(12) United States Patent
Holst et al.

(10) Patent No.: US 11,179,461 B2
(45) Date of Patent: Nov. 23, 2021

(54) II VACCINE ADJUVANT

(71) Applicant: UNIVERSITY OF COPENHAGEN, Copenhagen (DK)

(72) Inventors: Peter Johannes Holst, Copenhagen (DK); Cyrielle Elyette Fougeroux, Copenhagen (DK)

(73) Assignee: UNIVERSITY OF COPENHAGEN, Copenhagen (DK)

( * ) Notice: Subject to any disclaimer, the term of this patent is extended or adjusted under 35 U.S.C. 154(b) by 0 days.

(21) Appl. No.: 16/484,336

(22) PCT Filed: Mar. 19, 2018

(86) PCT No.: PCT/EP2018/056844
§ 371 (c)(1),
(2) Date: Aug. 7, 2019

(87) PCT Pub. No.: WO2018/172259
PCT Pub. Date: Sep. 27, 2018

(65) Prior Publication Data
US 2019/0374636 A1    Dec. 12, 2019

(30) Foreign Application Priority Data
Mar. 20, 2017 (GB) .................................. 1704417

(51) Int. Cl.
*A61K 39/39* (2006.01)
*A61K 39/12* (2006.01)
*C07K 14/05* (2006.01)
*C07K 14/11* (2006.01)
*C07K 14/045* (2006.01)
*C07K 14/025* (2006.01)
*A61K 39/00* (2006.01)

(52) U.S. Cl.
CPC .............. *A61K 39/39* (2013.01); *A61K 39/12* (2013.01); *A61K 2039/505* (2013.01); *A61K 2039/5256* (2013.01); *C07K 14/025* (2013.01); *C07K 14/045* (2013.01); *C07K 14/05* (2013.01); *C07K 14/11* (2013.01)

(58) Field of Classification Search
None
See application file for complete search history.

(56) References Cited

U.S. PATENT DOCUMENTS

| 2004/0058881 | A1 | 3/2004 | Humphreys et al. |
| 2010/0278904 | A1 | 11/2010 | Holst et al. |
| 2011/0293704 | A1 | 12/2011 | Holst et al. |
| 2016/0000904 | A1 | 1/2016 | Colloca et al. |
| 2016/0304582 | A1 | 10/2016 | Hill et al. |

FOREIGN PATENT DOCUMENTS

| WO | WO 2007/062656 A2 | 6/2007 |
| WO | WO 2010/057501 A1 | 5/2010 |
| WO | WO 2014/141176 A1 | 9/2014 |
| WO | WO 2017/025782 A1 | 2/2017 |
| WO | WO 2018/037045 A1 | 3/2018 |

OTHER PUBLICATIONS

Chen et al. Adv Drug Deliv Rev. Oct. 15, 2013; 65(10): 1357-1369.*
Becker et al., "Use of Recombinant Adenovirus for Metabolic Engineering of Mammalian Cells," Methods in Cell Biology, vol. 43, 1994, pp. 161-189.
Borghese et al., "CD74: An Emerging Opportunity as a Therapeutic Target in Cancer and Autoimmune Disease," Expert Opinion on Therapeutic Targets, vol. 15, No. 3, 2011 (Published online Jan. 6, 2011), pp. 237-251 (16 pages total).
Capone et al., "A Short Peptide from MHC Class II Invariant Chain Enhances CD8+ T Cell Responses by Promoting Antigen K48-linked Ubiquitination and Proteasomal Degradation," Poster presented at EMBO APP 10, 2019, 1 page.
Cham et al., "A Semi-automated Multiplex High-throughput Assay for Measuring IgG Antibodies Against Plasmodium falciparum erythrocyte Membrane Protein I (PfEMP I) Domains in Small Volumes of Plasma," Malaria Journal, vol. 7, No. 108, 2008 (Published Jun. 12, 2008), 8 pages.
Colloca et al., "Generation and Screening of a Large Collection of Novel Simian Adenovirus Allows the Identification of Vaccine Vectors Inducing Potent Cellular Immunity in Humans," Sci Transl Med., vol. 4, No. 115, Jan. 4, 2012, pp. 1-24.
Diebold et al., "MHC Class II Presentation of Endogenously Expressed Antigens by Transfected Dendritic Cells," Gene Therapy, vol. 8, 2001, pp. 487-493.
Fougeroux et al., "Modified MHC Class II-Associated invariant Chain Induces Increased Antibody Responses against Plasmodium falciparum Antigens after Adenoviral Vaccination," The Journal of Immunology, vol. 202, 2019 (Published online Mar. 4, 2019), pp. 2320-2331 (13 pages total).
Holst, "Augmentation of Adenovirus Induced Immune Responses," PhD Thesis, University of Copenhagen, Submitted Jul. 25, 2008, pp. 1-107 (133 pages total).
Hugo et al., "Fibroblasts Can Induce Thymocyte Positive Selection in vivo," Proc. Natl. Acad. Sci., vol. 90, Nov. 1993, pp. 10335-10339.
Mittendorf et al., "CD4+ T Cells in Antitumor Immunity: Utility of an Ii-Key HER$_2$/neu Hybrid Peptide Vaccine (AE37)," Expert Opinion on Biological Therapy, vol. 9, No. 1, 2009 (Published online Dec. 8, 2008), pp. 71-78 (9 pages total).
Morris et al., "Association of Intracellular Proteins With Folded Major Histocompatibility Complex Class I Molecules," Immunologic Research, vol. 30, No. 2, 2004, pp. 171-179.

(Continued)

*Primary Examiner* — Oluwatosin A Ogunbiyi
(74) *Attorney, Agent, or Firm* — Birch, Stewart, Kolasch & Birch, LLP

(57) ABSTRACT

The present invention relates to a vaccine comprising a nucleic acid construct such as a DNA construct especially a nucleic acid construct comprising sequences encoding invariant chain operatively linked to antigenic protein or peptide encoding sequences. The present vaccine stimulates an enhanced immune response.

15 Claims, 38 Drawing Sheets
Specification includes a Sequence Listing.

(56) References Cited

OTHER PUBLICATIONS

Nakano et al., "Positive Selection of T Cells Induced by Viral Delivery of Neopeptides to the Thymus," Science, vol. 275, Jan. 31, 1997, pp. 678-683 (7 pages total).
Pieters et al., "MHC Class II Restricted Antigen Presentation," Curr Opin Immunol., vol. 9, 1997, pp. 89-96.
Roy et al., "Complete Nucleotide Sequences and Genome Organization of Four Chimpanzee Adenoviruses," Virology, vol. 324, 2004 (Available online May 14, 2014), pp. 361-372.
Roy et al., "Creation of a Panel of Vectors Based on Ape Adenovirus Isolates," J Gene Med, vol. 13, 2011 (Published online Dec. 17, 2010), pp. 17-25.
Schröder et al., "The Multifaceted Roles of the Invariant Chain CD74—More than Just a Chaperone," Biochimica et Biophysica Acta, vol. 1863, 2016 (Available online Mar. 28, 2016), pp. 1269-1281.
Strubin et al., "Alternative Splicing and Alternative Initiation of Translation Explain the Four Forms of the Ia Antigen-associated Invariant Chain," The EMBO Journal, vol. 5, No. 13, 1986, pp. 3483-3488.
Stumptner-Cuvelette et al., "Multiple Roles of the Invariant Chain in MHC Class II Function," Biochimica et Biophysica Acta, vol. 1542, 2002, pp. 1-13.
Villadangos et al., "Degradation of Mouse Invariant Chain: Roles of Cathepsins S and D and the Influence of Major Histocompatibility Complex Polymorphism," J. Exp. Med., vol. 186. No. 4, Aug. 18, 1997, pp. 549-560, XP2328828.

\* cited by examiner

Intracellular - IT4var19

Extracellular - IT4var19

Extracellular - PFCLINvar30

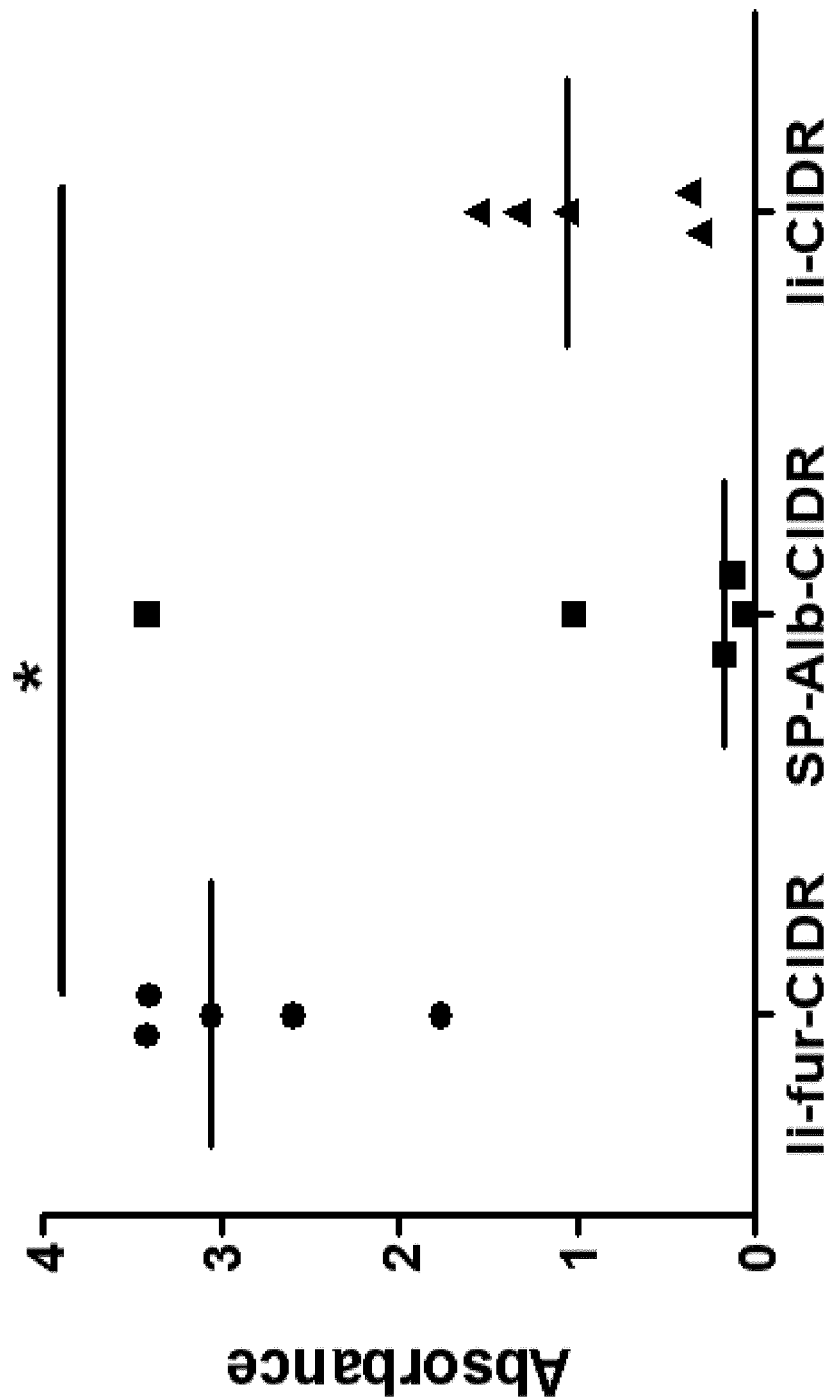

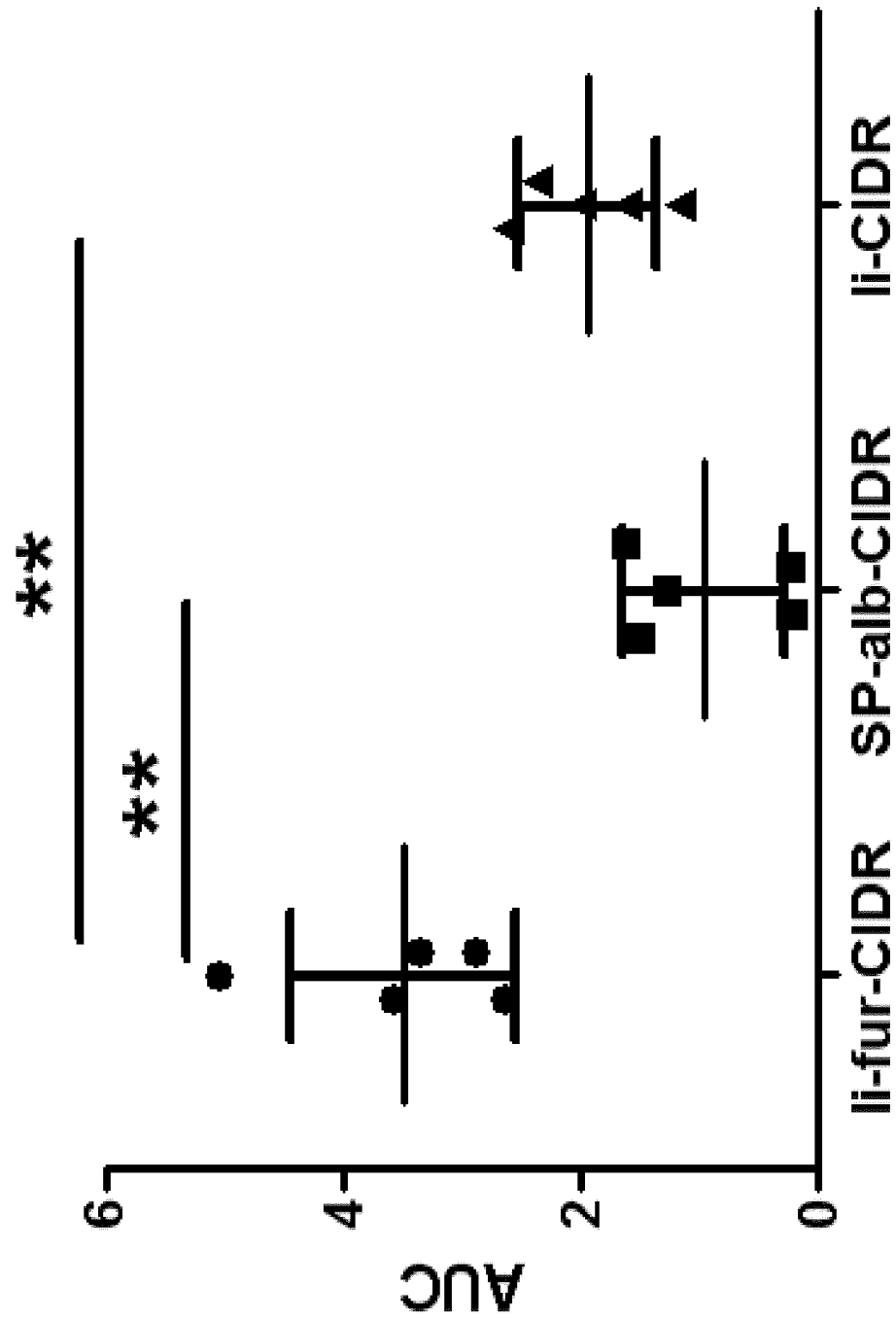

A

B

| | Ii-furin (secreted trimer) | Ii (membrane trimer) | SP-alb (Secreted monomer) | Δ17-Ii-fur (secreted trimer) | Ii-Cterm-fur (secreted monomer) |
|---|---|---|---|---|---|
| Ii | | | | | |
| Furin | Internal | - | - | internal | C-terminal |
| ESS | + | + | - | - | + |
| secretion | + | - | + | + | + |
| trimerisation | + | + | - | + | - |

A

B

Ii VACCINE ADJUVANT

REFERENCE TO SEQUENCE LISTING SUBMITTED VIA EFS-WEB

This application includes an electronically submitted sequence listing in .txt format. The .txt file contains a sequence listing entitled "-01-19 5979-0126PUS1_ST25.txt" created on Jan. 19, 2021 and is 146,972 bytes in size. The sequence listing contained in this .txt file is part of the specification and is hereby incorporated by reference herein in its entirety.

FIELD OF INVENTION

The present invention relates to a method for improving stimulation of an immune response.

BACKGROUND OF INVENTION

Despite current knowledge in the field of immunology especially regarding vaccine technologies no suitable vaccines are available against numerous pathogens. Widespread pandemics of HIV (Human Immunodeficiency Virus), HTLV (Human T-cell Lymphotropic Virus), tuberculosis and HCV (Hepatitis C virus) remain out of reach of effective vaccination, while Ebola and other emerging pathogens threaten to overwhelm our healthcare systems. Similarly, the rise in worldwide terrorism has expanded the potential epidemics to include lethal pathogens such as Lassa and Marburg.

Vaccines can be prophylactic (they are given before the actual infection occurs), or therapeutic (where they elicit or accelerate an immune response to a pathogen already in the body). Both methods of vaccination require the establishment of a solid immune response. The immune response that is activated by infection or vaccination depends on the interaction of several cell types, such as T-, B- and antigen-presenting cells as well as several different molecules, primarily antigens, MHC molecules, T- and B-cells receptors and many more.

Antigens include peptide fragments presented on the surface of antigen presenting cells by MHC molecules. Antigens can be of foreign, i.e. pathogenic origin, or stem from the organism itself, so-called auto-antigens. The MHC molecules are representatives of a polymorphous gene family encoded by a specific chromosomal region known as the "major histocompatibility complex", hence MHC. Two classes of MHC molecules exist, MHC class I (MHC-I) and MHC class II (MHC-II).

T-helper cells are stimulated by antigens presented by MHC class II (MHC-II) molecules residing on the surface of antigen-presenting cells. The MHC-II molecules are synthesized in the endoplasmatic reticulum. During synthesis, they combine with invariant chain (Ii) in a manner preventing the MHC-II molecules from being loaded with auto-antigens. The MHC-II molecule and the invariant chain are transported to the cell surface in a specific cellular compartment by signal sequences. As the compartment matures by the processing of its contents it progresses from being a lysosome, to a late endosome (after fusion with endocytotic vesicles) to an MHC class II compartment (MIIC). The endocytotic vesicle contains foreign antigen e.g. proteolytically cleaved bacterial peptide fragments. These fragments are by their degradation prepared to be loaded onto the MHC-II molecule. The MHC-II molecule is released by the invariant chain in a two part process wherein the invariant chain first is degraded proteolytically leaving only a peptide termed CLIP in the MHC-II binding domain, secondly by the removal of CLIP by an HLA-DM molecule. The MHC-II molecule is then free to bind the foreign antigens and present these on the cell surface after fusion of the MIIC vesicle to the plasma membrane. This initiates the humoral immune response as the presented antigen stimulates activation of a T-helper cell which in turn by several means activates a B cell, which ultimately differentiates into an antibody secreting cell.

T-helper cells can also participate in the cellular immune response when professional antigen presenting cells or activated tissue resident cells present antigen derived from intracellular organelles on MHC class II. In this way the $CD4^+$ T cells orchestrate inflammation by secreting cytokines and chemokines and provide stimulation for antigen presenting cells.

An important effector mechanism of the cellular immune response is initiated when the T-cell receptor of T-cytotoxic cells recognizes antigen bound to the MHC class I molecule on an antigen presenting cell. MHC-I molecules are typically not associated with a molecule of a functionality like the invariant chain that associates with MHC-II.

The processing of MHC-I into an antigen presenting molecule furthermore differs from that of MHC-II molecules in that the MHC-I molecule is loaded with antigen already in the endoplasmatic reticulum. The antigens presented by the MHC-I molecule are typically peptide fragments cleaved by the proteasome of proteins that have been synthesized by the antigen presenting cell itself. These proteins may be abnormal proteins encoded in the cell's own DNA or proteins derived from viruses or other pathogens that have infected the cell. An exception to this rule is present in a specialized subset of antigen presenting cells. These cells take up extracellular antigen and present them on MHC class I to stimulate cytotoxic T lymphocyte responses. In this cell subset, MHC class I molecules are also bound by the MHC class II associated invariant chain. The MHC class I-related proteolytic system is present in virtually all cells.

The functions of the two types of T cells are significantly different, as implied by their names. Cytotoxic T cells eradicate intracellular pathogens and tumors by direct lysis of cells and by secreting cytokines such as γ-interferon. The predominant cytotoxic T cell is the $CD8^+$ T cell, which also is antigen-specific. Helper T cells also can lyse cells, but their primary function is to secrete cytokines and chemokines that promote the activities of B cells (antibody-producing cells), antigen-presenting cells and other T cells and thus broadly enhance the immune response to foreign antigens, including antibody-mediated and cytotoxic T cell-mediated response mechanisms. $CD4^+$ T cells are the major helper T cell phenotype in the immune response.

Traditional vaccines rely on whole organisms, either pathogenic strains that have been killed or strains with attenuated pathogenicity. These vaccines run the risk of introducing the disease they are designed to prevent if the attenuation is insufficient or if enough organisms survive the killing step during vaccine preparation. Furthermore, such vaccines have reduced infectivity and are often insufficiently immunogenic, resulting in inadequate protection from the vaccination.

Molecular biological techniques have been used in an attempt to develop new vaccines based on individual antigenic proteins from pathogenic organisms. Conceptually, use of antigenic peptides rather than whole organisms would avoid pathogenicity while providing a vaccine containing the most immunogenic antigens. However, it has proven difficult to select the optimal antigen of a given protein or polypeptide and furthermore it has been found that pure peptides or carbohydrates tend to be weak immunogens.

Genetic (DNA or RNA) vaccines are new and promising candidates for the development of both prophylactic and therapeutic vaccines. The strength of the ensuing immune response is determined through a combination of the potency of the vector (i.e. naked DNA, viral vectors, live attenuated viruses etc.), the expression level of the antigen, and the recombinant antigen itself (i.e. high or low affinity MHC binders, structural determinants selecting for more or less limited T- or B-cell repertoire etc.). It is generally held to be true that efficient induction of immunological memory requires or benefits from the interactions of CD4+(helper cell) T-cells with CD8+(cytotoxic) T-cells and B-cells that mediate many of the effects of immune memory. However, one potential disadvantage of conventional DNA vaccines as compared to the virus vectored vaccines is their low immunogenicity in humans. One likely cause of this low immunogenicity is the restricted access of antigens formed within cells to the MHC II pathway for antigen processing and presentation to T helper cells and the antigen amount produced on professional antigen presenting cells.

SUMMARY OF INVENTION

In certain embodiments, the present invention provides for improved stimulation of the immune response in a manner that also in certain embodiments increases the kinetics of the response, simultaneously with both broadening and/or improving the response, while in some embodiments avoiding, among other things, the above mentioned disadvantages of the vaccination methods described in the state of the art. In particular, a novel system for a directed, specific and fast stimulation of the immune system is hereby made available in order to improve the vaccination of all animals.

By the present invention it was found that the antiviral $CD4^+$ and $CD8^+$ T-cell responses achieved by fusion of an antigen to the invariant chain were further improved by introducing a protease cleavage site within the invariant chain. Additionally, and surprisingly, it was found that upon cleavage of the fusion protein by a protease, the fusion proteins are secreted in the extracellular space without any substantial negative effect on other immune stimulating properties of the molecule. The constructs of the present invention therefore provide for a balanced immune response.

DESCRIPTION OF SEQUENCES

| | |
|---|---|
| SEQ ID No: 1 | Amino acid sequence for human invariant chain isoform p35 |
| SEQ ID No: 2 | Nucleotide sequence encoding human invariant chain isoform p35 |
| SEQ ID No: 3 | Amino acid sequence for human invariant chain isoform p33 |
| SEQ ID No: 4 | Amino acid sequence for human invariant chain isoform p43 |
| SEQ ID No: 5 | Nucleotide sequence encoding human invariant chain isoform p43 |
| SEQ ID No: 6 | Amino acid sequence for human invariant chain isoform p41 |
| SEQ ID No: 7 | Amino acid sequence for human invariant chain isoform c |
| SEQ ID No: 8 | Nucleotide sequence encoding human invariant chain isoform c |
| SEQ ID No: 9 | Amino acid sequence for murine invariant chain p31 |
| SEQ ID No: 10 | Nucleotide sequence encoding murine invariant chain p31 |
| SEQ ID No: 11 | Amino acid sequence for murine invariant chain p41 |
| SEQ ID No: 12 | Nucleotide sequence encoding murine invariant chain p41 |
| SEQ ID No: 13 | Amino acid sequence for *Cavia porcellus* invariant chain (UniProt accession number H0UZ94) |
| SEQ ID No: 14 | Amino acid sequence for *Heterocephalus glaber* invariant chain (UniProt accession number G5C391) |
| SEQ ID No: 15 | Amino acid sequence for *Fukomys damarensis* invariant chain (UniProt accession number A0A091E9W3) |
| SEQ ID No: 16 | Amino acid sequence for *Rattus norvegicus* second isoform invariant chain (UniProt accession number P10247-2) |
| SEQ ID No: 17 | Amino acid sequence for *Rattus norvegicus* first isoform invariant chain (UniProt accession number P10247) |
| SEQ ID No: 18 | Amino acid sequence for *Myotis lucifugus* invariant chain (UniProt accession number G1QEN4) |
| SEQ ID No: 19 | Amino acid sequence for *Myotis davidii* invariant chain (UniProt accession number L5LQM9) |
| SEQ ID No: 20 | Amino acid sequence for *Myotis brandtii* invariant chain (UniProt accession number S7N2W2) |
| SEQ ID No: 21 | Amino acid sequence for *Pteropus alecto* invariant chain (UniProt accession number L5L1G3) |
| SEQ ID No: 22 | Amino acid sequence for *Pan troglodytes verus* invariant chain (UniProt accession number A5A6L4) |
| SEQ ID No: 23 | Amino acid sequence for *Pongo abelii* invariant chain (UniProt accession number Q5RFJ4) |
| SEQ ID No: 24 | Amino acid sequence for *Pan troglodytes* invariant chain (UniProt accession number H2QRT2) |
| SEQ ID No: 25 | Amino acid sequence for *Gorilla gorilla gorilla* invariant chain (UniProt accession number G3R756) |
| SEQ ID No: 26 | Amino acid sequence for *Nomascus leucogenys* invariant chain (UniProt accession number G1RHB8) |
| SEQ ID No: 27 | Amino acid sequence for *Macaca mulatta* invariant chain (UniProt accession number I0FWR3) |
| SEQ ID No: 28 | Amino acid sequence for *Macaca fascicularis* invariant chain (UniProt accession number G7P8P8) |

| | |
|---|---|
| SEQ ID No: 29 | Amino acid sequence for *Macaca mulatta* invariant chain (UniProt accession number G7MVM5) |
| SEQ ID No: 30 | Amino acid sequence for *Macaca mulatta* invariant chain (UniProt accession number I0FWR4) |
| SEQ ID No: 31 | Amino acid sequence for *Macaca mulatta* invariant chain (UniProt accession number F7E9S4) |
| SEQ ID No: 32 | Amino acid sequence for *Papio anubis* invariant chain (UniProt accession number A0A096MM48) |
| SEQ ID No: 33 | Amino acid sequence for *Chlorocebus sabaeus* invariant chain (UniProt accession number A0A0D9RGK4) |
| SEQ ID No: 34 | Amino acid sequence for *Callithrix jacchus* invariant chain (UniProt accession number F7ENM4) |
| SEQ ID No: 35 | Amino acid sequence for *Felis catus* invariant chain (UniProt accession number M3VXS2) |
| SEQ ID No: 36 | Amino acid sequence for *Mustela putorius furo* invariant chain (UniProt accession number M3YQS4) |
| SEQ ID No: 37 | Amino acid sequence for *Loxodonta africana* invariant chain (UniProt accession number G3TJE1) |
| SEQ ID No: 38 | Amino acid sequence for *Loxodonta africana* invariant chain (UniProt accession number G3U7Y6) |
| SEQ ID No: 39 | Amino acid sequence for *Sus scrofa* invariant chain (UniProt accession number Q764N1) |
| SEQ ID No: 40 | Amino acid sequence for *Camelus ferus* invariant chain (UniProt accession number S9XLT6) |
| SEQ ID No: 41 | Amino acid sequence for *Bos mutus* invariant chain (UniProt accession number L8I7V9) |
| SEQ ID No: 42 | Amino acid sequence for *Bos taurus* invariant chain (UniProt accession number Q7JFY1) |
| SEQ ID No: 43 | Amino acid sequence for *Bos taurus* invariant chain (UniProt accession number Q29630) |
| SEQ ID No: 44 | Amino acid sequence for *Equus caballus* invariant chain (UniProt accession number F6TGS3) |
| SEQ ID No: 45 | Amino acid sequence for *Equus caballus* invariant chain (UniProt accession number Q9MXD5) |
| SEQ ID No: 46 | Amino acid sequence for *Oryctolagus cuniculus* invariant chain (UniProt accession number G1SKK3) |
| SEQ ID No: 47 | Amino acid sequence for *Otolemur garnettii* invariant chain (UniProt accession number H0WQB3) |
| SEQ ID No: 48 | Amino acid sequence for *Tupaia chinensis* invariant chain (UniProt accession number L9KN01) |
| SEQ ID No: 49 | Amino acid sequence for *Ictidomys tridecemlineatus* invariant chain (UniProt accession number I3MCR9) |
| SEQ ID No: 50 | Amino acid sequence for *Sarcophilus harrisii* invariant chain (UniProt accession number G3X0Q6) |
| SEQ ID NO: 51 | Amino acid sequence for the res linker |
| SEQ ID NO: 52 | Nucleotide sequence encoding the res linker |
| SEQ ID NO: 53 | Amino acid sequence for the HA tag |
| SEQ ID NO: 54 | Nucleotide sequence encoding the HA tag |
| SEQ ID NO: 55 | Nucleotide sequence encoding li/fur/Int |
| SEQ ID NO: 56 | Amino acid sequence of li/fur/Int |
| SEQ ID NO: 57 | Exemplary furin cleavage site |
| SEQ ID NO: 58 | Nucleotide sequence encoding SP-alb |
| SEQ ID NO: 59 | Amino acid sequence of SP-alb |
| SEQ ID NO: 60 | Nucleotide sequence encoding SP-alb-19-30 |
| SEQ ID NO: 61 | Amino acid sequence of SP-Alb-19-30 |
| SEQ ID NO: 62 | Nucleotide sequence encoding li-19-30 |
| SEQ ID NO: 63 | Amino acid sequence of li-19-30 |
| SEQ ID NO: 64 | Nucleotide sequence encoding li-fur-19-30 |
| SEQ ID NO: 65 | Amino acid sequence of li-fur-19-30 |
| SEQ ID NO: 66 | OVA257-264 (SIINFEKL) peptide sequence |
| SEQ ID NO: 67 | Peptide of the Melanoma associated retrovirus p15E protein |
| SEQ ID NO: 68 | IT4var19 antigen encoding polynucleotide sequence |
| SEQ ID NO: 69 | PFLCINvar30 antigen encoding polynucleotide sequence |

DESCRIPTION OF DRAWINGS

FIG. 6A-6F: Timeline of the antibody responses against IT4var19 and PFCLINvar30 induced after hAd5 with the Ii-fur adjuvant compared to controls. (A) and (B) show detection of antibodies recognizing IT4var19 (A) 2 weeks or (B) 6 weeks after immunization of Balb/C mice with Ad5-Ii-fur-IT4var19-PFCLINvar30 (N=5), Ad5-Sp-alb-IT4var19-PFCLINvar30 (N=5), Ad5-Ii-IT4var19-PFCLINvar30 (N=5) (serum was diluted to 1:50). (C) and (E) show the detection of antibodies recognizing IT4var19 10 weeks after immunization of Balb/C mice with Ad5-Ii-fur-IT4var19-PFCLINvar30 (N=5), Ad5-Sp-alb-IT4var19-PFCLINvar30 (N=5), Ad5-Ii-IT4var19-PFCLINvar30 (N=5). Serum was diluted to 1:50 and added to the wells in three-fold dilutions. Absorbance and dilutions were plotted on a log(X) axis (E), area under the curve were calculated and plotted on (C). (D) and (F) show the detection of antibodies recognizing PFCLINvar30, 10 weeks after immunization of Balb/C mice with Ad5-Ii-fur-IT4var19-PFCLINvar30 (N=5), Ad5-Sp-alb-IT4var19-PFCLINvar30 (N=5), Ad5-Ii-IT4var19-PFCLINvar30 (N=5). Serum was diluted to 1:50 and added to the wells in three-fold dilutions. Absorbance and dilutions were plotted on a log(X) axis (F), area under the curve were calculated and plotted on (D).

DETAILED DESCRIPTION OF THE INVENTION

Figure 1:
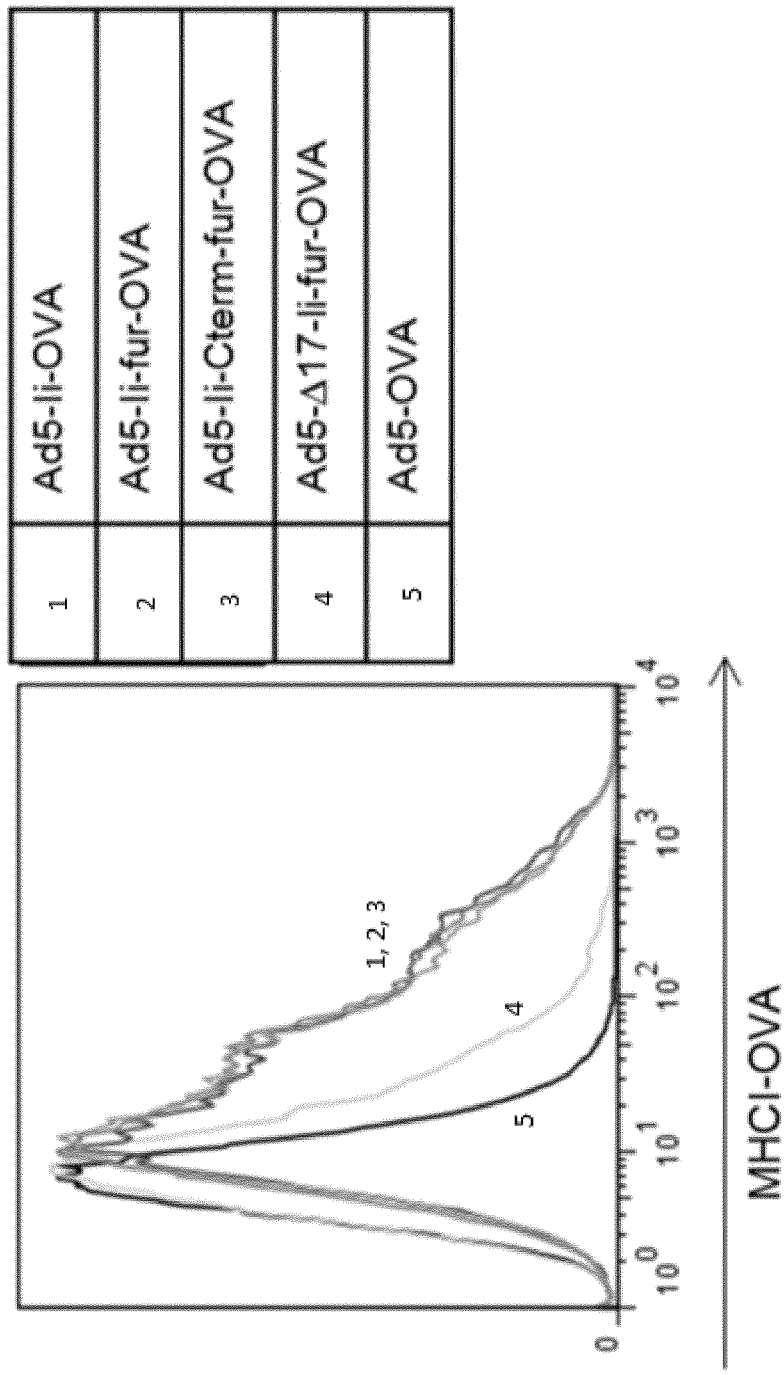
FIG. 1: Analysis of MHCI expression of OVA antigens with different adjuvants-MHCI presentation of OVA on the surface of JAWSII cells after infection with the different hAd5-OVA constructs.

The present invention relates to a vaccine comprising a nucleic acid construct such as a DNA construct, especially a nucleic acid construct comprising sequences encoding an invariant chain operatively linked to an antigenic protein or peptide, wherein a cleavage site for a protease has been introduced within the invariant chain.

In a first aspect, the invention relates to a nucleic acid construct comprising sequences encoding:
a. at least one invariant chain or variant thereof operatively linked to
b. at least one antigenic protein or peptide or an antigenic fragment thereof;
wherein
the C-terminal end of said invariant chain or variant thereof is operatively linked to the N-terminal end of said antigenic protein or peptide or antigenic fragment thereof;
said invariant chain or variant thereof comprises a protease cleavage site and optionally a trimerization (TRIM) domain located C-terminally of said protease cleavage site.

In a further aspect, the invention relates to a nucleic acid construct as described herein for use in stimulating an immune response.

In yet a further aspect, the invention relates to a nucleic acid construct as described herein for use as a primer for the stimulation of an immune response, thereby increasing the potency of a subsequently administered vaccine or a co-administered vaccine.

In yet a further aspect, the invention relates to a nucleic acid construct as described herein for use in boosting an immune response, thereby increasing the potency of a primer dose vaccine.

In yet another aspect, the invention relates to a chimeric protein comprising:
a. at least one invariant chain or variant thereof operatively linked to
b. at least one antigenic protein or peptide or an antigenic fragment thereof;
wherein
the part of the C-terminal end of said invariant chain or variant thereof is operatively linked to the N-terminal end of said antigenic protein or peptide or antigenic fragment thereof; and
said invariant chain or variant thereof comprises a protease cleavage site and optionally a trimerization (TRIM) domain located C-terminally of said protease cleavage site.

In yet another aspect, the invention relates to a delivery vehicle comprising the nucleic acid construct as described herein.

In yet another aspect, the invention relates to a method for administering the delivery vehicle described herein to an individual, wherein said administration is selected from the group consisting of needle injection, gene gun, jet injection, electroporation, ultrasound, and hydrodynamic delivery.

In yet another aspect, the invention relates to a method for administering the nucleic acid construct described herein to an individual, wherein said administration is selected from the group consisting of needle injection, gene gun, jet injection, electroporation, ultrasound, and hydrodynamic delivery.

In yet another aspect, the invention relates to a cell comprising the nucleic acid construct as described herein.

In yet another aspect, the invention relates to an antibody that can recognise the chimeric protein as described herein.

In yet another aspect, the invention relates to the use of the antibody described herein, in an assay for detecting proteins to which the antibody binds.

In yet another aspect, the invention relates to a composition comprising a nucleic acid sequence encoding:
a. at least one invariant chain or variant thereof;
b. at least one antigenic protein or peptide or an antigenic fragment thereof;
wherein
the C-terminal end of said invariant chain or variant thereof is operatively linked to the N-terminal end of said antigenic protein or peptide or antigenic fragment thereof;
said invariant chain or variant thereof comprises a protease cleavage site and optionally a trimerization (TRIM) domain located C-terminally of said protease cleavage site.

In yet another aspect, the invention relates to a composition comprising a nucleic acid sequence encoding:
a. at least one invariant chain or variant thereof;
b. at least one antigenic protein or peptide or an antigenic fragment thereof;
wherein
the C-terminal end of said invariant chain or variant thereof is operatively linked to the N-terminal end of said antigenic protein or peptide or antigenic fragment thereof;
said invariant chain or variant thereof comprises a protease cleavage site and optionally a trimerization (TRIM) domain located C-terminally of said protease cleavage site,
for use as a medicament.

In yet another aspect, the invention relates to a vaccine composition comprising a delivery vehicle as described herein for use as a medicament.

In yet another aspect, the invention relates to the use of a composition comprising a delivery vehicle as described herein in the manufacture of a medicament.

In yet another aspect, the invention relates to a delivery vehicle as described herein for use in the production of a vaccine.

In yet another aspect, the invention relates to a viral vector comprising a nucleic acid construct comprising sequences encoding:
c. at least one invariant chain operatively linked to
d. at least one antigenic protein or peptide or an antigenic fragment thereof;
wherein
the C-terminal end of said invariant chain or variant thereof is operatively linked to the N-terminal end of said antigenic protein or peptide or antigenic fragment thereof;

said invariant chain or variant thereof comprises a protease cleavage site and optionally a trimerization (TRIM) domain located C-terminally of said protease cleavage site.

In yet another aspect, the invention relates to an adenoviral vector comprising a nucleic acid construct comprising sequences encoding:
e. at least one invariant chain of any one of SEQ ID NOs: 1-8 operatively linked to
f. at least one antigenic protein or peptide or an antigenic fragment thereof;
wherein
the C-terminal end of said invariant chain is operatively linked to the N-terminal end of said antigenic protein or peptide or antigenic fragment thereof;
said invariant chain comprises a furin cleavage site and a trimerization (TRIM) domain located C-terminally of said protease cleavage site and N-terminally of said antigenic protein or peptide or an antigenic fragment thereof.

In yet another aspect, the invention relates to a kit in parts comprising:
a. a composition comprising a nucleic acid construct as described herein;
b. a medical instrument or other means for administering the composition; and
c. instructions on how to use the kit in parts.

In yet another aspect, the invention relates to a method for inducing an immune response in an animal, comprising administering to the animal a vaccine composition as described herein.

In yet another aspect, the invention relates to a method for genetic immunization comprising the steps of:
preparing a nucleic acid construct as described herein,
administering said nucleic acid construct to an individual.

In yet another aspect, the invention relates to a method for increasing the potency of a vaccine comprising the steps of:
a. providing the nucleic acid construct as described herein, or the composition as described herein;
b. priming the immune system of an individual by administering the nucleic acid construct or composition of step a) to an individual, thereby stimulating an immune response in an individual.

Definitions

Adenovirus: A group of double-stranded DNA containing viruses. Adenoviruses can be genetically modified making them replication incompetent or conditionally replication incompetent. In this form, as adenoviral constructs or adenovectors, they can be used as gene delivery vehicles for vaccination or gene therapy.

Adjuvant: Any substance whose admixture with an administered immunogenic determinant/antigen/nucleic acid construct increases or otherwise improves the immune response to said determinant.

Amino acid: Any synthetic or naturally occurring amino carboxylic acid, including any amino acid occurring in peptides and polypeptides including proteins and enzymes synthesized in vivo thus including modifications of the amino acids. The term amino acid is herein used synonymously with the term "amino acid residue" which is meant to encompass amino acids as stated which have been reacted with at least one other species, such as 2, for example 3, such as more than 3 other species. The generic term amino acid comprises both natural and non-natural amino acids any of which may be in the "D" or "L" isomeric form. Typically this term refers to any one of the 20 commonly found, naturally occurring amino acids.

Antibody: Immunoglobulin molecules and active portions of immunoglobulin molecules. Antibodies are for example intact immunoglobulin molecules or fragments thereof retaining the immunologic activity.

Antigen: Any substance that can bind to a clonally distributed immune receptor (T-cell or B-cell receptor). Usually a peptide, polypeptide or a multimeric polypeptide.

Antigens are preferably capable of eliciting an immune response.

Boost: To boost by a booster shot or dose is to give an additional dose of an immunizing agent, such as a vaccine, given at a time after the initial dose to sustain the immune response elicited by the previous dose of the same agent.

Carrier: Entity or compound to which antigens are coupled to aid in the induction of an immune response.

Chimeric protein: A genetically engineered protein that is encoded by a nucleotide sequence made by a splicing together of two or more complete or partial genes or a series of (non)random nucleic acids.

Complement: A complex series of blood proteins whose action "complements" the work of antibodies. Complement destroys bacteria, produces inflammation, and regulates immune reactions.

Cytokine: Growth or differentiation modulator, used non-determinative herein, and should not limit the interpretation of the present invention and claims. In addition to the cytokines, adhesion or accessory molecules, or any combination thereof, may be employed alone or in combination with the cytokines.

CTL: Cytotoxic T lymphocytes. A sub group of T-cells expressing CD8 along with the T-cell receptor and therefore able to respond to antigens presented by class I molecules.

Delivery vehicle: An entity whereby a nucleotide sequence or polypeptide or both can be transported from at least one media to another, such as a viral vector.

Fragment: is used to indicate a non-full length part of a nucleic acid or polypeptide. Thus, a fragment is itself also a nucleic acid or polypeptide, respectively.

Individual: Any species or subspecies of bird, mammal, fish, amphibian, or reptile. More suitably a mammal, more suitably a human.

Invariant chain: an integral membrane protein glycoprotein that associates with and stabilizes MHC II molecules in the endoplasmatic reticulum and subsequent cellular compartments. Here the term invariant chain covers all naturally occurring or artificially generated full length or fragmented homologous genes and proteins of a certain similarity to human invariant chain. Invariant chain is herein abbreviated Ii.

Isolated: used in connection with nucleic acids, polypeptides, and antibodies disclosed herein 'isolated' refers to these having been identified and separated and/or recovered from a component of their natural, typically cellular, environment. Nucleic acids, polypeptides, and antibodies of the invention are preferably isolated, and vaccines and other compositions of the invention preferably comprise isolated nucleic acids, polypeptides or isolated antibodies.

MHC: Major histocompatibility complex, two main subclasses of MHC, Class I and Class II exist.

Nucleic acid: A chain or sequence of nucleotides that convey genetic information. In regards to the present invention the nucleic acid is a deoxyribonucleic acid (DNA).

Nucleic acid construct: A genetically engineered nucleic acid. Typically comprising several elements such as genes or fragments of same, promoters, enhancers, terminators, polyA tails, linkers, polylinkers, operative linkers, multiple cloning sites (MCS), markers, STOP codons, other regulatory elements, internal ribosomal entry sites (IRES) or others.

Operative linker: A sequence of nucleotides or amino acid residues that bind together two parts of a nucleic acid construct or (chimeric) polypeptide in a manner securing the biological processing of the nucleic acid or polypeptide.

Pathogen: a specific causative agent of disease, especially a biological agent such as a virus, bacteria, prion or parasite that can cause disease to its host, also referred to as an infective agent.

Peptide: Plurality of covalently linked amino acid residues defining a sequence and linked by amide bonds. The term is used analogously with oligopeptide and poly-peptide. The natural and/or non-natural amino acids may be linked by peptide bonds or by non-peptide bonds. The term peptide also embraces post-translational modifications introduced by chemical or enzyme-catalyzed reactions, as are known in the art. The term can refer to a variant or fragment of a polypeptide.

Pharmaceutical carriers: also termed excipients, or stabilizers are non-toxic to the cell or individual being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™

Plurality: At least two.

Promoter: A binding site in a DNA chain at which RNA polymerase binds to initiate transcription of messenger RNA by one or more nearby structural genes.

Signal peptide: A short sequence of amino acids that determine the eventual location of a protein in the cell, also referred to as sorting peptide.

siRNA: Small interfering RNAs (siRNAs), which target (in a sequence-specific manner) endogenous RNAs for degradation, thereby reducing the amount of a gene product.

Surfactant: A surface active agent capable of reducing the surface tension of a liquid in which it is dissolved. A surfactant is a compound containing a polar group which is hydrophilic and a non polar group which is hydrophobic and often composed of a fatty chain.

Vaccine: A substance or composition capable of inducing an immune response in an animal. Also referred to as an immunogenic composition in the present text. An immune response being an immune response (humoral/antibody and/or cellular) inducing memory in an organism, resulting in the infectious agent, being met by a secondary rather than a primary response, thus reducing its impact on the host organism. A vaccine of the present invention may be given as or prophylactic and/or therapeutic medicament. The composition may comprise one or more of the following: antigen(s), nucleic acid constructs comprising one or more antigens operatively linked to Ii, carriers, adjuvants and pharmaceutical carriers.

Variant: a 'variant' of a given reference nucleic acid or polypeptide refers to a nucleic acid or polypeptide that displays a certain degree of sequence homology/identity to said reference nucleic acid or polypeptide but is not identical to said reference nucleic acid or polypeptide.

The Immune Response

Vaccines can be used prophylactically: they are given before the actual infection occurs; or therapeutically: where they elicit or accelerate an immune response to a pathogen already in the body. Both methods of vaccination require the establishment of a solid immune response. The immune response that is activated by infection or vaccination depends on the interaction of several cell types, such as T-, B- and antigen presenting cells as well as several different molecules, primarily antigens, MHC molecules, T- and B-cells receptors and many more.

Antigens include peptide fragments presented on the surface of antigen presenting cells by MHC molecules. Antigens can be of foreign, i.e. pathogenic origin, or stem from the organism itself, so called self or auto antigens. The MHC molecules are representatives of a polymorphous gene family encoded by a specific chromosomal region known as the "major histocompatibility complex", hence MHC. Two classes of MHC molecules exist, MHC class I (MHC-I) and MHC class II (MHC-II).

T-helper cells are stimulated by antigens presented by MHC class II (MHC-II) molecules residing on the surface of antigen presenting cells. The MHC-II molecules are synthesized in the endoplasmatic reticulum. During synthesis, they combine with invariant chain (Ii) in a manner preventing the MHC-II molecules from being loaded with auto-antigens. The MHC-II molecule is by signal sequences in the invariant chain transported to the cell surface in a specific cellular compartment. As the compartment matures by the processing of its contents it progresses from being a lysosome, to a late endosome (after fusion with endocytotic vesicles) to an MHC class II compartment (MIIC). The endocytotic vesicle contains foreign antigen e.g. proteolytically cleaved bacterial peptide fragments. These fragments are by their degradation prepared to be loaded onto the MHC-II molecule. The MHC-II molecule is released by the invariant chain in a two part process when the invariant chain first is degraded proteolytically leaving only a peptide termed CLIP in the MHC-II binding domain, secondly by the removal of CLIP by an HLA-DM molecule. The MHC-II molecule is then free to bind the foreign antigens and present these on the cell surface after fusion of the MIIC vesicle to the plasma membrane. This initiates the humoral immune response as the presented antigen stimulates activation of a T-helper cell which in turn by several means activates a B cell, which ultimately differentiates into an antibody secreting cell.

The cellular immune response is initiated when the T-cell receptor of T-cytotoxic cells recognizes antigen bound to the MHC class I molecule on an antigen presenting cell. MHC-I molecules are not associated with a molecule of a functionality like the invariant chain that associates with MHC-II. The processing of MHC-I into an antigen presenting molecule furthermore differs from that of MHC-II molecules in that the MHC-I molecule is loaded with antigen already in the endoplasmatic reticulum. The antigens presented by the MHC-I molecule are typically peptide fragments cleaved by the proteasome of proteins that have been synthesized by the antigen presenting cell itself. These proteins may be abnormal proteins encoded in the cells own DNA or proteins derived from viruses or other pathogens that have infected the cell and parasitize its protein synthesis machinery. The MHC class I-related proteolytic system is present in virtually all cells.

The functions of the two types of T cells are significantly different, as implied by their names. Cytotoxic T cells eradicate intracellular pathogens and tumors by direct lysis of cells and by secreting cytokines such as γ-interferon. The predominant cytotoxic T cell is the CD8$^+$ T cell, which also is antigen specific. Helper T cells also can lyse cells, but their primary function is to secrete cytokines that promote the activities of B cells (antibody-producing cells) and other T cells and thus they broadly enhance the immune response to foreign antigens, including antibody-mediated and cytotoxic T cell-mediated response mechanisms. CD4$^+$ T cells are the major helper T cell phenotype in the immune response.

Nucleic Acid Construct

An aspect of the invention relates to a nucleic acid construct comprising sequences encoding at least one invariant chain or variant thereof operatively linked to at least one antigenic protein or peptide or an antigenic fragment thereof; wherein the C-terminal end of said invariant chain or variant thereof is operatively linked to the N-terminal end of said antigenic protein or peptide or antigenic fragment thereof and wherein said invariant chain or variant thereof comprises a protease cleavage site and optionally a trimerization (TRIM) domain located C-terminally of said protease cleavage site.

By nucleic acid construct is understood a genetically engineered nucleic acid. The nucleic acid construct may be a non-replicating and linear nucleic acid, a circular expression vector, an autonomously replicating plasmid or viral expression vector. A nucleic acid construct may comprise several elements such as, but not limited to genes or fragments of same, promoters, enhancers, terminators, poly-A tails, linkers, polylinkers, operative linkers, multiple cloning sites (MCS), markers, STOP codons, internal ribosomal entry sites (IRES) and host homologous sequences for integration or other defined elements. It is to be understood that the nucleic acid construct according to the present invention may comprise all or a subset of any combination of the above-mentioned elements. Methods for engineering nucleic acid constructs are well known in the art (see, e.g., Molecular Cloning: A Laboratory Manual, Sambrook et al., eds., Cold Spring Harbor Laboratory, 2nd Edition, Cold Spring Harbor, N.Y., 1989).

The nucleic acid residues comprising the nucleic acid construct may in one embodiment be modified. Said modification may be selected from the group consisting of: acetylation, methylation, phosphorylation, ubiquitination, ribosylation, sulfurization, and others.

The nucleic acid construct according to the present invention may in one embodiment be composed of DNA. In another embodiment, the nucleic acid construct may be composed of a nucleic acid selected from the group consisting of deoxyribonucleic acid (DNA), ribonucleic acid (RNA), Locked Nucleic Acid (LNA), Peptide Nucleic Acid (PNA), Intercalating nucleic acid (INA), Twisted intercalating nucleic acid (TINA), Hexitol nucleic acids (HNA), arabinonucleic acid (ANA), cyclohexane nucleic acids (CNA), cyclohexenylnucleic acid (CeNA), Glycerol nucleic acid (GNA), threosyl nucleic acid (TNA), Gap-mers, Mixmers, Morpholinos, or a combination thereof.

Codon-Optimization and Degenerate Nucleic Acid Sequences

The expression of functional proteins in heterologous hosts is the cornerstone of modern biotechnology. Unfortunately, many proteins are difficult to express outside their original contexts. They may contain expression-limiting regulatory elements, come from organisms that use non-canonical nucleotide codes or from a gene rife with codons rarely used in the desired host. Improvements in the speed and efficiency of gene synthesis have rendered feasible complete gene redesign for maximum protein expression. For example, protein expression can improve dramatically when the codon frequency of the gene under study is matched to that of the host expression system. For example, a redesign strategy may include not only the use of optimum codon biases, but also the alteration of mRNA structural elements and the modification of translation and initiation regions. Techniques for codon optimization are known to the person skilled in the art, and may be performed by commercial suppliers such as GenScript Corporation.

It is understood, that the nucleic acid construct comprising invariant chain or a variant thereof according to the present invention may be codon-optimized in any way so as to produce—by translation into protein i.e. amino acids—an amino acid sequence comprising an invariant chain that corresponds to the amino acid sequence disclosed in any one of SEQ ID NOs: 1-50, and more suitably 1-8 (human invariant chains), or variants thereof according to the present invention.

Likewise, the nucleic acid construct comprising invariant chain according to the present invention may be codon-optimized in any way so as to produce—by translation into protein i.e. amino acids—an amino acid sequence comprising an invariant chain that corresponds to the amino acid sequence of any animal in which the nucleic acid construct may be used to prime an immune response; including any vertebrate, mammal, fish or bird; or variants thereof according to the present invention.

Codon Bias:

Codon bias has been identified as the single most important factor in prokaryotic gene expression. The degree to which a given codon appears in the genetic code varies significantly between organisms, between proteins expressed at high and low levels and even between different portions of the same operon. The reason for this is almost certainly because preferred codons correlate with the abundance of cognate tRNAs available within the cell. This relationship serves to optimize the translational system and to balance codon concentration with isoacceptor tRNA concentration.

Replace Infrequently Used Codons:

In general, the more rare codons that a gene contains, the less likely it is that the heterologous protein will be expressed at a reasonable level within that specific host system. These levels become even lower if the rare codons appear in clusters or in the N-terminal portion of the protein. Replacing rare codons with others that more closely reflect the host system's codon bias without modifying the amino acid sequence can increase the levels of functional protein expression.

Eliminate Problematic Codons:

Any codon that an organism uses less than 5% to 10% of the time may cause problems, regardless of where it is from. Again, close or adjacent codons can have more effect on protein expression than they could separately. Eliminating rare codons and codons that could be read as termination signals can prevent cases of low or nonexistent expression.

Express Viral Proteins in Mammalian Hosts:

Even viral genes can be successfully expressed in mammalian cell lines if the gene is properly prepared. Viral genes' dense information loads frequently result in overlapping reading frames. Many viral genes also encode cis-acting negative regulatory sequences within the coding sequence. Viral genes can be resynthesized not only to express only the desired protein but also to disrupt regulatory elements, thereby enhancing protein production. Viral codon optimization is especially useful in DNA vaccine research because it increases the immunogenicity of the target.

Other Constraints:

Although codon bias plays a large role in gene expression, the choice of expression vectors and transcriptional promoters is also important. The nucleotide sequences surrounding the N-terminal region of the protein are particularly sensitive, both to the presence of rare codons and to the identities of the codons immediately adjacent to the initiation AUG. There is also some interplay between translation and mRNA stability.

Degeneracy of the Genetic Code:

It follows from the above that the genetic code has redundancy but no ambiguity. For example, although codons GAA and GAG both specify glutamic acid (redundancy), neither of them specifies any other amino acid (no ambiguity) (see the codon table below for the full correlation). The codons encoding one amino acid may differ in any of their three positions. The degeneracy of the genetic code is what accounts for the existence of silent mutations. Degeneracy results because a triplet code of four bases designates 20 amino acids and a stop codon.

| Ala/A | GCU, GCC, GCA, GCG | Leu/L | UUA, UUG, CUU, CUC, CUA, CUG |
| --- | --- | --- | --- |
| Arg/R | CGU, CGC, CGA, CGG, AGA, AGG | Lys/K | AAA, AAG |
| Asn/N | AAU, AAC | Met/M | AUG |
| Asp/D | GAU, GAC | Phe/F | UUU, UUC |
| Cys/C | UGU, UGC | Pro/P | CCU, CCC, CCA, CCG |
| Gln/Q | CAA, CAG | Ser/S | UCU, UCC, UCA, UCG, AGU, AGC |
| Glu/E | GAA, GAG | Thr/T | ACU, ACC, ACA, ACG |
| Gly/G | GGU, GGC, GGA, GGG | Trp/W | UGG |
| His/H | CAU, CAC | Tyr/Y | UAU, UAC |
| Ile/I | AUU, AUC, AUA | Val/V | GUU, GUC, GUA, GUG |
| START | AUG | STOP | UAG, UGA, UAA |

The table shows the 20 amino acids, start and stop codons and the 64 possible codons. The direction of the mRNA is 5' to 3'.

Synonymous Substitution:

Silent mutations or substitutions are DNA mutations that do not result in a change to the amino acid sequence of a protein. They may occur in a non-coding region (outside of a gene or within an intron), or they may occur within an exon in a manner that does not alter the final amino acid sequence. The phrase silent mutation or substitution is often used interchangeably with the phrase synonymous mutation or substitution; however, synonymous mutations or substitutions are a subcategory of the former, occurring only within exons.

It is understood, that the nucleic acid construct comprising invariant chain or a variant thereof according to the present invention may comprise a synonymous substitution so as to produce—by translation into protein i.e. amino acids—an amino acid sequence comprising an invariant chain that corresponds to the amino acid sequence disclosed in any one of SEQ ID NOs: 1-50 or more suitably SEQ ID NOs: 1-8 (human invariant chains), or variants thereof according to the present invention.

Likewise, the nucleic acid construct comprising invariant chain according to the present invention may comprise a synonymous substitution so as to produce—by translation into protein i.e. amino acids—an amino acid sequence comprising an invariant chain that corresponds to the amino acid sequence of any animal in which the nucleic acid construct may be used to prime an immune response; including any vertebrate, mammal, fish or bird; or variants thereof according to the present invention.

Non-Synonymous Substitution into Synonymous Amino Acids:

A non-synonymous substitution causes a change in the amino acid. However, amino acids are grouped according to the properties of said amino acid, and the substitution of one amino acid with another amino acid may have no impact of the function or properties of the protein comprising said amino acid if the substitution results in a synonymous amino acid. Such substitutions may be denoted conservative substitution or mutation: A change in a DNA or RNA sequence that leads to the replacement of one amino acid with a biochemically similar one.

It is thus understood, that the nucleic acid construct comprising invariant chain or a variant thereof according to the present invention may comprise a non-synonymous substitution so as to produce—by translation into protein i.e. amino acids—an amino acid sequence comprising a variant of invariant chain, wherein said non-synonymous substitution results in the substitution of one or more amino acids which are synonymous.

Synonymous substitutions may comprise substitution of a hydrophobic amino acid with another hydrophobic amino acid; substitution of a hydrophilic amino acid with another hydrophilic amino acid; substitution of a polar amino acid with another polar amino acid; substitution of a non-polar amino acid with another non-polar amino acid; substitution of a positively charged amino acid with another positively charged amino acid; substitution of a negatively charged amino acid with another negatively charged amino acid; substitution of a neutral amino acid with another neutral amino acid; substitution of an ambiguous amino acid with its counterpart ambiguous charged amino acid such as isoleucine and leucine, asparagine and aspartic acid and glutamine and glutamic acid; substitution of an aromatic amino acid with another aromatic amino acid; substitution of an aliphatic amino acid with another aliphatic amino acid; or the substitution of any amino acid with alanine. These substitutions may be denoted equal-value substitution.

Splice Variants

Alternative splicing is the RNA splicing variation mechanism in which the exons of the primary gene transcript, the pre-mRNA, are separated and reconnected so as to produce alternative ribonucleotide arrangements. These linear combinations then undergo the process of translation where specific and unique sequences of amino acids are specified, resulting in isoform proteins or splice variants. In this way, alternative splicing uses genetic expression to facilitate the synthesis of a greater variety of proteins. In eukaryotes, alternative splicing is an important step towards higher efficiency, because information can be stored much more economically. Several proteins can be encoded in a DNA sequence whose length would only be enough for two proteins in the prokaryote way of coding.

The nucleic acid construct of the present invention may in one embodiment be designed so as to give rise to multiple antigenic peptides of fragments of antigenic peptides and/or multiple invariant chains or variants thereof.

In one embodiment, the nucleic acid construct according to the present invention comprises at least 1, such as 2, for example 3, such as 4, for example 5, such as 6, for example 7, such as 8, for example 9, such as 10, for example 11, such as 12, for example 13, such as 14, for example 15, such as 16, for example 17 such as 18, for example 19, such as 20 splice variants of an antigenic peptide or a fragment of said antigenic peptide.

The more than one antigenic peptide splice variants may encompass identical or non-identical antigenic peptides.

In another embodiment, the nucleic acid construct according to the present invention comprises at least 1, such as 2, for example 3, such as 4, for example 5, such as 6, for example 7, such as 8, for example 9, such as 10, for example 11, such as 12, for example 13, such as 14, for example 15, such as 16, for example 17 such as 18, for example 19, such as 20 splice variants of invariant chain or variants thereof.

Suitably the construct of the invention comprises a single invariant chain or variant thereof and a single antigenic peptide or a fragment of said antigenic peptide.

The more than one invariant chain splice variant may encompass identical or non-identical invariant chain or variants thereof.

In one embodiment, at least one splice variant of invariant chain comprises native full length invariant chain. In another embodiment, at least one splice variant of invariant chain comprises a variant of invariant chain. In yet another embodiment, at least one splice variant of invariant chain comprises a variant of invariant chain wherein said Ii does not comprise the LRMK amino acid residues of the Ii-KEY region. In another embodiment, at least one splice variant of invariant chain comprises a variant of invariant chain wherein said Ii does not comprise the M81 and M99 residues of the CLIP domain. In one embodiment the LRMK amino acid residues of the Ii-KEY region have been deleted or substituted. In a further embodiment, the invariant chain or variant thereof does not comprise the M81 and M99 residues of the CLIP domain.

It follows that the splice variant may comprise any combination of identical or non-identical antigenic peptides and/or identical or non-identical invariant chain or variants thereof.

In this manner it is possible to 'shuffle' sequences (exons) comprising different domains or regions of invariant chain, so as to obtain variants of invariant chain by alternative splicing. In this manner it is also possible to 'shuffle' sequences (exons) comprising different domains or regions of the antigenic peptide(s), so as to obtain variants of said antigenic peptide(s) by alternative splicing.

Invariant Chain

The term "invariant chain", also known as "Ii" or "CD74" refers to a non-polymorphic type II integral membrane protein. The protein has multiple functions in lymphocyte maturation and adaptive immune responses; in particular Ii ensures the targeting of newly synthesized MHC II to the endocytic pathway, where the complex can meet antigenic peptides. (Pieters J. (1997) Curr. Opin. Immunol., 9: 8996). Additionally, Ii has been shown to function as an MHC class I chaperone (Morris et al. (2004) Immunol. Res., 30: 171-179) and, by its endosomal targeting sequence, to facilitate stimulation of CD4+, but not CD8+ T-cells directed against covalently linked antigen (Diebold et al. (2001) Gene Ther. 8: 487-493).

For human invariant chain four different isoforms are known, generally termed p33, p35, p41 and p43 (Strubin et al., 1986, EMBO Journal, 5: 3483-3488). SEQ ID NO: 1 and SEQ ID NO: 2 correspond to the amino acid sequence and the nucleic acid sequence of human invariant chain p35 isoform, respectively. SEQ ID NO: 3 corresponds to the amino acid sequence of human invariant chain p33 isoform. SEQ ID NO: 4 and SEQ ID NO: 5 correspond to the amino acid sequence and the nucleic acid sequence of human invariant chain p43 isoform, respectively. SEQ ID NO: 6 corresponds to the amino acid sequence of human invariant chain p41 isoform. With respect to human p33 and p41 the human p35 and p43 isoforms contain an additional 16 residues at the N-terminus due to alternative initiation of translation. Compared to human p33 and p35 the human p41 and p43 isoforms comprise an additional domain (alternative splicing of exon 6b) inserted in frame in the C-terminal region of the invariant chain. The sequence of an additional human isoform c lacking two exons relative to human p33 and p35 is available in Genbank (Accession BC024272). SEQ ID NO: 7 and SEQ ID NO: 8 correspond to the amino acid sequence and the nucleic acid sequence of human invariant chain c isoform, respectively. Suitably the invariant chain is derived from human p33, p35, p41, p43 or c isoforms of invariant chain.

TABLE 1

Isoforms of human invariant chain

| Isoform | 16 AA at N-terminus | Additional domain | Polypeptide SEQ ID NO | Polynucleotide SEQ ID NO |
|---------|---------------------|-------------------|----------------------|--------------------------|
| p35 | + | − | 1 | 2 |
| p33 | − | − | 3 | — |
| p43 | + | + | 4 | 5 |
| p41 | − | + | 6 | — |
| c | + | − | 7 | 8 |

The invariant chain comprises several domains: a cytosolic domain which includes a sorting (targeting) peptide (also known as the "lysosomal targeting sequence", or "endolysosomal sorting sequence" ("ESS")) (positions 17 to 46 in human invariant chain SEQ ID NO: 1, positions 1 to 29 in the murine invariant chain SEQ ID NO: 9) preceded by an endoplasmic reticulum retention signal ("ERR" or "ER") in the human invariant chain p35 and p43 variants (positions 1 to 16 in human invariant chain SEQ ID NO: 1), a transmembrane domain ("TM", positions 47 to 72 in human invariant chain SEQ ID NO: 1, positions 30 to 55 in the murine invariant chain SEQ ID NO: 9), and a luminal domain which in itself comprises a KEY region (positions 93 to 96 in human invariant chain SEQ ID NO: 1, positions 76 to 79 in the murine invariant chain SEQ ID NO: 9), an adjacent CLIP region (positions 97 to 120 in human invariant chain SEQ ID NO 1, positions 80 to 103 in the murine invariant chain SEQ ID NO: 9). The CLIP region comprises a core CLIP peptide (positions 103 to 117 in human invariant chain SEQ ID NO: 1, positions 86 to 100 in the murine invariant chain SEQ ID NO: 9) and a trimerization domain (positions 134 to 208 in human invariant chain SEQ ID NO: 1, positions 117 to 191 in the murine invariant chain SEQ ID NO: 9; Mittendorf et al., (2009) Expert Opin. Biol. Ther., 9:71-78; Strumptner-Cuvelette and Benaroch, 2002, Biochem. Biophys. Acta, 1542: 1-13). The remainder of the luminal domain comprises two highly flexible regions situated between the transmembrane and KEY region (positions 73 to 92 in human invariant chain SEQ ID NO: 1, positions 56 to 75 in the murine invariant chain SEQ ID NO: 9) or downstream the trimerization domain (positions 209 to 232 in human invariant chain SEQ ID NO: 1, positions 192 to 215 in the murine invariant chain SEQ ID NO: 9).

Invariant chain has been characterized in several organisms such as chicken, cow, dog, mouse, rat and human. In one embodiment, the invariant chain is of vertebrate origin, more preferably of mammalian origin and most preferably of human origin. The employed invariant chain is preferably the invariant chain of the organism that is to receive the vaccination. In one embodiment the invariant chain and the host organisms or receivers of the treatment are of the same species.

For murine invariant chain only two isoforms (p31 and p41) are known corresponding to the human invariant chain isoforms p33 and p41, respectively. SEQ ID NO: 9 and SEQ ID NO: 10 correspond to the amino acid sequence and the nucleic acid sequence of murine invariant chain p31 isoform, respectively. SEQ ID NO: 11 and SEQ ID NO: 12 correspond to the amino acid sequence and the nucleic acid sequence of murine invariant chain p41 isoform, respectively. Suitably the fragment of invariant chain is derived from mouse p31 or p41 isoforms of invariant chain.

In one embodiment, the invariant chain is the polypeptide sequence recited in any one of SEQ ID NOs: 1-50. More suitably a human invariant chain of any one of SEQ ID NOs: 1-8.

Variants of Invariant Chain

A variant of invariant chain shares a level of sequence identity with invariant chain (such as any one or more of the invariant chain sequences of SEQ ID NOs: 1-50 or more suitably a human invariant chain of SEQ ID NOs: 1-8) or may be a fragment of invariant chain (such as any one or more of the invariant chain sequences of SEQ ID NOs: 1-50 or more suitably a human invariant chain of SEQ ID NOs: 1-8).

In one embodiment, the variant of invariant chain is a polypeptide sequence sharing at least 80%, more suitably at least 85%, more suitably at least 90%, more suitably at least 95%, more suitably at least 97%, more suitably at least 98%, more suitably at least 99% identity with any one or more of SEQ ID NOs: 1-50 or more suitably a human invariant chain of SEQ ID NOs: 1-8.

In one embodiment the variant is a fragment of at least 40 amino acids from any part of the invariant chain as set forth in any one of SEQ ID NO: 3. This includes a fragment including residues 1 to 40, 10 to 50, 20 to 60, 25 to 65, 30 to 70, 35 to 75, 40 to 80, 45 to 85, 50 to 90, 55 to 95, 60 to 100, 65 to 105, 70 to 110, 75 to 115, 80 to 120, 85 to 125, 90 to 130, 95 to 135, 100 to 140, 105 to 145, 110 to 150, 115 to 155, 120 to 160, 125 to 165, 130 to 170, 135 to 175, 140 to 180, 145 to 185, 150 to 190, 155 to 195, 160 to 200, 165 to 205, 170 to 210 and 175 to 216. It also includes fragments as any of the above listed expanding up to 5 residues to either side hereof. It further includes fragment of at least 50 residues, of at least 60 residues, of at least 70 residues, of at least 80 residues, of at least 90 residues, of at least 100 residues, of at least 110 residues, of at least 120 residues, of at least 130 residues, of at least 140 residues, of at least 150 residues, of at least 160 residues, of at least 170 residues, of at least 180 residues of at least 190 residues, of at least 200 residues and of at least 210 residues.

Any of the above described fragments of at least 85% sequence identity, for example at least 90% sequence identity, for example at least 91% sequence identity, such as at least 92% sequence identity, for example at least 93% sequence identity, such as at least 94% sequence identity, for example at least 95% sequence identity, such as at least 96% sequence identity, for example at least 97% sequence identity, such as at least 98% sequence identity, for example 99% sequence identity with SEQ ID NO: 3 are included within the scope of the present invention.

Suitably the invariant chain or variant thereof is capable of enhancing the immune response to the antigenic protein or peptide or an antigenic fragment thereof.

Polypeptide and Polynucleotide Sequence Comparison

For the purposes of comparing two closely-related polypeptide or polynucleotide sequences, the "% sequence identity" between a first sequence and a second sequence may be calculated. Polypeptide or polynucleotide sequences are said to be the same as or identical to other polypeptide or polynucleotide sequences, if they share 100% sequence identity over their entire length. Residues in sequences are numbered from left to right, i.e. from N- to C-terminus for polypeptides; from 5' to 3' terminus for polynucleotides. The terms "identical" or percentage "identity", in the context of two or more polypeptide sequences, refer to two or more sequences or sub-sequences that are the same or have a specified percentage of amino acid residues that are the same (i.e., 70% identity, optionally 75%, 80%, 85%, 90%, 95%, 98% or 99% identity over a specified region), when compared and aligned for maximum correspondence over a comparison window, or designated region as measured using one of the following sequence comparison algorithms or by manual alignment and visual inspection. This definition also refers to the compliment of a test sequence. Optionally, the identity exists over a region that is at least 250 amino acids in length, such as 300 amino acids or 350 amino acids. Suitably, the comparison is performed over a window corresponding to the entire length of the reference sequence (as opposed to the derivative sequence).

For sequence comparison, one sequence acts as the reference sequence, to which the test sequences are compared. When using a sequence comparison algorithm, test and reference sequences are entered into a computer, subsequent coordinates are designated, if necessary, and sequence algorithm program parameters are designated. Default program parameters can be used, or alternative parameters can be designated. The sequence comparison algorithm then calculates the percentage sequence identities for the test sequences relative to the reference sequence, based on the program parameters.

A "comparison window", as used herein, refers to a segment in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerised implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, J. Mol. Evol. 35:351-360 (1987). The method used is similar to the method described by Higgins & Sharp, CABIOS 5:151-153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., Nuc. Acids Res. 12:387-395 (1984)).

Another example of algorithm that is suitable for determining percent sequence identity and sequence similarity are the BLAST and BLAST 2.0 algorithms, which are described in Altschul et al., Nuc. Acids Res. 25:3389-3402 (1977) and Altschul et al., J. Mol. Biol. 215:403-410 (1990), respectively. Software for performing BLAST analyses is publicly available through the National Center for Biotechnology Information (website at www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighbourhood word score threshold (Altschul et al., supra). These initial neighbourhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

A "difference" between sequences refers to an insertion, deletion or substitution of a single residue in a position of the second sequence, compared to the first sequence. Two sequences can contain one, two or more such differences. Insertions, deletions or substitutions in a second sequence which is otherwise identical (100% sequence identity) to a first sequence result in reduced % sequence identity. For example, if the identical sequences are 9 residues long, one substitution in the second sequence results in a sequence identity of 88.9%. If the identical sequences are 17 amino acid residues long, two substitutions in the second sequence results in a sequence identity of 88.2%.

Alternatively, for the purposes of comparing a first, reference sequence to a second, comparison sequence, the number of additions, substitutions and/or deletions made to the first sequence to produce the second sequence may be ascertained. An addition is the addition of one residue into the first sequence (including addition at either terminus of the first sequence). A substitution is the substitution of one residue in the first sequence with one different residue. A deletion is the deletion of one residue from the first sequence (including deletion at either terminus of the first sequence).

In some embodiments, at least one region, peptide or domain of the at least one invariant chain is added to, removed from or substitutes a region, peptide or domain of the at least one invariant chain. Said region, peptide or domain may be derived from the at least one invariant chain, or from another protein. It may also be synthetic.

In one embodiment, a signal peptide is added to, removed from or replaces the sequence encoding the invariant chain. A signal peptide is a short sequence of amino acids that determines the eventual location of a protein in the cell, also referred to as a sorting peptide. Signal peptides that determine the location of proteins to subcellular compartments such as the endoplasmatic reticulum, golgi apparatus and the various compartments comprising the golgi apparatus, the nucleus, the plasma membrane, mitochondria and the various spaces and membranes herein, peroxisomes, lysosomes, endosomes and secretory vesicles among others are all included within the scope of the present disclosure. A preferred embodiment comprises alone the lysosomal targeting sequence of invariant chain. Another preferred embodiment comprises alone the KEY region of invariant chain. The signal peptide may be derived from the invariant chain.

In some embodiments, a TRIM domain is added to, removed from or replaces the TRIM domain of the at least one invariant chain. A TRIM domain is a trimerisation domain responsible for the trimerisation of the invariant chain. The TRIM domain of the human invariant chain set forth in SEQ ID NO: 3 corresponds to the region spanning from residues 134 to 208. The TRIM domain of the murine invariant chain set forth in SEQ ID NO: 9 corresponds to the region spanning from residues 118 to 192.

In one embodiment, the TRIM domain is derived from the invariant chain, such as the native TRIM domain found in the invariant chain. Suitably the TRIM domain has the same sequence as the TRIM domain in the invariant chain sequences recited in SEQ ID NO: 1-50 more suitably SEQ ID NO: 1-8. In another embodiment, it is derived from another protein. In yet another embodiment, it is synthetic. In some embodiments, the TRIM domain added to, removed from or replacing the TRIM domain of the invariant chain comprises the TRIM domain alone. In other embodiments, it comprises the TRIM domain together with the N-terminally adjacent sequence or the C-terminally adjacent sequence without any other regions or domains of invariant chain. Other preferred embodiments comprise alone the N-terminally or C-terminally adjacent sequences to the TRIM region but without the TRIM region itself. By adjacent is meant any amino acids within 10 residues of the TRIM region on the C-terminal side, within 20 residues, or within 24 residues, or amino acids within 10 residues of the TRIM region on the N-terminal side, within 20 residues, within 30 residues, within 40 residues, within 50 residues, within 75 residues or within 100 residues of the TRIM region.

Another embodiment relates to the removal, addition, or replacement of the CLIP region of the at least one invariant chain. As described above, the addition or replacement of the CLIP region includes the options of adding or replacing the existing CLIP region in the variant of the invariant chain or chains chosen, with CLIP regions from invariant chains of the same or other organisms or of variants of CLIP regions form the same or other organisms. The variant CLIP regions may, as follows from the above, be specifically generated mutant versions of the CLIP region, generated by single or multiple nucleic acid substitutions, deletions or additions. A preferred embodiment comprises the CLIP region alone, or the CLIP region together with the N-terminally adjacent sequence or the C-terminally adjacent sequence without any other regions or domains of invariant chain. Other preferred embodiments comprise alone the N-terminally or C-terminally adjacent sequences to the CLIP region but without the CLIP region itself. By adjacent is meant any amino acids within 10 residues of the CLIP region, within 20 residues, within 30 residues, within 40 residues, within 50 residues, within 75 residues or within 100 residues of the CLIP region.

Another embodiment relates to the removal, addition or replacement of the endosomal sorting signal of the at least one invariant chains. As described above, the addition or replacement of the endosomal sorting signal includes the options of adding or replacing the existing endosomal sorting signal in the variant of the invariant chain or chains chosen, with endosomal sorting signals from invariant chains of the same or other organisms or of variants of endosomal sorting signals form the same or other organisms. The variant endosomal sorting signal may, as follows from the above, be specifically generated mutant versions of the endosomal sorting signal, generated by single or multiple nucleic acid substitutions, deletions or additions. A preferred embodiment comprises the endosomal sorting signal alone, or the endosomal sorting signal together with the N-terminally adjacent sequence or the C-terminally adjacent sequence without any other regions or domains of invariant chain. Other preferred embodiments comprise alone the N-terminally or C-terminally adjacent sequences to the endosomal sorting signal but without the endosomal sorting signal itself. By adjacent is meant any amino acids within 10 residues of the endosomal sorting signal, within 20 residues, within 30 residues, within 40 residues, within 50 residues, within 75 residues or within 100 residues of the endosomal sorting signal.

In one embodiment, a transmembrane domain is added to, removed from or replaces the sequence encoding the invariant chain. A transmembrane domain is a short sequence of amino acids that allow a protein to be anchored in the cell membrane so that it is embedded therein.

In one embodiment of the present invention, all or part of the transmembrane domain of Ii may be replaced with the corresponding segment from any other protein, such as the chemokine receptor CCR6 TM6.

In another embodiment of the present invention, all or part of the transmembrane domain of Ii may be replaced with the corresponding segment from the chemokine receptor CCR6 TM6.

In some embodiments, the invariant chain fragment may further comprise a myriostylation site allowing or facilitating anchoring of the fragment to the membrane.

In particular embodiments, the invariant chain fragment comprises a signal peptide domain, a transmembrane domain and a trimerisation domain. Suitably the transmembrane domain has the same sequence as the transmembrane domain in any one of SEQ ID NOs: 1-50, more suitably SEQ ID NOs: 1-8. The transmembrane domain may comprise the region spanning from residues 50 to 115 of SEQ ID NO: 3.

Protease Cleavage Site

As used herein, a protease cleavage site refers to an intracellular protease cleavage site. Herein is disclosed a nucleic acid comprising sequences encoding at least one invariant chain or variant thereof, operatively linked to at least one antigenic protein or peptide or an antigenic fragment thereof, wherein the C-terminal end of said invariant chain is operatively linked to the N-terminal end of said antigenic protein or peptide or antigenic fragment thereof, and wherein the invariant chain or variant thereof comprises a protease cleavage site.

By protease cleavage site is understood a sequence of amino acids comprised within the invariant chain encoded by the nucleic acids disclosed herein, where the amino acid sequence can be recognised and processed by an intracellular protease. In other words, the polypeptide comprises a site which allows a protease to perform hydrolysis of peptide bonds within the polypeptide. Suitably the protease cleavage site is heterologous to the construct of the invention, i.e. does not naturally occur within components of the construct i.e. the invariant chain or the antigen protein or peptide or antigenic fragment thereof. Suitably cleavage occurs in the trans-Golgi network.

The protease cleavage site can be recognised by any intracellular protease. In some embodiments, the intracellular protease is a protease of the endoplasmic reticulum or a trans-Golgi network protease (most suitably a trans-Golgi network protease), suitably selected form the group consisting of furin and subtilisin-like proteases. Furin is a protease belonging to the family of subtilisin-like proprotein convertases, which process latent precursor proteins into their biologically active products. Furin is a calcium-dependent serine endoprotease that can efficiently cleave precursor proteins at their paired basic amino acid processing sites. Furin is enriched in the Golgi apparatus, where it functions to cleave other proteins into their mature, active forms. Furin cleaves proteins just downstream of a basic amino acid target sequence. In addition to processing cellular precursor proteins, furin is also utilized by a number of pathogens. For example, the envelope proteins of viruses such as HIV, influenza and dengue fever viruses must be cleaved by furin or furin-like proteases to become fully functional. Anthrax toxin, pseudomonas exotoxin, and papillomaviruses must likewise be processed by furin during their initial entry into host cells. Subtilisin-like proteases are proteases with a functionality similar to that of subtilisin, which is a non-specific protease belonging to the group of subtilases (serine proteases).

It has surprisingly been found that the insertion of a protease cleavage site within the invariant chain leads to the secretion of the invariant chain operatively linked to the antigenic protein or peptide or antigenic fragment thereof. In some embodiments, the protease cleavage site is a cleavage site for a subtilisin-like protease. In other embodiments, a preferred protease cleavage site is a furin cleavage site.

The skilled person knows how to design and introduce a sequence encoding a protease cleavage site such as a furin cleavage site in a nucleic acid. Proteases recognise their target by recognition sequences which are known in the art. In the case of furin, furin recognises numerous cleavage sites, of which an example is RXR/KR (SEQ ID NO: 70)(arginine, any amino acid, arginine or lysine, arginine). Databases for analysing furin cleavage sites are available and are known to the skilled person. It will be understood that in order to ensure proper cleavage, more than one protease cleavage site can be introduced. For example, the protease cleavage site may comprise two protease cleavage sites adjacent to one another. A preferred furin cleavage site is the sequence SGRRARRRARRSGR (SEQ ID NO: 57).

The protease cleavage site is comprised within the invariant chain or variant thereof. Within the scope of the present invention are nucleic acid constructs where the protease cleavage site is located at a terminal end of the invariant chain, such as at the C-terminal end or at the N-terminal end, and constructs where the protease cleavage site is internal to the invariant chain. In preferred embodiments, the introduction of the protease cleavage site does not disrupt the open reading frames of the nucleic acid construct.

The protease cleavage site may be inserted into the invariant chain (i.e. the presence of the protease cleavage site has not resulted in the deletion or substitution of any amino acids of the invariant chain), or alternatively the protease cleavage site may substitute one or more amino acids, or a complete region of, the invariant chain.

Suitably the protease cleavate site is located C-terminal of the ESS, more suitably C-terminal of the transmembrane domain, more suitably C-terminal of the KEY region, more suitably C-terminal of the CLIP region. In each case, N-terminal to the antigenic protein or peptide or antigenic fragment thereof.

Suitably the protease cleavage site is located between the ESS and the C-terminus of the invariant chain, more suitably between the transmembrane region and the C-terminus of the invariant chain, more suitably between the KEY region and the C-terminus of the invariant chain, more suitably between the CLIP region and the C-terminus of the invariant chain.

More suitably the protease cleavage site is located between the ESS and the TRIM domain, more suitably between the transmembrane region and the TRIM domain, more suitably between the KEY region and the TRIM domain, more suitably between the CLIP region and the TRIM domain.

As detailed above, the invariant chain may comprise a number of domains such as at least one TRIM domain, at least one signal peptide, at least one CLIP domain, at least one endosomal sorting signal and at least one myriostylation site. In some embodiments, the nucleic acid construct is designed in such a manner that the protease cleavage site is not comprised within any of the above-mentioned domains. In other embodiments, the nucleic acid construct is designed in such a manner that the protease cleavage site is comprised within any of the above-mentioned domains. The protease cleavage site may be inserted into the invariant chain or, alternatively, the protease cleavage site may replace a region naturally present in the invariant chain, so that the overall length of the invariant chain with the protease cleavage site is substantially the same as the overall length of the invariant chain without the protease cleavage site. In preferred embodiments, the region thus replaced does not exert an activity which is important or essential for the invariant chain. In preferred embodiments, the protease cleavage site replaces a region of the invariant chain which is not the TRIM domain, the signal peptide, the CLIP domain, the endosomal sorting signal or the myriostylation site.

In a preferred embodiment, the protease cleavage site is located between the CLIP domain and the TRIM domain. The protease cleavage site may for example be located immediately upstream of the TRIM domain or immediately downstream the CLIP domain. Without being bound by theory, it is hypothesized that the insertion of a protease cleavage site upstream of the TRIM domain does not challenge trimerisation of the invariant chain, and that the resulting polypeptide is trimeric.

The protease cleavage site may also be inserted upstream of the CLIP domain, for example immediately downstream of the endosomal sorting signal.

In another preferred embodiment, the protease cleavage site is located downstream of the TRIM domain, such as immediately downstream of the TRIM domain or such as in the C-terminal end of the invariant chain. In such embodiments, it is hypothesized that trimerisation of the invariant chain is challenged, and that the resulting polypeptide is monomeric.

Thus the emplacement of the protease cleavage site can be designed dependent on whether a monomeric or a trimeric form of the polypeptide encoded by the nucleic acid construct is desired.

Antigen

An antigen is a polypeptide which contains at least one epitope capable of eliciting an immune response. The terms antigen, antigenic sequence, antigenic protein, antigenic fragment and immunogen are used herein interchangeably. An epitope (also known as antigenic determinant) is that part of an antigenic sequence which is recognized by the immune system. Suitably, this recognition is mediated by the binding of antibodies, B cells, or T cells to the epitope in question. The epitopes bound by antibodies or B cells are referred to as B cell epitopes and the epitopes bound by T cells are referred to as T cell epitopes. Suitably binding is defined as binding with an association constant between the antibody or T cell receptor (TCR) and the respective epitope of $1 \times 10^5$ $M^{-1}$ or higher, or of $1 \times 10^6$ $M^{-1}$, $1 \times 10^7$ $M^{-1}$, $1 \times 10^8$ $M^{-1}$ or higher. The term "epitope" refers to conformational as well as non-conformational epitopes. Conformational and non-conformational epitopes are distinguished in that the binding to the former but not the latter is lost in the presence of denaturing solvents. T cell epitopes are non-conformational, i.e. they are linear, while B cell epitopes can be conformational or non-conformational. Linear B-cell epitopes typically vary between 5 to 20 amino acids in length.

Suitably the antigenic sequence is derived from a pathogen. An antigenic sequence is suitably derived from a pathogen selected from the group consisting of viruses, bacteria, protozoa and multicellular parasites. In an alternative embodiment the antigenic sequence is derived from a cancer cell.

In some embodiments, the at least one invariant chain is operatively linked to at least two, antigenic proteins or peptides or antigenic fragments thereof. Thus in some embodiments the number of antigenic proteins or peptides or antigenic fragments thereof is three, four, five, six, eight or ten or more. In some embodiments, each invariant chain element and each antigenic element are operatively linked to each other as defined below.

The antigen may be derived (such as obtained from) from a human or non-human pathogen including, e.g., bacteria, fungi, parasitic microorganisms or multicellular parasites which infect human and non-human vertebrates, or from a cancer cell or tumor cell. In one embodiment the antigen is a recombinant protein, such as a recombinant prokaryotic protein.

It is an object of the present invention to include but not limit the antigenic proteins or peptides or fragments of said proteins or peptides to stem from pathogenic organisms, cancer-specific polypeptides and antigens, and proteins or peptides associated with an abnormal physiological response.

More preferably it is an object of the present invention to include an antigen originating from any of the following types of pathogens: viruses, microorganisms and parasites. This includes pathogens of any animal known. It is preferable to have an antigen from a mammalian pathogen i.e. a pathogen that specifically targets mammalian animals. It is more preferred to have an antigen from a human pathogen. In general, any antigen that is found to be associated with a human pathogen may be used.

In another embodiment, it is preferable to have an antigen from an avian pathogen i.e. a pathogen that specifically targets birds or fowls. It is more preferred to have an antigen from a chicken (*Gallus gallus domesticus*). In general, any antigen that is found to be associated with an avian pathogen may be used.

In yet another embodiment, it is preferable to have an antigen from a piscine pathogen i.e. a pathogen that specifically targets fish. It is more preferred to have an antigen from a fish that may be bred in a fish farm. In general, any antigen that is found to be associated with a piscine pathogen may be used.

Viral Antigens

In a preferred embodiment at least one antigen may originate from, but is not limited to any of the following families of virus: Adenovirus, arenaviridae, astroviridae, bunyaviridae, caliciviridae, corona viridae, flaviviridae, herpesviridae, orthomyxoviridae, paramyxoviridae, picomaviridae, poxviridae, reoviridae, retroviridae, rhabdoviridae and toga viridae.

In some embodiments, at least one antigen may be derived from a virus selected from the group consisting of retroviruses, Flaviridae viruses, orthomyxoviruses, herpesviridae, arenaviruses, filoviridae, poxviridae and papovaviridae.

In one embodiment, at least one antigen or antigenic sequence may be derived from a retrovirus such as the Human Immunodeficiency Virus (HIV). In another embodiment, at least one antigen or antigenic sequence may be derived from a Flaviridae virus selected from the group consisting of: Dengue virus, hepatitis C virus and yellow fever virus. In another embodiment, at least one antigen or antigenic sequence may be derived from an orhomyxovirus is selected from: influenzavirus A, influenzavirus B and influenzavirus C. In another embodiment, at least one antigen or antigenic sequence may be derived from a herpesviridae virus is selected from the group consisting of: Herpes simplex virus, varicella-zoster virus, cytomegalovirus and Epstein-Barr virus. In another embodiment, at least one antigen or antigenic sequence may be derived from an arenavirus is selected from the group consisting of: Guanarito virus, Junin virus, Lassa virus, Lujo virus, Machupo virus, Sabia virus and Whitewater Arroyo virus. In another embodiment, at least one antigen or antigenic sequence may be derived from a filoviridae virus is selected from the group consisting of: Ebola virus and Marburg virus. In another embodiment, at least one antigen or antigenic sequence may be derived from a poxiviridae virus such as the smallpox virus. In another embodiment, at least one antigen or antigenic sequence may be derived from a papovaviridae virus such as a papillomavirus. In another embodiment, at least one antigen or antigenic sequence may be derived from a bacterium selected from the group of: *Mycobacterium tuberculosis, Bacillus anthracis, Staphylococcus* species and *Vibrio* species. In another embodiment, at least one antigen or antigenic sequence may be derived from a parasite selected from the group of: *Plasmodium* species, such as *P. falciparum, P. vivax, P. knowlesi*, or *P. malariae, Leishmania* species and *Trypanosoma* species, such as *T. brucei, T. cruzi, T. rhodesiense, T. vivax* or *T. congolense*.

In some embodiments the at least one antigenic protein or peptide is selected from the group of and/or may be at least one antigenic fragment of any of the following: vesicular stomatitis virus glycoprotein (VSV-GP), Influenza A NS-1 (non-structural protein 1), Influenza A M1 (matrix protein 1), Influenza A NP (nucleoprotein), LCMV NP, LCMV GP, Ebola GP, Ebola NP, murine gammaherpesvirus M2, M3 and ORF73 (such as MHV-68 M2, M3 and ORF73), chicken Ovalbumin (OVA), or a helper T-cell epitope.

Microorganism Antigens

In some embodiments the at least one antigenic protein or peptide or fragment of an antigenic protein or peptide is derived from a microorganism. More specifically at least one antigen may be derived from the one of the following from a non-exhaustive list: Anthrax (*Bacillus anthracis*), *Mycobacterium tuberculosis, Salmonella* (*Salmonella gallinarum, S. pullorum, S. typhi, S. enteridtidis, S. paratyphi, S. dublin, S. typhimurium*), *Clostridium botulinum, Clostridium perfringens, Corynebacterium diphtheriae, Bordetella pertussis, Campylobacter* such as *Campylobacter jejuni, Crytococcus neoformans, Yersinia pestis, Yersinia enterocolitica, Yersinia pseudotuberculosis, Listeria monocytogenes, Leptospira* species, *Legionella pneumophila, Borrelia burgdorferi, Streptococcus* species such as *Streptococcus pneumoniae, Neisseria meningitides, Haemophilus influenzae, Vibrio* species such as *Vibrio cholerae* O1, *V. cholerae* non-O1, *V. parahaemolyticus, V. parahaemolyticus, V. alginolyticus, V. furnissii, V. carchariae, V. hollisae, V. cincinnatiensis, V. metschnikovii, V. damsela, V. mimicus, V. fluvialis, V. vulnificus, Bacillus cereus, Aeromonas hydrophila, Aeromonas caviae, Aeromonas sobria, Aeromonas veronii, Plesiomonas shigelloides, Shigella* species such as *Shigella sonnei, S. boydii, S. flexneri*, and *S. dysenteriae*, Enterovirulent *Escherichia coli* EEC (*Escherichia coli*—enterotoxigenic (ETEC), *Escherichia coli*—enteropathogenic (EPEC), *Escherichia coli* O157:H7 enterohemorrhagic (EHEC), *Escherichia coli*—enteroinvasive (EIEC)), *Staphylococcus* species, such as *S. aureus* and especially the vancomycin intermediate/resistant species (VISA/VRSA) or the multidrug resistant species (MRSA), *Cryptosporidium parvum, Brucella* species such as *B. abortus, B. melitensis, B. ovis, B. suis*, and *B. canis, Burkholderia mallei* and *Burkholderia pseudomallei, Chlamydia psittaci, Coxiella burnetii, Francisella tularensis, Rickettsia prowazekii, Histoplasma capsulatum* and *Coccidioides immitis.*

In a preferred embodiment the at least one antigenic protein or peptide is from a microorganism selected from the group of: *Mycobacterium tuberculosis, Bacillus anthracis, Staphylococcus* species and *Vibrio* species.

Parasitic Antigen

One embodiment relates to a nucleic acid construct, wherein the at least one antigenic protein or peptide encoded is from a parasite.

Another embodiment of the present invention relates to a nucleic acid construct comprising combinations of at least two antigenic proteins or peptides from any of the above-mentioned pathogens.

Preferably the antigen is derived from, but not limited to, a parasite selected from the group of: *Plasmodium* species such as *Plasmodium malariae, Plasmodium ovale, Plasmodium vivax, Plasmodium falciparum, Endolimax nana, Giardia lamblia, Entamoeba histolytica, Cryptosporidium parvum, Blastocystis hominis, Trichomonas vaginalis, Toxoplasma gondii, Cyclospora cayetanensis, Cryptosporidium muris, Pneumocystis carinii, Leishmania donovani, Leishmania tropica, Leishmania braziliensis, Leishmania mexicana, Acanthamoeba* species such as *Acanthamoeba castellanii*, and *A. culbertsoni, Naegleria fowleri, Trypanosoma cruzi, Trypanosoma brucei rhodesiense, Trypanosoma brucei gambiense, Isospora belli, Balantidium coli*, Roundworm (*Ascaris lumbricoides*), Hookworm (*Necator Americanus, Ancylostoma* duodenal), Pinworm (*Enterobius vermicularis*), Roundworm (*Toxocara canis, Toxocara cati*), Heart worm (*Dirofilaria immitis*), Strongyloides (*Strongyloides stercoralis*), Trichinella (*Trichinella spiralis*), Filaria (*Wuchereria bancrofti, Brugia malayi, Onchocerca volvulus, Loa loa, Mansonella streptocerca, Mansonella perstans, Mansonella ozzardi*), Anisakine larvae (*Anisakis simplex* (herring worm), *Pseudoterranova* (*Phocanema, Terranova*) *decipiens* (cod or seal worm), *Contracaecum* species, *Hysterothylacium* (*Thynnascaris* species) *Trichuris trichiura*, Beef tapeworm (*Taenia saginata*), Pork tapeworm (*Taenia solium*), Fish tapeworm (*Diphyllobothrium latum*), Dog tapeworm (*Dipylidium caninum*), Intestinal fluke (*Fasciolopsis buski*), Blood fluke (*Schistosoma japonicum, Schistosoma mansoni*) *Schistosoma haematobium*), Liver fluke (*Clonorchis sinensis*), Oriental lung fluke (*Paragonimus westermani*), and Sheep liver fluke (*Fasciola hepatica*), *Nanophyetus salmincola* and *N. schikhobalowi*.

In a preferred embodiment the at least one antigenic protein or peptide is from a parasite selected from the group of: *Plasmodium* species, *Leishmania* species, and *Trypanosoma* species.

Domestic Animal Antigen

An aspect of the present invention relates antigens and/or antigenic sequences derived from diseases or agents that infect domestic animals, especially commercially relevant animals such as pigs, cows, horses, sheep, goats, llamas, rabbits, mink, mice, rats, dogs, cats, poultry such as chicken, turkeys, pheasants and others, fish such as trout, salmon and other farmed species. Examples of diseases or agents here of from which at least one antigen or antigenic sequence may be derived include, but are not limited to: Multiple species diseases such as: Anthrax, Aujeszky's disease, Bluetongue, Brucellosis such as: *Brucella abortus, Brucella melitensis* or *Brucella suis*; Crimean Congo haemorrhagic fever, Echinococcosis/hydatidosis, virus of the family Picornaviridae, genus Aphthovirus causing Foot and Mouth disease especially any of the seven immunologically distinct serotypes: A, O, C, SAT1, SAT2, SAT3, Asia1, or Heartwater, Japanese encephalitis, Leptospirosis, New world screwworm (*Cochliomyia hominivorax*), Old world screwworm (*Chrysomya bezziana*), Paratuberculosis, Q fever, Rabies, Rift Valley fever, Rinderpest, Trichinellosis, Tularemia, Vesicular stomatitis or West Nile fever; Cattle diseases such as: Bovine anaplasmosis, Bovine babesiosis, Bovine genital campylobacteriosis, Bovine spongiform encephalopathy, Bovine tuberculosis, Bovine viral diarrhoea, Contagious bovine pleuropneumonia, Enzootic bovine leukosis, Haemorrhagic septicaemia, Infectious bovine rhinotracheitis/infectious pustular vulvovaginitis, Lumpky skin disease, Malignant catarrhal fever, Theileriosis, Trichomonosis or Trypanosomosis (tsetse-transmitted); Sheep and goat diseases such as: Caprine arthritis/encephalitis, Contagious agalactia, Contagious caprine pleuropneumonia, Enzootic abortion of ewes (ovine chlamydiosis), Maedi-visna, Nairobi sheep disease, Ovine epididymitis (*Brucella ovis*), Peste des petits ruminants, Salmonellosis (*S. abortusovis*), Scrapie, Sheep pox and goat pox; Equine diseases such as: African horse sickness, Contagious equine metritis, Dourine, Equine encephalomyelitis (Eastern), Equine encephalomyelitis (Western), Equine infectious anaemia, Equine influenza, Equine piroplasmosis, Equine rhinopneumonitis, Equine viral arteritis, Glanders, Surra (*Trypanosoma evansi*) or Venezuelan equine encephalomyelitis; Swine diseases such as: African swine fever, Classical swine fever, Nipah virus encephalitis, Porcine cysticercosis, Porcine reproductive and respiratory syndrome, Swine vesicular disease or Transmissible gastroenteritis; Avian diseases such as: Avian chlamydiosis, Avian infectious bronchitis, Avian infectious laryngotracheitis, Avian mycoplasmosis (*M. gallisepticum*), Avian mycoplasmosis (*M. synoviae*), Duck virus hepatitis, Fowl cholera, Fowl typhoid, Highly pathogenic avian influenza this being any Influenzavirus A or B and especially H5N1, Infectious bursal disease (Gumboro disease), Marek's disease, Newcastle disease, *Pullorum* disease or Turkey rhinotracheitis; Lagomorph and rodent diseases such as: Virus enteritis, Myxomatosis or Rabbit haemorrhagic disease; Fish diseases such as: Epizootic haematopoietic necrosis, Infectious haematopoietic necrosis, Spring viraemia of carp, Viral haemorrhagic septicaemia, Infectious pancreatic necrosis, Infectious salmon anaemia, Epizootic ulcerative syndrome, Bacterial kidney disease (Renibacterium salmoninarum), Gyrodactylosis (*Gyrodactylus salaris*), Red sea bream iridoviral disease; or other diseases such as Camelpox or Leishmaniosis.

Yet another embodiment relates to the at least one antigenic protein or peptide or fragment of said antigenic protein or peptide being an antigenic peptide or protein with at least 85% identity to any of the above described antigens. The homology or identity between amino acids may be calculated by any of the previously mentioned BLOSUM scoring matrices.

Cancer Antigens

An embodiment relates to a nucleic acid construct, wherein the at least one antigenic protein or peptide or fragment of an antigenic protein or peptide is from a cancer-specific polypeptide or cancer antigen.

Many protein/glycoproteins have been identified and linked to certain types of cancer; these are referred to as cancer specific polypeptides, tumor-associated antigens or cancer antigens. In general, any antigen that is found to be associated with cancer tumors may be used. One way in which cancer specific antigens may be found is by subtraction analyses such as various micro array analyses, such as DNA microarray analysis. Herein the gene expression pattern (as seen in the level of RNA or protein encoded by said genes) between healthy and cancerous patients, between groups of cancerous patients or between healthy and cancerous tissue in the same patient is compared. The genes that have approximately equal expression levels are "subtracted" from each other leaving the genes/gene products that differ between the healthy and cancerous tissue. This approach is known in the art and may be used as a method of identifying novel cancer antigens or to create a gene expression profile specific for a given patient or group of patients. Antigens this identified, both single antigen and the combinations in which they may have been found fall within the scope of the present invention.

Preferably the at least one antigen is derived from, but not limited to, a cancer specific polypeptide selected from the group of: MAGE-3, MAGE-1, gp100, gp75, TRP-2, tyrosinase, MART-1, CEA, Ras, p53, B-Catenin, gp43, GAGE-1, BAGE-1, PSA, MUC-1, 2, 3, and HSP-70, TRP-1, gp100/pmel17, .beta.-HCG, Ras mutants, p53 mutants, HMW melanoma antigen, MUC-18, HOJ-1, cyclin-dependent kinase 4 (Cdk4), Caspase 8, HER-2/neu, Human papilloma virus HPV type 6, 11, 16, 18, 31 and 33, Bcr-Abl tyrosine kinase, carcinoembryonic antigen (CEA), telomerase, and SV40 Large T.

One embodiment relates to a nucleic acid construct, wherein, the at least one antigenic protein or peptide or fragment of an antigenic protein or peptide is from a cancer-specific polypeptide selected from the group of: p53, HER-2/neu, telomerase, and melanoma antigen.

Antigen Associated with an Abnormal Physiological Response

One embodiment relates to a nucleic acid construct, wherein the at least one antigenic protein or peptide or fragment of an antigenic protein or peptide is from a polypeptide associated with an abnormal physiological response. Such an abnormal physiological response includes, but is not limited to autoimmune diseases, allergic reactions, cancers and congenital diseases. A non-exhaustive list of examples of hereof includes diseases such rheumatoid arthritis, systemic lupus erythematosus, multiple sclerosis, psoriasis and Crohn's disease.

It is within the scope of the invention to combine two or more of any of the herein mentioned antigens.

Operative Linker

An aspect of the present invention relates to the nucleic acid construct wherein the at least one invariant chain or variant thereof is operatively linked to at least one antigenic protein or peptide or an antigenic fragment thereof, wherein the C-terminal end of the invariant chain is operatively linked to the N-terminal end of the antigenic protein or peptide. The operative linker is thus placed between the invariant chain and the antigenic protein or peptide or antigenic fragment thereof.

The operative linker between the invariant chain and the antigenic protein or peptide or fragment of antigenic protein or peptide either is a direct link or a link mediated by a spacer region. By the term operative linker is understood a sequence of nucleotides or amino acid residues that binds together two parts of a nucleic acid construct or chimeric polypeptide in a manner securing the biological processing of the nucleic acid or polypeptide. If the operative linker is a direct link, the two nucleic acids each encoding either an open reading frame or a fragment of an open reading frame are placed immediately adjacent to each other and thereby also in frame. If the operative linker is mediated by a spacer region, a series of nucleotides are inserted between the nucleotides encoding the at least one invariant chain and the at least one antigenic peptide, respectively. Within the scope of the present disclosure are embodiments wherein the spacer region merely is a series of nucleotides linking the at least two elements of the present invention in a manner retaining the open reading frames, or the spacer region may encode one or more signals or separate elements as defined herein below.

Suitably the invariant chain is indirectly linked to the antigenic sequence by a spacer region which is a linker sequence. Suitably the linker sequence comprises or more suitably consists of glycine and serine, more suitably the linker sequence comprises or more suitably consists of the sequence GlySer. Alternatively, the linker sequence comprises or consists of the 'AscI' linker, which is a linker having the polypeptide sequence ArgArgAla, encoded by polynucleotide sequence AGGCGCGCC. Alternatively, the linker sequence comprises or more suitably consists of the 'res' linker, which is a linker having the polypeptide sequence SerAspArgTyrLeuAsnArgArgAla (SEQ ID NO: 51), encoded by polynucleotide sequence AGCGATCGCTATTTAAATAGGCGCGCC (SEQ ID NO: 52). Alternatively, the linker sequence comprises or more suitably consists of the human influenza hemagglutinin (HA) tag (polypeptide SEQ ID NO: 53, polynucleotide SEQ ID NO: 54).

Suitably the linker sequence consists of 50 or fewer, more suitably 30 or fewer, more suitably 10 or fewer, more suitably 5 or fewer residues.

In another embodiment the operative linker comprises a spacer region encoding at least one helper epitope for class II MHC molecules. An example of a helper epitope is an immunogenic determinant such as Diphtheria toxin. Especially Diphtheria toxin B fragment COOH-terminal region has been shown to be immunogenic in mice. Furthermore, HSP70, in part or in whole, as well as other immunogenic peptides, such as influenza viral or immunogenic sequences or peptides with an anchoring motif to HLA class I and class II molecules, also may be encoded in the spacer region of the nucleic acid construct.

In yet another embodiment the operative linker of the nucleic acid construct may comprise at least one siRNA or miRNA encoding sequence. siRNAs (small interfering RNAs) and miRNAs (microRNAs) target endogenous RNAs, in a sequence-specific manner, for degradation. An siRNA or miRNA encoded within the nucleic acid construct of the present invention may thus be chosen to target an undesirable gene product.

In another embodiment the operative linker comprises at least one polylinker or multiple cloning site (MCS). Polylinkers and MCS's are series of nucleotides comprising restriction enzyme recognition sequences, i.e. sites where a restriction enzyme cut the DNA in blunt or staggered manner facilitating the subcloning of other fragments/sequences of DNA into the nucleic acid construct. The recognition sequences of the polylinkers/MCS's are typically unique meaning that they are not found elsewhere on the nucleic acid construct. The operative linker may furthermore comprise one or more stop or termination codons that signals the release of the nascent polypeptide from the ribosome. The operative linker may also comprise at least one IRES (Internal Ribosomal Entry Site) and/or at least one promoter. An IRES is a nucleotide sequence that allows for translation initiation in the middle of a messenger RNA (mRNA) sequence as part of the greater process of protein synthesis. A promoter is a DNA sequence that enables a gene to be transcribed. The promoter is recognized by RNA polymerase, which then initiates transcription, as detailed below. The promoter may be unidirectional or bidirectional.

In a preferred embodiment the operative linker spanning the region between the invariant chain and the at least one antigen is an operative linker comprising at least one polylinker, at least one promoter, and optionally also at least one IRES. These elements may be placed in any order. In a further preferred embodiment, the STOP codon of the invariant chain has been deleted, and the polylinker has been cloned into the vector in a manner conserving the open reading frame allowing for in frame reading of the at least one antigen that is inserted into the polylinker. This has the advantage of facilitating subcloning of multiple antigens into the same construct in one step or in multiple cloning steps and allowing for the simultaneous expression of multiple antigens in the same frame as the invariant chain. A STOP codon may be inserted after the polylinker for translation termination. This embodiment may be combined with any of the above helper epitopes, mi/siRNAs or any of the other elements herein described.

In a preferred embodiment, the operative linker, which is placed between the at least one invariant chain and the at least one antigenic protein or peptide or fragment thereof, is preferably such that as to ensure the readability of the open reading frame of the construct, so that the antigenic peptide is: preceded by at least one operative linker, which is itself preceded by at least one invariant chain or variant thereof. The at least one antigenic peptide encoding sequence preferably is placed at the terminal part of the invariant chain and an operative linker is inserted herein between. The terminal part is the first or last residue of the invariant chain or fragment hereof.

In some embodiments, the invariant chain is operatively linked to one antigenic protein or peptide or antigenic fragment thereof and the antigenic protein or peptide or antigenic fragment thereof is operatively linked to at least one further antigenic protein or peptide or antigenic fragment thereof, wherein the antigenic proteins or peptide or antigenic fragments thereof are operatively linked to each other as defined herein.

Combinations

It is within the scope of the present invention that the nucleic acid construct encodes a plurality of elements, the elements being the at least one invariant chain and the at least one antigenic protein or peptide or fragment of said protein or peptide. It therefore falls within the scope of the present invention to have a plurality of invariant chains each of these being operatively linked to each other and to a plurality of antigenic proteins or peptides or fragments of antigenic proteins or peptides, wherein these also are operatively linked. The elements of the nucleic acid construct must thus be operatively linked to each other. Several series of invariant chains each operatively linked to one antigenic protein or peptide or fragment of said protein or peptide, each of these series being operatively linked to each other are encompassed within the present invention. Each of the invariant chains may comprise a protease cleavage site as defined above. Thus embodiments with multiple protease cleavage sites are also disclosed herein.

Advantages and very important aspects of the present invention relate to the fact that any type of immune response e.g. T cell mediated and antibody mediated responses, can be initiated, both with epitopes known to be weak antigens, with polypeptides of unknown antigenic properties, and with multiple epitopes/antigens simultaneously. The insertion of a protease site leads to secretion of the antigen as a monomer or as a trimer, and this leads to an improved immune response.

It is therefore also within the scope of the present invention that a preferred embodiment is a nucleic acid construct encoding at least one invariant chain operatively linked to a plurality of antigenic proteins or peptides or fragment of proteins or peptides, such as two, three, four, five, six, eight, ten, twelve or more antigenic proteins or peptides or fragment of proteins or peptides, where the invariant chain comprises a protease cleavage site.

The nucleic acid construct may comprise additional elements. These include but are not limited to: internal ribosomal entry sites (IRES), genes encoding proteins related to antigen presentation such as LAMP, calreticulin and Hsp70, genes encoding proteins that are related to intracellular spreading such as VP22, HIV Tat, Cx43 or other connexins and intercellular gap-junction constituents, genes encoding natural killer cell (NK-cell) activation molecules such as H60 and cytokines, chicken ovalbumin, or any T-helper cell epitope.

In one embodiment the nucleic acid construct comprises at least one gene encoding a protein related to antigen presentation such as LAMP, LIMP, calreticulin or Hsp70.

In another embodiment the nucleic acid construct comprises at least one gene encoding a protein related to intracellular spreading such as VP22, Cx43, HIV Tat, other connexins or intercellular gap-junction constituents.

Promoter

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7-20 bp of DNA, and containing one or more recognition sites for transcriptional activator proteins. At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV 40 late genes, a discrete element overlying the start site itself helps to fix the place of initiation.

Additional promoter elements regulate the frequency of transcriptional initiation. Typically, these are located in the region 30-110 bp upstream of the start site, although a number of promoters have recently been shown to contain functional elements downstream of the start site as well. The spacing between elements is flexible, so that promoter function is preserved when elements are inverted or moved relative to one another. In the tk promoter, the spacing between elements can be increased to 50 bp apart before activity begins to decline. Depending on the promoter, it appears that individual elements can function either cooperatively or independently to activate transcription. Any promoter that can direct transcription initiation of the sequences encoded by the nucleic acid construct may be used in the invention.

An aspect of the present invention comprises the nucleic acid construct wherein the at least one operatively linked invariant chain and antigenic protein or peptide encoding sequence is preceded by a promoter enabling expression of the construct.

It is a further aspect that the promoter is selected from the group of constitutive promoters, inducible promoters, organism specific promoters, tissue specific promoters and cell type specific promoters.

Examples of promoters include, but are not limited to: constitutive promoters such as: simian virus 40 (SV40) early promoter, a mouse mammary tumor virus promoter, a human immunodeficiency virus long terminal repeat promoter, a Moloney virus promoter, an avian leukaemia virus promoter, an Epstein-Barr virus immediate early promoter, a Rous sarcoma virus (RSV) promoter, a human actin promoter, a human myosin promoter, a human haemoglobin promoter, cytomegalovirus (CMV) promoter and a human muscle creatine promoter, inducible promoters such as: a metallothionine promoter, a glucocorticoid promoter, a progesterone promoter, and a tetracycline promoter (tet-on or tet-off), tissue specific promoters such as: HER-2 promoter and PSA associated promoter and bidirectional promoters, that are capable of initiating transcription in either direction from the promoter.

Advantages of using an inducible promoter include the option of providing a "dormant" vaccine that can be activated at will. This may be of use if the vaccination preferably only is induced locally vs. systemically within a body (e.g. in cases involving cancer), or the vaccine is detrimental to the health of the recipient at the time of vaccination.

In a preferred embodiment the nucleic acid construct comprises a promoter selected from the group of: CMV promoter, SV40 promoter and RSV promoter. Particularly preferred are the CMV promoter and SV40 promoter.

Delivery Vehicle

In one aspect, the present disclosure relates to the nucleic acid construct as described in any of the above, comprised within a delivery vehicle. A delivery vehicle is an entity whereby a nucleotide sequence or polypeptide or both can be transported from at least one media to another. Delivery vehicles are generally used for expression of the sequences encoded within the nucleic acid construct and/or for the intracellular delivery of the construct or the polypeptide encoded therein. It is within the scope of the present invention that the delivery vehicle is a vehicle selected from the group of: RNA based vehicles, DNA based vehicles/vectors, lipid-based vehicles, virally based vehicles and cell based vehicles. Examples of such delivery vehicles include, but are not limited to: biodegradable polymer microspheres, lipid based formulations such as liposome carriers, coating the construct onto colloidal gold particles, lipopolysaccharides, polypeptides, polysaccharides, and pegylation of viral vehicles.

A preferred embodiment regards delivery of the nucleic acid construct as naked DNA by mechanical or electrical techniques. Especially the coating of the nucleic acid construct upon gold particles is a favoured embodiment. The delivery of the nucleic acid construct upon gold particles is done by ballistic transfer using particle bombardment equipment such as a gene gun.

A more preferred embodiment comprises a virus as a delivery vehicle, where the virus is selected from the non-exhaustive group of: adenoviruses, retroviruses, lentiviruses, adeno-associated viruses, herpesviruses, vaccinia viruses, foamy viruses, cytomegaloviruses, Semliki forest virus, poxviruses, MVA based vectors, RNA virus vector and DNA virus vector. Such viral vectors are well known in the art.

Viral vectors are often made up of two components, a modified viral genome and a coat structure surrounding it, although sometimes viral vectors are introduced in naked form or coated with proteins other than viral proteins. Most current vectors have coat structures similar to a wild-type virus. This structure packages and protects the viral nucleic acid and provides the means to bind and enter target cells.

Preferably, viral vectors are modified from wild-type viral genomes to disable the growth of the virus in a target cell while enabling the virus to grow in a host cell (e.g. such as a packaging or helper cell) used to prepare infectious particles. Vector nucleic acids generally essential cis-acting viral sequences for replication and packaging in a helper line and expression control sequences for regulating the expression of a polynucleotide being delivered to a target cell. Other viral functions are expressed in trans in specific packaging or helper cell lines as known in the art.

Adenovirus

In a more preferred embodiment the vehicle comprising the nucleic acid construct as described herein is an adenovirus. The adenoviral genome consists of a linear double-stranded DNA molecule of approximately 36 kb carrying more than about thirty genes necessary to complete the viral replication cycle. The early genes are divided into 4 regions (E1 to E4) that are essential for viral replication with the exception of the E3 region, which is believed to modulate the anti-viral host immune response. The E1 region (EIA and EIB) encodes proteins responsible for the regulation of transcription of the viral genome. Expression of the E2 region genes (E2A and E2B) leads to the synthesis of the polypeptides needed for viral replication. The proteins encoded by the E3 region prevent cytolysis by cytotoxic T cells and tumor necrosis factor. The proteins encoded by the E4 region are involved in DNA replication, late gene expression and splicing and host cell shut off. The late genes generally encode structural proteins contributing to the viral capsid. In addition, the adenoviral genome carries at cis-acting 5' and 3' ITRs (Inverted Terminal Repeat) and packaging sequences essential for DNA replication. The ITRs harbor origins of DNA replication while the encapsidation region is required for the packaging of adenoviral DNA into infectious particles (see for example US 2004/0157307).

In the most preferred embodiment of the present invention the vehicle comprising the nucleic acid construct as described herein is a replication defective adenovirus or a conditionally replication deficient adenovirus. Adenoviral vectors can be engineered to be conditionally replicative (CRAd vectors) in order to replicate selectively in specific cells (e.g., such as proliferative cells). In another aspect, an adenoviral vector is replication-defective for the E1 function (e.g., by total or partial deletion or mutagenesis of E1). The adenoviral backbone of the vector may comprise additional modifications (deletions, insertions or mutations in one or more viral genes). An example of an E2 modification is illustrated by the thermosensitive mutation localized on the DBP (DNA Binding Protein) encoding gene. The adenoviral sequence may also be deleted of all or part of the E4 region. Additional deletions within the non-essential E3 region may allow the size of the polynucleotide being delivered to be increased. However, it may be advantageous to retain all or part of the E3 sequences coding for polypeptides (e.g., such as gp19k) allowing the virus to escape the immune system or inflammatory reactions. Second generation vectors retaining the ITRs and packaging sequences and comprising substantial genetic modifications to abolish the residual synthesis of the viral antigens also may be used in order to improve long-term expression of the expressed gene in the transduced cells. The nucleic acid construct being introduced into the cell may be inserted in any location of the viral genome, with the exception of the cis-acting sequences (see for example US 2004/0157307).

Adenoviruses can be derived from any human or animal source, in particular canine, avian, bovine, murine, ovine, feline, porcine or simian sources or alternatively, may be a hybrid virus. Any serotype can be employed. However, the human adenoviruses are preferred and such viruses are available, for example, from the ATCC (American Type Culture Collection).

A preferred embodiment of the present invention comprises an adenovirus such as: Ovine adenovirus, Canine adenovirus type II, Modified vaccinia Ankara (MVA) or MVA-BN.

Suitably the adenovirus of use in the present invention is derived from a human adenovirus. Examples of human-derived adenoviruses are Ad1, Ad2, Ad4, Ad5, Ad6, Ad11, Ad19, Ad24, Ad34 and Ad35. Although Ad5-based vectors have been used extensively in a number of gene therapy trials, there may be limitations on the use of Ad5 and other human group C adenoviral vectors due to preexisting immunity in the general population due to natural infection. Ad5 and other human group C members tend to be among the most seroprevalent serotypes. Additionally, immunity to existing vectors may develop as a result of exposure to the vector during treatment. These types of preexisting or developed immunity to seroprevalent vectors may limit the effectiveness of gene therapy or vaccination efforts. Alternative adenovirus serotypes, thus constitute very important targets in the pursuit of gene delivery systems capable of evading the host immune response.

Alternatively the adenoviral vector of use in the present invention is derived from a non-human simian adenovirus. Numerous adenoviruses have been isolated from non-human simians such as chimpanzees, bonobos, rhesus macaques and gorillas, and vectors derived from these adenoviruses induce strong immune responses to transgenes encoded by these vectors (Colloca et al. (2012) *Sci. Transl. Med.* 4:1-9; Roy et al. (2004) *Virol.* 324: 361-372; Roy et al. (2010) *J. of Gene Med.* 13:17-25). Certain advantages of vectors based on non-human simian adenoviruses include the relative lack of cross-neutralising antibodies to these adenoviruses in the target population. For example, cross-reaction of certain chimpanzee adenoviruses with pre-existing neutralizing antibody responses is only present in 2% of the target population compared with 35% in the case of certain candidate human adenovirus vectors.

Suitably, the adenovirus is derived from a non-human simian adenovirus which is a chimpanzee adenovirus such as ChAd3, ChAd63, ChAd83, ChAd155, Pan 5, Pan 6, Pan 7 (also referred to as C7) or Pan 9. Examples of such strains are described in WO03/000283, WO2005/071093, WO2010/086189 and GB1510357.5 and are also available from the American Type Culture Collection, 10801 University Boulevard, Manassas, Va. 20110-2209, and other sources. Alternatively, adenovirus may be derived from non-human simian adenoviruses isolated from bonobos, such as PanAd1, PanAd2 or PanAd3. Examples of such vectors described herein can be found for example in WO2005/071093 and WO2010/086189. They may also be derived from adenoviruses isolated from gorillas as described in WO2013/52799, WO2013/52811 and WO2013/52832.

Adenoviral particles or empty adenoviral capsids also can be used to transfer nucleic acid constructs or nucleic acid based delivery vectors by a virus-mediated co-internalization process. This process can be accomplished in the presence of cationic agent(s) such as polycarbenes or lipid vesicles comprising one or more lipid layers.

Adenoviral particles may be prepared and propagated according to any conventional technique in the field of the art using a complementation cell line or a helper virus, which supplies in trans the missing viral genes necessary for viral replication. The adenoviral particles can be recovered from the culture supernatant but also from the cells after lysis and optionally further purified according to standard techniques (e.g. chromatography and ultracentrifugation).

Cell-type specific targeting may be achieved with vectors derived from adenoviruses having a broad host range by the modification of viral surface proteins. For example, the specificity of infection of adenoviruses is determined by the attachment to cellular receptors present at the surface of permissive cells. In this regard, the fiber and penton present at the surface of the adenoviral capsid play a critical role in cellular attachment. Thus, cell targeting of adenoviruses can be carried out by genetic modification of the viral gene encoding fiber and/or penton, to generate modified fiber and/or penton capable of specific interaction with unique cell surface receptors.

An aspect of the present invention relates to an adenoviral vector comprising a nucleotide construct encoding at least one antigen and at least one protein or peptide or fragment of a protein or peptide which stimulates an MHC-I response.

A further aspect of the present invention relates to an adenoviral vector, wherein the nucleotide construct encodes at least one protein or peptide or fragment of a protein or peptide which stimulates an MHC-II response.

Preferably, the adenoviral vector comprises sequences, wherein the at least one antigen is operatively linked to the at least one MHC response stimulating protein or peptide or fragment of an MHC response stimulating protein or peptide. The MHC stimulating protein or peptide or fragment of protein or peptide is preferably an MHC associated protein or peptide. Such an MHC associated peptide can be but is not limited being selected from the group of: ER localizing peptide, Golgi localizing peptide, endosomal peptide loading compartment localizing peptide, lysosomal, MIIC, CIIV, melanosomes, secretory granules, and Birbeck granules.

More preferably the adenoviral vector comprises an endosomal peptide loading compartment localizing peptide. Such an endosomal peptide loading compartment localizing peptide can be, but is not limited to being, selected from the group of: sorting signal peptides, LAMP, LIMP and invariant chain.

Most preferably the adenoviral vector comprises at least one MHC response stimulating protein or peptide or fragment of protein or peptide and said MHC response stimulating protein or peptide or fragment of protein or peptide is invariant chain.

The adenoviral vector may furthermore comprise proteins that assist in the spreading of the virus or the construct comprised therein. Such proteins include connexins, gap-junction related proteins and pore-forming proteins. A preferred embodiment of the present invention comprises an adenoviral vector encoding or otherwise comprising any one or more of the following proteins related to intercellular spreading: VP22, Cx43 and HIV Tat.

Recombinant Cell

An aspect of the present invention relates to a cell comprising the nucleic acid construct as defined in any of the above. Such a recombinant cell can be used a tool for in vitro research, as a delivery vehicle for the nucleic acid construct or as part of a gene therapy regime. The nucleic acid construct and nucleic acid based vectors according to the invention can be introduced into cells by techniques well known in the art and which include microinjection of DNA into the nucleus of a cell, transfection, electroporation, lipofection/liposome fusion and particle bombardment. Suitable cells include autologous and non-autologous cells, and may include xenogenic cells.

In a preferred embodiment the nucleic acid construct of the present invention is comprised within an antigen presenting cell (APC). Any cell that presents antigens on its surface in association with an MHC molecule is considered an antigen presenting cell. Such cells include but are not limited to macrophages, dendritic cells, B cells, hybrid APCs, and foster APCs. Methods of making hybrid APCs are well known in the art.

In a more preferred embodiment the APC is a professional antigen presenting cell and most preferably the APC is an MHC-I and/or MHC-II expressing cell.

The APC according to any of the above may be a stem cell obtained from a patient. After introducing the nucleic acid construct of the invention, the stem cell may be reintroduced into the patient in an attempt to treat the patient of a medical condition. Preferably, the cell isolated from the patient is a stem cell capable of differentiating into an antigen presenting cell.

It is furthermore included within the scope of the present invention to that the antigen presenting cell comprising the nucleic acid construct of the present invention does not express any co-stimulatory signals and the antigenic protein or peptide or antigenic fragment of said protein or peptide is an auto-antigen.

Chimeric Proteins and Antibodies

An object of the present invention is the chimeric protein encoded by the nucleic acid constructs as described herein above, comprising at least one operatively linked invariant chain and at least one antigenic protein or peptide or fragment of said antigenic protein or peptide, wherein the C-terminal end of said invariant chain or variant thereof is operatively linked to the N-terminal end of said antigenic protein or peptide or antigenic fragment thereof, and wherein said invariant chain or variant thereof comprises a protease cleavage site and optionally a TRIM domain located C-terminally of said protease cleavage site. By chimeric protein is understood a genetically engineered protein that is encoded by a nucleotide sequence made by a splicing together of two or more complete or partial genes or a series of (non)random nucleic acids.

An aspect of the present invention relates to an antibody that can recognize the chimeric protein as defined herein above. By the term antibody is understood immunoglobulin molecules and active portions of immunoglobulin molecules. Antibodies are for example intact immunoglobulin molecules or fragments thereof retaining the immunologic activity. Such antibodies can be used for the passive immunization of an animal, or for use in an assay for detecting proteins to which the antibody binds.

Vaccine Compositions

An aspect of the present invention relates to a composition comprising a nucleic acid sequence encoding at least one invariant chain operatively linked to at least one antigenic protein or peptide or fragment of said antigenic protein or peptide, wherein the C-terminal end of said invariant chain or variant thereof is operatively linked to the N-terminal end of said antigenic protein or peptide or antigenic fragment thereof, and wherein said invariant chain or variant thereof comprises a protease cleavage site and optionally a TRIM domain located C-terminally of said protease cleavage site. The vaccine may thus comprise a nucleic acid construct as defined in any of the above. The vaccine may furthermore be used as a medicament.

Nucleic Acid Construct Compositions

An aspect of the present invention relates to a composition comprising a nucleic acid sequence encoding at least one invariant chain or variants thereof operatively linked to at least one antigenic protein or peptide or fragment of said antigenic protein or peptide. The composition may thus comprise a nucleic acid construct as defined in any of the above. The composition may furthermore be used as a medicament.

The nucleic acid construct composition according to the invention can be formulated according to known methods such as by the admixture of one or more pharmaceutically acceptable carriers, also known as excipients or stabilizers with the active agent. These excipients may be acceptable for administration to any individual/animal, preferably to vertebrates and more preferably to humans as they are non-toxic to the cell or individual being exposed thereto at the dosages and concentrations employed. Often the physiologically acceptable carrier is an aqueous pH buffered solution. Examples of such excipients, carriers and methods of formulation may be found e.g. in Remington's Pharmaceutical Sciences (Maack Publishing Co, Easton, Pa.). Examples of physiologically acceptable carriers include but are not limited to: buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

To formulate a pharmaceutically acceptable composition suitable for effective administration, such compositions will according to the invention contain an effective amount of the nucleic acid construct, the nucleic acid construct comprised within a delivery vehicle or the chimeric protein encoded within the nucleic acid construct as described herein. Often, if priming the immune response with protein or polypeptides as encoded by the nucleic acid construct of the present invention, a carrier will be used as a scaffold by coupling the proteins or peptides hereto and thus aiding in the induction of an immune response. The carrier protein may be any conventional carrier including any protein suitable for presenting immunogenic determinants. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles. Such carriers are well known to those of ordinary skill in the art. Additionally, these carriers may function as immunostimulating agents ("adjuvants"). Immunisation of the animal may be carried out with adjuvants and/or pharmaceutical carriers. Conventional carrier proteins include, but are not limited to, keyhole limpet hemocyanin, serum proteins such as transferrin, bovine serum albumin, or human serum albumin, an ovalbumin, immunoglobulins, or hormones, such as insulin. The carrier may be present together with an adjuvant or independently here from.

In the following, nucleic acid construct composition or composition are meant to encompass compositions useful for prophylactic and therapeutic use, including stimulating an immune response in a patient. It is further contemplated that the composition of the invention does not induce any systemic or local toxicity reactions or any other side effects.

In one preferred embodiment, the phrase 'composition' as used herein refers to a composition for priming an immune response.

In a preferred embodiment the nucleic acid construct is packaged. Packaging means for the nucleic acid construct include means selected from, but not limited to the group of: RNA based or DNA based vectors, lipid based carriers, viral expression vectors, viral delivery vectors, coating of colloidal gold particles and biodegradable polymer microspheres.

Any of the previously mentioned delivery means may thus be used for packing purposes for use in a composition.

In one embodiment the packaging means of the nucleic acid construct is a viral expression vector selected from, but not limited to the group of: adenovirus, retrovirus, lentivirus, adeno-associated virus, herpes virus, vaccinia virus and DNA virus vector. The viral vector may be a replication deficient or conditionally replication deficient viral vector.

An aspect of the invention relates to a composition comprising at least two vectors. This encompasses that any one or two different nucleic acid constructs as described may be packed into at least two vectors, these vectors being of a type as described in any of the above. The invention furthermore relates to a composition comprising three, four, five or six vectors. Again, these vectors may differ from one another or not, and may carry identical or different nucleic acid constructs as described herein above.

A further aspect of the present invention relates to a composition comprising at least one chimeric protein as encoded by any of the nucleic acid constructs described herein. When a chimeric protein or polypeptide is to be used as an immunogen, it may be produced by expression of any one or more of the nucleic acid constructs described above in a recombinant cell or it may be prepared by chemical synthesis by methods known in the art. As described in the above, such chimeric proteins and/or peptides may be coupled to carriers to increase the immunologic response to the proteins/peptides and may be administered with or without an adjuvant and/or excipient.

In one embodiment, the present invention relates to the use of the nucleic acid construct as described herein for the production of a composition.

Enhancing an Immune Response: Traditional Adjuvants

Adjuvants may be included in the composition to enhance the specific immune response. Thus, it is particular important to identify an adjuvant that when combined with the antigen(s)/nucleic acid constructs and/or delivery vehicles (any of which may also be referred to as immunogenic determinant), results in a composition capable of inducing a strong specific immunological response. The immunogenic determinant may also be mixed with two or more different adjuvants prior to immunisation. Compositions are also referred to as immunogenic compositions in the present text.

A large number of adjuvants have been described and used for the generation of antibodies in laboratory animals, such as mice, rats and rabbits. In such setting the tolerance of side effect is rather high as the main aim is to obtain a strong antibody response. For use and for approval for use in pharmaceuticals, and especially for use in humans it is required that the components of the composition, including the adjuvant, are well characterized. It is further required that the composition has minimal risk of any adverse reaction, such as granuloma, abscesses or fever.

An embodiment of the present invention relates to a composition comprising an adjuvant. In a preferred embodiment the composition is suitable for administration to a mammal, such as a human being. Therefore the preferred adjuvant is suitable for administration to a mammal and most preferably is suitable for administration to a human being.

In another preferred embodiment the composition is suitable for administration to a bird or a fish, and most preferably to a chicken (*Gallus gallus domesticus*). Therefore the preferred adjuvant is suitable for administration to a bird or a fish.

The choice of adjuvant may further be selected by its ability to stimulate the type of immune response desired, B-cell or/and T-cell activation and the composition may be formulated to optimize distribution and presentation to the relevant lymphatic tissues.

Adjuvants pertaining to the present invention may be grouped according to their origin, be it mineral, bacterial, plant, synthetic, or host product. The first group under this classification is the mineral adjuvants, such as aluminum compounds. Antigens precipitated with aluminum salts or antigens mixed with or adsorbed to performed aluminum compounds have been used extensively to augment immune responses in animals and humans. Aluminium particles have been demonstrated in regional lymph nodes of rabbits seven days following immunization, and it may be that another significant function is to direct antigen to T cell containing areas in the nodes themselves. Adjuvant potency has been shown to correlate with intimation of the draining lymph nodes. While many studies have confirmed that antigens administered with aluminium salts lead to increased humoral immunity, cell mediated immunity appears to be only slightly increased, as measured by delayed-type hypersensitivity. Aluminium hydroxide has also been described as activating the complement pathway. This mechanism may play a role in the local inflammatory response as well as immunoglobulin production and B cell memory. Furthermore, aluminum hydroxide can protect the antigen from rapid catabolism. Primarily because of their excellent record of safety, aluminum compounds are presently the only adjuvants used in humans.

Another large group of adjuvants is those of bacterial origin. Adjuvants with bacterial origins can be purified and synthesized (e.g. muramyl dipeptides, lipid A) and host mediators have been cloned (Interleukin 1 and 2). The last decade has brought significant progress in the chemical purification of several adjuvants of active components of bacterial origin: *Bordetella pertussis, Mycobacterium tuberculosis*, lipopoly-saccharide, Freund's Complete Adjuvant (FCA) and Freund's Incomplete Adjuvant (Difco Laboratories, Detroit, Mich.) and Merck Adjuvant 65 (Merck and Company, Inc., Rahway, N.J.). Additionally suitable adjuvants in accordance with the present invention are e.g. Titermax Classical adjuvant (SIGMA-ALDRICH), ISCOMS, Quil A, ALUN, see U.S. Pat. Nos. 58,767 and 5,554,372, Lipid A derivatives, choleratoxin derivatives, HSP derivatives, LPS derivatives, synthetic peptide matrixes, GMDP, and other as well as combined with immunostimulants (U.S. Pat. No. 5,876,735). *B. pertussis* is of interest as an adjuvant in the context of the present invention due to its ability to modulate cell-mediated immunity through action on T-lymphocyte populations. For lipopolysaccharide and Freund's Complete Adjuvant, adjuvant active moieties have been identified and synthesized which permit study of structure-function relationships. These are also considered for inclusion in immunogenic compositions according to the present invention.

Lipopolysaccharide (LPS) and its various derivatives, including lipid A, have been found to be powerful adjuvants in combination with liposomes or other lipid emulsions. It is not yet certain whether derivatives with sufficiently low toxicity for general use in humans can be produced. Freund's Complete Adjuvant is the standard in most experimental studies.

Mineral oil may be added to the immunogenic composition in order to protect the antigen from rapid catabolism.

Many other types of materials can be used as adjuvants in immunogenic compositions according to the present invention. They include plant products such as saponin, animal products such as chitin and numerous synthetic chemicals.

Adjuvants according to the present invention can also been categorized by their proposed mechanisms of action. This type of classification is necessarily somewhat arbitrary because most adjuvants appear to function by more than one mechanism. Adjuvants may act through antigen localization and delivery, or by direct effects on cells making up the immune system, such as macrophages and lymphocytes. Another mechanism by which adjuvants according to the invention enhance the immune response is by creation of an antigen depot. This appears to contribute to the adjuvant activity of aluminum compounds, oil emulsions, liposomes, and synthetic polymers. The adjuvant activity of lipopolysaccharides and muramyl dipeptides appears to be mainly mediated through activation of the macrophage, whereas *B. pertussis* affects both macrophages and lymphocytes. Further examples of adjuvants that may be useful when incorporated into immunogenic compositions according to the present invention are described in U.S. Pat. No. 5,554,372.

Adjuvants useful in compositions according to the present invention may thus be mineral salts, such as aluminium hydroxide and aluminium or calcium phosphates gels, oil emulsions and surfactant based formulations such as MF59 (microfluidized detergent stabilized oil in water emulsion), QS21 (purified saponin), AS02 (SBAS2, oil-in-water emulsion+monophosphoryl lipid A (MPL)+QS21), Montanide ISA 51 and ISA-720 (stabilized water in oil emulsion), Adjuvant 65 (containing peanut oil, mannide monooleate and aluminum monostearate), RIBI ImmunoChem Research Inc., Hamilton, Utah), particulate adjuvants, such as virosomes (unilamellar liposomal cehicles incorporating influenza haemagglutinin), AS04 (Al salt with MPL), ISCOMS (structured complex of saponins and lipids (such as cholesterol), polyactide co-glycolide (PLG), microbial derivatives (natural and synthetic) such as monophosphoryl lipid A (MPL), Detox (MPL+*M. Phlei* cell wall skeleton), AGP (RC-529 (synthetic acylated monosaccharide)), DC_chol (lipoidal immunostimulators able to self-organize into liposomes), OM-174 (lipid A derivative), CpG motifs (synthetic oligonucleotides containing immunostimulatory CpG motifs), modified bacterial toxins, LT and CT, with non-toxic adjuvant effects, Endogenous human immunomodulators, e.g., hGM-CSF or hIL-12 or Immudaptin (C3d tandem array), inert vehicles such as gold particles.

Additional examples of adjuvants comprise: Immunostimulatory oil emulsions (for example, water-in-oil, oil-in-water, water-in-oil-in-water such as e.g. Freund's incomplete adjuvant such as Montainde®, Specol, mineral salts such e.g. as $Al(OH)_3$, $AlPO_4$, microbial products, Saponins such as Qual A, synthetic products, as well as adjuvant formulations, and immune stimulatory complexes (ISCOMs) and cytokines, heat-inactivated bacteria/components, nanobeads, LPS, LTA. A list of other commonly used adjuvants is disclosed on pages 6-8 in WO 2003/089471, the list being hereby incorporated by reference.

Immunogenic compositions according to the invention may also contain diluents such as buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with non-specific serum albumin are exemplary appropriate diluents.

Adjuvants are generally included in the immunogenic compositions in an amount according to the instructions of the manufacturer.

Enhancing an Immune Response: Non-Traditional Adjuvants

Cytokine Modulation

For a vaccine to be effective, it must induce an appropriate immune response for a given pathogen. This can be accomplished by modifications to the form of antigen expressed (i.e. intracellular vs. secreted), the method and route of delivery, and the dose of DNA delivered. However, it can also be accomplished by the co-administration of plasmid DNA (pDNA) encoding immune regulatory molecules, e.g. cytokines, lymphokines or co-stimulatory molecules. These "genetic adjuvants", along with any of the 'traditional adjuvants' or 'other immunstimulatory adjuvants' as outlined herein, may be administered a number of ways:
- as a mixture of 2 separate plasmids, one encoding the immunogen and the other encoding the cytokine;
- as a single bi- or polycistronic vector, separated by spacer regions; or
- as a plasmid-encoded chimera, or fusion protein; or
- in its native form, i.e. a protein or nucleotide.

In general, co-administration of pro-inflammatory agents (such as various interleukins, tumor necrosis factor, and GM-CSF) plus TH2 inducing cytokines increase antibody responses, whereas pro-inflammatory agents and TH1 inducing cytokines decrease humoral responses and increase cytotoxic responses (which is more important in viral protection, for example). Co-stimulatory molecules like B7-1, B7-2 and CD40L are also sometimes used.

This concept has been successfully applied in topical administration of pDNA encoding IL-10. Plasmid encoded B7-1 (a ligand on APCs) has successfully enhanced the immune response in anti-tumor models, and mixing plasmids encoding GM-CSF and the circumsporozoite protein of *P. yoelii* (PyCSP) has enhanced protection against subsequent challenge (whereas plasmid-encoded PyCSP alone did not). GM-CSF may cause dendritic cells to present antigen more efficiently, and enhance IL-2 production and TH cell activation, thus driving the increased immune response. This can be further enhanced by first priming with a pPyCSP and pGM-CSF mixture, and later boosting with a recombinant poxvirus expressing PyCSP. However, co-injection of plasmids encoding GM-CSF (or IFN-γ, or IL-2) and a fusion protein of *P. chabaudi* merozoite surface protein 1 (C-terminus)-hepatitis B virus surface protein (PcMSP1-HBs) actually abolished protection against challenge, compared to protection acquired by delivery of pPcMSP1-HBs alone.

Other Immunostimulatory Adjuvants

In one embodiment, any of the following may be used as an immunostimulatory adjuvant to the nucleic acid construct or composition according to the present invention:

LPS (lipopolysaccharide), Poly-IC (poly-inositol cytosine) or any other adjuvant that resembles double-stranded RNA, LL37, RIG-1 helicase, IL-12, IL-18, CCL-1, CCL-5, CCL-19, CCL-21, GM-CSF, CX3CL, CD86, PD-1, secreted PD-1, IL10-R, secreted IL10-R, IL21, ICOSL, 41BBL, CD40L and any other protein or nucleic acid sequence that stimulates an immune response.

In one embodiment, the immunostimulatory adjuvant is fused to an adenoviral fiber protein. For example, CX3CL may be fused to adenoviral fiber proteins.

Immunostimulatory CpG Motifs

Plasmid DNA itself appears to have an adjuvant effect on the immune system. Plasmid DNA has derived from bacteria been found to trigger innate immune defense mechanisms, the activation of dendritic cells, and the production of TH1 cytokines. This is due to recognition of certain CpG dinucleotide sequences which are immuno-stimulatory. CpG stimulatory (CpG-S) sequences occur twenty times more frequently in bacterially derived DNA than in eukaryotes. This is because eukaryotes exhibit "CpG suppression"—i.e. CpG dinucleotide pairs occur much less frequently than expected. Additionally, CpG-S sequences are hypomethylated. This occurs frequently in bacterial DNA, while CpG motifs occurring in eukaryotes are all methylated at the cytosine nucleotide. In contrast, nucleotide sequences which inhibit the activation of an immune response (termed CpG neutralising, or CpG-N) are over represented in eukaryotic genomes. The optimal immunostimulatory sequence has been found to be an unmethylated CpG dinucleotide flanked by two 5' purines and two 3' pyrimidines. Additionally, flanking regions outside this immunostimulatory hexamer are optionally guanine-rich to ensure binding and uptake into target cells.

The innate immune system works synergistically with the adaptive immune system to mount a response against the DNA encoded protein. CpG-S sequences induce polyclonal B-cell activation and the upregulation of cytokine expression and secretion. Stimulated macrophages secrete IL-12, IL-18, TNF-α, IFN-α, IFN-β and IFN-γ, while stimulated B-cells secrete IL-6 and some IL-12. Manipulation of CpG-S and CpG-N sequences in the plasmid backbone of DNA vaccines can ensure the success of the immune response to the encoded antigen, and drive the immune response toward a TH1 phenotype. This is useful if a pathogen requires a TH response for protection. CpG-S sequences have also been used as external adjuvants for both DNA and recombinant protein vaccination with variable success rates. Other organisms with hypomethylated CpG motifs have also demonstrated the stimulation of polyclonal B-cell expansion. However, the mechanism behind this may be more complicated than simple methylation—hypomethylated murine DNA has not been found to mount an immune response.

Formulations of DNA

The efficiency of DNA immunization can be improved by stabilising DNA against degradation, and increasing the efficiency of delivery of DNA into antigen presenting cells. This may be achieved by coating biodegradable cationic microparticles (such as poly(lactide-co-glycolide) formulated with cetyltrimethylammonium bromide) with DNA. Such DNA-coated microparticles can be as effective at raising CTL as recombinant vaccinia viruses, especially when mixed with alum. Particles 300 nm in diameter appear to be most efficient for uptake by antigen presenting cells.

Administration

Nucleic acid constructs and compositions according to the invention may be administered to an individual in therapeutically effective amounts. The effective amount may vary according to a variety of factors such as the individual's condition, weight, sex and age. Other factors include the mode of administration.

In one embodiment, the nucleic acid construct according to the present invention may be delivered to a subject in the form of DNA, RNA, LNA, PNA, INA, TINA, HNA, ANA, CNA, CeNA, GNA, TNA, Gap-mers, Mix-mers, Morpholinos or any combination thereof.

In one embodiment, the nucleic acid construct according to the present invention may be delivered to a subject in the form of DNA.

In another embodiment, the nucleic acid construct according to the present invention may be delivered to a subject in the form of RNA. Thus, the nucleic acid construct may be transcribed into RNA prior to administration.

In yet another embodiment, the nucleic acid construct according to the present invention may be delivered to a subject in the form of protein. Thus, the nucleic acid construct may be translated into protein prior to administration.

In the embodiment in which the nucleic acid construct according to the present invention is delivered to a subject in the form of a protein, the protein may have been modified to increase stabilization and/or to optimize delivery into the cell. The protein may have increased stability due to the presence of disulfide bonds (for example, U.S. Pat. No. 5,102,985 treated solutions of proteins in reduced form with hydrogen peroxide to generate proteins having an intramolecular disulfide bridge in 90-96% yield), an increase in polar residues, surface charge optimization, surface salt bridges, encapsulation (e.g. with mesoporous silicate), or the protein may be linked to heat-shock proteins (such as Hsp-60, Hsp-70, Hsp-90, Hsp-20, Hsp-27, Hsp-84 and others), HIV tat translocation domain, adenoviral fiber proteins, or any other proteins or domains.

The pharmaceutical or veterinary compositions may be provided to the individual by a variety of routes such as subcutaneous (sc or s.c.), intraperitoneal (i.p.), topical, oral and intramuscular (im or i.m.). Administration of pharmaceutical compositions is accomplished orally or parenterally. Methods of parenteral delivery include topical, intra-arterial (directly to the tissue), intramuscular, intracerebrally (ic or i.c.), subcutaneous, intramedullary, intrathecal, intraventricular, intravenous (iv or i.v.), intraperitoneal, or intranasal administration. The present invention also has the objective of providing suitable topical, oral, systemic and parenteral pharmaceutical formulations for use in the methods of priming an immune response with the composition.

For example, the compositions can be administered in such oral dosage forms as tablets, capsules (each including timed release and sustained release formulations), pills, powders, granules, elixirs, tinctures, solutions, suspensions, aerosols, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts. An effective but non-toxic amount of the composition, comprising any of the herein described compounds can be employed. Also any and all conventional dosage forms that are known in the art to be appropriate for formulating injectable immunogenic peptide composition are encompassed, such as lyophilized forms and solutions, suspensions or emulsion forms containing, if required, conventional pharmaceutically acceptable carriers, diluents, preservatives, adjuvants, buffer components, etc.

In one embodiment, the composition for priming and/or the subsequent booster vaccine is given as a slow or sustained release formulation.

Preferred modes of administration of the nucleic acid construct or composition according to the invention include, but are not limited to systemic administration, such as intravenous or subcutaneous administration, intradermal administration, intramuscular administration, intranasal administration, oral administration, rectal administration, vaginal administration, pulmonary administration and generally any form of mucosal administration. Furthermore, it is within the scope of the present invention that the means for any of the administration forms mentioned in the herein are included in the present invention.

A nucleic acid construct or composition according to the present invention can be administered once, or any number of times such as two, three, four or five times.

In a preferred embodiment, the nucleic acid construct or composition is administered once, followed by administration of a suitable vaccine.

In another preferred embodiment, the nucleic acid construct or composition is administered as a series of administrations prior to administering the vaccine. Such a series may comprise administering the nucleic acid construct or composition daily, every second day, every third day, every fourth day, every fifth day, every sixth day, weekly, bi weekly or every third week for a total of one, two, three, four or five times.

In one embodiment, the time period between administering first the nucleic acid construct or composition for priming the immune system and secondly the vaccine for boosting is at least one day apart, such as at least two days apart, for example three days apart, such as at least four days apart, for example five days apart, such as at least six days apart, for example seven days apart, such as at least eight days apart, for example nine days apart, such as at least ten days apart, for example fifteen days apart, such as at least twenty days apart, for example twenty-five days apart.

Priming with the nucleic acid construct or composition is thus intended to be further boosted by administering a vaccine. Administration may be in a form or body part different from the previous administration or similar to the previous administration.

The booster shot is either a homologous or a heterologous booster shot. A homologous booster shot is a where the first and subsequent administrations comprise the same constructs and more specifically the same delivery vehicle. A heterologous booster shot is where identical constructs are comprised within different vectors.

A preferred administration form of the composition according to the present invention is administering the composition to the body area, inside or out, most likely to be the receptacle of a given infection. The receptacle of infection is the body area that the infection is received by, e.g. regarding influenza, the receptacle of infection is the lungs.

The nucleic acid construct or composition of the present invention can be administered to any organism to which it may be beneficial, especially any animal such as a vertebrate animal. It falls within the scope of the present invention that the means and modes of administration of the composition are adapted to the recipient.

A preferred recipient of the composition is a mammal and the mammal is in a more preferred embodiment of the present invention selected from the group of: cows, pigs, horses, sheep, goats, llamas, mice, rats, monkeys, dogs, cats, ferrets and humans. In the most preferred embodiment the mammal is a human.

Another preferred recipient of the composition is any vertebrate from the class ayes (bird), such as *Gallus gallus domesticus* (chicken).

An embodiment of the present invention includes a composition further comprising a second active ingredient. The second active ingredient is selected from, but not limited to the group of adjuvants, antibiotics, chemotherapeutics, antiallergenics, cytokines, complement factors and co-stimulatory molecules of the immune system.

Another embodiment of the present invention comprises a kit of parts, wherein the kit includes at least one nucleic acid construct or composition according to any of the above, a means for administering said nucleic acid construct or composition and the instruction on how to do so. It is within the scope of the present invention to include multiple dosages of the same composition or several different compositions. In a preferred embodiment the kit of parts further comprises a second active ingredient. In a more preferred embodiment, said second active ingredient is a suitable vaccine, i.e. a vaccine capable of boosting the immune response raised by previous priming of said immune response.

The present invention further comprises a method for potentiating an immune response in an animal, comprising administering to the animal a nucleic acid construct or composition according to any of the above, followed by administering a suitable vaccine, thereby priming and boosting the immune system of a subject.

The immune response may be, but is not limited to, any of the following types of responses: an MHC-I dependent response, an MHC-I and/or MHC-II dependent response, a T-cell dependent response, a $CD4^+$ T-cell dependent response, a $CD4^+$ T cell independent response, a $CD8^+$ T-cell dependent response and a B cell dependent immune response. Suitable vaccines are those that are capable of boosting the immune system subsequent to the priming of the immune system with the nucleic acid construct or composition according to the present invention.

In a further embodiment, the present invention relates to a method of treatment of an individual in need thereof, comprising administering the composition as described herein above to treat a clinical condition in said individual.

Increasing the Potency of a Vaccine

An embodiment of the invention relates to a nucleic acid construct encoding at least one invariant chain or variant thereof and at least one antigenic protein or peptide or fragment of an antigenic protein or peptide operatively linked as described above. In some embodiments, the at least one antigenic protein or peptide or fragment of an antigenic protein or peptide is from a virus, bacteria or parasite.

It is not always straightforward to develop prime-boost regimens using nucleic acid constructs comprising invariant chain or variant thereof.

In some embodiments there is provided a nucleic acid construct encoding at least one invariant chain and a viral, bacterial or parasitic antigen or a fragment thereof, as described above, for priming an immune response, wherein said priming is followed by a subsequent booster vaccination with a vaccine. Said variant of invariant chain may be any variant as specified elsewhere herein, comprising invariant chain wherein some domains have been altered by e.g. deletion or substitution of amino acids or regions.

In one embodiment, the present invention is directed to the use of a nucleic acid construct for increasing the potency of a vaccine or for priming an immune response.

In one embodiment, the present invention discloses a method for increasing the potency of a vaccine or for priming an immune response comprising the steps of:
a. providing a nucleic acid construct comprising invariant chain or a variant thereof and an antigenic peptide or fragment thereof as described herein,
b. priming the immune system of a subject by administering the nucleic acid construct of step a) thereby stimulating an immune response in said subject, and
c. boosting the immune response of step b) by administering a suitable vaccine.

In one embodiment, the present invention discloses a method for increasing the potency of a vaccine or for priming an immune response comprising the steps of:
a. providing a nucleic acid construct comprising a variant of invariant chain and an antigenic peptide or fragment thereof as described herein, b. priming the immune system of a subject by administering the nucleic acid construct of step a) thereby stimulating an immune response in said subject, and
c. boosting the immune response of step b) by administering a suitable vaccine, wherein said variant of invariant chain comprises alteration of the TRIM region by e.g. deletion or substitution.

In one embodiment, the present invention discloses a method for increasing the potency of a vaccine or for priming an immune response comprising the steps of:
a. providing a nucleic acid construct comprising a variant of invariant chain and an antigenic peptide or fragment thereof as described herein,
b. priming the immune system of a subject by administering the nucleic acid construct of step a) thereby stimulating an immune response in said subject, and
c. boosting the immune response of step b) by administering a suitable vaccine, wherein said variant of invariant chain comprises alteration of the endosomal sorting signal by e.g. deletion or substitution.

In one embodiment, the present invention discloses a method for increasing the potency of a vaccine or for priming an immune response comprising the steps of:
a. providing a nucleic acid construct comprising a variant of invariant chain and an antigenic peptide or fragment thereof as described herein,
b. priming the immune system of a subject by administering the nucleic acid construct of step a) thereby stimulating an immune response in said subject, and
c. boosting the immune response of step b) by administering a suitable vaccine, wherein said variant of invariant chain comprises alteration of the signal peptide by e.g. deletion or substitution.

In one embodiment, the present invention discloses a method for increasing the potency of a vaccine or for priming an immune response comprising the steps of:
a. providing a nucleic acid construct comprising a variant of invariant chain and an antigenic peptide or fragment thereof as described herein,
b. priming the immune system of a subject by administering the nucleic acid construct of step a) thereby stimulating an immune response in said subject, and
c. boosting the immune response of step b) by administering a suitable vaccine, wherein said variant of invariant chain is a variant of any one of SEQ ID NOs: 1-8 and does not comprise the first 17 amino acids.

The vaccine of which the potency is increased can be a vaccine directed at any of the diseases or disorders listed above. In some embodiments, the vaccine is a cancer vaccine. In other embodiments, the vaccine is directed to an abnormal physiological response.

Vaccine Types

One aspect of the present invention relates to the priming of an immune response in a subject by administering a nucleic acid construct comprising Ii-linked antigen as described above, followed by a subsequent booster achieved by administering to the same subject a suitable vaccine.

Suitable vaccines according to the present invention preferably have at least one identical feature in common with the nucleic acid construct used for priming of an immune response. Said identical feature may be comprised in part or all of an invariant chain, part or all of an antigenic peptide, part or all of a backbone structure such as part or all of a promoter region, part or all of an enhancer, part or all of a terminator, part or all of a poly-A tail, part or all of a linker, part or all of a polylinker, part or all of an operative linker, part or all of a multiple cloning site (MCS), part or all of a marker, part or all of a STOP codon, part or all of an internal ribosomal entry site (IRES) and part or all of a host homologous sequence for integration or other defined elements.

In a preferred embodiment, the identical feature is part or all of an antigenic peptide or a ubiquitous helper T cell epitope. In a most preferred embodiment, the identical feature is part or all of an antigenic peptide.

In another preferred embodiment, the identical feature is part or all of invariant chain.

Vaccines may be regarded as traditional or innovative. Any of the herein cited types of vaccines may be used in the subsequent booster step according to the present invention.

Traditional vaccines, or first generation vaccines, rely on whole organisms; either pathogenic strains that have been killed, or strains with attenuated pathogenicity.

Molecular biological techniques have been used to develop new vaccines, second generation vaccines, based on individual antigenic proteins from the pathogenic organisms. Conceptually, use of antigenic peptides rather than whole organisms would avoid pathogenicity while providing a vaccine containing the most immunogenic antigens. These include toxoid-based vaccines based on inactivated toxic compound are well-known, and subunit vaccines based on a fragment of an inactivated or attenuated pathogenic strain.

Conjugate vaccines: Certain bacteria have polysaccharide outer coats that are poorly immunogenic. By linking these outer coats to proteins (e.g. toxins), the immune system can be led to recognize the polysaccharide as if it was a protein antigen.

Recombinant vector vaccine: By combining the physiology of one micro-organism and the DNA of the other, immunity can be created against diseases that have complex infection processes.

Synthetic vaccines are composed mainly or wholly of synthetic peptides, carbohydrates or antigens.

DNA (or genetic) vaccines, or third generation vaccines, are new and promising candidates for the development of both prophylactic and therapeutic vaccines. DNA vaccines are made up of a small, circular piece of DNA (a plasmid) that has been genetically engineered to produce one or more antigens from a micro-organism. The vaccine DNA is injected into the cells of the body, where the "inner machinery" of the host cells "reads" the DNA and converts it into pathogenic proteins. Because these proteins are recognised as foreign, they are processed by the host cells and displayed on their surface, to alert the immune system, which then triggers a range of immune responses. The strength of the ensuing immune response is determined through a combination of the potency of the vector (i.e. naked DNA, viral vectors, live attenuated viruses etc.), the expression level of the antigen, and the recombinant antigen it self (i.e. high or low affinity MHC binders, structural determinants selecting for more or less limited T- or B-cell repertoire etc.). It is generally held to be true, that efficient induction of immunological memory requires or benefits from the interactions of $CD4^+$ (helper cell) T-cells with $CD8^+$ (cytotoxic) T-cells and B-cells that mediate many of the effects of immune memory.

In one embodiment of the present invention, priming of an immune response with a nucleic acid construct according to the present invention is followed by the subsequent administration of a first generation or traditional vaccine for boosting said immune response.

In one embodiment of the present invention, priming of an immune response with a nucleic acid construct according to the present invention is followed by the subsequent administration of a second generation vaccine for boosting said immune response.

In one embodiment of the present invention, priming of an immune response with a nucleic acid construct according to the present invention is followed by the subsequent administration of a third generation or DNA vaccine for boosting said immune response.

The use of invariant chain in DNA vaccine constructs to increase immunogenicity is well-known in the art. In one embodiment of the present invention, priming of an immune response with a nucleic acid construct according to the present invention is followed by the subsequent administration of a DNA vaccine comprising invariant chain or a variant thereof for boosting said immune response.

In one embodiment of the present invention, priming of an immune response with a nucleic acid construct according to the present invention is followed by the subsequent administration of an adenoviral vaccine for boosting said immune response.

Vaccines may further be monovalent (also called univalent) or multivalent (also called polyvalent). A monovalent vaccine is designed to immunize against a single antigen or single microorganism. A multivalent or polyvalent vaccine is designed to immunize against two or more strains of the same microorganism, or against two or more microorganisms.

In a further embodiment, a buffer is added to the vaccine composition. The pH of a liquid preparation is adjusted in view of the components of the composition and necessary suitability for administration to the subject. Suitably, the pH of a liquid mixture is at least 4, at least 5, at least 5.5, at least 5.8, at least 6. The pH of the liquid mixture may be less than 9, less than 8, less than 7.5 or less than 7. In other embodiments, pH of the liquid mixture is between 4 and 9, between 5 and 8, such as between 5.5 and 8. Consequently, the pH will suitably be between 6-9, such as 6.5-8.5. In a particularly preferred embodiment the pH is between 5.8 and 6.4.

An appropriate buffer may be selected from acetate, citrate, histidine, maleate, phosphate, succinate, tartrate and TRIS. In one embodiment, the buffer is a phosphate buffer such as Na/Na$_2$PO$_4$, Na/K$_2$PO$_4$ or K/K$_2$PO$_4$. The buffer can be present in the liquid mixture in an amount of at least 6 mM, at least 10 mM or at least 40 mM. The buffer can be present in the liquid mixture in an amount of less than 100 mM, less than 60 mM or less than 40 mM.

It is well known that for parenteral administration solutions should have a pharmaceutically acceptable osmolality to avoid cell distortion or lysis. A pharmaceutically acceptable osmolality will generally mean that solutions will have an osmolality which is approximately isotonic or mildly hypertonic. Suitably the compositions of the present invention when reconstituted will have an osmolality in the range of 250 to 750 mOsm/kg, for example, the osmolality may be in the range of 250 to 550 mOsm/kg, such as in the range of 280 to 500 mOsm/kg. In a particularly preferred embodiment the osmolality may be in the range of 280 to 310 mOsm/kg.

Osmolality may be measured according to techniques known in the art, such as by the use of a commercially available osmometer, for example the Advanced® Model 2020 available from Advanced Instruments Inc. (USA). An "isotonicity agent" is a compound that is physiologically tolerated and imparts a suitable tonicity to a formulation to prevent the net flow of water across cell membranes that are in contact with the formulation. In some embodiments, the isotonicity agent used for the composition is a salt (or mixtures of salts), conveniently the salt is sodium chloride, suitably at a concentration of approximately 150 nM. In other embodiments, however, the composition comprises a non-ionic isotonicity agent and the concentration of sodium chloride in the composition is less than 100 mM, such as less than 80 mM, e.g. less than 50 mM, such as less 40 mM, less than 30 mM and especially less than 20 mM. The ionic strength in the composition may be less than 100 mM, such as less than 80 mM, e.g. less than 50 mM, such as less 40 mM or less than 30 mM. In a particular embodiment, the non-ionic isotonicity agent is a polyol, such as sucrose and/or sorbitol. The concentration of sorbitol may e.g. between about 3% and about 15% (w/v), such as between about 4% and about 10% (w/v). Adjuvants comprising an immunologically active saponin fraction and a TLR4 agonist wherein the isotonicity agent is salt or a polyol have been described in WO2012/080369.

Suitably, a human dose volume is used of between 0.05 ml and 1 ml, such as between 0.1 and 0.5 ml, in particular a dose volume of about 0.5 ml, or 0.7 ml. The volumes of the compositions used may depend on the delivery route and location, with smaller doses being given by the intradermal route. A unit dose container may contain an overage to allow for proper manipulation of materials during administration of the unit dose.

For parenteral administration in particular, compositions should be sterile. Sterilisation can be performed by various methods although is conveniently undertaken by filtration through a sterile grade filter. By "sterile grade filter" it is meant a filter that produces a sterile effluent after being challenged by microorganisms at a challenge level of greater than or equal to 1×10$^7$/cm$^2$ of effective filtration area. Sterile grade filters are well known to the person skilled in the art of the invention for the purpose of the present invention, sterile grade filters have a pore size between 0.15 and 0.25 urn, suitably 0.18-0.22 um, such as 0.2 or 0.22 urn.

Kits of Parts

In one aspect, the invention relates to a kit of parts comprising a composition comprising a nucleic acid construct as disclosed herein, a medical instrument or other means for administering the composition and instructions for use.

EXAMPLES

Materials and Methods

Vaccine Design

Figure 14:
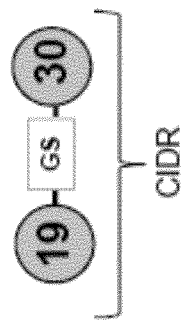
Figure 15:
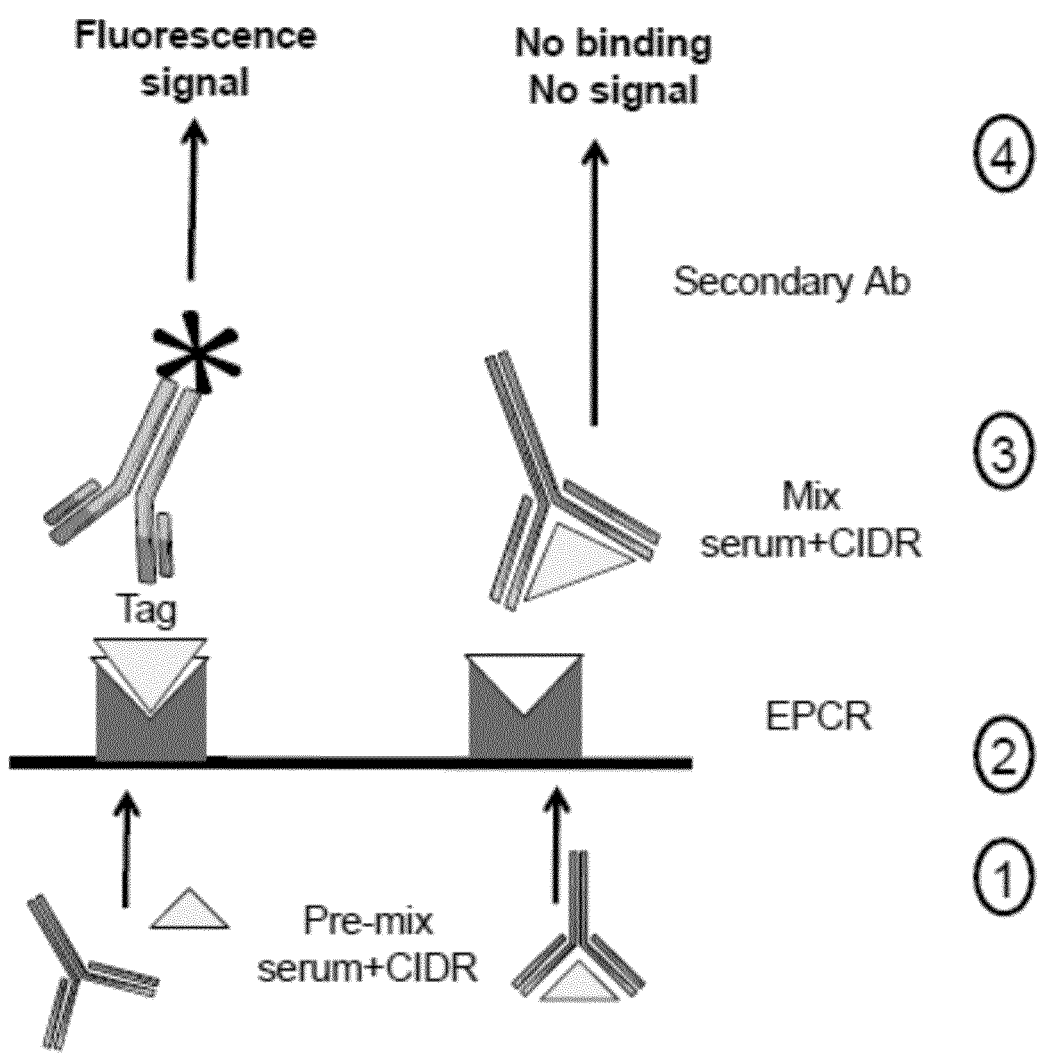
Figure 16:
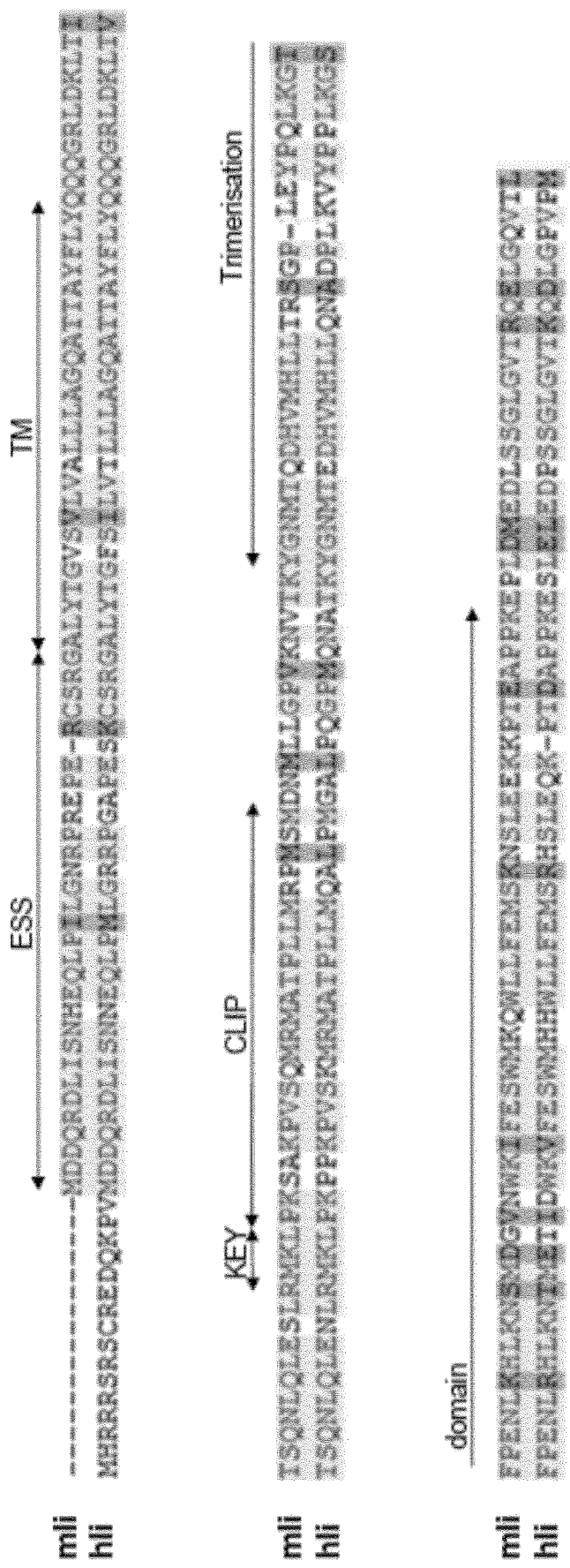

Malarial antigens IT4var19 (SEQ ID NO: 68, also referred to herein as 'CIDR1.1-IT4var19', or simply '19') and PFCLINvar30 (SEQ ID NO: 69, also referred to herein as CIDR1.1-PFCLINvar30, or simply '30') were cloned into CMV-based shuttle vectors containing the sequence coding for Ii-fur (SEQ ID NO: 5) or Ii (isoform 2, p31, SEQ ID NO: 9) or SP-alb (SEQ ID NO: 7). The different adenoviral constructs were designed based on Replication-deficient E1 deleted human adenovirus type 5 (Ad5, also referred to as hAd5). The invariant chain was inserted either as a full length protein (Ii), or with a deletion in the ESS domain (Δ17-Ii). The recognition site for the furin was either inserted before (Ii-fur) or after (Ii-Cterm-fur) the trimerisation domain. One construct was made with no invariant chain but engineered for secretion of the antigens using the albumin signal peptide (SP-alb). For antigen presentation studies, the different adenovirus constructs were inserted with OVA. For immunogenicity studies, the same constructs were engineered with IT4var19 ("19") and PFCLInvar30 ("30"), linked by a G-S linker and fused to the C terminus of the invariant chain or to the signal peptide of the albumin (SP-alb) (see top part of FIG. 14). For these constructs The huAd5 vectors were produced by homologous recombination in BJ5183 cells. The inserted adjuvant-antigens were flanked by the CMV promoter (huCMV) and a simian virus 40 (SV40) polyadenylation signal. In vitro expression of the encoded antigens was places under the control of a tetracycline operator. The adenoviral viruses were purified using a caesium chloride gradient as described according to Becker et al 1994, after amplification. All viruses were sequenced and titered.

Analysis of MHC-I OVA and MHCII-OVA Presentation

Figure 21A:
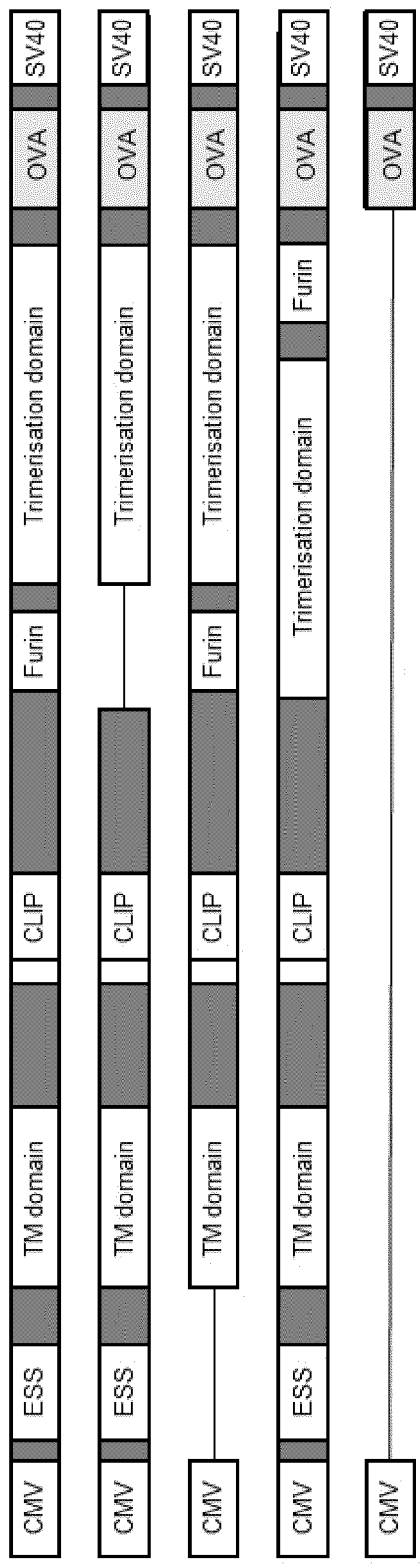
Figure 21B:
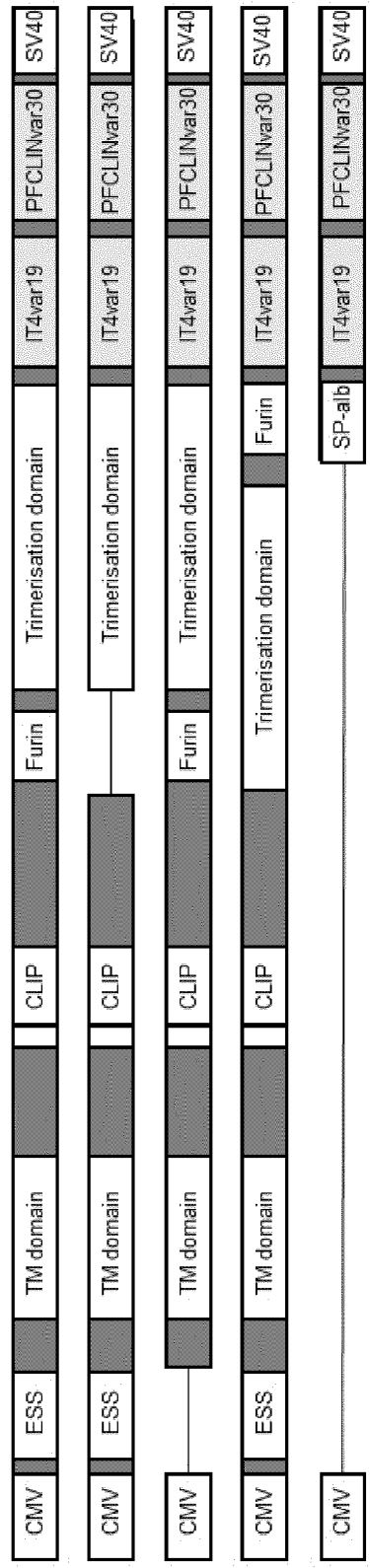

For MHCI antigen presentation, JAWSII cells were infected with 250M01/cell of the different Ad5 constructs inserted with OVA (FIG. 21A). The next day cells were washed and stained with anti-mouse H2 kb-bound to MHC-displayed OVA fragment SIINFEKL (SEQ ID NO: 66). Phycoerythrin (PE) fluorescence was analyzed by FACS Calibur, and data were interpreted using flowjo. For MHCII antigen presentation, 105 JAWS cell were infected with 250M01/cell of the different Ad5 constructs inserted with OVA (see FIG. 21A). The next day cells were washed and incubated with $4 \times 10^4$ BO-97.10 (a cell line which specifically recognises MHCII bound to OVA (Hugo et al 1993)). After 96 h of co-culture, supernatant was harvested and IL-2 level measured by ELISA (using the IL-2 Ready Set and Go assay (ebioscience, 88-7024-86)).

Analyses of T Cell Responses

T cell responses were initially assessed by footpad swelling measurement in Balb/c mice after vaccination in the right hind paw. Mice were vaccinated with Ad5-Ii-fur-IT4var19-PFCLINvar30 (n=5), Ad5-SP-Alb-IT4var19-PFCLINvar30 (n=5) and Ad5-Ii-IT4var19-PFCLINvar30 (n=5). Footpad swelling was measured with a caliper every day and the increase as compared to the unvaccinated paw was plotted to compare the different vaccinated groups. After vaccination, cells and cytokines are recruited to the site where the antigen has been introduced to trigger the immune response. By immunizing in the loose tissue behind the footpad the immune response towards vector and vaccine antigen causes swelling that can be measured by a caliper. The quantitation is interpreted as an indicator of the strength of the cellular immune response.

Detection of Proteins in Supernatant and Cell Cytosol

Secretion of the antigens was investigated by infecting either COS7 cells with 10 IFU/cell or VERO cells with 50 IFU/cell with the different Ad5 constructs inserted with IT4var19 and PFCLINvar30 overnight with medium replaced to serum free medium after 24 hours. Supernatant and cells were harvested 48 h after infection and cells were lysed with NP40 and protease inhibitor cocktail. Supernatant was concentrated using vivaspin columns. Supernatants were run on SDS-PAGE and recognized by immunized rat serum. Primary antibody was recognized with an anti-rat-alkaline phosphatase antibody revealed with BCIP/NBT tablets. Folding of IT4var19 and PFCLINvar30 in supernatant and cell lysate was investigating by testing the binding to their natural ligand EPCR. Nunc maxisorp plates were coated with 3 μg/mL EPCR ectodomain and supernatant and cell lysates were added to the wells. Interaction of the two proteins was revealed by recognition of either IT4var19 or PFLCINvar30 with immunized rat serum. Rat antibodies were recognized with horseradish peroxidase (HRP)-conjugated polyclonal rabbit anti-rat. Optical density was measured at 450 nm using an ELISA plate reader (VersaMax Molecular Devices).

Vaccination in Mice for Assessment of Antibody Responses

Balb/c or in some cases C57BL/6 mice were vaccinated on day 0 with $2 \times 10^9$ particles intra-muscularly with the different CIDR constructs (N=5 per group) and boosted 8 weeks after with a homologous boost ($2 \times 10^9$ particles intra-muscularly). Blood samples were harvested 2 weeks, 6 weeks and 10 weeks after the first vaccination.

Analyses of Antibody Responses: Recognition ELISA:

Serum was isolated from blood samples and antibody responses were analysed by ELISA. Nunc Maxisorp plates were coated with 5 μg/ml IT4var19 or PFCLINvar30 proteins. Serum was added to the wells and diluted accordingly to the required read out. Antibodies recognizing specifically IT4var19 and PFCLINvar30 were detected with horseradish peroxidase (HRP)-conjugated polyclonal rabbit anti-mouse Ig (P260 DAKO, Denmark). Wells were revealed using TMB plus (Kem-En-Tec Diagnostics, 4395A). Optical density was measured at 450 nm using an ELISA plate reader (VersaMax Molecular Devices).

Analyses of Antibody Responses: Inhibition ELISA:

Serum was isolated from blood samples and antibody responses were analysed by ELISA. Nunc Maxisorp plates were coated with 3 μg/ml ECPR. Serum and IT4var19 or PFcIinvar30 proteins were mixed and then tested for the ability of the antibody to prevent binding to EPCR. Binding between IT4var19 or PFcIinvar30 and EPCR was identified by HRP Ig anti-his-tag. Wells were revealed using TMB plus (Kem-En-Tec Diagnostics, 4395A). Optical density was measured at 450 nm using an ELISA plate reader (VersaMax Molecular Devices).

Analyses of Cross-Reactive Antibodies by Luminex:

Cross reactive antibodies were detected in serum of Balb/c mice 10 weeks after vaccination by multiplex. 1/50 diluted serum was incubated with beads coated with different CIDR proteins, and binding to the beads was detected by luminescence, as described by Cham et al 2008.

Measurement of Tumor Progression In Vivo:

C57BL/6 mice were immunized with $2 \times 10^7$ IFU in the footpad with either Ad5-Ii-furin-p15E (N=5) or Ad5-Ii-p15E (N=5). On day 155 mice were challenged iv. with $2 \times 10^5$ B16F10gp cells (murine melanoma cell line expressing the immunodominant epitope of the glycoprotein (GP) of lymphocytic choriomeningitis virus (LCMV)). 14 days after challenge, lungs were isolated and fixed o/n in a solution of 2% PFA in PBS. Metastases were counted as black nodules on the surface of the lungs.

Assessment of Anti-p15E Antibody Responses

A peptide of the Melanoma associated retrovirus (MelARV) p15E protein (Sequence: CFYADHTGLVRDS-MAKLRERLSQRQKLFESQQGWFEGLFNKSP (SEQ ID NO: 67), conjugated to BSA) was purchased from Schafer-N(Copenhagen, Denmark). Nunc MaxiSorp ELISA plates were coated o/n with 2 ug/mL μL peptide solution (in PBS) per well and subsequently blocked with a 0.5% BSA solution for 2 h at 37° C. Serum was diluted to 1:25 and added to the wells in two-fold dilutions and incubated for 3 h at 37° C. Specific antibodies were detected using a HRP-coupled goat anti-mouse IgG antibody (Dako, P0447) and revealed with TMB plus (Kem-En-Tec Diagnostics, 4395A). Optical density was measured at 450 nm using an ELISA plate reader (VersaMax Molecular Devices).

Statistical Analysis

Nonparametric Mann-Whitney tests were performed for comparing analysis antibody responses between the different groups. Sera from week 10 (for recognition) were diluted 2 fold and analyzed with a nonlinear regression curve, and areas under the curve (AUC) were calculated and plotted for comparison. Statistical analyses were performed using Graph Pad Prism. p-values <0.05 were considered significant. Footpad swelling was analysed with one-way analysis of variance followed by a Newman-Keuls test.

Example 1A: MHCI-OVA Presentation

JAWSII cells were cultured, infected, fixed and stained as described in the materials and methods section above and were analysed by flow cytometry. The results are shown in FIG. 1 and show that the Ii-fur-Ag complex does not affect MHC-I presentation. However, the d17-Ii-fur-OVA inserted Ad5 showed a decreased presentation of OVA construct even though the endosomal sorting pathway is not normally overlapping the MHCI sorting pathway, but rather the MHCII.

Example 1B: T Cell Response

After vaccination, cells and cytokines are recruited to the site where the antigen has been introduced to trigger the immune response. By immunizing in the loose tissue behind the footpad the immune response towards vector and vaccine antigen causes swelling that can be measured by a caliper. The quantitation is interpreted as an indicator of the strength of the cellular immune response.

Figure 2:
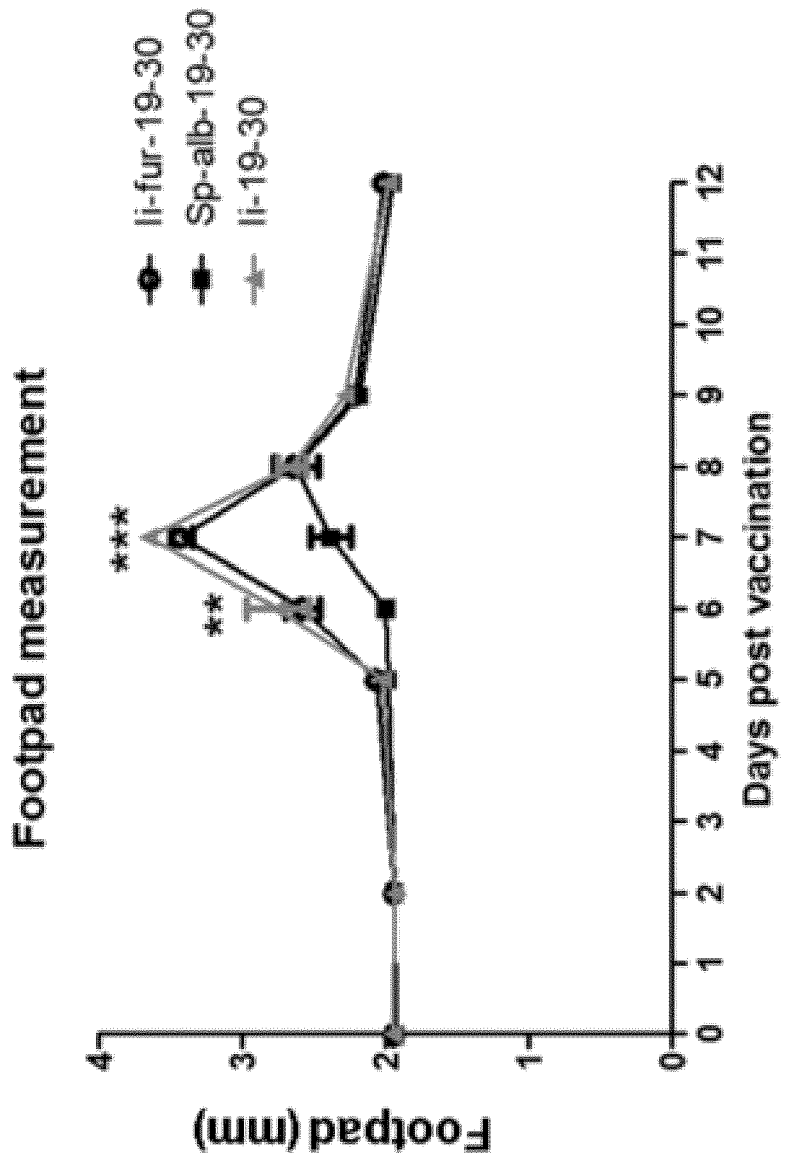
FIG. 2: Analysis of MHCI expression of OVA antigens with different adjuvants-footpad swelling measurements representing T cell recruitment after immunization in the right footpad with the hAd5-IT4var19-PFCLINvar30 constructs.

After vaccination the footpads of mice vaccinated with Ii and Ii-fur constructs were more swollen than in mice vaccinated with SPalb construct (FIG. 2), showing that with Ii and Ii-fur constructs the immune response was more intense than with the SPalb construct. Vaccination with Ii- and Ii-fur constructs resulted in very similar levels of swelling indicating very similar T cell responses.

Example 2: MHCII-OVA Presentation

Figure 3:
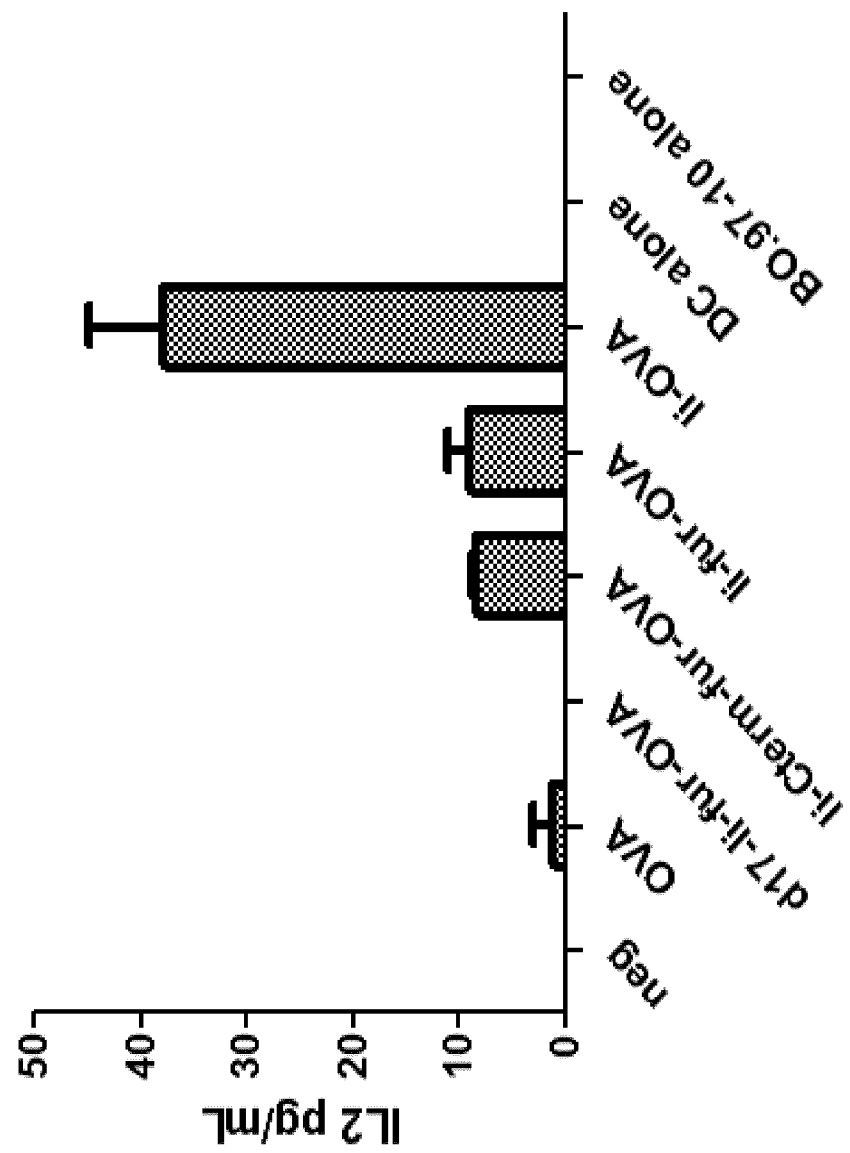
FIG. 3: Analysis of MHCII expression of OVA antigens with different adjuvants. This figure shows IL-2 levels representing MHCII presentation of OVA on the surface of JAWSII cells infected with the different hAd5-OVA constructs and recognized by T-cells specific for MHCII-OVA.

Ii-fur constructs showed increased MHCII presentation of OVA on the surface of DC like cells. However, presentation was lower than the Ii-construct, since the secretion of the Ii-fur complex, lowers the re-uptake by the endosomes thus MHCII presentation (FIG. 3).

Example 3: Expression of Encoded Proteins

Figures 4A, 4B:
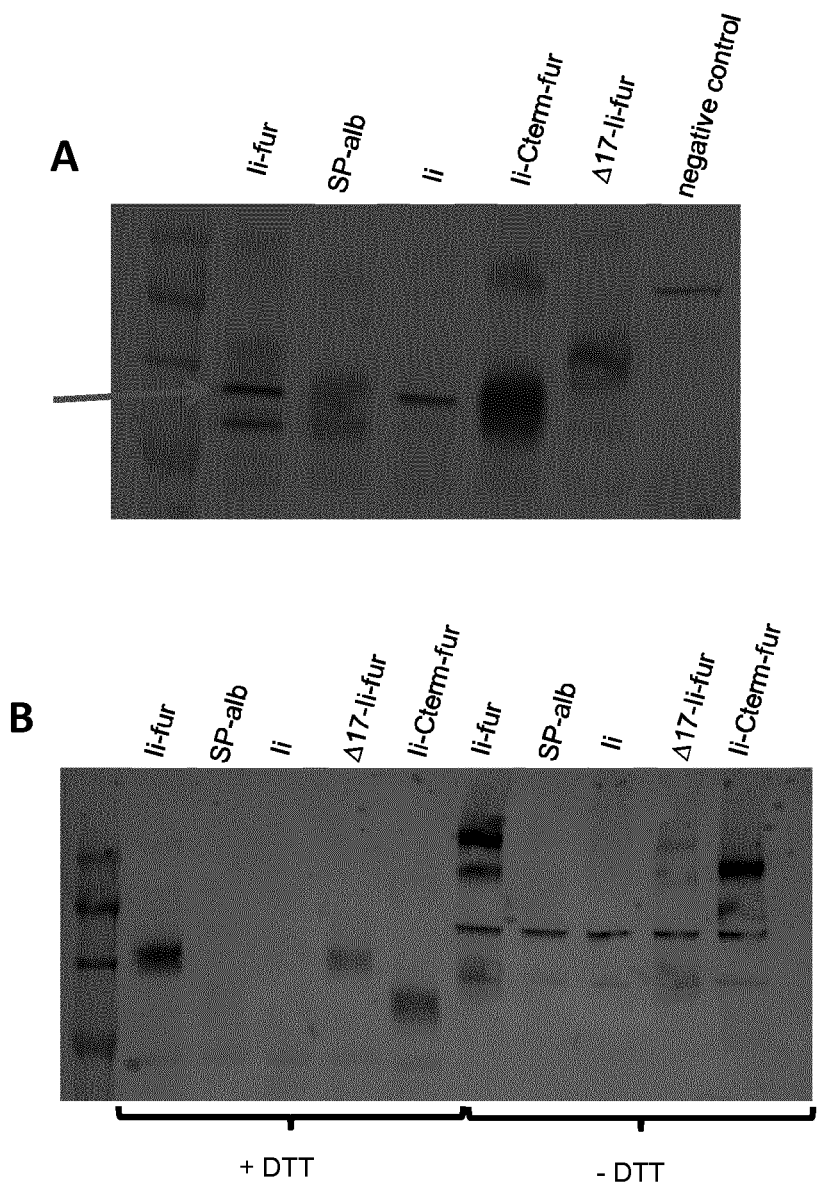
FIGS. 4A and 4B: Analysis of the expression of encoded antigens IT4var19 and PFCIinvar30. (A) illustrates identification of PFCLINvar30 by western blot in the SN (supernatant) of infected VERO cells with the different hAd5-IT4var19-PFCLINvar30 viruses. VERO cells were infected with 50 MOI/cell and SN was harvested 48 h after. (B) illustrates identification of PFCLINvar30 by western blot in denaturing and non-denaturing conditions in the supernatant, after infection of COS7 cells with hAd5-IT4var19-PFCLINvar30.
Figure 5A:
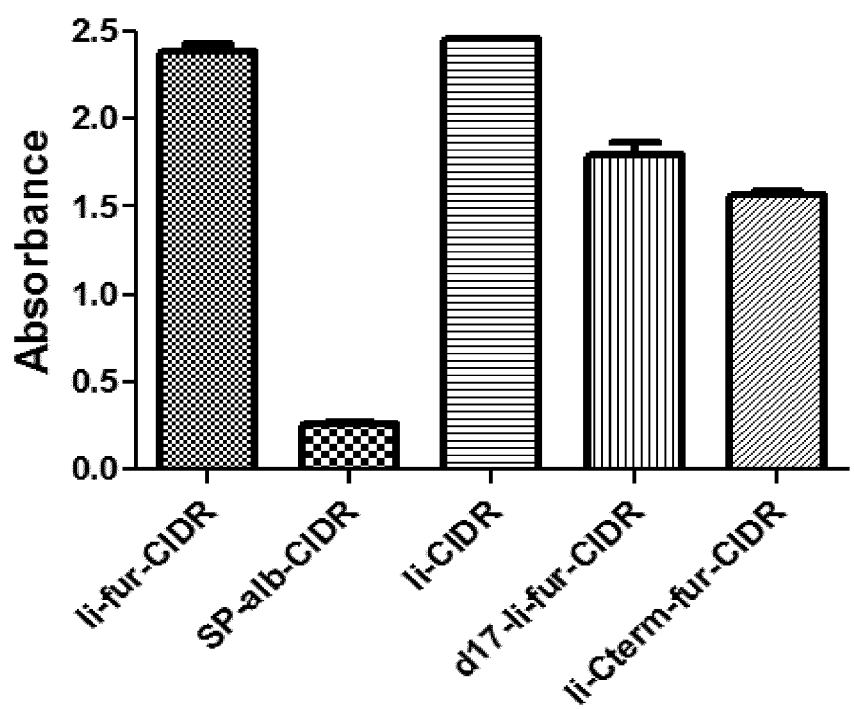
FIG. 5A-5D: Analysis of the expression of encoded antigens IT4var19 and PFCIinvar30. These graphs illustrate the analysis of binding to EPCR by expressed proteins in the supernatant or cell lysates, after infection of COS7 cells with hAd5-IT4var19-PFCLINvar30.
Figure 5B:
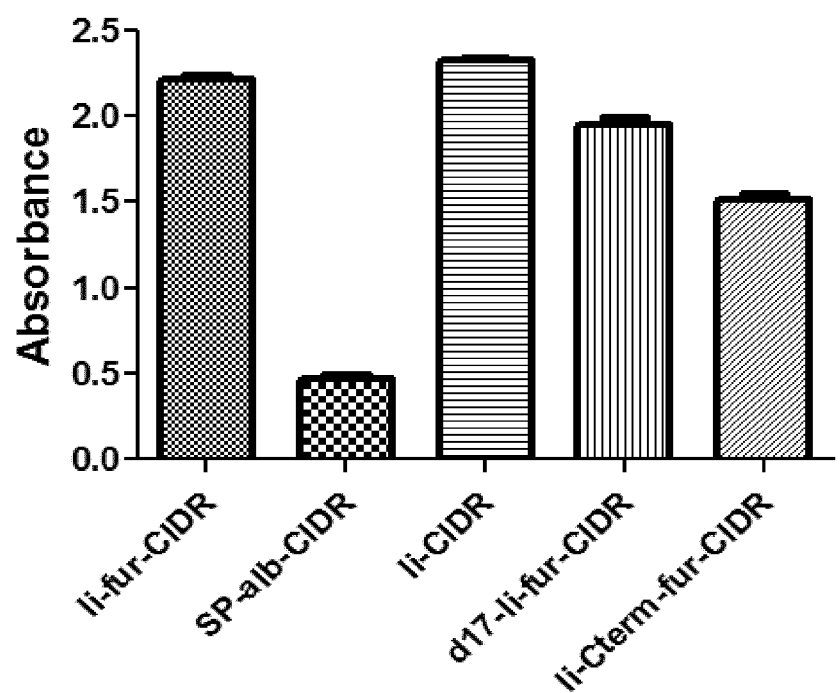
Figure 5C:
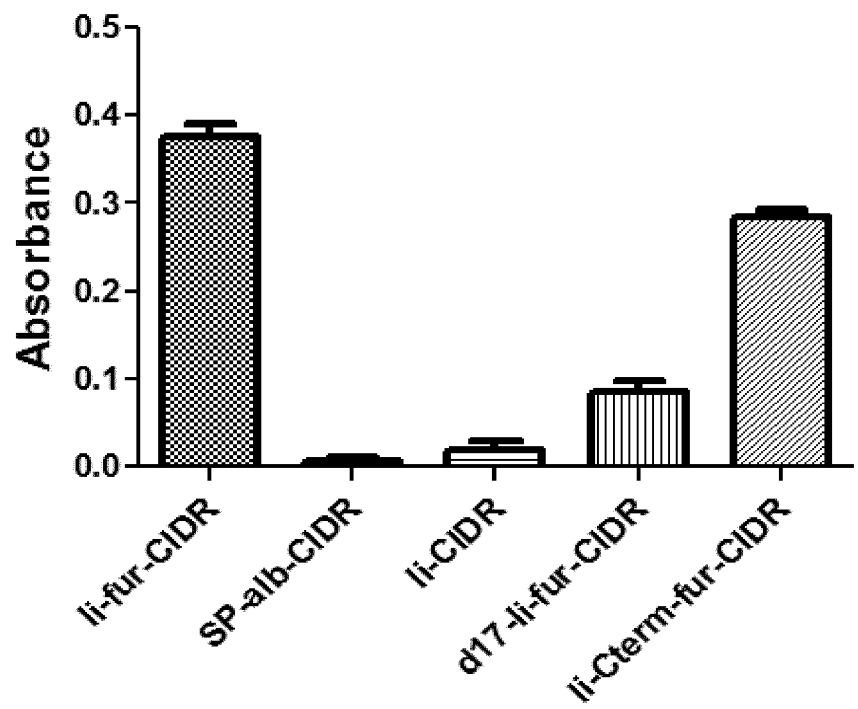
Figure 5D:
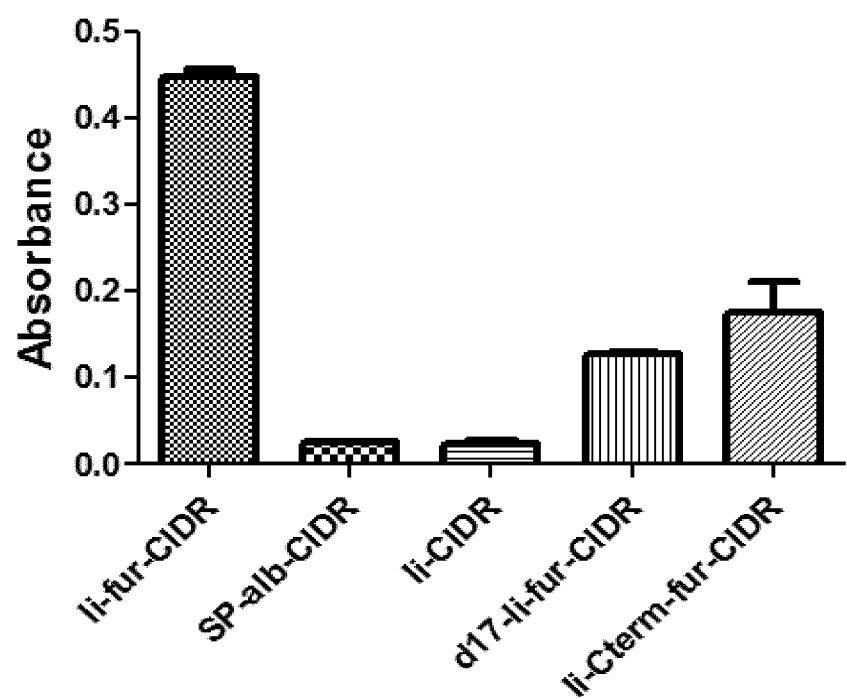
Figure 6B:
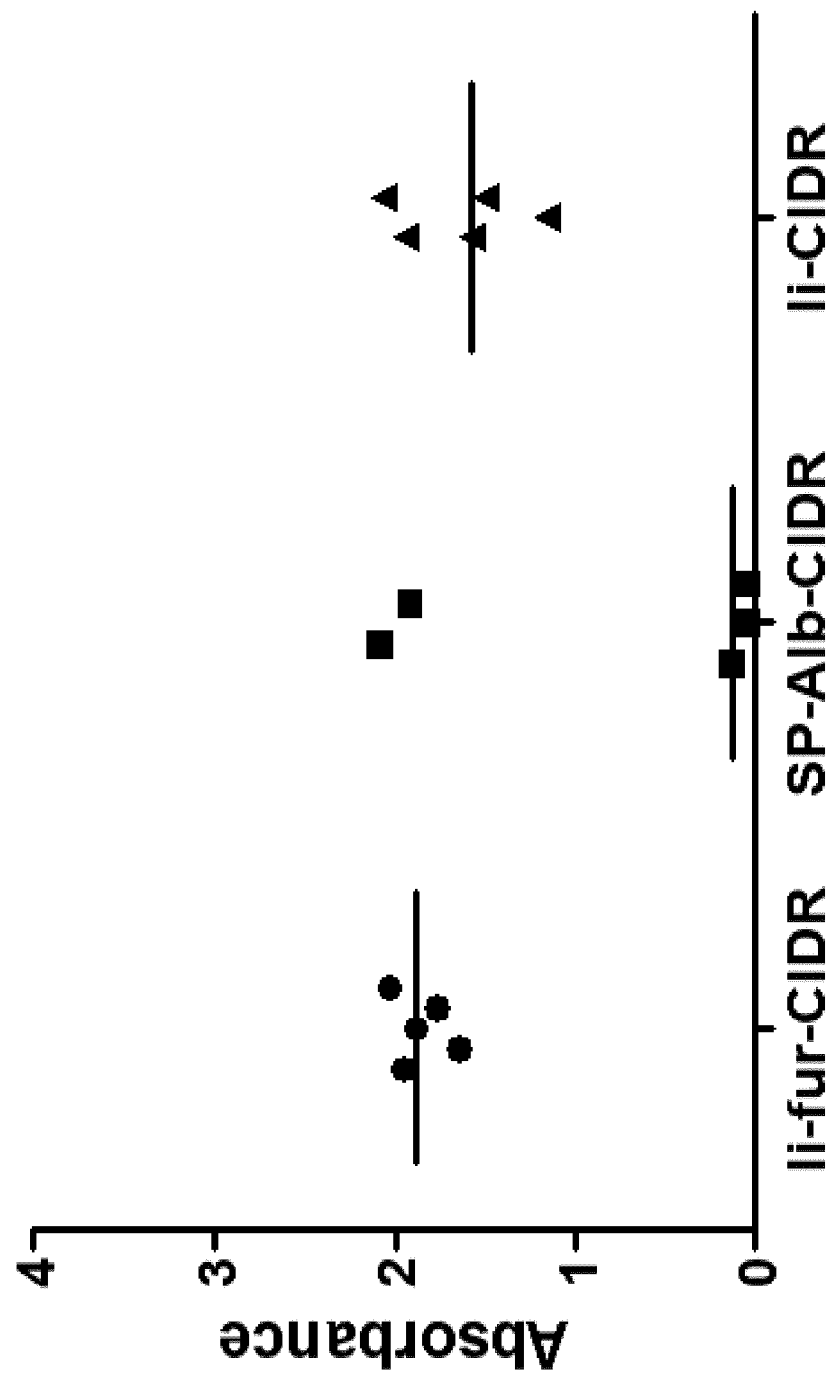
Figure 6C:
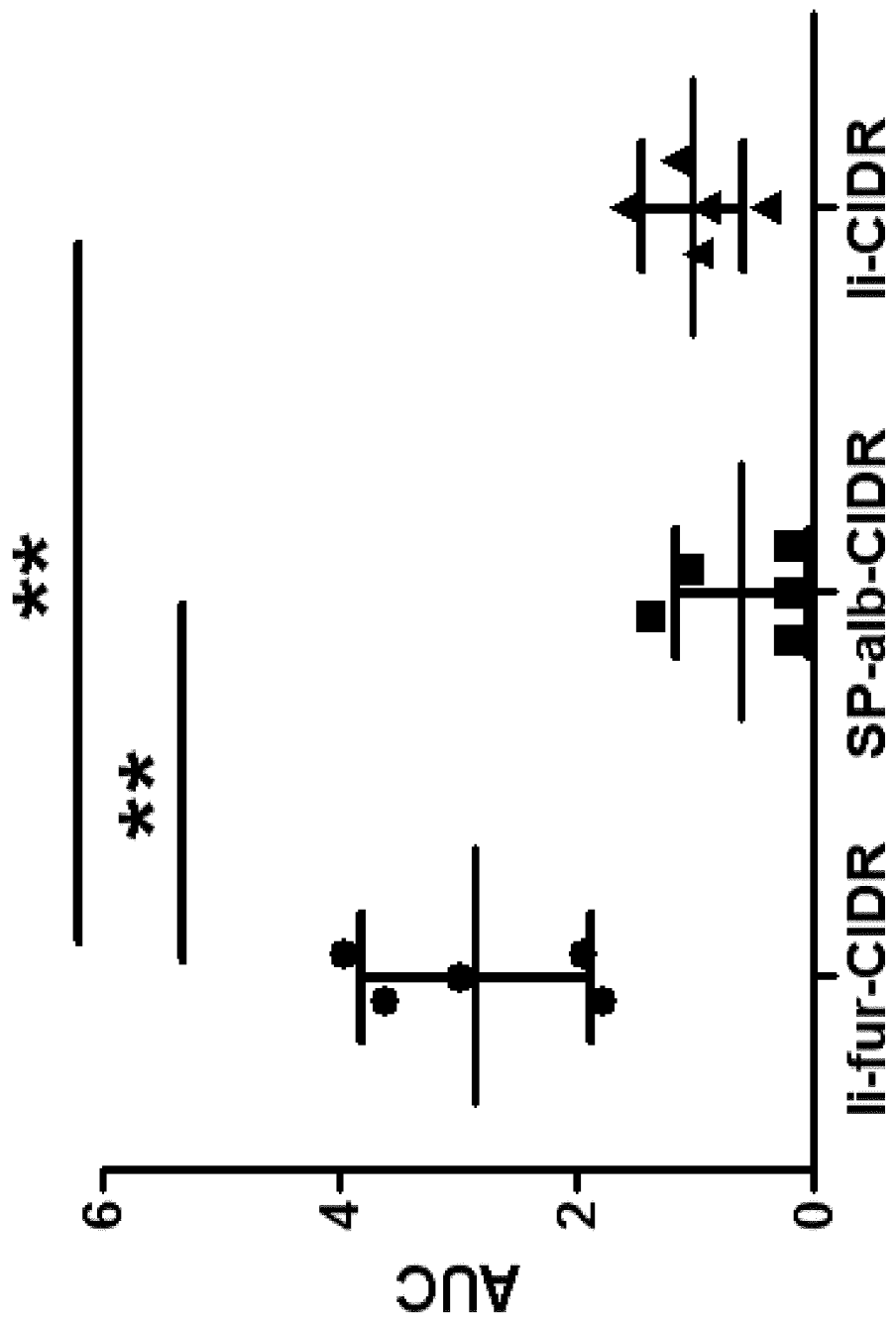
Figure 6E:
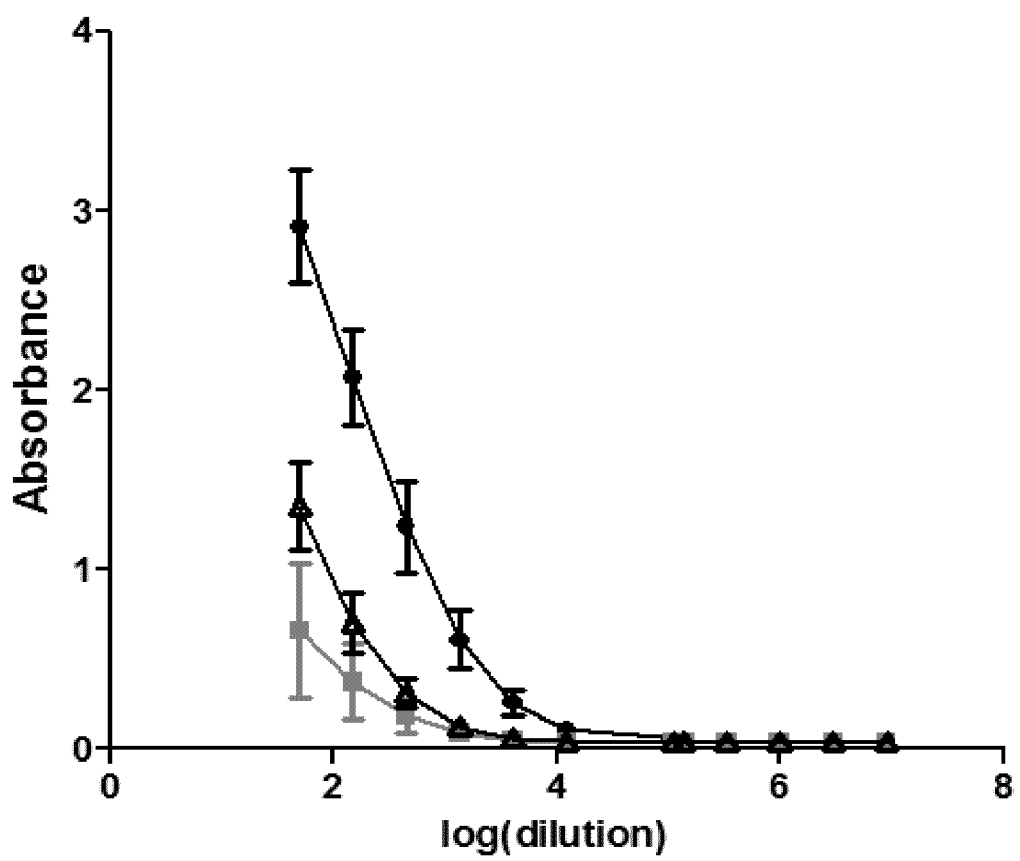
Figure 6F:
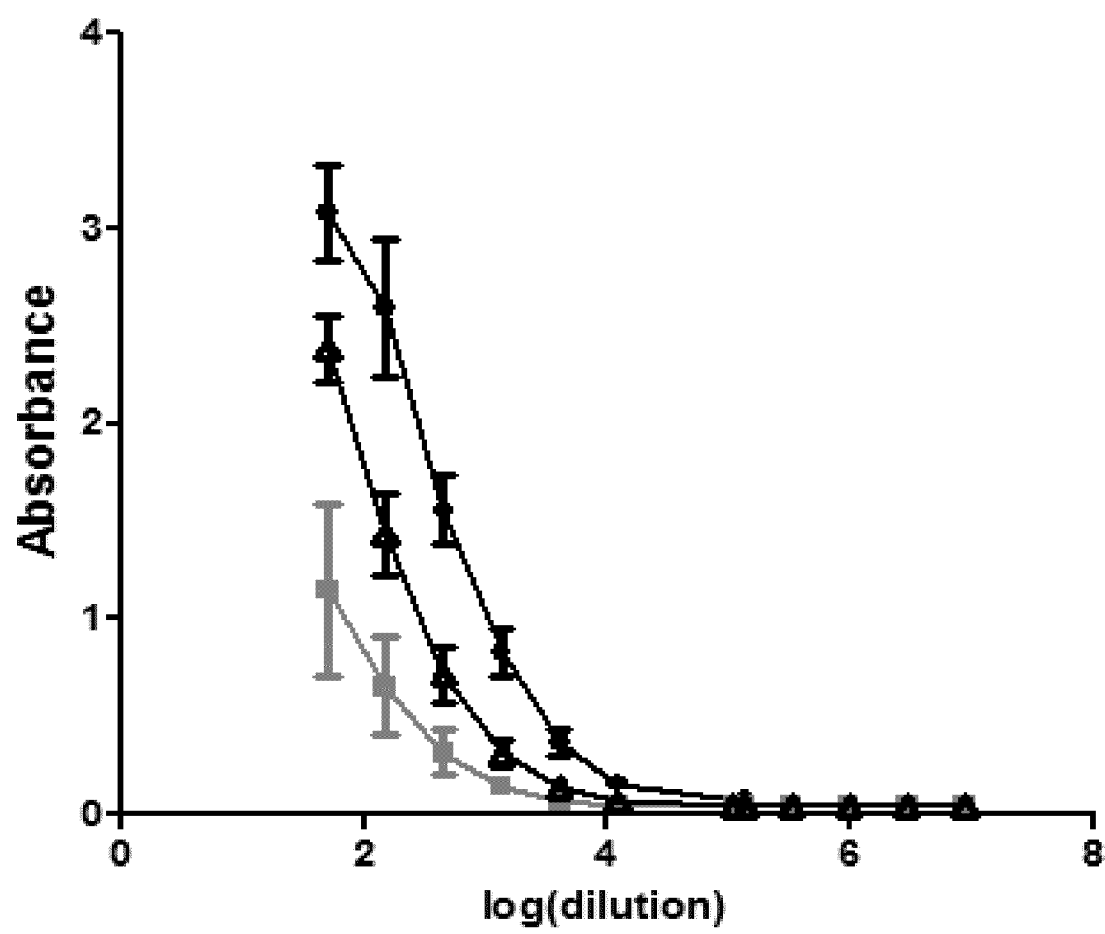
Figure 7A:
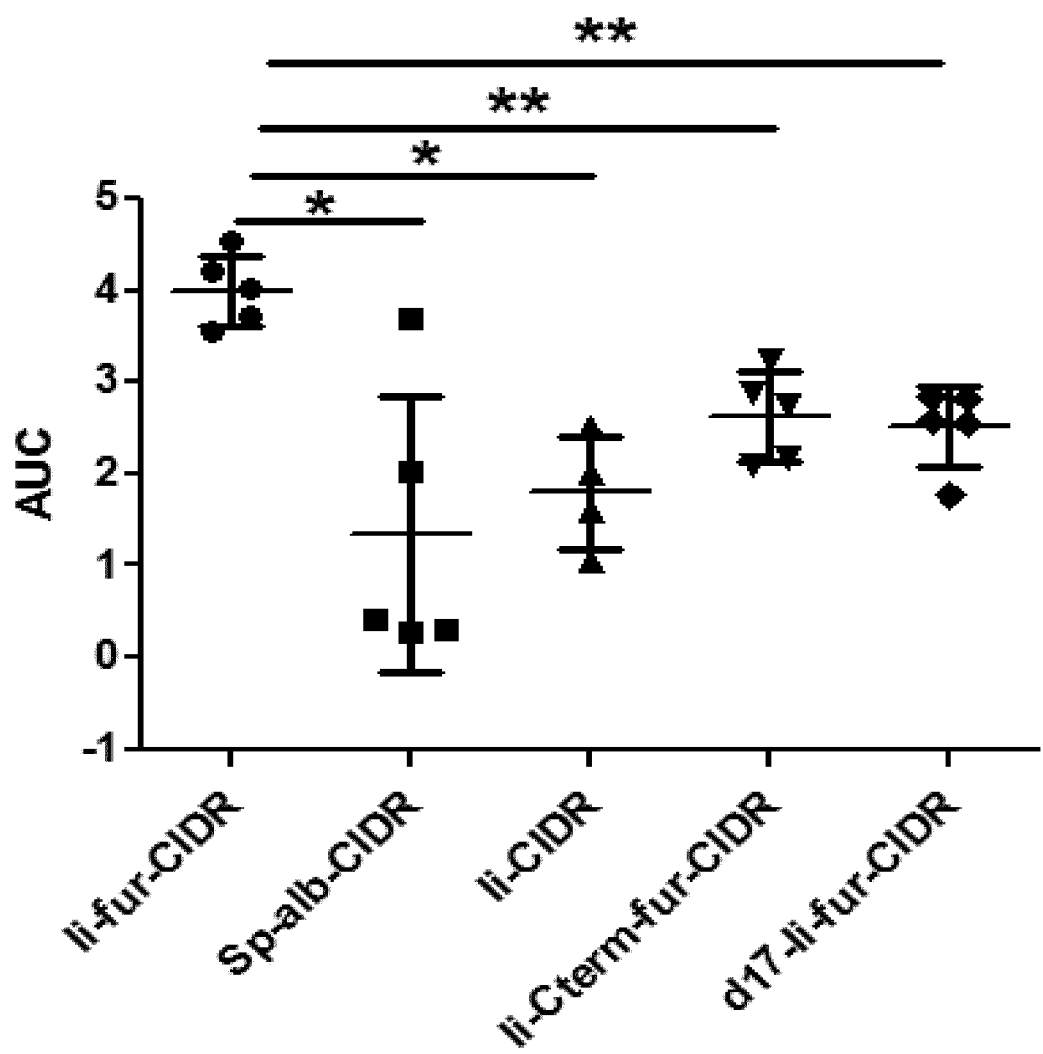
FIG. 7A-7D: Antibodies against IT4var19 and PFCLINvar30 induced after hAd5 vaccination for comparison of the Ii-fur adjuvant compared to controls. (A) and (C) show the detection of antibodies recognizing IT4var19 10 weeks after immunization of Balb/C mice with Ad5-Ii-fur-IT4var19-PFCLINvar30 (N=5), Ad5-Sp-alb-IT4var19-PFCLINvar30 (N=5), Ad5-Ii-IT4var19-PFCLINvar30 (N=5), Ad5-Ii-Cterm-fur-IT4var19-PFCLINvar30 (N=5), Ad5-d17-Ii-fur-IT4var19-PFCLINvar30 (N=5). Serum was diluted to 1:5 and added to the wells in two-fold dilutions. Absorbance and dilutions were plotted on a log(X) axis (C), areas under the curves were calculated and plotted on (A). (B) and (D) show detection of antibodies recognizing PFCLINvar30 10 weeks after immunization of Balb/C mice with Ad5-Ii-fur-IT4var19-PFCLINvar30 (N=5), Ad5-Sp-alb-IT4var19-PFCLINvar30 (N=5), Ad5-Ii-IT4var19-PFCLINvar30 (N=5), Ad5-Ii-Cterm-fur-IT4var19-PFCLINvar30 (N=5), Ad5-417-Ii-fur-IT4var19-PFCLINvar30 (N=5). Serum was diluted to 1:5 and added to the wells in two-fold dilutions. Absorbance and dilutions were plotted on a log(X) axis (D), areas under the curves were calculated and plotted on (C).
Figure 7B:
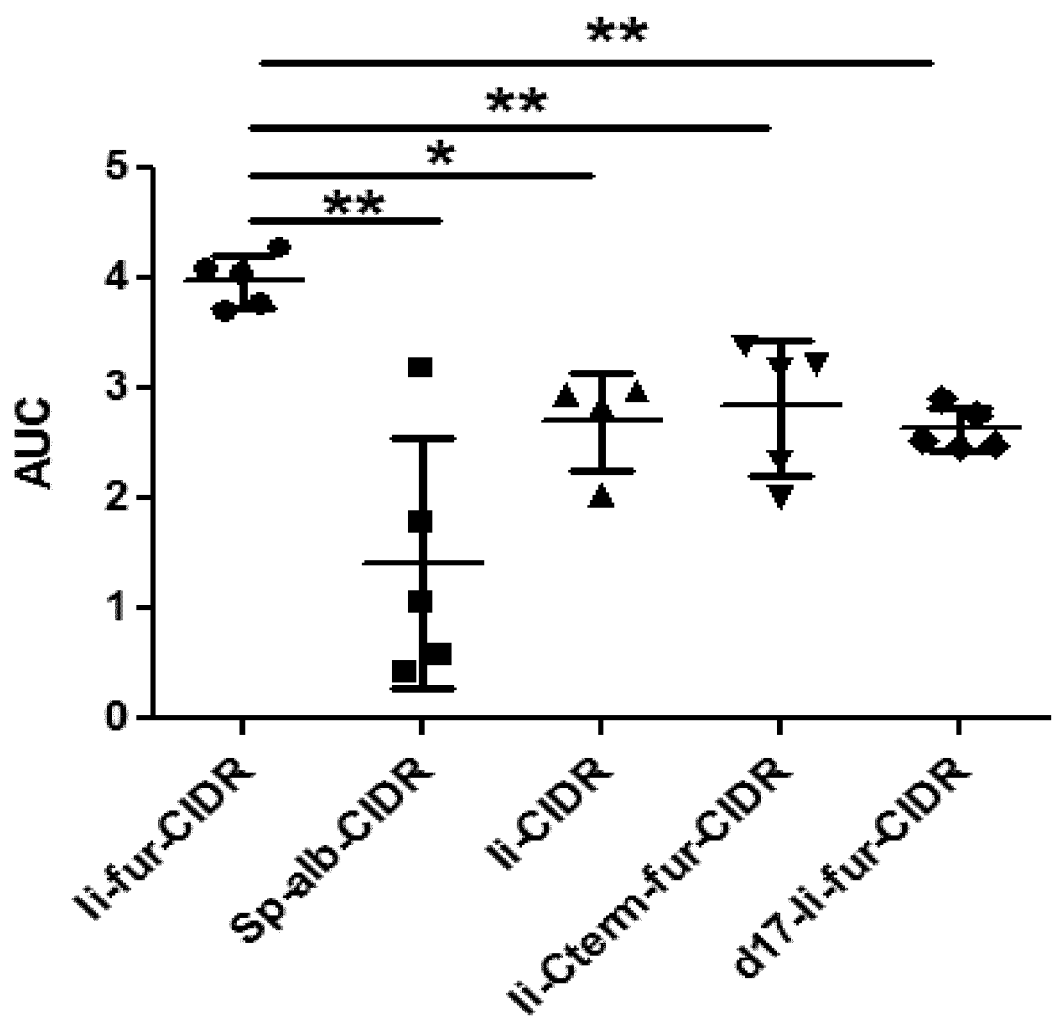
Figure 7C:
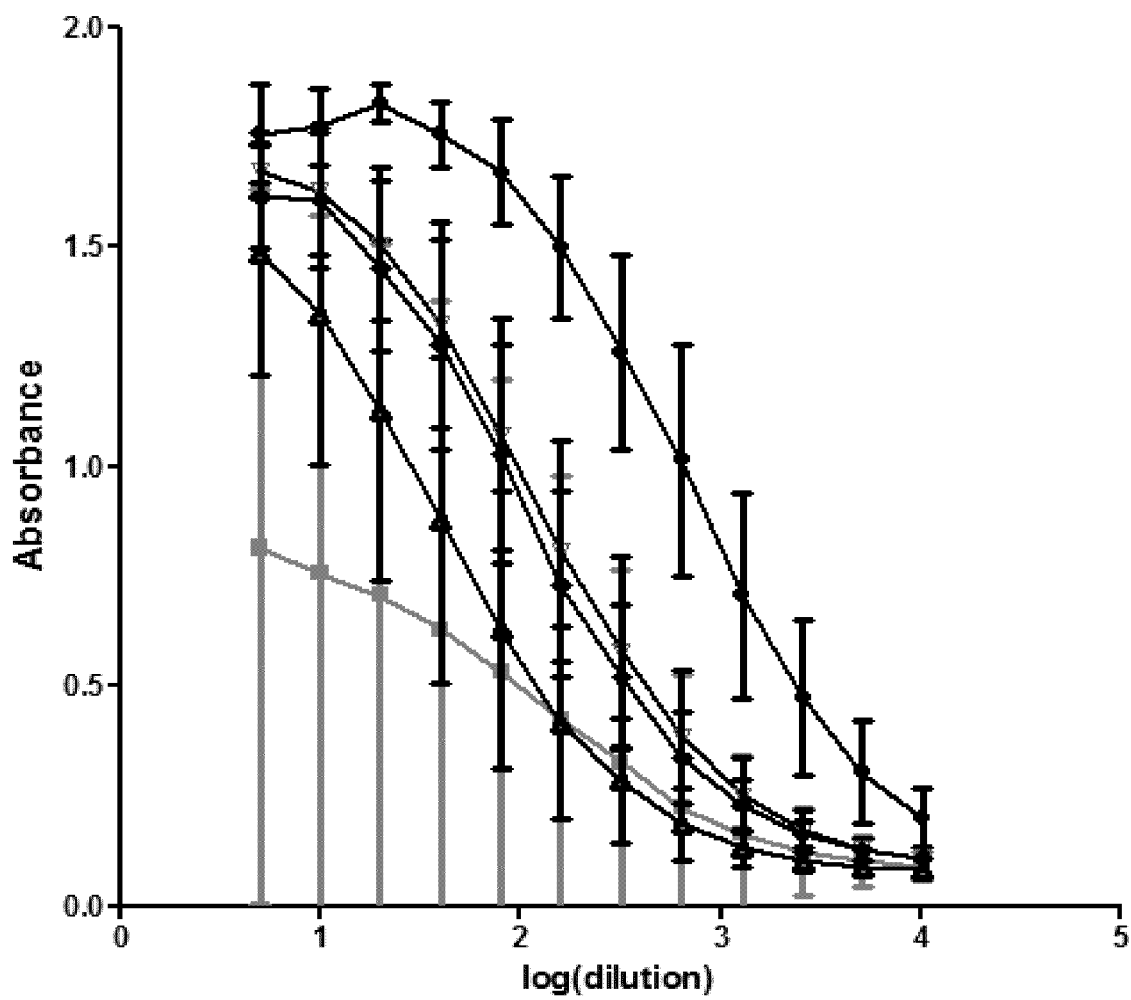
Figure 7D:
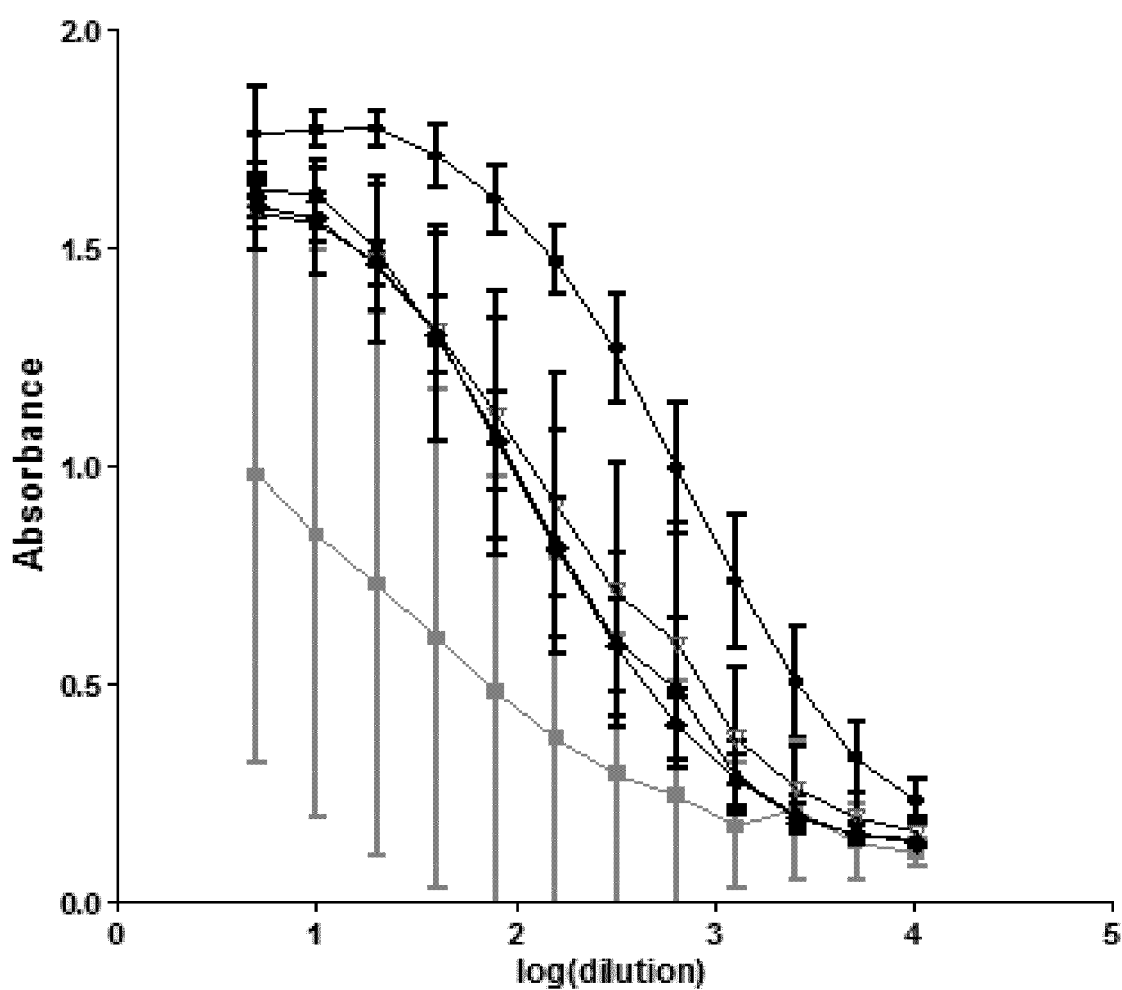

FIG. 4A shows that the coupled antigens designed to be secreted via the furin recognition site and the albumin signal peptide could be detected in the supernatant of infected cells, with the Ii-Cterm-fur being the most effective.

Figure 18:
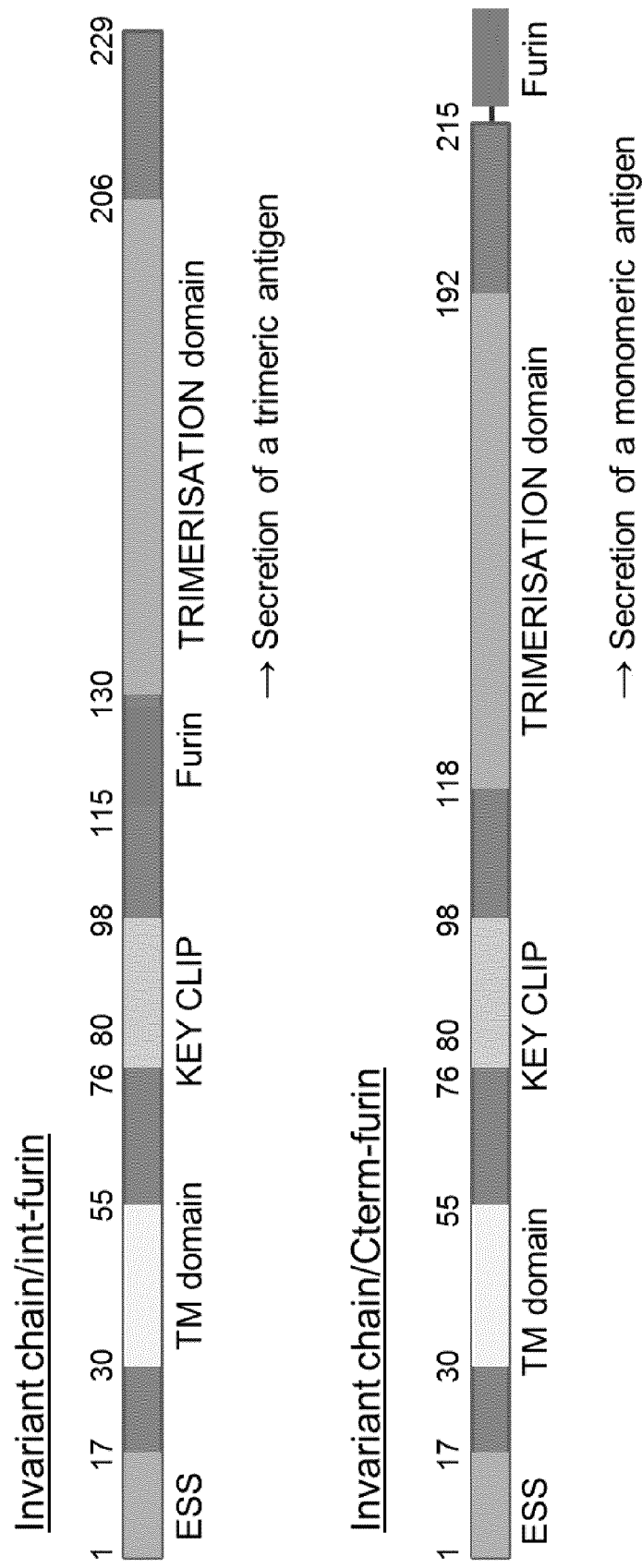
Figure 19:
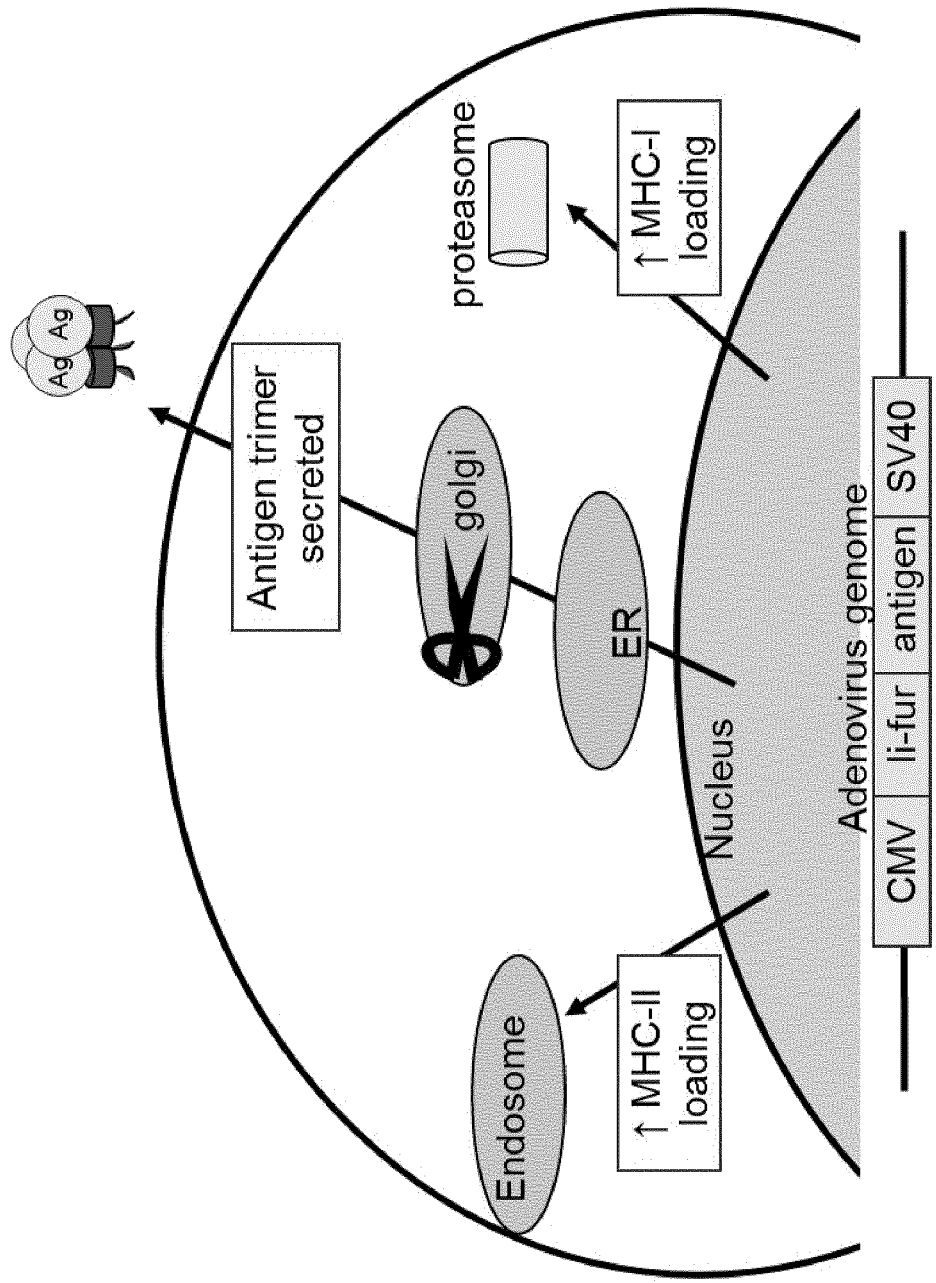
Figure 20:
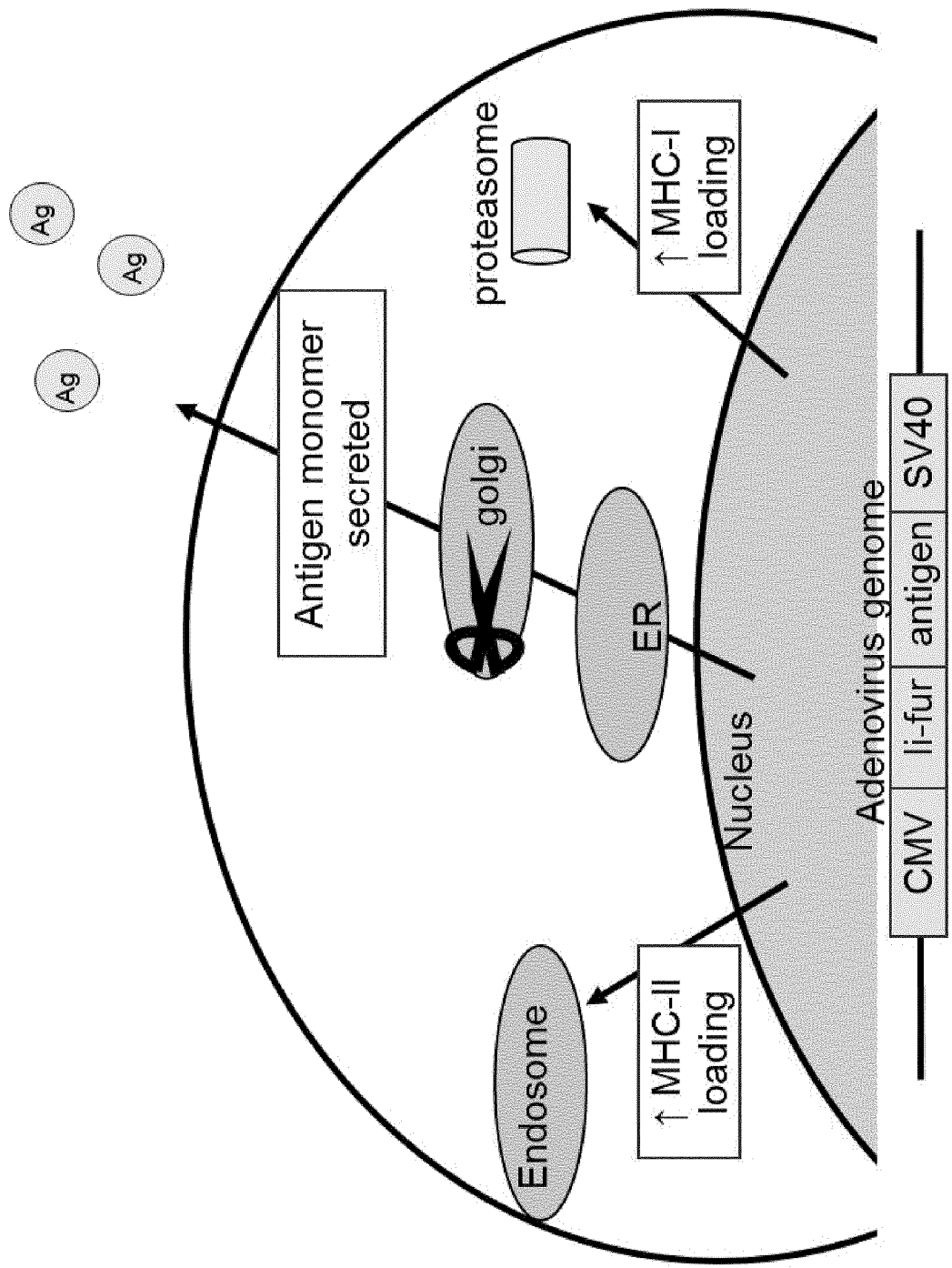

FIG. 4B shows that in non-denaturing conditions, a trimer could be detected with the Ii-fur and d17-Ii-fur. This is because the trimerisation domain is present in the Ii thus the encoded antigens are secreted as a trimer (see also FIGS. 18-20).

Example 4: Expression of Encoded Proteins

It can be seen from FIG. 5 that binding to EPCR with both encoded antigens, IT4var19 and PFCLINvar30, was detected in the supernatant and cell lysates. Ii-fur-CIDR constructs induced higher levels of secreted antigens in the SN as compared to SP while the Ii-CIDR was secreted at minimal levels, but retained at high levels intracellularly. These findings also confirmed that the conformation of the antigens is maintained and accessibility of the EPCR binding epitopes is not prevented by the trimerization induced by the invariant chain.

Example 5: Timeline of the Antibody Response

The enhanced response provided by the Ii-fur adjuvant was detected as early as 2 weeks post vaccination, where the antibody response was increased compared to monomer secretion (SP-alb) and membrane trimer (Ii) (FIG. 6). This shows that Ii-fur adjuvant triggers an accelerated and enhanced immune response. Ten weeks post vaccination, and 2 weeks post homologous boost, the antibody response was significantly increased in comparison to the two other constructs for each encoded antigen.

Example 6: Increased Antibody Response

FIG. 7 illustrates that when comparing the Ii-fur construct to the mutated constructs, both presence of the ESS and trimerization provide optimal adjuvant effect on antibody response, as it can be seen that deletion of each sequence leads to a decrease of the immune response.

Example 7: Increased Inhibition Response

Figure 8A:
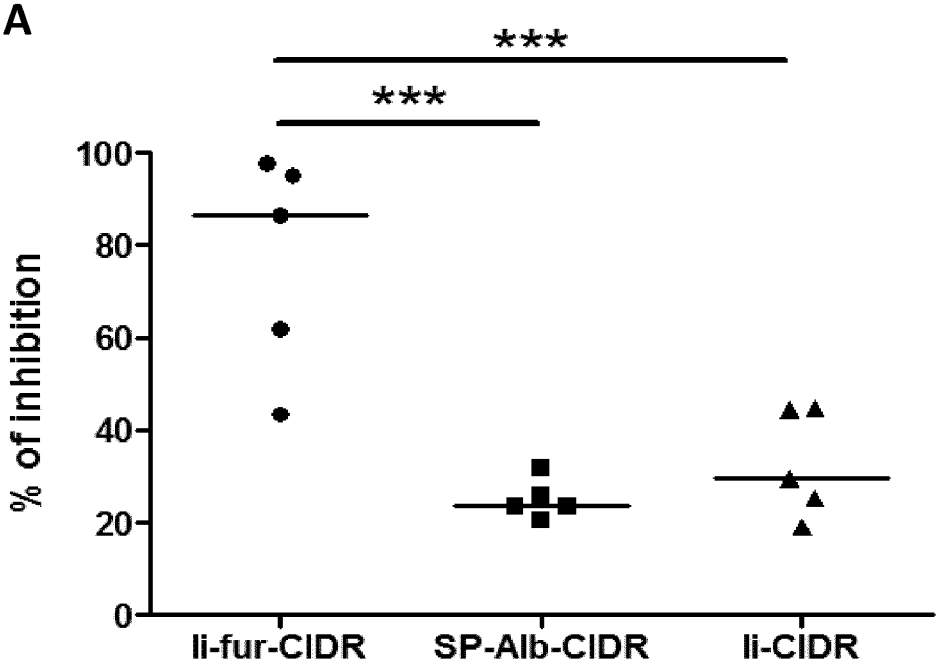
FIG. 8A-8B: Measurement of inhibitory antibodies against IT4var19 and PFCLINvar30 induced after Ad5 vaccination for comparison of Ii adjuvants. (A) shows the detection of antibodies inhibiting the binding of IT4var19 to EPCR from week 10 serum after immunization of Balb/C mice with FIG. 21A-21B: Illustration of the different Ad5 constructs used in the examples. (A) shows the five hAd5 vectors which were designed, all encoding IT4var19-PFCLINvar30 (CIDR1.1) and different form of the invariant chain-furin or a secretion signal. The inserted antigens were flanked by the human CMV promoter (huCMV) and a simian virus 40 (SV40) polyadenylation signal. (B) shows the five hAd5 vectors which were designed, all encoding chOVA and different forms of the invariant chain-furin. The inserted antigens were flanked by the human CMV promoter (huCMV) and a simian virus 40 (SV40) polyadenylation signal.
Figure 8B:
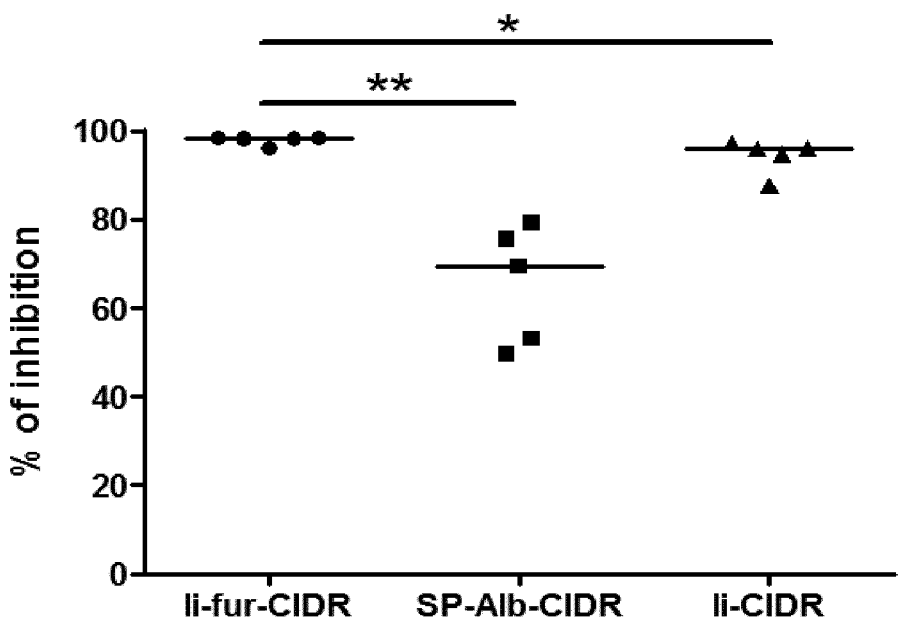
Figure 9A:
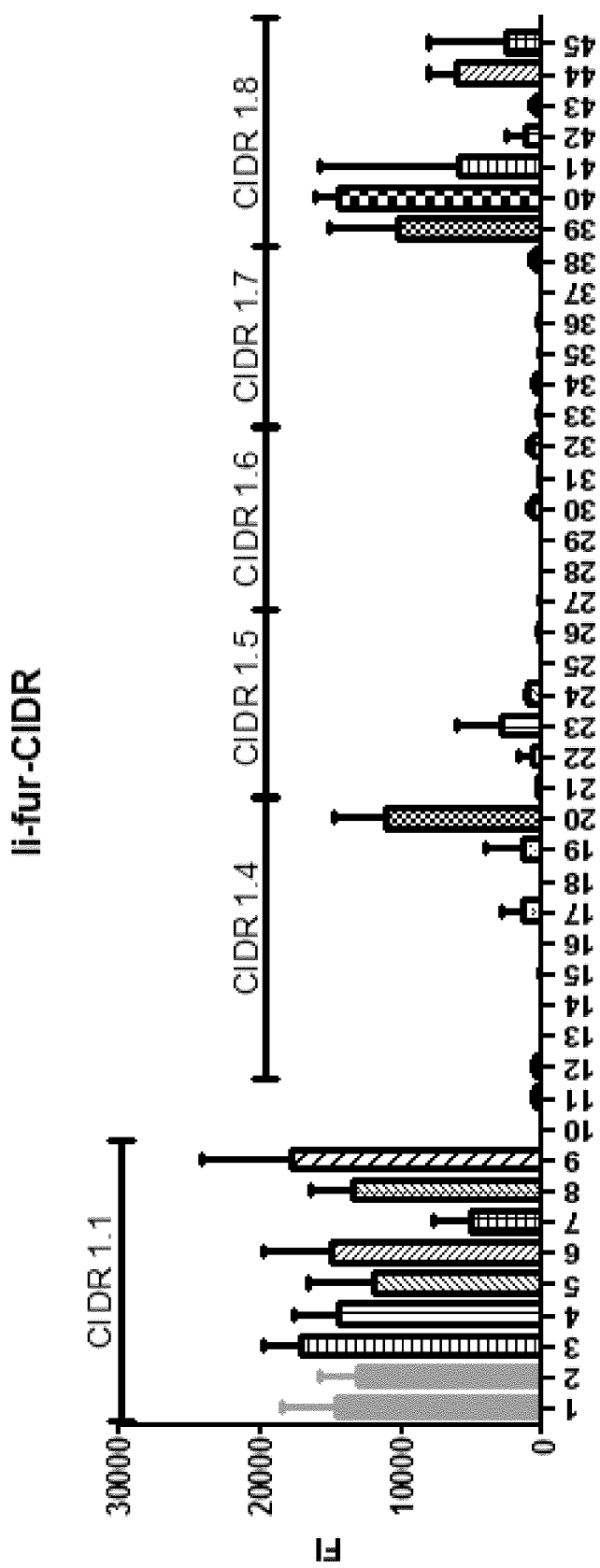
Figure 9B:
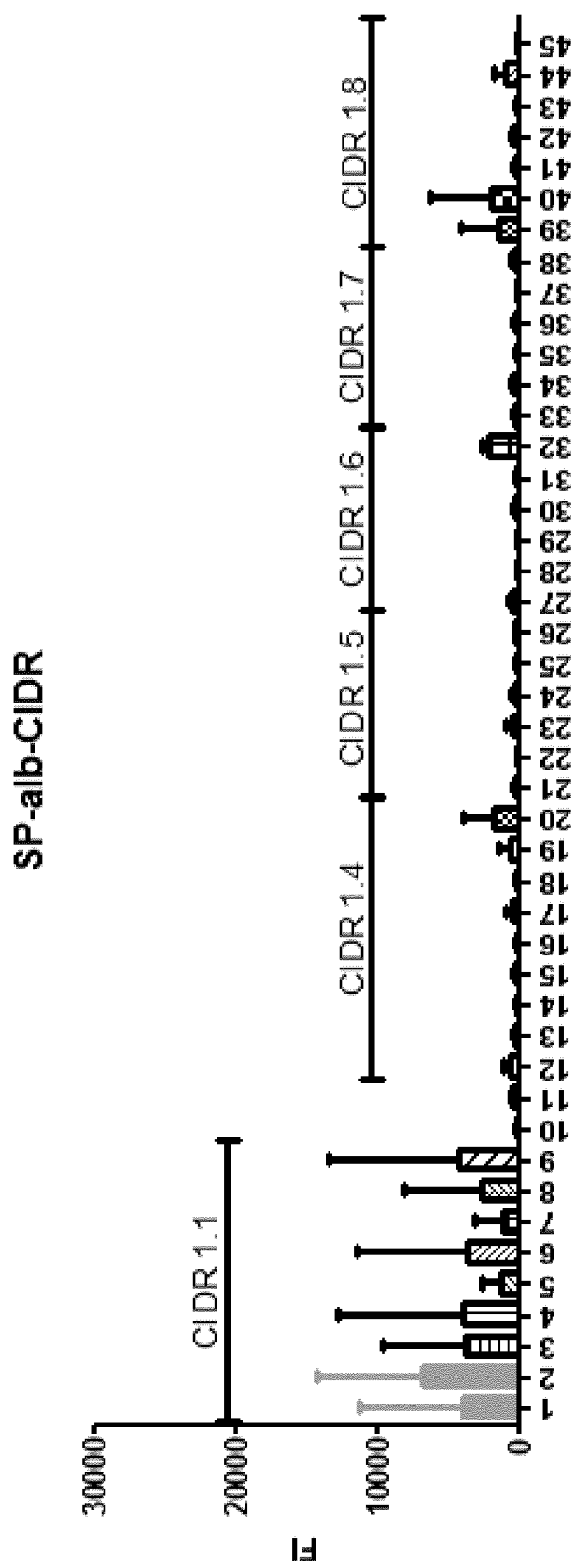
Figure 9C:
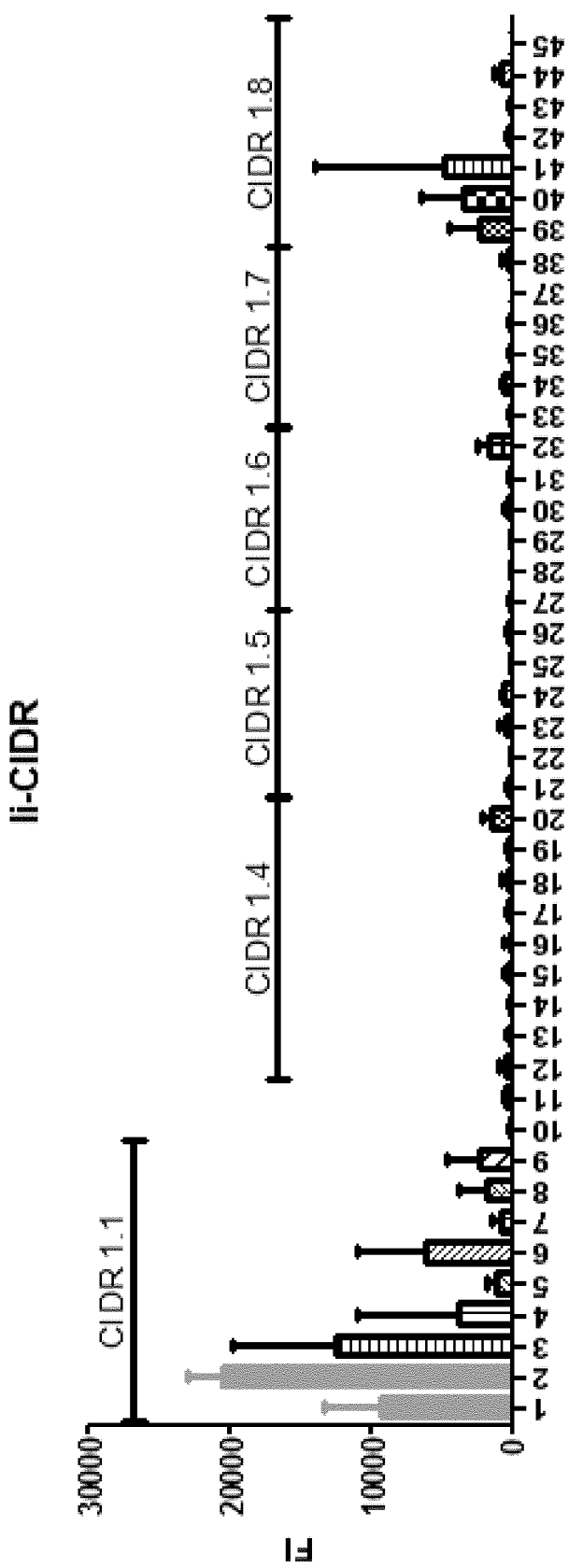
Figure 9D:
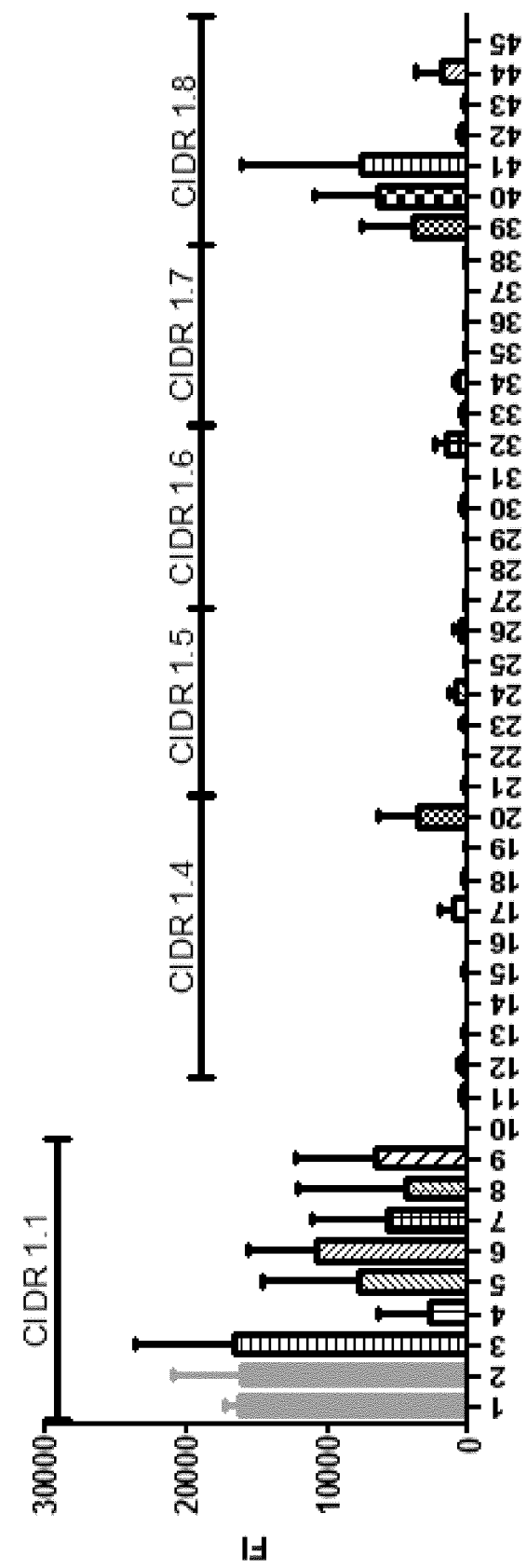
Figure 9E:
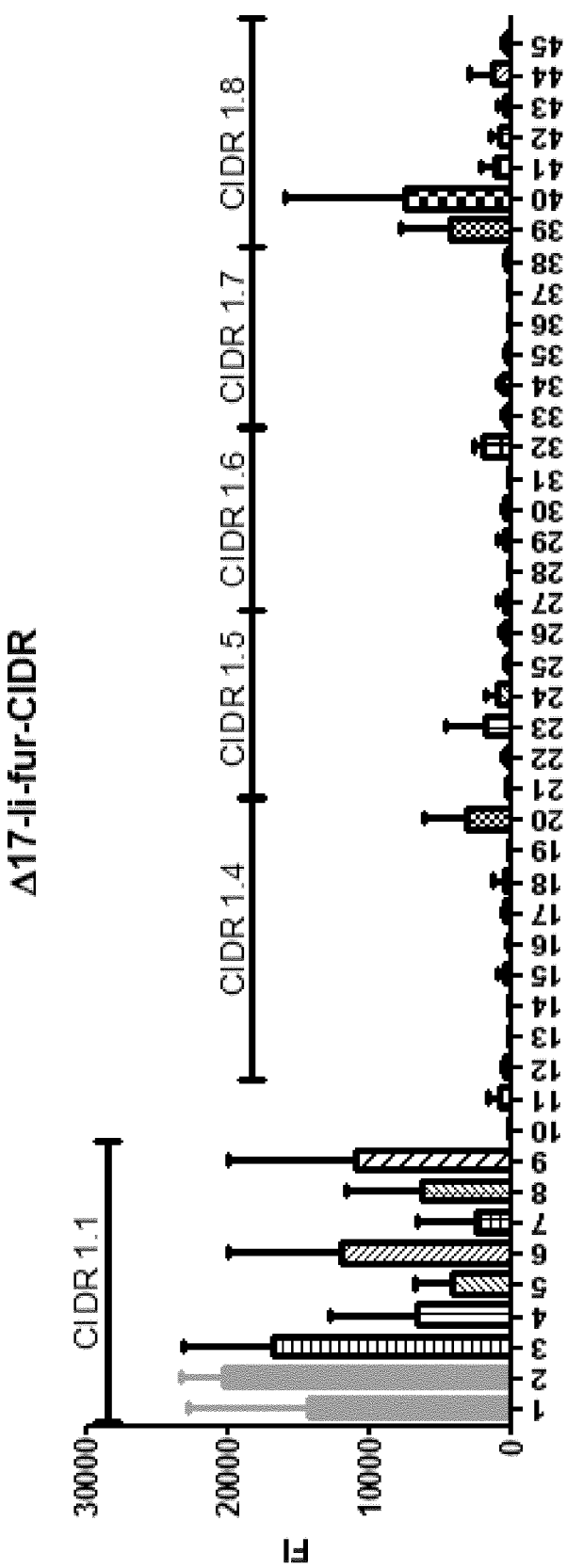

As can be seen in FIG. 8, antibodies generated after vaccination were able to prevent IT4var19 and PFCLINvar30 from binding to their natural ligand (EPCR), showing that not only was the antibody response increased but was also more efficient with the Ii and Ii-fur constructs. Thus it can be concluded that the Ii-fur adjuvant not only induced faster production and higher levels of antibody, but also antibodies with increased functionality compared to Ii alone or the secreted antigen with SP-alb.

Example 8: Cross-Reactivity of the Increased Antibody Response

It was found that the intensity of the induced cross-reactivity was higher when mice were vaccinated with the construct containing the Ii-fur adjuvant compared to the other constructs, especially the cross-reactivity with CIDR1.1 (FIG. 9). Recognition of genetically further "var" genes (from CIDR1.4, 1.7 and 1.8) was also increased using this adjuvant, compared to Ii alone or the secreted version of the antigen. Thus, the tethering of the antigens to the Ii-fur not only triggered a higher and more functional antibody response, but also allows more consistent cross-reactivity of the induced antibodies. Here again, it is shown that both trimerisation and ESS domains provide for optimal adjuvant effect.

Examples 9 and 10: Antibody Responses Induced in C57BL/6

Figures 10A, 10B:
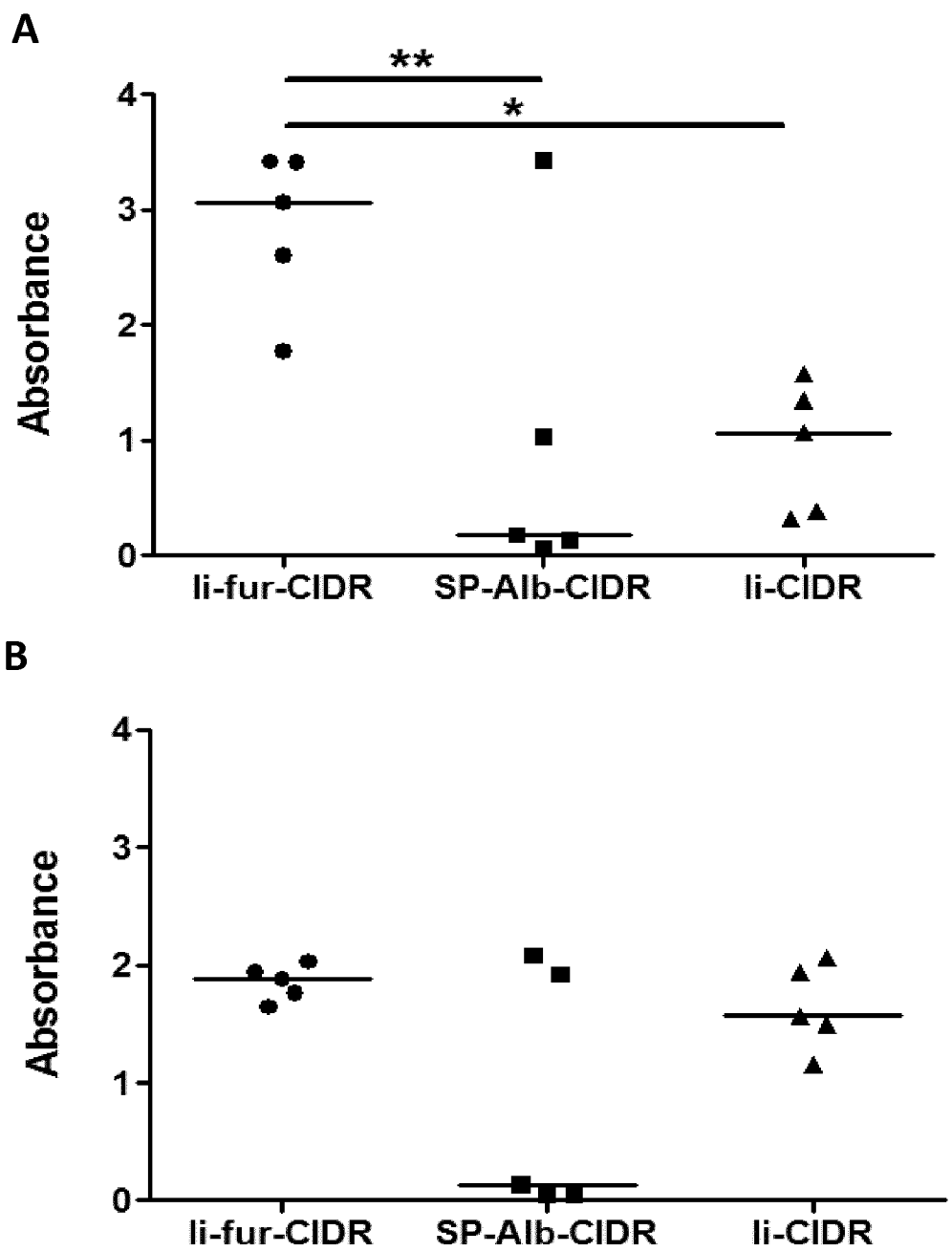
Figure 10C:
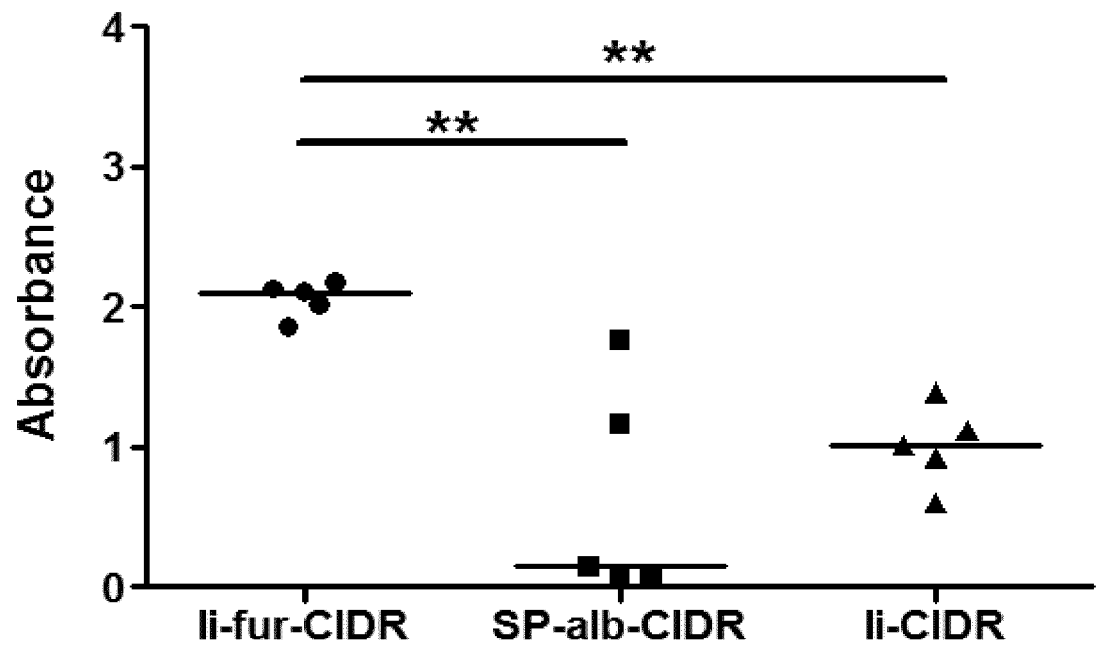
Figure 10D:
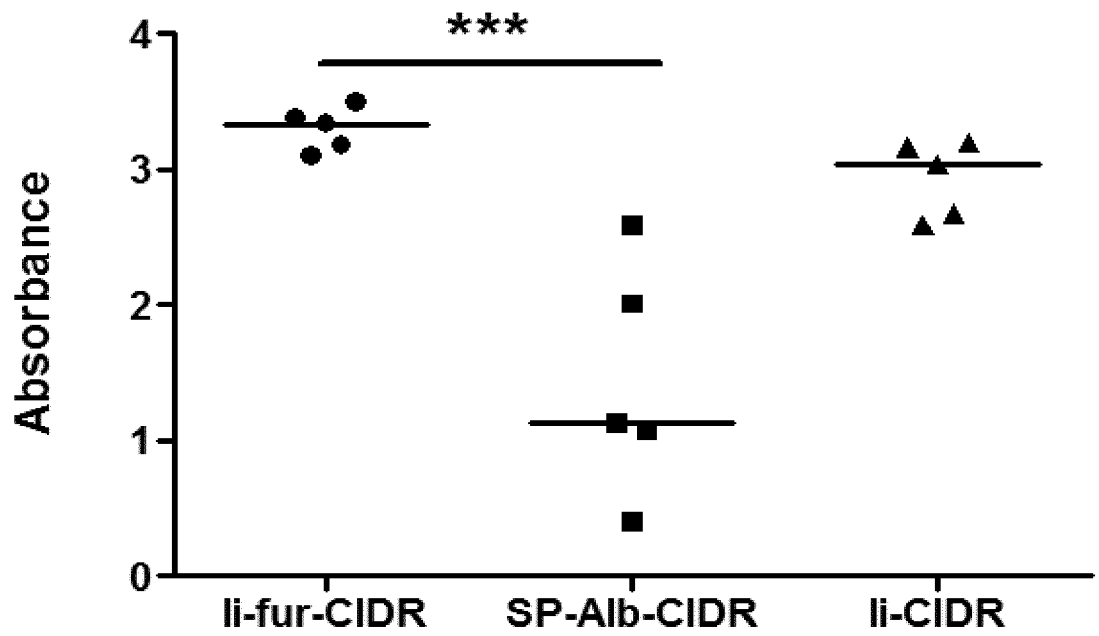
Figure 11A:
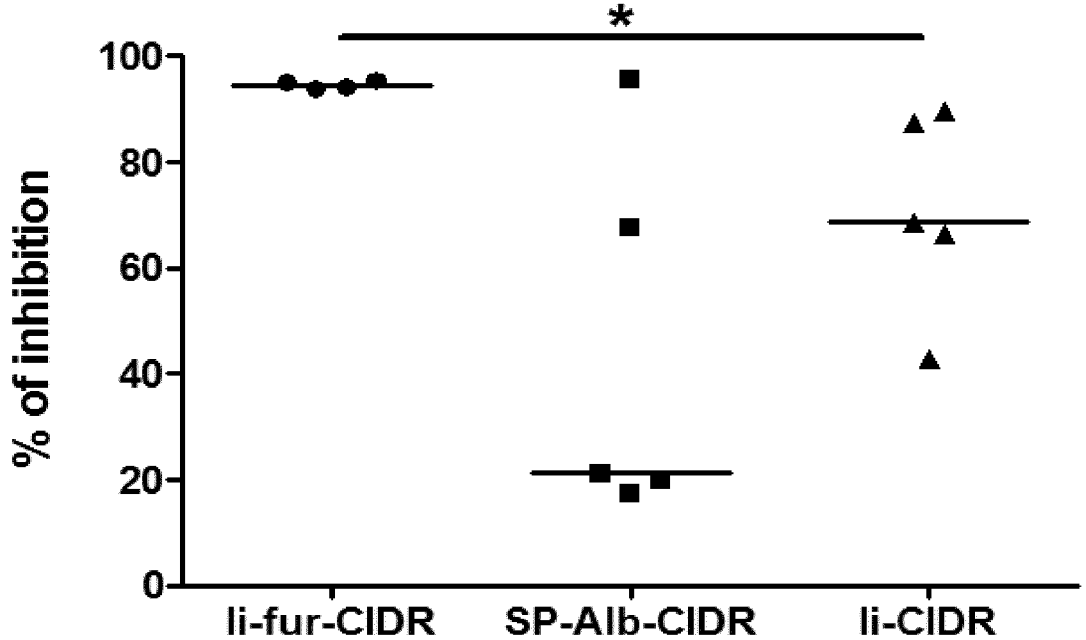
Figure 11B:
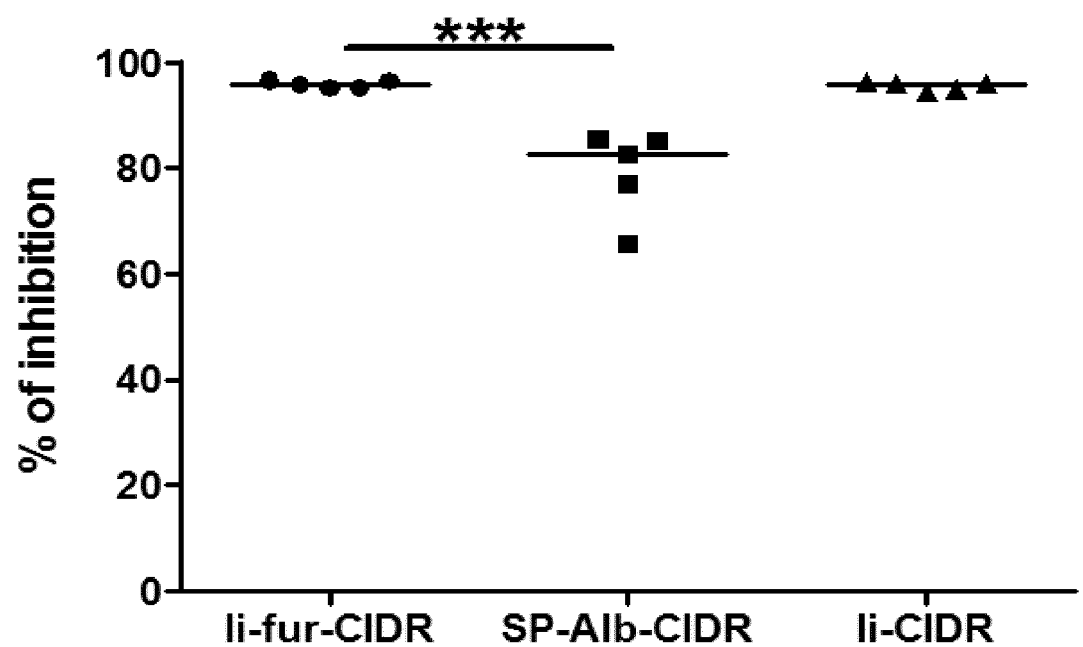

These figures show that all the antibody results (recognition and inhibition data) obtained with Balb/C mice and shown above, where reproducible in a different strain of mice, here C57BL/6 mice (FIGS. 10 and 11).

Example 11: Analysis of the Adjuvant Effect of the Ii-Fur on a Different Antigen (p15E in MelARV)

Figure 12A:
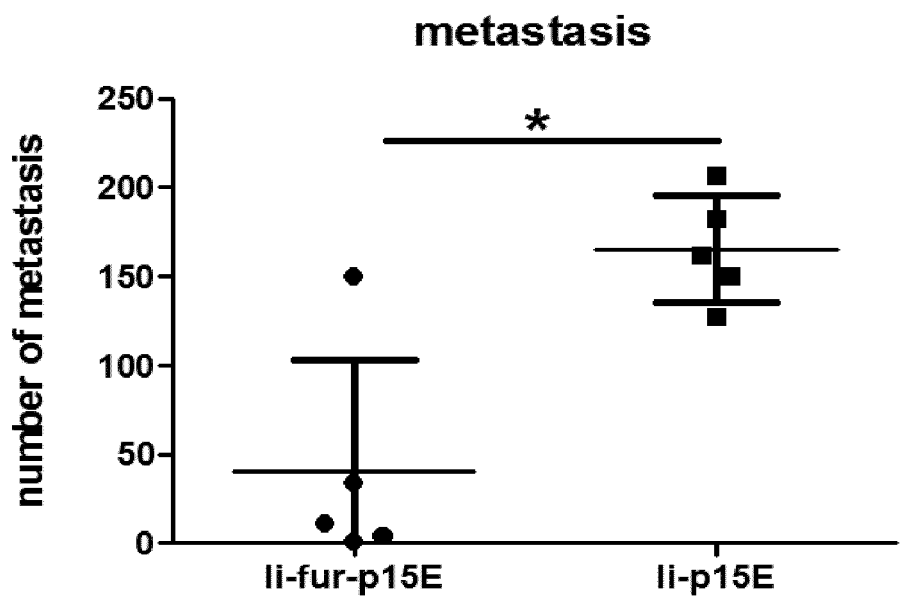
Figure 12B:
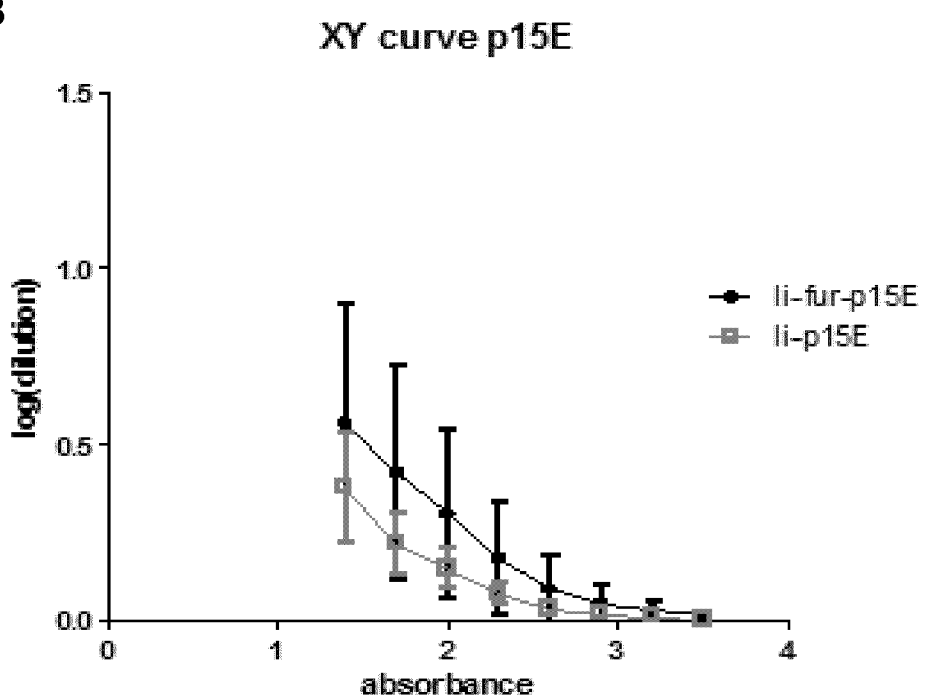
Figure 12C:
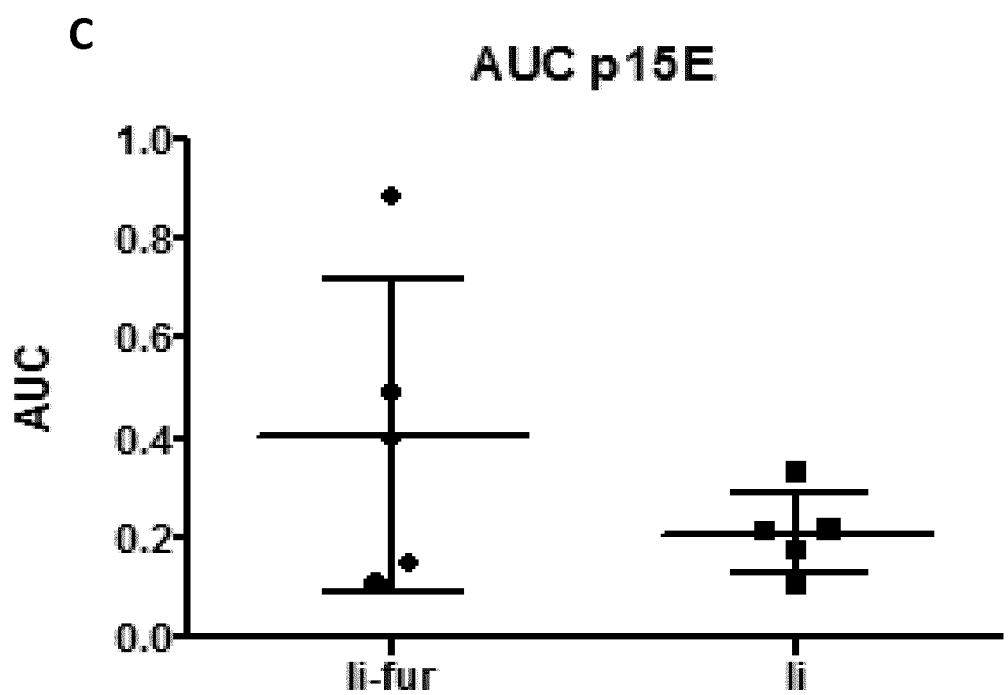
Figure 13:
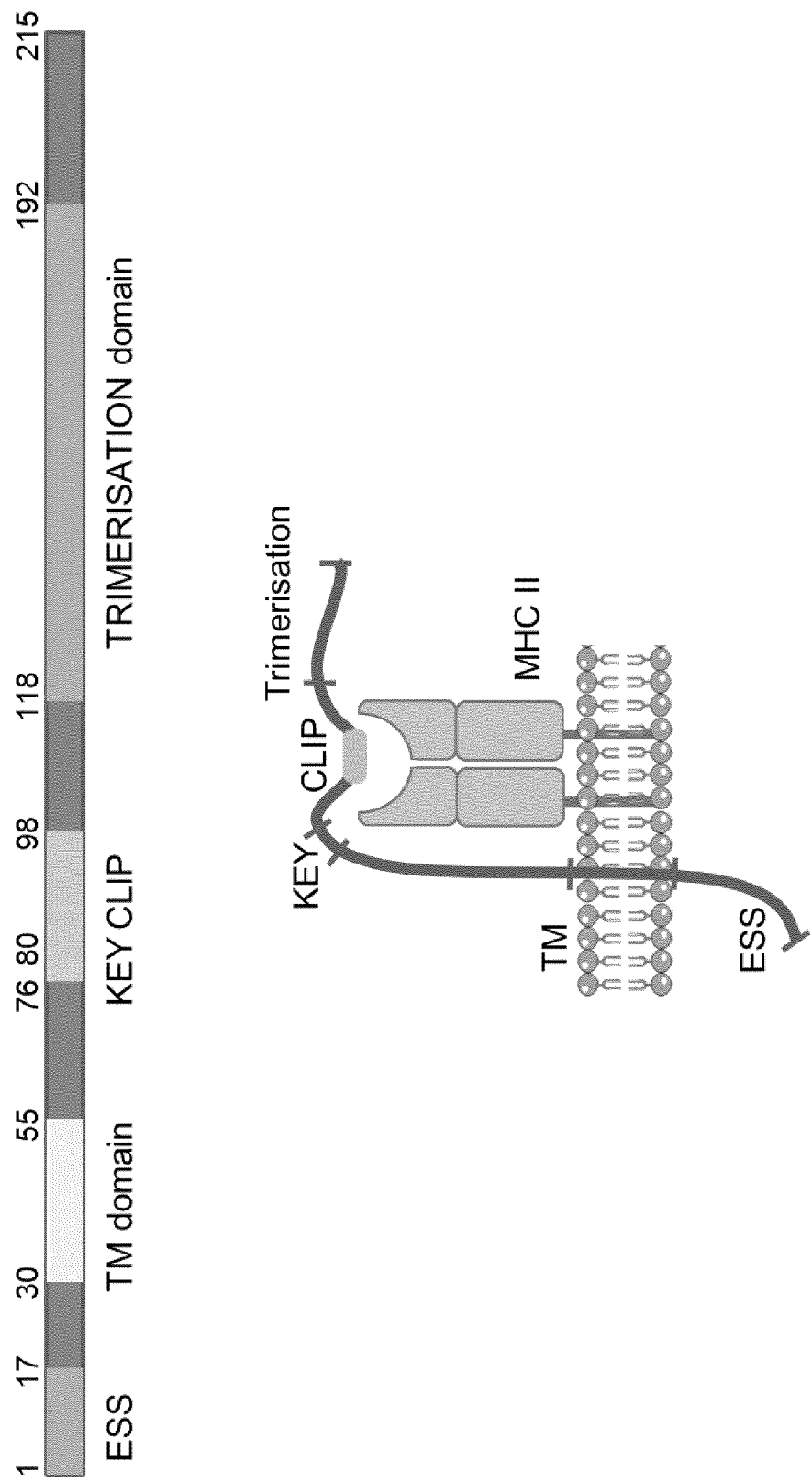

Mice vaccinated with the Ii-fur construct showed a significant decrease of tumor metastasis compared to the Ad5-Ii group (FIG. 12). Unfortunately 12 weeks after the Ad5 immunization it was not possible to detect a difference of antibody levels between the 2 groups as the detection was quite low.

Figure 17:
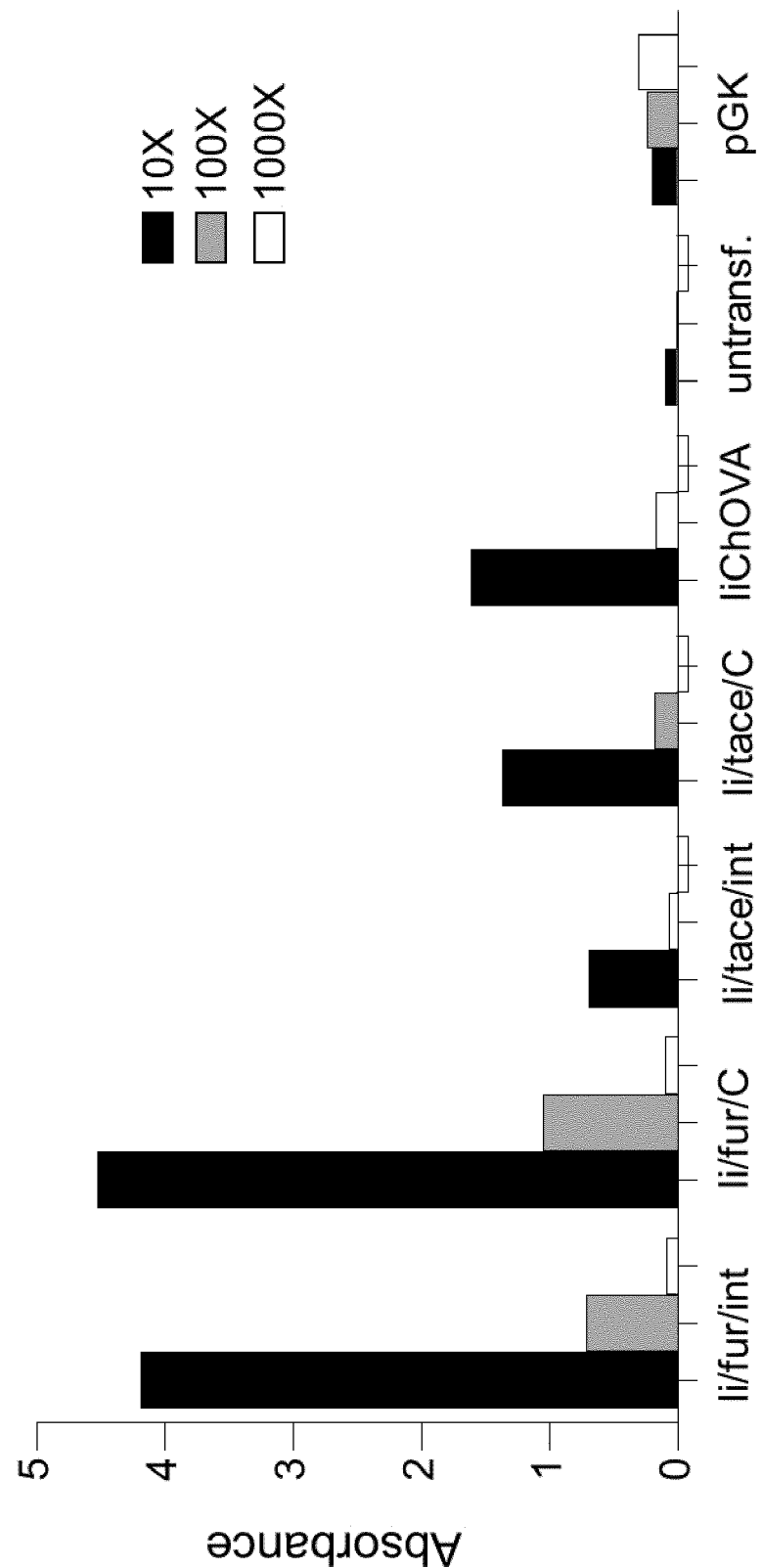

Example 12: ELISA on Cell Supernatants from Invariant Chain OVA Linked Constructs COS7 cells were seeded in 6-well plates with half a million cells per plate and transfected the next day with 2 ug of each plasmid using lipofectamine. Two days post transfection the supernatant was harvested and tested for OVA content by ELISA. The plasmids used were as follows: (1) antigen with internal furin recognition site (Ii/fur/int); (2) antigen with C-terminal furin recognition site (Ii/fur/C); (3) antigen with internal TACE fusion protease recognition site (Ii/tace/int); (4) antigen with C-terminal TACE recognition site (Ii/tace/C); native IiChOVA served as non-cleaved control (IiChOVA) and pGK and untransfected cells (untransgec.) served as negative controls. The absorbance of different dilutions (factor 10, factor 100 and factor 1000) is shown. It can be seen that the furin recognition sites lead to secretion of the OVA antigen, whereas the TACE recognition site does not efficiently lead to secretion of the OVA antigen (FIG. 17).

REFERENCES

Becker et al. (1994) Use of recombinant adenovirus for metabolic engineering of mammalian cells. *Methods Cell Biol* 43 Pt A, 161-189

Cham et al. (2008). A semi-automated multiplex high-throughput assay for measuring IgG antibodies against *Plasmodium falciparum* erythrocyte membrane protein 1 (PfEMP1) domains in small volumes of plasma. Malar J 7, 108

Colloca et al. (2012) Vaccine vectors derived from a large collection of simian adenoviruses induce potent cellular immunity across multiple species Sci. *Transl. Med.* 4:1-9

Diebold et al (2001). MHC class II presentation of endogenously expressed antigens by transfected dendritic cells. *Gene Ther.* 8:487-493.

Hugo et al. (1993) Fibroblasts can induce thymocyte positive selection in vivo. *Proc Natl Acad Sci USA* 90, (21), 10335-10339

Mittendorf et al., (2009) CD4[+] T Cells in Antitumor Immunity: Utility of an Li-Key HER2/neu Hybrid Peptide Vaccine (AE37) *Expert Opin. Biol. Ther.,* 9:71-78

Morris et al (2004). Association of intracellular proteins with folded major histocompatibility complex class I molecules. *Immunol. Res.* 30:171-179.

Pieters (1997). MHC class II restricted antigen presentation. *Curr. Opin. Immunol.* 9:89-96.

Roy et al. (2004) Complete nucleotide sequences and genome organization of four chimpanzee adenoviruses *Virol.* 324: 361-372

Roy et al. (2010) Creation of a panel of vectors based on ape adenovirus isolates *J. of Gene Med.* 13:17-25

Sambrook et al., eds., Molecular Cloning: A Laboratory Manual, Cold Spring Harbor Laboratory, 2nd Edition, Cold Spring Harbor, N.Y., 1989.

Strubin et al. (1986) Alternative splicing and alternative initiation of translation explain the four forms of the Ia antigen-associated invariant chain *EMBO Journal,* 5: 3483-3488

Strumptner-Cuvelette, P., and P. Benaroch. (2002). Multiple roles of the invariant chain in MHC class II function. *Biochem. Biophys. Acta.,* 1542:1-13.

The invention claimed is:

1. A nucleic acid construct comprising sequences encoding:
   a. at least one invariant chain or variant thereof operatively linked to
   b. at least one antigenic protein or peptide or an antigenic fragment thereof;
   wherein
      the C-terminal end of said invariant chain or variant thereof is operatively linked to the N-terminal end of said antigenic protein or peptide or antigenic fragment thereof;
      said invariant chain or variant thereof comprises a protease cleavage site for a protease selected from the group consisting of furin and subtilisin-like proteases, and optionally a trimerization (TRIM) domain located C-terminally of said protease cleavage site, wherein the protease cleavage site is located between the MHC-II interaction peptide (CLIP) region and the C-terminus of the invariant chain.

2. The nucleic acid construct according to claim 1, wherein the encoded at least one invariant chain shares at least 90% identity to any one of SEQ ID NOs: 1, 3, 4, 6, 7, 9, 11 or 13-50.

3. The nucleic acid construct according to claim 2, wherein the encoded at least one invariant chain is identical to any one of SEQ ID NOs: 1, 3, 4, 6, 7, 9, 11 or 13-50.

4. The nucleic acid construct according to claim 1, wherein the encoded variant of invariant chain is a fragment of SEQ ID NO: 3 of at least 40 amino acids and has at least 85% identity to the same fragment of SEQ ID NO: 3.

5. The nucleic acid construct according to claim 1, wherein the encoded at least one invariant chain comprises a region encoding a transmembrane domain.

6. The nucleic acid construct according to claim 1, wherein the at least one antigenic protein or peptide or an antigenic fragment thereof is derived from a pathogen selected from the group consisting of viruses, bacteria, protozoa and multicellular parasites.

7. The nucleic acid construct according to claim 1, wherein at least one antigenic protein or peptide or an antigenic fragment thereof is from a cancer-specific polypeptide.

8. The nucleic acid construct according to claim 1, wherein the invariant chain and the antigenic protein or peptide or antigenic fragment thereof are linked by a direct link or a link mediated by a spacer region.

9. The nucleic acid according to claim 1, wherein the nucleic acid is comprised within a delivery vehicle, wherein the delivery vehicle is selected from the group of: RNA based vehicles, DNA based vehicles/vectors, lipid based vehicles, polymer-based vehicles and virally derived DNA or RNA vehicles.

10. The nucleic acid according to claim 9, wherein the delivery vehicle is an adenovirus.

11. The nucleic acid according to claim 1 wherein the protease cleavage site is a furin cleavage site.

12. The nucleic acid according to claim 11 wherein the furin cleavage site comprises or consists of the sequence RXR/KR (SEQ ID NO: 70) wherein X is any of the 20 naturally occurring amino acids.

13. The nucleic acid according to claim 12 wherein the furin cleavage site comprises SEQ ID NO: 57.

14. A method for inducing an immune response in an animal, comprising administering to the animal composition comprising the nucleic acid according to claim 1 which is operably linked to a promoter for expression of said nucleic acid.

15. The nucleic acid according to claim 13 wherein the furin cleavage site consists of SEQ ID NO: 57.

* * * * *

SEQUENCE LISTING

```
<160> NUMBER OF SEQ ID NOS: 70

<210> SEQ ID NO 1
<211> LENGTH: 232
<212> TYPE: PRT
<213> ORGANISM: Homo sapiens

<400> SEQUENCE: 1

Met His Arg Arg Arg Ser Arg Ser Cys Arg Glu Asp Gln Lys Pro Val
1               5                   10                  15

Met Asp Asp Gln Arg Asp Leu Ile Ser Asn Asn Glu Gln Leu Pro Met
            20                  25                  30

Leu Gly Arg Arg Pro Gly Ala Pro Glu Ser Lys Cys Ser Arg Gly Ala
        35                  40                  45

Leu Tyr Thr Gly Phe Ser Ile Leu Val Thr Leu Leu Leu Ala Gly Gln
    50                  55                  60

Ala Thr Thr Ala Tyr Phe Leu Tyr Gln Gln Gln Gly Arg Leu Asp Lys
65                  70                  75                  80

Leu Thr Val Thr Ser Gln Asn Leu Gln Leu Glu Asn Leu Arg Met Lys
                85                  90                  95

Leu Pro Lys Pro Pro Lys Pro Val Ser Lys Met Arg Met Ala Thr Pro
            100                 105                 110

Leu Leu Met Gln Ala Leu Pro Met Gly Ala Leu Pro Gln Gly Pro Met
        115                 120                 125

Gln Asn Ala Thr Lys Tyr Gly Asn Met Thr Glu Asp His Val Met His
    130                 135                 140

Leu Leu Gln Asn Ala Asp Pro Leu Lys Val Tyr Pro Pro Leu Lys Gly
145                 150                 155                 160

Ser Phe Pro Glu Asn Leu Arg His Leu Lys Asn Thr Met Glu Thr Ile
                165                 170                 175

Asp Trp Lys Val Phe Glu Ser Trp Met His His Trp Leu Leu Phe Glu
            180                 185                 190

Met Ser Arg His Ser Leu Glu Gln Lys Pro Thr Asp Ala Pro Pro Lys
        195                 200                 205
```

Glu Ser Leu Glu Leu Glu Asp Pro Ser Ser Gly Leu Gly Val Thr Lys
            210                 215                 220

Gln Asp Leu Gly Pro Val Pro Met
225                 230

<210> SEQ ID NO 2
<211> LENGTH: 699
<212> TYPE: DNA
<213> ORGANISM: Homo sapiens

<400> SEQUENCE: 2

```
atgcacagga ggagaagcag gagctgtcgg gaagatcaga agccagtcat ggatgaccag    60
cgcgacctta tctccaacaa tgagcaactg cccatgctgg gccggcgccc tggggccccg   120
gagagcaagt gcagccgcgg agccctgtac acaggctttt ccatcctggt gactctgctc   180
ctcgctggcc aggccaccac cgcctacttc ctgtaccagc agcagggccg gctggacaaa   240
ctgacagtca cctcccagaa cctgcagctg gagaacctgc gcatgaagct tcccaagcct   300
cccaagcctg tgagcaagat gcgcatggcc accccgctgc tgatgcaggc gctgcccatg   360
ggagccctgc ccaggggcc catgcagaat gccaccaagt atggcaacat gacagaggac   420
catgtgatgc acctgctcca gaatgctgac cccctgaagg tgtacccgcc actgaagggg   480
agcttcccgg agaacctgag acaccttaag aacaccatgg agaccataga ctggaaggtc   540
tttgagagct ggatgcacca ttggctcctg tttgaaatga gcaggcactc cttggagcaa   600
aagcccactg acgctccacc gaaagagtca ctggaactgg aggacccgtc ttctgggctg   660
ggtgtgacca agcaggatct gggcccagtc cccatgtga                          699
```

<210> SEQ ID NO 3
<211> LENGTH: 216
<212> TYPE: PRT
<213> ORGANISM: Homo sapiens

<400> SEQUENCE: 3

Met Asp Asp Gln Arg Asp Leu Ile Ser Asn Asn Glu Gln Leu Pro Met
1               5                   10                  15

Leu Gly Arg Arg Pro Gly Ala Pro Glu Ser Lys Cys Ser Arg Gly Ala
            20                  25                  30

Leu Tyr Thr Gly Phe Ser Ile Leu Val Thr Leu Leu Ala Gly Gln
        35                  40                  45

Ala Thr Thr Ala Tyr Phe Leu Tyr Gln Gln Gln Gly Arg Leu Asp Lys
    50                  55                  60

Leu Thr Val Thr Ser Gln Asn Leu Gln Leu Glu Asn Leu Arg Met Lys
65                  70                  75                  80

Leu Pro Lys Pro Pro Lys Pro Val Ser Lys Met Arg Met Ala Thr Pro
                85                  90                  95

Leu Leu Met Gln Ala Leu Pro Met Gly Ala Leu Pro Gln Gly Pro Met
            100                 105                 110

Gln Asn Ala Thr Lys Tyr Gly Asn Met Thr Glu Asp His Val Met His
        115                 120                 125

Leu Leu Gln Asn Ala Asp Pro Leu Lys Val Tyr Pro Pro Leu Lys Gly
    130                 135                 140

Ser Phe Pro Glu Asn Leu Arg His Leu Lys Asn Thr Met Glu Thr Ile
145                 150                 155                 160

Asp Trp Lys Val Phe Glu Ser Trp Met His His Trp Leu Leu Phe Glu
                165                 170                 175

Met Ser Arg His Ser Leu Glu Gln Lys Pro Thr Asp Ala Pro Pro Lys
            180                 185                 190

Glu Ser Leu Glu Leu Glu Asp Pro Ser Ser Gly Leu Gly Val Thr Lys
            195                 200                 205

Gln Asp Leu Gly Pro Val Pro Met
            210                 215

<210> SEQ ID NO 4
<211> LENGTH: 296
<212> TYPE: PRT
<213> ORGANISM: Homo sapiens

<400> SEQUENCE: 4

Met His Arg Arg Arg Ser Arg Ser Cys Arg Glu Asp Gln Lys Pro Val
1               5                   10                  15

Met Asp Asp Gln Arg Asp Leu Ile Ser Asn Asn Glu Gln Leu Pro Met
            20                  25                  30

Leu Gly Arg Arg Pro Gly Ala Pro Glu Ser Lys Cys Ser Arg Gly Ala
        35                  40                  45

Leu Tyr Thr Gly Phe Ser Ile Leu Val Thr Leu Leu Leu Ala Gly Gln
    50                  55                  60

Ala Thr Thr Ala Tyr Phe Leu Tyr Gln Gln Gln Gly Arg Leu Asp Lys
65                  70                  75                  80

Leu Thr Val Thr Ser Gln Asn Leu Gln Leu Glu Asn Leu Arg Met Lys
                85                  90                  95

Leu Pro Lys Pro Pro Lys Pro Val Ser Lys Met Arg Met Ala Thr Pro
            100                 105                 110

Leu Leu Met Gln Ala Leu Pro Met Gly Ala Leu Pro Gln Gly Pro Met
        115                 120                 125

Gln Asn Ala Thr Lys Tyr Gly Asn Met Thr Glu Asp His Val Met His
    130                 135                 140

Leu Leu Gln Asn Ala Asp Pro Leu Lys Val Tyr Pro Pro Leu Lys Gly
145                 150                 155                 160

Ser Phe Pro Glu Asn Leu Arg His Leu Lys Asn Thr Met Glu Thr Ile
                165                 170                 175

Asp Trp Lys Val Phe Glu Ser Trp Met His His Trp Leu Leu Phe Glu
            180                 185                 190

Met Ser Arg His Ser Leu Glu Gln Lys Pro Thr Asp Ala Pro Pro Lys
        195                 200                 205

Val Leu Thr Lys Cys Gln Glu Glu Val Ser His Ile Pro Ala Val His
    210                 215                 220

Pro Gly Ser Phe Arg Pro Lys Cys Asp Glu Asn Gly Asn Tyr Leu Pro
225                 230                 235                 240

Leu Gln Cys Tyr Gly Ser Ile Gly Tyr Cys Trp Cys Val Phe Pro Asn
                245                 250                 255

Gly Thr Glu Val Pro Asn Thr Arg Ser Arg Gly His His Asn Cys Ser
            260                 265                 270

Glu Ser Leu Glu Leu Glu Asp Pro Ser Ser Gly Leu Gly Val Thr Lys
        275                 280                 285

Gln Asp Leu Gly Pro Val Pro Met
    290                 295

<210> SEQ ID NO 5
<211> LENGTH: 891
<212> TYPE: DNA
<213> ORGANISM: Homo sapiens

<400> SEQUENCE: 5

```
atgcacagga ggagaagcag gagctgtcgg gaagatcaga agccagtcat ggatgaccag      60
cgcgaccttA tctccaacaa tgagcaactg cccatgctgg gccggcgccc tgggccccg     120
gagagcaagt gcagccgcgg agccctgtac acaggctttt ccatcctggt gactctgctc    180
ctcgctggcc aggccaccac cgcctacttc ctgtaccagc agcagggccg gctggacaaa    240
ctgacagtca cctcccagaa cctgcagctg agaaacctgc gcatgaagct tcccaagcct    300
cccaagcctg tgagcaagat gcgcatggcc accccgctgc tgatgcaggc gctgcccatg    360
ggagccctgc cccaggggcc catgcagaat gccaccaagt atggcaacat gacagaggac    420
catgtgatgc acctgctcca gaatgctgac ccctgaagg tgtacccgcc actgaagggg    480
agcttcccgg agaacctgag acaccttaag aacaccatgg agaccataga ctggaaggtc    540
tttgagagct ggatgcacca ttggctcctg tttgaaatga gcaggcactc cttggagcaa    600
aagcccactg acgctccacc gaaagtactg accaagtgcc aggaagaggt cagccacatc    660
cctgctgtcc acccgggttc attcaggccc aagtgcgacg agaacggcaa ctatctgcca    720
ctccagtgct atgggagcat cggctactgc tggtgtgtct cccccaacgg cacgagggtc    780
cccaacacca gaagccgcgg gcaccataac tgcagtgagt cactggaact ggaggacccg    840
tcttctgggc tgggtgtgac caagcaggat ctgggcccag tccccatgtg a             891
```

<210> SEQ ID NO 6
<211> LENGTH: 280
<212> TYPE: PRT
<213> ORGANISM: Homo sapiens

<400> SEQUENCE: 6

```
Met Asp Asp Gln Arg Asp Leu Ile Ser Asn Asn Glu Gln Leu Pro Met
1               5                   10                  15

Leu Gly Arg Arg Pro Gly Ala Pro Glu Ser Lys Cys Ser Arg Gly Ala
            20                  25                  30

Leu Tyr Thr Gly Phe Ser Ile Leu Val Thr Leu Leu Ala Gly Gln
        35                  40                  45

Ala Thr Thr Ala Tyr Phe Leu Tyr Gln Gln Gln Gly Arg Leu Asp Lys
    50                  55                  60

Leu Thr Val Thr Ser Gln Asn Leu Gln Leu Glu Asn Leu Arg Met Lys
65                  70                  75                  80

Leu Pro Lys Pro Pro Lys Pro Val Ser Lys Met Arg Met Ala Thr Pro
                85                  90                  95

Leu Leu Met Gln Ala Leu Pro Met Gly Ala Leu Pro Gln Gly Pro Met
            100                 105                 110

Gln Asn Ala Thr Lys Tyr Gly Asn Met Thr Glu Asp His Val Met His
        115                 120                 125

Leu Leu Gln Asn Ala Asp Pro Leu Lys Val Tyr Pro Pro Leu Lys Gly
    130                 135                 140

Ser Phe Pro Glu Asn Leu Arg His Leu Lys Asn Thr Met Glu Thr Ile
145                 150                 155                 160

Asp Trp Lys Val Phe Glu Ser Trp Met His His Trp Leu Leu Phe Glu
                165                 170                 175

Met Ser Arg His Ser Leu Glu Gln Lys Pro Thr Asp Ala Pro Pro Lys
            180                 185                 190

Val Leu Thr Lys Cys Gln Glu Glu Val Ser His Ile Pro Ala Val His
        195                 200                 205
```

```
Pro Gly Ser Phe Arg Pro Lys Cys Asp Glu Asn Gly Asn Tyr Leu Pro
    210                 215                 220
Leu Gln Cys Tyr Gly Ser Ile Gly Tyr Cys Trp Cys Val Phe Pro Asn
225                 230                 235                 240
Gly Thr Glu Val Pro Asn Thr Arg Ser Arg Gly His His Asn Cys Ser
                245                 250                 255
Glu Ser Leu Glu Leu Glu Asp Pro Ser Ser Gly Leu Gly Val Thr Lys
            260                 265                 270
Gln Asp Leu Gly Pro Val Pro Met
            275                 280
```

<210> SEQ ID NO 7
<211> LENGTH: 160
<212> TYPE: PRT
<213> ORGANISM: Homo sapiens

<400> SEQUENCE: 7

```
Met His Arg Arg Ser Arg Ser Cys Arg Glu Asp Gln Lys Pro Val
1               5                   10                  15
Met Asp Asp Gln Arg Asp Leu Ile Ser Asn Asn Glu Gln Leu Pro Met
                20                  25                  30
Leu Gly Arg Arg Pro Gly Ala Pro Glu Ser Lys Cys Ser Arg Gly Ala
            35                  40                  45
Leu Tyr Thr Gly Phe Ser Ile Leu Val Thr Leu Leu Leu Ala Gly Gln
        50                  55                  60
Ala Thr Thr Ala Tyr Phe Leu Tyr Gln Gln Gln Gly Arg Leu Asp Lys
65                  70                  75                  80
Leu Thr Val Thr Ser Gln Asn Leu Gln Leu Glu Asn Leu Arg Met Lys
                85                  90                  95
Leu Pro Lys Pro Pro Lys Pro Val Ser Lys Met Arg Met Ala Thr Pro
            100                 105                 110
Leu Leu Met Gln Ala Leu Pro Met Gly Ala Leu Pro Gln Gly Pro Met
        115                 120                 125
Gln Asn Ala Thr Lys Tyr Gly Asn Met Thr Glu Asp His Val Met His
130                 135                 140
Leu Leu Gln Ser His Trp Asn Trp Arg Thr Arg Leu Leu Gly Trp Val
145                 150                 155                 160
```

<210> SEQ ID NO 8
<211> LENGTH: 483
<212> TYPE: DNA
<213> ORGANISM: Homo sapiens

<400> SEQUENCE: 8

```
atgcacagga ggagaagcag gagctgtcgg gaagatcaga agccagtcat ggatgaccag      60
cgcgacctta tctccaacaa tgagcaactg cccatgctgg gccggcgccc tggggccccg     120
gagagcaagt gcagccgcgg agccctgtac acaggctttt ccatcctggt gactctgctc     180
ctcgctggcc aggccaccac cgcctacttc ctgtaccagc agcagggccg gctggacaaa     240
ctgacagtca cctcccagaa cctgcagctg agaaacctgc gcatgaagct tcccaagcct     300
cccaagcctg tgagcaagat gcgcatggcc accccgctgc tgatgcaggc gctgcccatg     360
ggagccctgc cccaggggcc catgcagaat gccaccaagt atggcaacat gacagaggac     420
catgtgatgc acctgctcca gagtcactgg aactggagga ccgtcttct gggctgggtg     480
tga                                                                  483
```

<210> SEQ ID NO 9
<211> LENGTH: 215
<212> TYPE: PRT
<213> ORGANISM: Murine

<400> SEQUENCE: 9

Met Asp Asp Gln Arg Asp Leu Ile Ser Asn His Glu Gln Leu Pro Ile
1               5                   10                  15

Leu Gly Asn Arg Pro Arg Glu Pro Glu Arg Cys Ser Arg Gly Ala Leu
            20                  25                  30

Tyr Thr Gly Val Ser Val Leu Val Ala Leu Leu Leu Ala Gly Gln Ala
        35                  40                  45

Thr Thr Ala Tyr Phe Leu Tyr Gln Gln Gln Gly Arg Leu Asp Lys Leu
    50                  55                  60

Thr Ile Thr Ser Gln Asn Leu Gln Leu Glu Ser Leu Arg Met Lys Leu
65                  70                  75                  80

Pro Lys Ser Ala Lys Pro Val Ser Gln Met Arg Met Ala Thr Pro Leu
                85                  90                  95

Leu Met Arg Pro Met Ser Met Asp Asn Met Leu Leu Gly Pro Val Lys
            100                 105                 110

Asn Val Thr Lys Tyr Gly Asn Met Thr Gln Asp His Val Met His Leu
        115                 120                 125

Leu Thr Arg Ser Gly Pro Leu Glu Tyr Pro Gln Leu Lys Gly Thr Phe
    130                 135                 140

Pro Glu Asn Leu Lys His Leu Lys Asn Ser Met Asp Gly Val Asn Trp
145                 150                 155                 160

Lys Ile Phe Glu Ser Trp Met Lys Gln Trp Leu Leu Phe Glu Met Ser
                165                 170                 175

Lys Asn Ser Leu Glu Glu Lys Lys Pro Thr Glu Ala Pro Lys Glu
            180                 185                 190

Pro Leu Asp Met Glu Asp Leu Ser Ser Gly Leu Gly Val Thr Arg Gln
        195                 200                 205

Glu Leu Gly Gln Val Thr Leu
    210                 215

<210> SEQ ID NO 10
<211> LENGTH: 648
<212> TYPE: DNA
<213> ORGANISM: Murine

<400> SEQUENCE: 10
atggatgacc aacgcgacct catctctaac catgaacagt tgcccatact gggcaaccgc      60
cctagagagc agaaaggtg cagccgtgga gctctgtaca ccggtgtctc tgtcctggtg     120
gctctgctct tggctgggca ggccaccact gcttacttcc tgtaccagca cagggccgc     180 ctagacaagc tgaccatcac ctcccagaac ctgcaactgg agagccttcg catgaagctt     240
ccgaaatctg ccaaacctgt gagccagatg cggatggcta ctcccttgct gatgcgtcca     300
atgtccatgg ataacatgct ccttgggcct gtgaagaacg ttaccaagta cggcaacatg     360
acccaggacc atgtgatgca tctgctcacg aggtctggac ccctggagta cccgcagctg     420
aaggggacct tcccagagaa tctgaagcat cttaagaact ccatggatgg cgtgaactgg     480
aagatcttcg agagctggat gaagcagtgg ctccttgtttg agatgagcaa gaactccctg     540
gaggagaaga agcccaccga ggctccaacct aaagagccac tggacatgga agacctatct     600
tctggcctgg gagtgaccag gcaggaactg ggtcaagtca ccctgtga            648

<210> SEQ ID NO 11
<211> LENGTH: 279
<212> TYPE: PRT
<213> ORGANISM: Murine

<400> SEQUENCE: 11

```
Met Asp Asp Gln Arg Asp Leu Ile Ser Asn His Glu Gln Leu Pro Ile
1               5                   10                  15

Leu Gly Asn Arg Pro Arg Glu Pro Glu Arg Cys Ser Arg Gly Ala Leu
            20                  25                  30

Tyr Thr Gly Val Ser Val Leu Val Ala Leu Leu Leu Ala Gly Gln Ala
        35                  40                  45

Thr Thr Ala Tyr Phe Leu Tyr Gln Gln Gln Gly Arg Leu Asp Lys Leu
    50                  55                  60

Thr Ile Thr Ser Gln Asn Leu Gln Leu Glu Ser Leu Arg Met Lys Leu
65                  70                  75                  80

Pro Lys Ser Ala Lys Pro Val Ser Gln Met Arg Met Ala Thr Pro Leu
                85                  90                  95

Leu Met Arg Pro Met Ser Met Asp Asn Met Leu Leu Gly Pro Val Lys
            100                 105                 110

Asn Val Thr Lys Tyr Gly Asn Met Thr Gln Asp His Val Met His Leu
        115                 120                 125

Leu Thr Arg Ser Gly Pro Leu Glu Tyr Pro Gln Leu Lys Gly Thr Phe
    130                 135                 140

Pro Glu Asn Leu Lys His Leu Lys Asn Ser Met Asp Gly Val Asn Trp
145                 150                 155                 160

Lys Ile Phe Glu Ser Trp Met Lys Gln Trp Leu Leu Phe Glu Met Ser
                165                 170                 175

Lys Asn Ser Leu Glu Glu Lys Lys Pro Thr Glu Ala Pro Pro Lys Val
            180                 185                 190

Leu Thr Lys Cys Gln Glu Glu Val Ser His Ile Pro Ala Val Tyr Pro
        195                 200                 205

Gly Ala Phe Arg Pro Lys Cys Asp Glu Asn Gly Asn Tyr Leu Pro Leu
    210                 215                 220

Gln Cys His Gly Ser Thr Gly Tyr Cys Trp Cys Val Phe Pro Asn Gly
225                 230                 235                 240

Thr Glu Val Pro His Thr Lys Ser Arg Gly Arg His Asn Cys Ser Glu
                245                 250                 255

Pro Leu Asp Met Glu Asp Leu Ser Ser Gly Leu Gly Val Thr Arg Gln
            260                 265                 270

Glu Leu Gly Gln Val Thr Leu
        275
```

<210> SEQ ID NO 12
<211> LENGTH: 840
<212> TYPE: DNA
<213> ORGANISM: Murine

<400> SEQUENCE: 12
atggatgacc aacgcgacct catctctaac catgaacagt tgcccatact gggcaaccgc    60
cctagagagc cagaaaggtg cagccgtgga gctctgtaca ccggtgtctc tgtcctggtg   120
gctctgctct tggctgggca ggccaccact gcttacttcc tgtaccagca acagggccgc   180
ctagacaagc tgaccatcac ctcccagaac ctgcaactgg agagccttcg catgaagctt   240

```
ccgaaatctg ccaaacctgt gagccagatg cggatggcta ctcccttgct gatgcgtcca    300
atgtccatgg ataacatgct ccttgggcct gtgaagaacg ttaccaagta cggcaacatg    360
acccaggacc atgtgatgca tctgctcacg aggtctggac ccctggagta cccgcagctg    420
aaggggacct tcccagagaa tctgaagcat cttaagaact ccatggatgg cgtgaactgg    480
aagatcttcg agagctggat gaagcagtgg ctcttgtttg agatgagcaa gaactccctg    540
gaggagaaga agcccaccga ggctccacct aaagtactga ccaagtgcca ggaagaagtc    600
agccacatcc ctgccgtcta cccgggtgcg ttccgtccca gtgcgacga gaacggtaac     660 tatttgccac tccagtgcca cgggagcact ggctactgct ggtgtgtgtt ccccaacggc    720
actgaggttc ctcacaccaa gagccgcggg cgccataact gcagtgagcc actggacatg    780
gaagacctat cttctggcct gggagtgacc aggcaggaac tgggtcaagt caccctgtga    840
```

\<210\> SEQ ID NO 13
\<211\> LENGTH: 280
\<212\> TYPE: PRT
\<213\> ORGANISM: Cavia porcellus

\<400\> SEQUENCE: 13

```
Met Glu Asp Gln His Asp Leu Ile Ser Asn His Glu Gln Leu Pro Met
1               5                   10                  15

Leu Gly Gln Arg Pro Gly Ala Gln Asp Gly Lys Cys Ser Arg Gly Ala
            20                  25                  30

Leu Tyr Thr Gly Phe Ser Val Leu Val Ala Leu Leu Leu Ala Gly Gln
        35                  40                  45

Ala Thr Thr Ala Tyr Phe Leu Tyr Gln Gln Gln Gly Arg Leu Asp Lys
    50                  55                  60

Leu Thr Val Thr Ser Gln Asn Leu Gln Leu Glu Asn Leu Arg Met Lys
65                  70                  75                  80

Met Pro Lys Pro Pro Lys Pro Val Ser Gln Met Arg Met Ala Thr Pro
                85                  90                  95

Leu Leu Met Arg Ala Leu Pro Met Glu Val Met His Lys Gly Pro Val
            100                 105                 110

Gln Asn Ala Thr Lys Tyr Gly Asn Thr Thr Gln Asp Tyr Val Met His
        115                 120                 125

Thr Leu Leu Lys Ser Asp Pro Leu Lys Val Tyr Pro Gln Leu Gln Gly
    130                 135                 140

Ser Phe Leu Glu Asn Leu Lys His Leu Lys Asn Thr Met Glu Ser Leu
145                 150                 155                 160

Asp Trp Lys Val Phe Glu Ser Trp Met His His Trp Leu Leu Phe Glu
                165                 170                 175

Met Ser Arg Asn Ser Pro Glu Glu Lys Pro Thr Glu Ala Pro Pro Lys
            180                 185                 190

Val Leu Ser Lys Cys Gln Glu Glu Val Ser His Ile Pro Ala Val His
        195                 200                 205

Pro Gly Thr Phe Arg Pro Gln Cys Asp Glu Asn Gly Asn Tyr Met Pro
    210                 215                 220

Leu Gln Cys His Gly Ser Thr Gly Tyr Cys Trp Cys Val Phe Pro Asn
225                 230                 235                 240

Gly Thr Glu Val Pro His Thr Arg Ser His Gly His His Asn Cys Ser
                245                 250                 255

Glu Pro Leu Glu Ala Glu Asp Leu Ser Ser Gly Leu Gly Val Thr Lys
            260                 265                 270
```

```
Gln Glu Leu Gly Gln Ala Ser Leu
        275                 280

<210> SEQ ID NO 14
<211> LENGTH: 329
<212> TYPE: PRT
<213> ORGANISM: Heterocephalus glaber

<400> SEQUENCE: 14

Met Glu Asp Gln Arg Asp Leu Ile Ser Asn His Glu Gln Leu Pro Met
1               5                   10                  15

Leu Gly Gln Arg Leu Gly Ala Gln Asp Arg Lys Cys Ser Arg Gly Ala
            20                  25                  30

Leu Tyr Thr Gly Phe Ser Val Leu Val Ala Leu Leu Leu Ala Gly Gln
        35                  40                  45

Ala Thr Thr Ala Tyr Phe Leu Tyr Gln Gln Gln Gly Arg Leu Asp Lys
    50                  55                  60

Leu Thr Val Thr Ser Gln Asn Leu Gln Leu Glu Asn Leu Arg Met Lys
65                  70                  75                  80

Met Pro Gln Ser Pro Lys Pro Val Ser Gln Met Arg Val Ala Thr Pro
                85                  90                  95

Leu Leu Met Arg Ala Leu Pro Met Glu Gly Leu Leu Gln Gly Pro Met
            100                 105                 110

Gln Gln Asn Ala Thr Lys Tyr Gly Asn Met Thr Gln Asp His Val Met
        115                 120                 125

His Met Leu Leu Lys Ser Asp Pro Leu Lys Val Tyr Pro Gln Leu Glu
    130                 135                 140

Gly Ser Phe Leu Asp Asn Leu Lys His Leu Lys Asn Thr Met Glu Ser
145                 150                 155                 160

Leu Asp Trp Lys Val Phe Glu Ser Trp Met His His Trp Leu Leu Phe
                165                 170                 175

Glu Met Ser Arg Asn Ser Pro Gly Glu Lys Pro Thr Glu Ala Pro Pro
            180                 185                 190

Lys Val Leu Ser Lys Cys Gln Glu Val Ser His Ile Pro Ala Val
        195                 200                 205

His Pro Gly Thr Phe Arg Pro Gln Cys Asp Glu Asn Gly Asn Tyr Met
    210                 215                 220

Pro Leu Gln Cys His Gly Ser Thr Gly Tyr Cys Trp Cys Val Phe Pro
225                 230                 235                 240

Asn Gly Thr Glu Val Pro Gln Thr Arg Ser Arg Gly His His Asn Cys
                245                 250                 255

Ser Glu Pro Leu Glu Ala Glu Asp Leu Ser Ser Gly Leu Gly Met Thr
            260                 265                 270

Lys Gln Glu Leu Gly Pro Ala His Leu Ala Ala Arg Ala Lys Asp Ser
        275                 280                 285

Ser Val Arg Lys Arg Thr Cys Thr Arg Cys Leu Gly Leu Ser His Arg
    290                 295                 300

Leu Leu Cys Arg Leu Leu Leu Gly Glu Lys Gly Asp Arg Leu Trp
305                 310                 315                 320

Ser Leu Leu Phe Leu Ser Ile Ala Ala
                325

<210> SEQ ID NO 15
<211> LENGTH: 298
<212> TYPE: PRT
```

<213> ORGANISM: Fukomys damarensis

<400> SEQUENCE: 15

| Met | Glu | Asp | Gln | Arg | Asp | Leu | Ile | Ser | Asn | His | Glu | Gln | Leu | Pro | Met |
|---|---|---|---|---|---|---|---|---|---|---|---|---|---|---|---|
| 1 | | | | 5 | | | | | 10 | | | | | 15 | |

Leu Gly Gln Arg Pro Ala Ala Gln Asp Arg Lys Cys Ser Arg Gly Ala
            20              25              30

Leu Tyr Thr Gly Phe Ser Ile Leu Val Ala Leu Leu Leu Ala Gly Gln
        35              40              45

Ala Thr Thr Ala Tyr Phe Leu Tyr Gln Gln Gln Gly Arg Leu Asp Lys
50              55              60

Leu Thr Val Thr Ser Gln Asn Leu Gln Leu Glu Asn Leu Arg Met Lys
65              70              75              80

Met Pro Lys Ser Ser Lys Pro Met Thr Gln Met Arg Val Ala Thr Pro
            85              90              95

Met Leu Met Arg Ala Leu Pro Met Glu Gly Leu Leu Gln Gly Pro Met
        100            105            110

Gln Asn Ala Thr Lys Tyr Gly Asn Met Thr Gln Asp His Val Met His
        115            120            125

Thr Leu Leu Gln Ser Asp Pro Leu Lys Val Tyr Pro Gln Leu Thr Gly
    130              135            140

Ser Phe Leu Glu Asn Leu Lys His Leu Lys Asn Thr Met Gln Ser Leu
145              150              155              160

Asp Trp Lys Val Phe Glu Ser Trp Met His His Trp Leu Leu Phe Glu
            165            170            175

Met Ser Arg Asn Ser Pro Glu Lys Pro Thr Glu Ala Pro Pro Lys Val
        180            185            190

Leu Ser Lys Cys Gln Glu Glu Val Ser His Ile Pro Ala Val His Pro
        195            200            205

Gly Thr Phe Arg Pro Gln Cys Asp Glu Asn Gly Asn Tyr Met Pro Leu
    210              215            220

Gln Cys His Gly Ser Thr Gly Tyr Cys Trp Cys Val Phe Pro Asn Gly
225              230              235              240

Thr Glu Val Pro His Thr Arg Ser Arg Gly His His Asn Cys Ser Asp
            245            250            255

Pro Leu Glu Ala Glu Asp Leu Ser Ser Gly Leu Gly Val Thr Lys Gln
        260            265            270

Glu Leu Gly Pro Gly Leu Cys Leu Ala Lys Leu Val Ile Ser Ser Gln
        275            280            285

Gly Arg Gly Ser Trp Lys Asn Lys Arg Gly
    290              295

<210> SEQ ID NO 16
<211> LENGTH: 216
<212> TYPE: PRT
<213> ORGANISM: Rattus norvegicus

<400> SEQUENCE: 16

Met Asp Asp Gln Arg Asp Leu Ile Ser Asn His Glu Gln Leu Pro Ile
1              5              10              15

Leu Gly Gln Arg Ala Arg Ala Pro Glu Ser Asn Cys Asn Arg Gly Val
            20              25              30

Leu Tyr Thr Ser Val Ser Val Leu Val Ala Leu Leu Leu Ala Gly Gln
        35              40              45

Ala Thr Thr Ala Tyr Phe Leu Tyr Gln Gln Gln Gly Arg Leu Asp Lys

```
            50                  55                  60

Leu Thr Val Thr Ser Gln Asn Leu Gln Leu Glu Asn Leu Arg Met Lys
 65                  70                  75                  80

Leu Pro Lys Ser Ala Lys Pro Val Ser Pro Met Arg Met Ala Thr Pro
                 85                  90                  95

Leu Leu Met Arg Pro Leu Ser Met Asp Asn Met Leu Gln Ala Pro Val
                100                 105                 110

Lys Asn Val Thr Lys Tyr Gly Asn Met Thr Gln Asp His Val Met His
                115                 120                 125

Leu Leu Thr Lys Ser Gly Pro Val Asn Tyr Pro Gln Leu Lys Gly Ser
            130                 135                 140

Phe Pro Glu Asn Leu Lys His Leu Lys Asn Ser Met Asn Gly Leu Asp
145                 150                 155                 160

Trp Lys Val Phe Glu Ser Trp Met Lys Gln Trp Leu Leu Phe Glu Met
                165                 170                 175

Ser Lys Asn Ser Leu Glu Glu Lys Gln Pro Thr Gln Thr Pro Pro Lys
            180                 185                 190

Glu Pro Leu Asp Met Glu Asp Pro Ser Ser Gly Leu Gly Val Thr Lys
            195                 200                 205

Gln Asp Met Gly Gln Met Phe Leu
        210                 215

<210> SEQ ID NO 17
<211> LENGTH: 280
<212> TYPE: PRT
<213> ORGANISM: Rattus norvegicus

<400> SEQUENCE: 17

Met Asp Asp Gln Arg Asp Leu Ile Ser Asn His Glu Gln Leu Pro Ile
  1               5                  10                  15

Leu Gly Gln Arg Ala Arg Ala Pro Glu Ser Asn Cys Asn Arg Gly Val
                 20                  25                  30

Leu Tyr Thr Ser Val Ser Val Leu Val Ala Leu Leu Leu Ala Gly Gln
             35                  40                  45

Ala Thr Thr Ala Tyr Phe Leu Tyr Gln Gln Gly Arg Leu Asp Lys
         50                  55                  60

Leu Thr Val Thr Ser Gln Asn Leu Gln Leu Glu Asn Leu Arg Met Lys
 65                  70                  75                  80

Leu Pro Lys Ser Ala Lys Pro Val Ser Pro Met Arg Met Ala Thr Pro
                 85                  90                  95

Leu Leu Met Arg Pro Leu Ser Met Asp Asn Met Leu Gln Ala Pro Val
                100                 105                 110

Lys Asn Val Thr Lys Tyr Gly Asn Met Thr Gln Asp His Val Met His
                115                 120                 125

Leu Leu Thr Lys Ser Gly Pro Val Asn Tyr Pro Gln Leu Lys Gly Ser
            130                 135                 140

Phe Pro Glu Asn Leu Lys His Leu Lys Asn Ser Met Asn Gly Leu Asp
145                 150                 155                 160

Trp Lys Val Phe Glu Ser Trp Met Lys Gln Trp Leu Leu Phe Glu Met
                165                 170                 175

Ser Lys Asn Ser Leu Glu Glu Lys Gln Pro Thr Gln Thr Pro Pro Lys
            180                 185                 190

Val Leu Thr Lys Cys Gln Glu Glu Val Ser His Ile Pro Asp Val His
            195                 200                 205
```

```
Pro Gly Ala Phe Arg Pro Lys Cys Asp Glu Asn Gly Asn Tyr Met Pro
    210                 215                 220
Leu Gln Cys His Gly Ser Thr Gly Tyr Cys Trp Cys Val Phe Pro Asn
225                 230                 235                 240
Gly Thr Glu Val Pro His Thr Lys Ser Arg Gly Arg His Asn Cys Ser
                245                 250                 255
Glu Pro Leu Asp Met Glu Asp Pro Ser Ser Gly Leu Gly Val Thr Lys
            260                 265                 270
Gln Asp Met Gly Gln Met Phe Leu
            275                 280

<210> SEQ ID NO 18
<211> LENGTH: 280
<212> TYPE: PRT
<213> ORGANISM: Myotis lucifugus

<400> SEQUENCE: 18

Met Glu Asp Gln Arg Asp Leu Ile Ser Asn His Glu Gln Leu Pro Met
1               5                   10                  15
Leu Gly Gln Arg Pro Gly Ala Gln Glu Ser Lys Cys Ser Arg Gly Ala
                20                  25                  30
Leu Tyr Thr Gly Phe Ser Val Leu Val Ala Leu Leu Leu Ala Gly Gln
            35                  40                  45
Ala Thr Thr Ala Tyr Phe Leu Tyr Gln Gln Gly Arg Leu Asp Lys
50                  55                  60
Leu Thr Val Thr Ser Gln Asn Leu Gln Leu Glu Asn Met Arg Met Lys
65                  70                  75                  80
Leu Pro Lys Ser Ala Lys Pro Val Gly Lys Met Arg Val Ala Thr Pro
                85                  90                  95
Met Leu Met Gln Ala Leu Pro Met Asp Gly Leu Leu Gln Gly Pro Met
            100                 105                 110
Gln Asn Ala Thr Lys Tyr Gly Asn Thr Thr Met Asp His Val Met His
        115                 120                 125
Leu Leu Leu Lys Ala Asp Pro Leu Lys Val Tyr Pro Gln Met Lys Gly
130                 135                 140
Ser Phe Pro Glu Asn Leu Lys His Leu Lys Lys Thr Met Glu Gly Leu
145                 150                 155                 160
Asp Trp Lys Ile Phe Glu Ser Trp Met His Gln Trp Leu Leu Phe Glu
                165                 170                 175
Met Ser Lys Asn Ser Leu Gly Glu Lys Leu Thr Glu Gly Ser Pro Lys
            180                 185                 190
Val Leu Thr Lys Cys Leu Glu Glu Ala Ser Arg Ile Pro Ala Ile His
        195                 200                 205
Pro Gly Arg Phe Lys Pro Gln Cys Asp Glu Asn Gly Asn Tyr Met Pro
    210                 215                 220
Leu Gln Cys Phe Gly Ser Ile Gly Tyr Cys Trp Cys Val Phe Pro Asn
225                 230                 235                 240
Gly Thr Glu Val Pro His Thr Arg Ser Arg Gly Arg His Asn Cys Ser
                245                 250                 255
Glu Pro Leu Asp Met Glu Asp Leu Ser Ser Gly Leu Gly Val Thr Lys
            260                 265                 270
Gln Asp Leu Val Gln Ala Thr Met
        275                 280

<210> SEQ ID NO 19
```

<211> LENGTH: 323
<212> TYPE: PRT
<213> ORGANISM: Myotis davidii

<400> SEQUENCE: 19

Met Glu Asp Gln Arg Asp Leu Ile Ser Asn His Glu Gln Leu Pro Met
1               5                   10                  15

Leu Gly Gln Arg Pro Gly Ala Gln Glu Ser Lys Cys Ser Arg Gly Ala
            20                  25                  30

Leu Tyr Thr Gly Phe Ser Val Leu Val Ala Leu Leu Leu Ala Gly Gln
        35                  40                  45

Ala Thr Thr Ala Tyr Phe Leu Tyr Gln Gln Gly Arg Leu Asp Lys
    50                  55                  60

Leu Thr Val Thr Ser Gln Asn Leu Gln Leu Glu Asn Leu Arg Met Lys
65                  70                  75                  80

Leu Pro Lys Ser Ala Lys Pro Val Gly Lys Met Arg Val Ala Thr Pro
                85                  90                  95

Met Leu Met Gln Ala Leu Pro Met Glu Gly Leu Leu Gln Gly Pro Met
            100                 105                 110

Gln Asn Ala Thr Lys Tyr Gly Asn Thr Thr Met Asp His Val Met His
        115                 120                 125

Leu Leu Leu Lys Ala Asp Pro Leu Lys Val Tyr Pro Gln Met Lys Gly
130                 135                 140

Ser Phe Pro Glu Asn Leu Lys His Leu Lys Lys Thr Met Glu Gly Leu
145                 150                 155                 160

Asp Trp Lys Ile Phe Glu Ser Trp Met His Gln Trp Leu Leu Phe Glu
                165                 170                 175

Met Ser Lys Asn Ser Leu Gly Glu Lys Leu Thr Glu Gly Ser Pro Lys
            180                 185                 190

Val Leu Thr Gln Cys Leu Glu Glu Ala Ser Arg Ile Pro Ala Ile His
        195                 200                 205

Pro Gly Arg Phe Lys Pro Gln Cys Asp Glu Asn Gly Asn Tyr Met Pro
    210                 215                 220

Leu Gln Cys Phe Gly Ser Ile Gly Tyr Cys Trp Cys Val Phe Pro Asn
225                 230                 235                 240

Gly Thr Glu Val Pro His Thr Arg Ser Arg Gly Arg His Asn Cys Ser
                245                 250                 255

Glu Pro Leu Asp Met Glu Asp Leu Ser Ser Gly Leu Gly Val Thr Lys
            260                 265                 270

Gln Asp Leu Val Gln Ala Ile Glu Asp Thr Ser Thr Gln Ser Ala Leu
        275                 280                 285

His Gly His Ser Phe Leu Ala Leu Phe Arg Pro Pro Asn Leu Ala Thr
    290                 295                 300

Tyr Phe Ser Pro Leu His Ala Leu Leu Pro Pro Ser Pro Thr Leu His
305                 310                 315                 320

Leu Ile Ser

<210> SEQ ID NO 20
<211> LENGTH: 295
<212> TYPE: PRT
<213> ORGANISM: Myotis brandtii

<400> SEQUENCE: 20

Met Leu Gly Gln Arg Pro Gly Ala Gln Glu Ser Lys Cys Ser Arg Gly
1               5                   10                  15

```
Ala Leu Tyr Thr Gly Phe Ser Val Leu Val Ala Leu Leu Ala Gly
             20                  25                  30

Gln Ala Thr Thr Ala Tyr Phe Leu Tyr Gln Gln Gly Arg Leu Asp
             35                  40                  45

Lys Leu Thr Val Thr Ser Gln Asn Leu Gln Leu Glu Asn Leu Arg Met
 50                  55                  60

Lys Leu Pro Lys Ser Ala Lys Pro Val Gly Lys Met Arg Val Ala Thr
 65                  70                  75                  80

Pro Met Leu Met Gln Ala Leu Pro Met Glu Gly Leu Leu Gln Gly Pro
             85                  90                  95

Met Gln Asn Ala Thr Lys Tyr Gly Asn Thr Thr Met Asp His Val Met
            100                 105                 110

His Leu Leu Lys Ala Asp Pro Leu Lys Val Tyr Pro Gln Met Lys
            115                 120                 125

Gly Ser Phe Pro Glu Asn Leu Lys His Leu Lys Lys Thr Met Glu Gly
            130                 135                 140

Leu Asp Trp Lys Ile Phe Glu Ser Trp Met His Gln Trp Leu Leu Phe
145                 150                 155                 160

Glu Met Ser Lys Asn Ser Leu Gly Glu Lys Leu Thr Glu Gly Ser Pro
            165                 170                 175

Lys Val Leu Thr Lys Cys Leu Glu Glu Ala Ser Arg Ile Pro Ala Ile
            180                 185                 190

His Pro Gly Arg Phe Lys Pro Gln Cys Asp Glu Asn Gly Asn Tyr Met
            195                 200                 205

Pro Leu Gln Cys Phe Gly Ser Ile Gly Tyr Cys Trp Cys Val Phe Pro
210                 215                 220

Asn Gly Thr Glu Val Pro His Thr Arg Ser Arg Gly Arg His Asn Cys
225                 230                 235                 240

Ser Glu Pro Leu Asp Met Glu Asp Leu Ser Ser Gly Leu Gly Val Thr
            245                 250                 255

Lys Gln Asp Leu Val Gln Glu Ile Thr Ser Glu Gln Gln Ile Arg Arg
            260                 265                 270

Ala Leu Leu Pro Lys Pro Pro Ser Ile Ser Arg His Thr Arg Pro Lys
            275                 280                 285

Glu Leu Asp His Glu Leu Gly
            290                 295

<210> SEQ ID NO 21
<211> LENGTH: 299
<212> TYPE: PRT
<213> ORGANISM: Pteropus alecto

<400> SEQUENCE: 21

Met Glu Asp Gln Arg Asp Leu Ile Ser Asn His Glu Gln Leu Pro Met
 1               5                  10                  15

Leu Gly Gln Arg Pro Gly Ala Pro Glu Arg Asn Cys Ser Arg Gly Ala
             20                  25                  30

Leu Tyr Thr Gly Phe Ser Val Leu Val Ala Leu Leu Ala Gly Gln
             35                  40                  45

Ala Thr Thr Ala Tyr Phe Leu Tyr Gln Gln Gly Arg Leu Asp Lys
 50                  55                  60

Leu Thr Val Thr Ser Gln Asn Leu Gln Leu Glu Asn Leu Arg Met Lys
 65                  70                  75                  80

Leu Pro Lys Ser Ala Lys Pro Val Ser Lys Met Arg Val Ala Thr Pro
             85                  90                  95
```

```
Met Leu Met Gln Ala Leu Pro Met Asp Gly Val Leu Gln Gly Pro Met
                100                 105                 110

Gln Asn Ala Thr Lys Tyr Gly Asn Ser Thr Leu Asp His Val Met His
            115                 120                 125

Leu Leu Leu Lys Ser Asp Pro Leu Lys Val Tyr Pro Gln Leu Lys Gly
        130                 135                 140

Ser Phe Pro Glu Asn Leu Lys Arg Leu Arg Asn Thr Met Glu Gly Leu
145                 150                 155                 160

Asp Trp Lys Ala Phe Glu Asn Trp Met His Gln Trp Leu Leu Phe Glu
                165                 170                 175

Met Ser Lys Asn Ser Leu Glu Glu Lys Pro Lys Pro Thr Gln Val Pro
            180                 185                 190

Thr Lys Val Leu Thr Lys Cys Leu Glu Glu Val Ser Arg Ile Pro Ala
        195                 200                 205

Ile His Pro Gly Met Phe Lys Pro Lys Cys Asp Glu Asn Gly Asn Tyr
210                 215                 220

Met Pro Leu Gln Cys Tyr Gly Ser Ile Gly Tyr Cys Trp Cys Val Phe
225                 230                 235                 240

Pro Asn Gly Thr Glu Val Pro His Thr Arg Ser Arg Lys Arg Ser Asn
                245                 250                 255

Cys Ser Glu Pro Val Asp Met Glu Asp Leu Ser Ser Gly Leu Gly Val
            260                 265                 270

Thr Lys Gln Asp Leu Ser Gln Gly Lys Gly Ala Cys Arg Gly Asp Ala
        275                 280                 285

Gln His Gly Thr Thr Leu Val His Ser Pro Thr
290                 295

<210> SEQ ID NO 22
<211> LENGTH: 232
<212> TYPE: PRT
<213> ORGANISM: Pan troglodytes verus

<400> SEQUENCE: 22

Met His Arg Arg Arg Ser Arg Ser Cys Arg Glu Asp Gln Lys Pro Val
1               5                   10                  15

Met Asp Asp Gln Arg Asp Leu Ile Ser Asn Asn Glu Gln Leu Pro Met
            20                  25                  30

Leu Gly Arg Arg Pro Gly Ala Pro Glu Ser Lys Cys Ser Arg Gly Ala
        35                  40                  45

Leu Tyr Thr Gly Phe Ser Ile Leu Val Thr Leu Leu Leu Ala Gly Gln
    50                  55                  60

Ala Thr Thr Ala Tyr Phe Leu Tyr Gln Gln Gln Gly Arg Leu Asp Lys
65                  70                  75                  80

Leu Thr Val Thr Ser Gln Asn Leu Gln Leu Glu Asn Leu Arg Met Lys
                85                  90                  95

Leu Pro Lys Pro Pro Lys Pro Val Ser Lys Met Arg Met Ala Thr Pro
            100                 105                 110

Leu Leu Met Gln Ala Leu Pro Met Gly Ala Leu Pro Gln Gly Pro Met
        115                 120                 125

Gln Asn Ala Thr Lys Tyr Gly Asn Met Thr Glu Asp His Val Met His
    130                 135                 140

Leu Leu Gln Asn Ala Asp Pro Leu Lys Val Tyr Pro Pro Leu Lys Gly
145                 150                 155                 160

Ser Phe Pro Glu Asn Leu Arg His Leu Lys Asn Thr Met Glu Thr Ile
```

```
                    165                 170                 175

Asp Trp Lys Val Phe Glu Ser Trp Met His His Trp Leu Leu Phe Glu
            180                 185                 190

Met Ser Arg His Ser Leu Glu Gln Lys Pro Thr Glu Ala Pro Pro Lys
        195                 200                 205

Glu Ser Leu Glu Leu Glu Asp Pro Ser Ser Gly Leu Gly Val Thr Lys
    210                 215                 220

Gln Asp Leu Gly Pro Val Pro Met
225                 230

<210> SEQ ID NO 23
<211> LENGTH: 232
<212> TYPE: PRT
<213> ORGANISM: Pongo abelii

<400> SEQUENCE: 23

Met His Arg Arg Arg Ser Arg Ser Cys Arg Glu Asp Gln Lys Pro Val
1               5                   10                  15

Met Asp Asp Gln Arg Asp Leu Ile Ser Asn Asn Glu Gln Leu Pro Met
            20                  25                  30

Leu Gly Arg Arg Pro Gly Ala Pro Glu Ser Lys Cys Gly Arg Gly Ala
        35                  40                  45

Leu Tyr Thr Gly Phe Ser Ile Leu Val Thr Leu Leu Leu Ala Gly Gln
    50                  55                  60

Ala Thr Thr Ala Tyr Phe Leu Tyr Gln Gln Gln Gly Arg Leu Asp Lys
65                  70                  75                  80

Leu Thr Val Thr Ser Gln Asn Leu Gln Leu Glu Asn Leu Arg Met Lys
                85                  90                  95

Leu Pro Lys Pro Pro Lys Pro Val Ser Lys Met Arg Met Ala Thr Pro
            100                 105                 110

Leu Leu Met Gln Ala Leu Pro Met Gly Ala Leu Pro Arg Gly Pro Met
        115                 120                 125

Gln Asn Ala Thr Lys Tyr Gly Asn Met Thr Glu Asp His Val Met His
    130                 135                 140

Leu Leu Gln Asn Ala Asp Pro Leu Lys Val Tyr Pro Pro Leu Lys Gly
145                 150                 155                 160

Ser Phe Pro Glu Asn Leu Arg His Leu Lys Asn Thr Met Glu Thr Ile
                165                 170                 175

Asp Trp Lys Val Phe Glu Ser Trp Met His His Trp Leu Leu Phe Glu
            180                 185                 190

Met Ser Arg His Ser Leu Glu Gln Lys Pro Thr Glu Ala Pro Pro Lys
        195                 200                 205

Glu Ser Leu Glu Leu Glu Asp Pro Ser Ser Gly Leu Gly Val Thr Lys
    210                 215                 220

Gln Asp Leu Gly Pro Val Pro Met
225                 230

<210> SEQ ID NO 24
<211> LENGTH: 232
<212> TYPE: PRT
<213> ORGANISM: Pan troglodytes

<400> SEQUENCE: 24

Met His Arg Arg Arg Ser Arg Ser Cys Arg Glu Asp Gln Lys Pro Val
1               5                   10                  15

Met Asp Asp Gln Arg Asp Leu Ile Ser Asn Asn Glu Gln Leu Pro Met
```

```
                    20                  25                  30
Leu Gly Arg Arg Pro Gly Ala Pro Glu Ser Lys Cys Ser Arg Gly Ala
                35                  40                  45
Leu Tyr Thr Gly Phe Ser Ile Leu Val Thr Leu Leu Leu Ala Gly Gln
         50                  55                  60
Ala Thr Thr Ala Tyr Phe Leu Tyr Gln Gln Gln Gly Arg Leu Asp Lys
 65                  70                  75                  80
Leu Thr Val Thr Ser Gln Asn Leu Gln Leu Glu Asn Leu Arg Met Lys
                 85                  90                  95
Leu Pro Lys Pro Pro Lys Pro Val Ser Lys Met Arg Met Ala Thr Pro
            100                 105                 110
Leu Leu Met Gln Ala Leu Pro Met Gly Ala Leu Pro Gln Gly Pro Met
        115                 120                 125
Gln Asn Ala Thr Lys Tyr Gly Asn Met Thr Glu Asp His Val Met His
    130                 135                 140
Leu Leu Gln Asn Ala Asp Pro Leu Lys Val Tyr Pro Pro Leu Lys Gly
145                 150                 155                 160
Ser Phe Pro Glu Asn Leu Arg His Leu Lys Asn Thr Met Glu Thr Ile
                165                 170                 175
Asp Trp Lys Val Phe Glu Ser Trp Met His His Trp Leu Leu Phe Glu
            180                 185                 190
Met Ser Arg His Ser Leu Glu Gln Lys Pro Thr Glu Ala Pro Pro Lys
        195                 200                 205
Glu Ser Leu Glu Leu Glu Asp Pro Ser Ser Gly Leu Gly Val Thr Lys
    210                 215                 220
Gln Asp Leu Gly Pro Ala Pro Leu
225                 230

<210> SEQ ID NO 25
<211> LENGTH: 296
<212> TYPE: PRT
<213> ORGANISM: Gorilla gorilla gorilla

<400> SEQUENCE: 25

Met His Arg Arg Ser Ser Arg Ser Cys Arg Glu Asp Gln Lys Pro Val
  1               5                  10                  15
Met Asp Asp Gln Arg Asp Leu Ile Ser Asn Asn Glu Gln Leu Pro Met
                 20                  25                  30
Leu Gly Arg Arg Pro Gly Ala Pro Glu Ser Lys Cys Ser Arg Gly Ala
                35                  40                  45
Leu Tyr Thr Gly Phe Ser Ile Leu Val Thr Leu Leu Leu Ala Gly Gln
         50                  55                  60
Ala Thr Thr Ala Tyr Phe Leu Tyr Gln Gln Gln Gly Arg Leu Asp Lys
 65                  70                  75                  80
Leu Thr Val Thr Ser Gln Asn Leu Gln Leu Glu Asn Leu Arg Met Lys
                 85                  90                  95
Leu Pro Lys Pro Pro Lys Pro Val Ser Lys Met Arg Met Ala Thr Pro
            100                 105                 110
Leu Leu Met Gln Ala Leu Pro Met Gly Ala Leu Pro Gln Gly Pro Met
        115                 120                 125
Gln Asn Ala Thr Lys Tyr Gly Asn Met Thr Glu Asp His Val Met His
    130                 135                 140
Leu Leu Gln Asn Ala Asp Pro Leu Lys Val Tyr Pro Pro Leu Lys Gly
145                 150                 155                 160
```

```
Ser Phe Pro Glu Asn Leu Arg His Leu Lys Asn Thr Met Glu Thr Ile
                165                 170                 175

Asp Trp Lys Val Phe Glu Ser Trp Met His His Trp Leu Leu Phe Glu
            180                 185                 190

Met Ser Arg His Ser Leu Glu Gln Lys Pro Thr Glu Ala Pro Pro Lys
        195                 200                 205

Val Leu Thr Lys Cys Gln Glu Val Ser His Ile Pro Ala Val His
    210                 215                 220

Pro Gly Ser Phe Arg Pro Thr Cys Asp Glu Asn Gly Asn Tyr Leu Pro
225                 230                 235                 240

Leu Gln Cys Tyr Gly Ser Ile Gly Tyr Cys Trp Cys Val Phe Pro Asn
                245                 250                 255

Gly Thr Glu Val Pro Asn Thr Arg Ser Arg Gly His His Asn Cys Ser
            260                 265                 270

Glu Ser Leu Glu Leu Glu Asp Pro Ser Ser Gly Leu Gly Val Thr Lys
        275                 280                 285

Gln Asp Leu Ser Pro Val Pro Met
    290                 295

<210> SEQ ID NO 26
<211> LENGTH: 296
<212> TYPE: PRT
<213> ORGANISM: Nomascus leucogenys

<400> SEQUENCE: 26

Met His Arg Arg Ser Ser Arg Ser Cys Arg Glu Asp Gln Lys Pro Val
1               5                   10                  15

Met Asp Asp Gln Arg Asp Leu Ile Ser Asn Asn Glu Gln Leu Pro Met
            20                  25                  30

Leu Gly Arg Arg Pro Gly Ala Pro Glu Ser Lys Cys Ser Arg Gly Ala
        35                  40                  45

Leu Tyr Thr Gly Phe Ser Ile Leu Val Thr Leu Leu Leu Ala Gly Gln
    50                  55                  60

Ala Thr Thr Ala Tyr Phe Leu Tyr Gln Gln Gln Gly Arg Leu Asp Lys
65                  70                  75                  80

Leu Thr Val Thr Ser Gln Asn Leu Gln Leu Glu Asn Leu Arg Met Lys
                85                  90                  95

Leu Pro Lys Pro Pro Lys Pro Val Ser Lys Met Arg Met Ala Thr Pro
            100                 105                 110

Leu Leu Met Gln Ala Leu Pro Met Gly Ala Leu Pro Arg Gly Pro Met
        115                 120                 125

Gln Asn Ala Thr Lys Tyr Gly Asn Met Thr Glu Asp His Val Met His
    130                 135                 140

Leu Leu Gln Asn Ala Asp Pro Leu Lys Val Tyr Pro Pro Leu Lys Gly
145                 150                 155                 160

Ser Phe Pro Glu Asn Leu Arg His Leu Lys Asn Thr Met Glu Thr Ile
                165                 170                 175

Asp Trp Lys Val Phe Glu Ser Trp Met His His Trp Leu Leu Phe Glu
            180                 185                 190

Met Ser Arg His Ser Leu Glu Gln Lys Pro Thr Glu Ala Pro Pro Lys
        195                 200                 205

Val Leu Thr Lys Cys Gln Glu Val Ser His Ile Pro Ala Val His
    210                 215                 220

Pro Gly Ser Phe Arg Pro Lys Cys Asp Glu Asn Gly Asn Tyr Leu Pro
225                 230                 235                 240
```

```
Leu Gln Cys Tyr Gly Ser Ile Gly Tyr Cys Trp Cys Val Phe Pro Asn
                245                 250                 255

Gly Thr Glu Val Pro Asn Thr Arg Ser Arg Gly His His Asn Cys Ser
            260                 265                 270

Glu Ser Leu Glu Leu Glu Asp Pro Ser Ser Gly Leu Gly Val Thr Lys
        275                 280                 285

Gln Asp Leu Gly Pro Val Pro Ile
    290                 295

<210> SEQ ID NO 27
<211> LENGTH: 230
<212> TYPE: PRT
<213> ORGANISM: Macaca mulatta

<400> SEQUENCE: 27

Met Tyr Arg Ser Ser Arg Arg Ser Cys Gln Glu Asp Gln Lys Pro Val
1               5                   10                  15

Met Asp Asp Gln Arg Asp Leu Ile Ser Asn Asn Glu Gln Leu Pro Met
            20                  25                  30

Leu Gly Arg Arg Pro Gly Thr Pro Glu Ser Lys Cys Ser Arg Gly Ala
        35                  40                  45

Leu Tyr Thr Gly Phe Ser Ile Leu Val Thr Leu Leu Leu Ala Gly Gln
    50                  55                  60

Ala Thr Thr Ala Tyr Phe Leu Tyr Gln Gln Gln Gly Arg Leu Asp Lys
65                  70                  75                  80

Leu Thr Val Thr Thr Gln Ser Leu Gln Leu Glu Asn Leu Arg Met Lys
                85                  90                  95

Leu Pro Lys Pro Pro Lys Pro Val Ser Lys Met Arg Met Ala Thr Pro
            100                 105                 110

Leu Leu Met Gln Ala Leu Pro Met Gly Ala Gln Gly Pro Met Gln Asn
        115                 120                 125

Ala Thr Lys Tyr Gly Asn Met Thr Glu Asp His Val Met His Leu Leu
    130                 135                 140

Gln Asn Ala Asp Pro Leu Lys Val Tyr Pro Pro Leu Lys Gly Ser Phe
145                 150                 155                 160

Pro Glu Asn Leu Arg His Leu Lys Ser Thr Met Glu Thr Leu Asp Trp
                165                 170                 175

Lys Val Phe Glu Ser Trp Met His His Trp Leu Leu Phe Glu Met Ser
            180                 185                 190

Lys His Ser Leu Glu Gln Lys Pro Thr Glu Ala Pro Pro Lys Glu Ser
        195                 200                 205

Leu Glu Leu Glu Asp Pro Ser Ser Gly Leu Gly Val Thr Lys Gln Asp
    210                 215                 220

Leu Gly Pro Val Pro Met
225                 230

<210> SEQ ID NO 28
<211> LENGTH: 346
<212> TYPE: PRT
<213> ORGANISM: Macaca fascicularis

<400> SEQUENCE: 28

Met Tyr Arg Ser Ser Arg Arg Ser Cys Gln Glu Asp Gln Lys Pro Val
1               5                   10                  15

Met Asp Asp Gln Arg Asp Leu Ile Ser Asn Asn Glu Gln Leu Pro Met
            20                  25                  30
```

Leu Gly Arg Arg Pro Gly Thr Pro Glu Ser Lys Cys Ser Arg Gly Ala
        35                  40                  45

Leu Tyr Thr Gly Phe Ser Ile Leu Val Thr Leu Leu Leu Ala Gly Gln
    50                  55                  60

Ala Thr Thr Ala Tyr Phe Leu Tyr Gln Gln Gln Gly Arg Leu Asp Lys
65                  70                  75                  80

Leu Thr Val Thr Thr Gln Ser Leu Gln Leu Glu Asn Leu Arg Met Lys
                85                  90                  95

Leu Pro Lys Pro Pro Lys Pro Val Ser Lys Met Arg Met Ala Thr Pro
            100                 105                 110

Leu Leu Met Gln Ala Leu Pro Met Gly Ala Gln Gly Pro Met Gln Asn
        115                 120                 125

Ala Thr Lys Tyr Gly Asn Met Thr Glu Asp His Val Met His Leu Leu
130                 135                 140

Gln Asn Ala Asp Pro Leu Lys Val Tyr Pro Pro Leu Lys Gly Ser Phe
145                 150                 155                 160

Pro Glu Asn Leu Arg His Leu Lys Ser Thr Met Glu Thr Leu Asp Trp
                165                 170                 175

Lys Val Phe Glu Ser Trp Met His His Trp Leu Leu Phe Glu Met Ser
            180                 185                 190

Lys His Ser Leu Glu Gln Lys Pro Thr Glu Ala Pro Pro Lys Val Leu
        195                 200                 205

Thr Lys Cys Gln Glu Glu Val Ser Arg Ile Pro Ala Val His Pro Gly
    210                 215                 220

Ser Phe Arg Pro Lys Cys Asp Glu Asn Gly Asn Tyr Leu Pro Leu Gln
225                 230                 235                 240

Cys Tyr Gly Ser Thr Gly Tyr Cys Trp Cys Val Phe Pro Asn Gly Thr
                245                 250                 255

Glu Val Pro Asn Thr Arg Ser Arg Gly His Gln Asn Cys Ser Glu Ser
            260                 265                 270

Leu Glu Leu Glu Asp Pro Ser Ser Gly Leu Gly Val Thr Lys Gln Asp
        275                 280                 285

Leu Gly Pro Val His Thr Gln Asp Ile Ile Leu Ser Phe Met Phe Ile
    290                 295                 300

His Phe Leu Pro Ser Pro Pro Gln Asn His Gly Glu Leu Asp Val Arg
305                 310                 315                 320

Gly Asn Ser Leu Leu Thr Phe Leu Asp Leu Leu Cys Leu Pro Gln Leu
                325                 330                 335

Phe Thr Met His Leu Gln Gly Ala Cys Pro
            340                 345

<210> SEQ ID NO 29
<211> LENGTH: 346
<212> TYPE: PRT
<213> ORGANISM: Macaca mulatta

<400> SEQUENCE: 29

Met Tyr Arg Ser Ser Arg Ser Cys Gln Glu Asp Gln Lys Pro Val
1               5                   10                  15

Met Asp Asp Gln Arg Asp Leu Ile Ser Asn Asn Glu Leu Pro Met
            20                  25                  30

Leu Gly Arg Arg Pro Gly Thr Pro Glu Ser Lys Cys Ser Arg Gly Ala
        35                  40                  45

Leu Tyr Thr Gly Phe Ser Ile Leu Val Thr Leu Leu Leu Ala Gly Gln
    50                  55                  60

```
            50                  55                  60
Ala Thr Thr Ala Tyr Phe Leu Tyr Gln Gln Gln Gly Arg Leu Asp Lys
 65                  70                  75                  80

Leu Thr Val Thr Thr Gln Ser Leu Gln Leu Glu Asn Leu Arg Met Lys
                 85                  90                  95

Leu Pro Lys Pro Pro Lys Pro Val Ser Lys Met Arg Met Ala Thr Pro
            100                 105                 110

Leu Leu Met Gln Ala Leu Pro Met Gly Ala Gln Gly Pro Met Gln Asn
        115                 120                 125

Ala Thr Lys Tyr Gly Asn Met Thr Glu Asp His Val Met His Leu Leu
    130                 135                 140

Gln Asn Ala Asp Pro Leu Lys Val Tyr Pro Pro Leu Lys Gly Ser Phe
145                 150                 155                 160

Pro Glu Asn Leu Arg His Leu Lys Ser Thr Met Glu Thr Leu Asp Trp
                165                 170                 175

Lys Val Phe Glu Ser Trp Met His His Trp Leu Leu Phe Glu Met Ser
            180                 185                 190

Lys His Ser Leu Glu Gln Lys Pro Thr Glu Ala Pro Pro Lys Val Leu
        195                 200                 205

Thr Lys Cys Gln Glu Glu Val Ser Arg Ile Pro Ala Val His Pro Gly
    210                 215                 220

Ser Phe Arg Pro Lys Cys Asp Glu Asn Gly Asn Tyr Leu Pro Leu Gln
225                 230                 235                 240

Cys Tyr Gly Ser Thr Gly Tyr Cys Trp Cys Val Phe Pro Asn Gly Thr
                245                 250                 255

Glu Val Pro Asn Thr Arg Ser Arg Gly His Gln Asn Cys Ser Glu Ser
            260                 265                 270

Leu Glu Leu Glu Asp Pro Ser Ser Gly Leu Gly Val Thr Lys Gln Asp
        275                 280                 285

Leu Gly Pro Val His Thr Gln Asp Ile Ile Leu Ser Phe Met Phe Ile
    290                 295                 300

His Phe Leu Pro Ser Pro Gln Asn His Gly Glu Leu Asp Val Arg
305                 310                 315                 320

Gly Asn Ser Leu Leu Thr Phe Leu Asp Leu Leu Cys Leu Pro Gln Leu
                325                 330                 335

Phe Thr Met His Leu Gln Gly Ala Cys Pro
            340                 345

<210> SEQ ID NO 30
<211> LENGTH: 294
<212> TYPE: PRT
<213> ORGANISM: Macaca mulatta

<400> SEQUENCE: 30

Met Tyr Arg Ser Ser Arg Ser Cys Gln Glu Asp Gln Lys Pro Val
 1               5                  10                  15

Met Asp Asp Gln Arg Asp Leu Ile Ser Asn Asn Glu Gln Leu Pro Met
                 20                  25                  30

Leu Gly Arg Arg Pro Gly Thr Pro Glu Ser Lys Cys Ser Arg Gly Ala
            35                  40                  45

Leu Tyr Thr Gly Phe Ser Ile Leu Val Thr Leu Leu Leu Ala Gly Gln
        50                  55                  60

Ala Thr Thr Ala Tyr Phe Leu Tyr Gln Gln Gln Gly Arg Leu Asp Lys
 65                  70                  75                  80
```

```
Leu Thr Val Thr Thr Gln Ser Leu Gln Leu Glu Asn Leu Arg Met Lys
                85                  90                  95

Leu Pro Lys Pro Pro Lys Pro Val Ser Lys Met Arg Met Ala Thr Pro
            100                 105                 110

Leu Leu Met Gln Ala Leu Pro Met Gly Ala Gln Gly Pro Met Gln Asn
            115                 120                 125

Ala Thr Lys Tyr Gly Asn Met Thr Glu Asp His Val Met His Leu Leu
            130                 135                 140

Gln Asn Ala Asp Pro Leu Lys Val Tyr Pro Pro Leu Lys Gly Ser Phe
145                 150                 155                 160

Pro Glu Asn Leu Arg His Leu Lys Ser Thr Met Glu Thr Leu Asp Trp
                165                 170                 175

Lys Val Phe Glu Ser Trp Met His His Trp Leu Leu Phe Glu Met Ser
            180                 185                 190

Lys His Ser Leu Glu Gln Lys Pro Thr Glu Ala Pro Pro Lys Val Leu
            195                 200                 205

Thr Lys Cys Gln Glu Glu Val Ser Arg Ile Pro Ala Val His Pro Gly
            210                 215                 220

Ser Phe Arg Pro Lys Cys Asp Glu Asn Gly Asn Tyr Leu Pro Leu Gln
225                 230                 235                 240

Cys Tyr Gly Ser Thr Gly Tyr Cys Trp Cys Val Phe Pro Asn Gly Thr
                245                 250                 255

Glu Val Pro Asn Thr Arg Ser Arg Gly His Gln Asn Cys Ser Glu Ser
            260                 265                 270

Leu Glu Leu Glu Asp Pro Ser Ser Gly Leu Gly Val Thr Lys Gln Asp
            275                 280                 285

Leu Gly Pro Val Pro Met
        290

<210> SEQ ID NO 31
<211> LENGTH: 270
<212> TYPE: PRT
<213> ORGANISM: Macaca mulatta

<400> SEQUENCE: 31

Met Tyr Arg Ser Ser Arg Arg Ser Cys Gln Glu Asp Gln Lys Pro Val
1               5                   10                  15

Met Asp Asp Gln Arg Asp Leu Ile Ser Asn Asn Glu Gln Leu Pro Met
            20                  25                  30

Leu Gly Arg Arg Pro Gly Thr Pro Glu Ser Lys Cys Ser His Gly Ala
            35                  40                  45

Leu Tyr Thr Gly Phe Ser Ile Leu Val Thr Leu Leu Leu Ala Gly Gln
50                  55                  60

Ala Thr Thr Ala Tyr Phe Leu Tyr Gln Gln Gln Gly Arg Leu Asp Lys
65                  70                  75                  80

Leu Thr Val Thr Thr Gln Ser Leu Gln Leu Glu Asn Leu Arg Met Lys
                85                  90                  95

Leu Pro Lys Pro Pro Lys Pro Val Ser Lys Met Arg Met Ala Thr Pro
            100                 105                 110

Leu Leu Met Gln Ala Leu Pro Met Gly Ala Gln Gly Pro Met Gln Asn
            115                 120                 125

Ala Thr Lys Tyr Gly Asn Met Thr Glu Asp His Val Met His Leu Leu
            130                 135                 140

Gln Asn Ala Asp Pro Leu Lys Val Tyr Pro Pro Leu Lys Gly Ser Phe
145                 150                 155                 160
```

```
Pro Glu Asn Leu Arg His Leu Lys Ser Thr Met Glu Thr Leu Asp Trp
            165                 170                 175

Lys Val Phe Glu Ser Trp Met His His Trp Leu Leu Phe Glu Met Ser
            180                 185                 190

Lys His Ser Leu Glu Gln Lys Pro Thr Glu Ala Pro Pro Lys Val Leu
            195                 200                 205

Thr Lys Cys Gln Glu Glu Val Ser Arg Ile Pro Ala Val His Pro Gly
            210                 215                 220

Ser Phe Arg Pro Lys Cys Asp Glu Asn Gly Asn Tyr Leu Pro Leu Gln
225                 230                 235                 240

Cys Tyr Gly Ser Thr Gly Tyr Cys Trp Cys Val Phe Pro Asn Gly Thr
            245                 250                 255

Glu Val Pro Asn Thr Arg Ser Arg Gly His Gln Asn Cys Ser
            260                 265                 270

<210> SEQ ID NO 32
<211> LENGTH: 294
<212> TYPE: PRT
<213> ORGANISM: Papio anubis

<400> SEQUENCE: 32

Met Tyr Arg Ser Ser Arg Arg Ser Cys Gln Glu Asp Gln Lys Pro Val
1               5                   10                  15

Met Asp Asp Gln Arg Asp Leu Ile Ser Asn Asn Glu Gln Leu Pro Met
            20                  25                  30

Leu Gly Arg Arg Pro Gly Thr Pro Glu Ser Lys Cys Ser Arg Gly Ala
            35                  40                  45

Leu Tyr Thr Gly Phe Ser Ile Leu Val Thr Leu Leu Leu Ala Gly Gln
            50                  55                  60

Ala Thr Thr Ala Tyr Phe Leu Tyr Gln Gln Gln Gly Arg Leu Asp Lys
65                  70                  75                  80

Leu Thr Val Thr Thr Gln Asn Leu Gln Leu Glu Asn Leu Arg Met Lys
            85                  90                  95

Leu Pro Lys Pro Pro Lys Pro Val Ser Lys Met Arg Met Ala Thr Pro
            100                 105                 110

Leu Leu Met Gln Ala Leu Pro Met Gly Ala Gln Gly Pro Met Gln Asn
            115                 120                 125

Ala Thr Lys Tyr Gly Asn Met Thr Glu Asp His Val Met His Leu Leu
            130                 135                 140

Gln Asn Ala Asp Pro Leu Lys Val Tyr Pro Pro Leu Lys Gly Ser Phe
145                 150                 155                 160

Pro Glu Asn Leu Arg His Leu Lys Ser Thr Met Glu Thr Leu Asp Trp
            165                 170                 175

Lys Val Phe Glu Ser Trp Met His His Trp Leu Leu Phe Glu Met Ser
            180                 185                 190

Lys His Ser Leu Glu Gln Lys Pro Thr Glu Ala Pro Pro Lys Val Leu
            195                 200                 205

Thr Lys Cys Gln Glu Glu Val Ser Arg Ile Pro Ala Val His Pro Gly
            210                 215                 220

Ser Phe Arg Pro Lys Cys Asp Glu Asn Gly Asn Tyr Leu Pro Leu Gln
225                 230                 235                 240

Cys Tyr Gly Ser Thr Gly Tyr Cys Trp Cys Val Phe Pro Asn Gly Thr
            245                 250                 255

Glu Val Pro Asn Thr Arg Ser Arg Gly His Gln Asn Cys Ser Glu Ser
```

```
                260                 265                 270
Leu Glu Leu Glu Asp Pro Ser Ser Gly Leu Gly Val Thr Lys Gln Asp
            275                 280                 285

Leu Gly Pro Val Pro Met
        290

<210> SEQ ID NO 33
<211> LENGTH: 294
<212> TYPE: PRT
<213> ORGANISM: Chlorocebus sabaeus

<400> SEQUENCE: 33

Met Tyr Arg Ser Ser Arg Arg Ser Cys Gln Glu Asp Gln Lys Pro Val
1               5                   10                  15

Met Asp Asp Gln Arg Asp Leu Ile Ser Asn Asn Glu Gln Leu Pro Met
            20                  25                  30

Leu Gly Arg Arg Pro Gly Thr Pro Glu Ser Lys Cys Ser Arg Gly Ala
        35                  40                  45

Leu Tyr Thr Gly Phe Ser Ile Leu Val Thr Leu Leu Leu Ala Gly Gln
    50                  55                  60

Ala Thr Thr Ala Tyr Phe Leu Tyr Gln Gln Gln Gly Arg Leu Asp Lys
65                  70                  75                  80

Leu Thr Val Thr Thr Gln Asn Leu Gln Leu Glu Asn Leu Arg Met Lys
                85                  90                  95

Leu Pro Lys Pro Pro Lys Pro Val Ser Lys Met Arg Met Ala Thr Pro
            100                 105                 110

Leu Leu Met Gln Ala Leu Pro Met Gly Ala Gln Gly Pro Met Gln Asn
        115                 120                 125

Ala Thr Lys Tyr Gly Asn Met Thr Glu Asp His Val Met His Leu Leu
    130                 135                 140

Gln Asn Ala Asp Pro Leu Lys Val Tyr Pro Pro Leu Lys Gly Ser Phe
145                 150                 155                 160

Pro Glu Asn Leu Arg His Leu Lys Ser Thr Met Glu Thr Leu Asp Trp
                165                 170                 175

Lys Val Phe Glu Ser Trp Met His His Trp Leu Leu Phe Glu Met Ser
            180                 185                 190

Lys His Ser Leu Glu Gln Lys Pro Thr Glu Ala Pro Pro Lys Val Leu
        195                 200                 205

Thr Lys Cys Gln Glu Glu Val Ser Arg Ile Pro Ala Val His Pro Gly
    210                 215                 220

Thr Phe Arg Pro Lys Cys Asp Glu Asn Gly Asn Tyr Leu Pro Leu Gln
225                 230                 235                 240

Cys Tyr Gly Ser Thr Gly Tyr Cys Trp Cys Val Phe Pro Asn Gly Thr
                245                 250                 255

Glu Val Pro Asn Thr Arg Ser Arg Gly His Gln Asn Cys Ser Glu Ser
            260                 265                 270

Leu Glu Leu Glu Asp Pro Ser Ser Gly Leu Gly Val Thr Lys Gln Asp
        275                 280                 285

Leu Gly Pro Val Pro Met
    290

<210> SEQ ID NO 34
<211> LENGTH: 295
<212> TYPE: PRT
<213> ORGANISM: Callithrix jacchus
```

```
<400> SEQUENCE: 34

Val Phe Arg Arg Ile Ser Arg Asn Cys Trp Glu Asp Gln Lys Pro Met
1               5                   10                  15

Asp Asp Gln Arg Asp Leu Ile Ser Asn Asn Glu Gln Leu Pro Met Leu
            20                  25                  30

Gly Gln Arg Pro Gly Ala Pro Glu Ser Lys Cys Ser Arg Gly Ala Val
        35                  40                  45

Tyr Thr Val Phe Ser Ile Leu Val Ala Leu Leu Leu Ala Gly Gln Ala
    50                  55                  60

Thr Thr Ala Tyr Phe Leu Tyr Gln Gln Gln Gly Arg Leu Asp Lys Leu
65                  70                  75                  80

Thr Val Thr Ser Gln Asn Leu Gln Leu Glu Asn Leu Arg Met Lys Leu
                85                  90                  95

Pro Lys Pro Ala Lys Pro Leu Ser Gln Met Arg Met Ala Thr Pro Leu
            100                 105                 110

Leu Met Gln Ala Leu Pro Met Ala Gly Leu Pro Gln Lys Pro Met Gln
        115                 120                 125

Asn Ala Thr Lys His Gly Asn Met Thr Glu Asp His Val Met His Leu
    130                 135                 140

Leu Leu Asn Ala Asp Pro Leu Lys Val Tyr Pro Pro Leu Lys Gly Ser
145                 150                 155                 160

Leu Ser Glu Asn Leu Lys His Leu Lys Asn Thr Met Glu Thr Met Asp
                165                 170                 175

Trp Lys Val Phe Glu Ser Trp Leu His His Trp Leu Leu Phe Glu Met
            180                 185                 190

Ser Lys His Ser Leu Glu Gln Lys Pro Thr Glu Ala Pro Pro Lys Ala
        195                 200                 205

Leu Thr Lys Cys Gln Glu Val Ser His Ile Pro Asp Val His Pro
    210                 215                 220

Gly Ser Phe Arg Pro Lys Cys Asp Glu Asn Gly Asn Tyr Leu Pro Leu
225                 230                 235                 240

Gln Cys Tyr Gly Ser Ile Gly Tyr Cys Trp Cys Val Phe Pro Asn Gly
                245                 250                 255

Thr Glu Val Pro Asn Thr Arg Ser Arg Gly His His Asn Cys Ser Glu
            260                 265                 270

Ser Leu Glu Leu Glu Asp Pro Ser Ser Gly Leu Gly Val Thr Lys Gln
        275                 280                 285

Asp Leu Gly Pro Ala Pro Leu
    290                 295

<210> SEQ ID NO 35
<211> LENGTH: 280
<212> TYPE: PRT
<213> ORGANISM: Felis catus

<400> SEQUENCE: 35

Met Glu Asp Gln Arg Asp Leu Ile Ser Asn His Glu Gln Leu Pro Ile
1               5                   10                  15

Leu Gly Gln Arg Pro Ala Ala Pro Glu Ser Lys Cys Ser Arg Gly Ala
            20                  25                  30

Leu Tyr Thr Gly Phe Ser Val Leu Val Ala Leu Leu Leu Ala Gly Gln
        35                  40                  45

Ala Thr Thr Ala Tyr Phe Leu Tyr Gln Gln Gln Gly Arg Leu Asp Lys
    50                  55                  60
```

```
Leu Thr Val Thr Ala Gln Asn Leu Gln Leu Glu Asn Leu Arg Met Lys
 65                  70                  75                  80

Leu Pro Lys Pro Ala Lys Pro Leu Asn Lys Leu Arg Val Ala Thr Pro
                 85                  90                  95

Met Leu Met Gln Thr Met Pro Val Arg Gly Leu Leu Gln Ala Pro Met
            100                 105                 110

Gln Asn Ala Thr Lys Tyr Gly Asn Met Thr Gln Asp His Val Met His
        115                 120                 125

Met Leu Leu Glu Gly Asp Pro Leu Lys Val Tyr Pro Gln Leu Lys Gly
    130                 135                 140

Asn Phe Pro Glu Asn Leu Lys His Leu Lys Asn Thr Met Gly Thr Leu
145                 150                 155                 160

Asp Trp Lys Val Phe Glu Asn Trp Met Tyr Gln Trp Leu Leu Phe Glu
                165                 170                 175

Met Ser Lys Asn Ser Leu Glu Lys His Pro Ala Asp Ile Pro Leu Lys
            180                 185                 190

Val Leu Thr Lys Cys Gln Glu Val Ser Arg Ile Pro Ala Val His
        195                 200                 205

Pro Gly Thr Phe Arg Pro Gln Cys Asp Glu Asn Gly Asn Tyr Lys Pro
    210                 215                 220

Leu Gln Cys Tyr Gly Ser Thr Gly Tyr Cys Trp Cys Val Phe Pro Asn
225                 230                 235                 240

Gly Thr Glu Val Pro His Ser Arg Ser His Gly His Arg Asn Cys Ser
                245                 250                 255

Glu Ser Val Asp Val Glu Asp Leu Ser Ser Gly Leu Gly Met Thr Lys
            260                 265                 270

Pro Asp Leu Gly Gln Ala Pro Leu
        275                 280

<210> SEQ ID NO 36
<211> LENGTH: 279
<212> TYPE: PRT
<213> ORGANISM: Mustela putorius furo

<400> SEQUENCE: 36

Met Glu Asp Gln Arg Asp Leu Ile Ser Asn His Glu Gln Leu Pro Met
 1               5                  10                  15

Leu Gly Gln Arg Pro Ser Ala Pro Glu Ser Lys Cys Ser Arg Gly Ala
             20                  25                  30

Leu Tyr Thr Gly Phe Ser Val Leu Val Ala Leu Leu Leu Ala Gly Gln
         35                  40                  45

Ala Thr Thr Ala Tyr Phe Leu Tyr Gln Gln Gln Gly Arg Leu Asp Lys
 50                  55                  60

Leu Thr Val Thr Ser Gln Asn Leu Gln Leu Glu Asn Leu Arg Met Lys
 65                  70                  75                  80

Leu Pro Lys Pro Pro Lys Pro Leu His Lys Met Arg Ala Ala Thr Pro
                 85                  90                  95

Met Leu Met Gln Ala Leu Pro Met Pro Asp Leu Leu Gln Glu Pro Leu
            100                 105                 110

Gln Asn Ala Thr Lys Tyr Gly Asn Met Thr Gln Asp His Val Met His
        115                 120                 125

Val Leu Leu Glu Thr Asp Pro Leu Lys Val Tyr Pro Lys Leu Lys Gly
    130                 135                 140

Ser Phe Leu Glu Asn Leu Lys His Leu Lys Asn Thr Met Gly Pro Leu
145                 150                 155                 160
```

Glu Trp Lys Val Phe Glu Ser Trp Met Tyr Gln Trp Leu Leu Phe Glu
            165                 170                 175

Met Ser Lys Asn Ser Leu Glu Asn Lys Pro Glu Val Pro Leu Lys Ala
            180                 185                 190

Leu Thr Gln Cys Gln Glu Val Ser Arg Val Pro Ala Val His Pro
            195                 200                 205

Gly Thr Phe Arg Pro Gln Cys Asp Glu Asn Gly Asn Tyr Lys Pro Leu
            210                 215                 220

Gln Cys Tyr Gly Ser Thr Gly Tyr Cys Trp Cys Val Phe Pro Asn Gly
225                 230                 235                 240

Thr Glu Val Pro His Thr Arg Ser Arg Gly His His Asn Cys Arg Glu
            245                 250                 255

Pro Leu Asp Met Glu Asp Leu Ser Ser Gly Leu Gly Met Thr Lys Gln
            260                 265                 270

Asp Leu Gly Gln Val Ala Val
            275

<210> SEQ ID NO 37
<211> LENGTH: 280
<212> TYPE: PRT
<213> ORGANISM: Loxodonta africana

<400> SEQUENCE: 37

Met Glu Asp Gln Arg Asp Leu Ile Ser Asn His Glu Gln Leu Pro Ile
1               5                   10                  15

Leu Gly Gln Arg Pro Gln Ala Pro Glu Ser Lys Cys Ser Arg Gly Ala
            20                  25                  30

Leu Tyr Thr Gly Phe Ser Val Leu Val Ala Leu Leu Leu Ala Gly Gln
            35                  40                  45

Ala Thr Thr Ala Tyr Phe Leu Tyr Gln Gln Gln Gly Arg Leu Asp Lys
        50                  55                  60

Leu Thr Val Thr Ala Gln Asn Leu Gln Leu Glu Asn Leu Arg Met Lys
65                  70                  75                  80

Leu Pro Lys Pro Ala Met Pro Met Ser Lys Met Arg Met Ala Thr Pro
            85                  90                  95

Leu Leu Met Arg Ala Leu Pro Met Glu Ala Leu Pro His Gly Pro Met
            100                 105                 110

Gln Asn Ala Thr Lys Tyr Gly Asn Met Pro Gln Asp Tyr Val Met His
            115                 120                 125

Met Leu Leu Arg Thr Asp Pro Leu Lys Val Tyr Pro Gln Leu Lys Gly
            130                 135                 140

Thr Leu Pro Glu Asn Leu Lys His Leu Lys Asn Thr Met Asp Gly Leu
145                 150                 155                 160

Asp Trp Lys Ala Phe Glu Asn Trp Met His Gln Trp Leu Leu Phe Glu
            165                 170                 175

Met Ser Lys Asn Ser Val Glu Glu Lys Pro Thr Glu Ala Pro Thr Lys
            180                 185                 190

Ala Leu Thr Lys Cys Gln Glu Val Ser Arg Ile Pro Ala Ile His
            195                 200                 205

Pro Gly Val Tyr Arg Pro Lys Cys Asp Glu Asn Gly Asn Tyr Leu Pro
            210                 215                 220

Leu Gln Cys Tyr Gly Ser Thr Gly Tyr Cys Trp Cys Val Phe Pro Asn
225                 230                 235                 240

Gly Thr Glu Val Pro His Thr Arg Ser Arg Gly His His Asn Cys Ser

```
                    245                 250                 255
Glu Pro Leu Glu Leu Glu Asp Leu Ser Ser Gly Val Asp Met Thr Lys
            260                 265                 270
Gln Gly Val Gly Glu Glu Thr Leu
            275                 280

<210> SEQ ID NO 38
<211> LENGTH: 280
<212> TYPE: PRT
<213> ORGANISM: Loxodonta africana

<400> SEQUENCE: 38

Met Glu Asp Gln Arg Asp Leu Ile Ser Asn His Glu Gln Leu Pro Ile
1               5                  10                  15
Leu Gly Gln Arg Pro Gln Ala Pro Glu Ser Lys Cys Ser Arg Gly Ala
            20                  25                  30
Leu Tyr Thr Gly Phe Ser Val Leu Val Ala Leu Leu Leu Ala Gly Gln
        35                  40                  45
Ala Thr Thr Ala Tyr Phe Leu Tyr Gln Gln Gln Gly Arg Leu Asp Lys
    50                  55                  60
Leu Thr Val Thr Ala Gln Asn Leu Gln Leu Glu Asn Leu Arg Met Lys
65                  70                  75                  80
Leu Pro Lys Pro Ala Met Pro Met Ser Lys Met Arg Met Ala Thr Pro
                85                  90                  95
Leu Leu Met Arg Ala Leu Pro Met Glu Ala Leu Pro His Gly Pro Met
            100                 105                 110
Gln Asn Ala Thr Lys Tyr Gly Asn Met Pro Gln Asp Tyr Val Met His
        115                 120                 125
Met Leu Leu Arg Thr Asp Pro Leu Lys Val Tyr Pro Gln Leu Lys Gly
    130                 135                 140
Thr Leu Pro Glu Asn Leu Lys His Leu Lys Asn Thr Met Asp Gly Leu
145                 150                 155                 160
Asp Trp Lys Ala Phe Glu Asn Trp Met His Gln Trp Leu Leu Phe Glu
                165                 170                 175
Met Ser Lys Asn Ser Val Glu Glu Lys Pro Thr Glu Ala Pro Thr Lys
            180                 185                 190
Ala Leu Thr Lys Cys Gln Glu Glu Val Ser Arg Ile Pro Ala Ile His
        195                 200                 205
Pro Gly Val Tyr Arg Pro Lys Cys Asp Glu Asn Gly Asn Tyr Leu Pro
    210                 215                 220
Leu Gln Cys Tyr Gly Ser Thr Gly Tyr Cys Trp Cys Val Phe Pro Asn
225                 230                 235                 240
Gly Thr Glu Val Pro His Thr Arg Ser Arg Gly His His Asn Cys Ser
                245                 250                 255
Glu Pro Leu Glu Leu Glu Asp Leu Ser Ser Gly Val Asp Met Thr Lys
            260                 265                 270
Gln Gly Val Gly Glu Gly Leu Leu
        275                 280

<210> SEQ ID NO 39
<211> LENGTH: 214
<212> TYPE: PRT
<213> ORGANISM: Sus scrofa

<400> SEQUENCE: 39

Met Glu Asp Gln Arg Asp Leu Ile Ser Asn His Glu Gln Leu Pro Met
```

```
1               5                   10                  15
Leu Gly Gln Arg Pro Gly Ala Pro Glu Ser Lys Cys Ser Arg Gly Ala
                20                  25                  30
Leu Tyr Thr Gly Phe Ser Val Leu Val Ala Leu Leu Ala Gly Gln
            35                  40                  45
Ala Thr Thr Ala Tyr Phe Leu Tyr Gln Gln Gln Gly Arg Leu Asp Lys
        50                  55                  60
Leu Thr Val Thr Ser Gln Asn Leu Gln Leu Glu Ser Leu Arg Met Lys
65                  70                  75                  80
Leu Pro Lys Pro Ser Lys Pro Leu Ser Lys Met Arg Val Ser Ala Pro
                85                  90                  95
Met Leu Met Gln Ala Leu Pro Met Glu Gly Pro Glu Pro Met Arg Asn
                100                 105                 110
Ala Thr Lys Tyr Gly Asn Met Thr Gln Asp His Val Met His Leu Leu
            115                 120                 125
Leu Lys Ser Asp Pro Leu Gly Val Tyr Pro Lys Leu Lys Gly Ser Leu
        130                 135                 140
Pro Glu Asn Leu Lys His Leu Lys Asn Thr Met Asp Gly Val Asn Trp
145                 150                 155                 160
Lys Leu Phe Glu Asn Trp Leu Arg Gln Trp Leu Leu Phe Glu Met Ser
                165                 170                 175
Lys Asn Ser Leu Glu Glu Thr Pro Phe Glu Val Pro Pro Lys Asp Pro
                180                 185                 190
Leu Glu Thr Glu Asp Leu Ser Ser Gly Leu Gly Val Thr Lys Gln Asp
            195                 200                 205
Leu Gly Gln Val Ile Leu
        210

<210> SEQ ID NO 40
<211> LENGTH: 340
<212> TYPE: PRT
<213> ORGANISM: Camelus ferus

<400> SEQUENCE: 40

Met Glu Asp Gln Arg Asp Leu Ile Ser Asn His Glu Gln Leu Pro Ile
1               5                   10                  15
Leu Gly Gln Arg Pro Ala Ala Pro Glu Ser Lys Cys Ser Arg Gly Ala
                20                  25                  30
Leu Tyr Thr Gly Phe Ser Val Leu Met Ala Leu Leu Ala Gly Gln
            35                  40                  45
Ala Thr Thr Ala Tyr Phe Leu Tyr Gln Gln Gln Gly Arg Leu Asp Lys
        50                  55                  60
Leu Thr Ile Thr Ser Gln Asn Leu Gln Leu Glu Asn Leu Arg Met Lys
65                  70                  75                  80
Leu Pro Lys Pro Ala Lys Pro Leu Ser Gln Met Arg Met Ala Thr Pro
                85                  90                  95
Met Leu Met Gln Ala Leu Pro Met Gln Gly Pro Gln Leu Met Gln Asn
                100                 105                 110
Ala Thr Lys Tyr Gly Asn Met Thr Gln Asp His Val Met His Leu Leu
            115                 120                 125
Leu Lys Ala Asp Pro Leu Lys Val Tyr Pro Gln Leu Lys Gly Ser Leu
        130                 135                 140
Pro Glu Asn Leu Lys His Leu Lys Asn Thr Met Asp Gly Met Asn Trp
145                 150                 155                 160
```

-continued

Lys Leu Phe Glu Asn Trp Met His Tyr Trp Leu Leu Phe Glu Met Ser
            165                 170                 175

Lys Asn Ser Gln Glu Glu Gln Pro Phe Glu Val Pro Thr Lys Ala Leu
        180                 185                 190

Thr Lys Cys Gln Glu Glu Val Ser Arg Ile Pro Ala Ile His Pro Gly
        195                 200                 205

Thr Phe Arg Pro Lys Cys Asp Glu Asn Gly Asn Tyr Met Pro Leu Gln
        210                 215                 220

Cys Tyr Gly Ser Ile Gly Tyr Cys Trp Cys Val Phe Pro Asn Gly Thr
225                 230                 235                 240

Glu Val Pro His Thr Arg Ser Arg Gly His His Asn Cys Ser Asp Pro
                245                 250                 255

Leu Glu Met Glu Asp Leu Ser Ser Gly Leu Gly Val Thr Lys Pro Asp
            260                 265                 270

Leu Gly Gln Gly Pro Thr His Glu Ala Leu Ser Ser Ser Leu Gly Pro
        275                 280                 285

Arg Gln Met Leu Glu Leu Pro Ser Cys Pro Pro Arg Val Val Asn Asp
        290                 295                 300

Gln Gln Gly Phe Gln Thr Gln Glu Ala Tyr Leu Pro Pro Gly Val Leu
305                 310                 315                 320

Gln Thr Val Cys Ser Ala Val Phe Phe Cys Glu Glu Arg Gly Met Thr
                325                 330                 335

Gly Ser Arg Thr
            340

<210> SEQ ID NO 41
<211> LENGTH: 268
<212> TYPE: PRT
<213> ORGANISM: Bos mutus

<400> SEQUENCE: 41

Met Glu Asp Gln Arg Asp Leu Ile Ser Asn His Glu Gln Leu Pro Met
1               5                   10                  15

Leu Gly Gln Arg Pro Gly Ala Gln Glu Ser Lys Cys Ser Arg Gly Ala
            20                  25                  30

Leu Tyr Thr Gly Phe Ser Val Leu Val Ala Leu Leu Leu Ala Gly Gln
        35                  40                  45

Ala Thr Thr Ala Tyr Phe Leu Tyr Gln Gln Gly Arg Leu Asp Lys
    50                  55                  60

Leu Thr Val Thr Ser Gln Asn Leu Gln Leu Glu Asn Leu Arg Met Lys
65                  70                  75                  80

Leu Pro Lys Pro Ala Lys Pro Met Ser Gln Met Arg Met Ala Thr Pro
                85                  90                  95

Met Leu Met Arg Ala Leu Pro Met Ala Gly Pro Glu Pro Met Lys Asn
            100                 105                 110

Ala Thr Lys Tyr Gly Asn Met Thr Gln Asp His Val Met His Leu Leu
        115                 120                 125

Leu Lys Ala Asp Pro Leu Lys Val Tyr Pro Gln Leu Lys Gly Ser Leu
    130                 135                 140

Pro Glu Asn Leu Lys His Leu Lys Asp Ser Met Asp Gly Leu Asp Trp
145                 150                 155                 160

Lys Leu Phe Glu Ser Trp Leu His Gln Trp Leu Leu Phe Glu Met Ser
                165                 170                 175

Lys Asn Ser Leu Glu Glu Lys Pro Phe Glu Gly Pro Pro Lys Val Leu
            180                 185                 190

Thr Gln Cys Gln Glu Val Ser Arg Ile Pro Ala Ile His Pro Gly
            195                 200                 205

Val Phe Lys Pro Asn Cys Asp Glu Asn Gly Asn Tyr Met Pro Leu Gln
210                 215                 220

Cys Tyr Gly Ser Ile Gly Tyr Cys Trp Cys Val Phe Pro Asn Gly Thr
225                 230                 235                 240

Glu Val Pro His Thr Arg Ser Arg Gly His Arg Asn Cys Ser Asp Pro
                245                 250                 255

Met Glu Met Glu Tyr Pro Ser Ser Gly Leu Gly Val
            260                 265

<210> SEQ ID NO 42
<211> LENGTH: 190
<212> TYPE: PRT
<213> ORGANISM: Bos taurus

<400> SEQUENCE: 42

Ile Ser Asn His Glu Gln Leu Pro Met Leu Gly Gln Arg Pro Gly Ala
1               5                   10                  15

Gln Glu Ser Lys Cys Ser Arg Gly Ala Leu Tyr Thr Gly Phe Ser Val
            20                  25                  30

Leu Val Ala Leu Leu Leu Ala Gly Gln Ala Thr Thr Ala Tyr Phe Leu
        35                  40                  45

Tyr Gln Gln Gln Gly Arg Leu Asp Lys Leu Thr Val Thr Ser Gln Asn
    50                  55                  60

Leu Gln Leu Glu Asn Leu Arg Met Lys Leu Pro Lys Pro Ala Lys Pro
65                  70                  75                  80

Met Ser Gln Met Arg Met Ala Thr Pro Met Leu Met Arg Ala Leu Pro
                85                  90                  95

Met Ala Gly Pro Glu Pro Met Lys Asn Ala Thr Lys Tyr Gly Asn Met
            100                 105                 110

Thr Gln Asp His Val Met His Leu Leu Leu Lys Ala Asp Pro Leu Lys
        115                 120                 125

Val Tyr Pro Gln Leu Lys Gly Ser Leu Pro Glu Asn Leu Lys His Leu
    130                 135                 140

Lys Asp Ser Met Asp Gly Leu Asp Trp Lys Leu Phe Glu Ser Trp Leu
145                 150                 155                 160

His Gln Trp Leu Leu Phe Glu Met Ser Lys Asn Ser Leu Glu Glu Lys
                165                 170                 175

Pro Phe Glu Gly Pro Pro Lys Pro Met Glu Met Glu Tyr
            180                 185                 190

<210> SEQ ID NO 43
<211> LENGTH: 204
<212> TYPE: PRT
<213> ORGANISM: Bos taurus

<400> SEQUENCE: 43

Met Glu Asp Gln Arg Asp Leu Ile Ser Asn His Glu Gln Leu Pro Met
1               5                   10                  15

Leu Gly Gln Arg Pro Gly Ala Gln Glu Ser Lys Cys Ser Arg Gly Ala
            20                  25                  30

Leu Tyr Thr Gly Phe Ser Val Leu Val Ala Leu Leu Leu Ala Gly Gln
        35                  40                  45

Ala Thr Thr Ala Tyr Phe Leu Tyr Gln Gln Gln Gly Arg Leu Asp Lys
    50                  55                  60

```
Leu Thr Val Thr Ser Gln Asn Leu Gln Leu Glu Asn Leu Arg Met Lys
 65                  70                  75                  80

Leu Pro Lys Pro Ala Lys Pro Met Ser Gln Met Arg Met Ala Thr Pro
                 85                  90                  95

Met Leu Met Arg Ala Leu Pro Met Ala Gly Pro Glu Pro Met Lys Asn
            100                 105                 110

Ala Thr Lys Tyr Gly Asn Met Thr Gln Asp His Val Met His Leu Leu
            115                 120                 125

Leu Lys Ala Asp Pro Leu Lys Val Tyr Pro Gln Leu Lys Gly Ser Leu
130                 135                 140

Pro Glu Asn Leu Lys His Leu Lys Asp Ser Met Asp Gly Leu Asp Trp
145                 150                 155                 160

Lys Leu Phe Glu Ser Trp Leu His Gln Trp Leu Leu Phe Glu Met Ser
                165                 170                 175

Lys Asn Ser Leu Glu Glu Lys Pro Phe Glu Gly Pro Pro Lys Asp Pro
            180                 185                 190

Met Glu Met Glu Tyr Pro Ser Ser Gly Leu Gly Val
            195                 200

<210> SEQ ID NO 44
<211> LENGTH: 208
<212> TYPE: PRT
<213> ORGANISM: Equus caballus

<400> SEQUENCE: 44

Met Glu Asp Gln Arg Asp Leu Ile Ser Asn His Glu Gln Val Pro Ile
 1               5                  10                  15

Leu Gly Gln Arg Pro Ala Ala Pro Glu Arg Lys Cys Ser Arg Gly Ala
                20                  25                  30

Leu Tyr Thr Gly Phe Ser Val Leu Val Ala Leu Leu Leu Ala Gly Gln
            35                  40                  45

Ala Thr Thr Ala Tyr Phe Leu Phe Gln Gln Gln Gly Arg Leu Asp Lys
 50                  55                  60

Leu Thr Val Thr Ala Gln Asn Leu Gln Leu Glu Lys Leu Arg Met Lys
 65                  70                  75                  80

Leu Pro Lys Ser Ala Lys Pro Val Ser Lys Ile Arg Val Ala Thr Pro
                 85                  90                  95

Met Leu Met Gln Ala Leu Pro Met Glu Gly Leu Ser His Gly Pro Met
            100                 105                 110

Gln Asn Ala Thr Lys Tyr Gly Asn Thr Thr Gln Asp His Val Met His
            115                 120                 125

Leu Leu Leu Arg Ala Asp Pro Leu Lys Val Tyr Pro Gln Leu Lys Gly
130                 135                 140

Ser Phe Gln Glu Asn Leu Lys His Leu Lys Ser Thr Met Asp Gly Leu
145                 150                 155                 160

Asp Trp Lys Val Phe Glu Asn Trp Met His Trp Leu Leu Phe Glu
                165                 170                 175

Met Ser Arg Asn Ser Leu Glu Glu Lys Pro Thr Gln Gly Pro Thr Lys
            180                 185                 190

Glu Pro Leu Glu Ile Glu Asp Leu Ser Ser Gly Val Gly Met Ala Lys
            195                 200                 205

<210> SEQ ID NO 45
<211> LENGTH: 208
<212> TYPE: PRT
```

<213> ORGANISM: Equus caballus

<400> SEQUENCE: 45

Met Glu Asp Gln Arg Asp Leu Ile Ser Asn His Glu Gln Val Pro Ile
1               5                   10                  15

Leu Gly Gln Arg Pro Ala Ala Pro Glu Arg Lys Cys Ser Arg Gly Ala
            20                  25                  30

Leu Tyr Thr Gly Phe Ser Val Leu Val Ala Leu Leu Leu Ala Gly Gln
        35                  40                  45

Ala Thr Thr Ala Tyr Phe Leu Phe Gln Gln Gln Gly Arg Pro Asp Lys
    50                  55                  60

Leu Thr Val Thr Ala Gln Asn Leu Gln Leu Glu Ser Leu Arg Met Lys
65                  70                  75                  80

Leu Pro Lys Ser Ala Lys Pro Val Ser Lys Ile Arg Val Ala Thr Pro
                85                  90                  95

Met Leu Met Gln Ala Leu Pro Met Glu Gly Leu Ser His Gly Pro Met
            100                 105                 110

Gln Asn Ala Thr Lys Tyr Gly Asn Thr Thr Gln Asp His Val Met His
        115                 120                 125

Leu Leu Leu Arg Ala Asp Pro Leu Lys Val Tyr Pro Gln Leu Lys Gly
    130                 135                 140

Ser Phe Gln Glu Asn Leu Lys His Leu Lys Ser Thr Met Asp Gly Leu
145                 150                 155                 160

Asp Trp Lys Val Phe Glu Asn Trp Met His Gln Trp Leu Leu Phe Glu
                165                 170                 175

Met Ser Arg Asn Ser Leu Glu Glu Lys Pro Thr Gln Gly Pro Thr Lys
            180                 185                 190

Glu Pro Leu Glu Ile Glu Asp Leu Ser Ser Gly Val Gly Met Ala Lys
        195                 200                 205

<210> SEQ ID NO 46
<211> LENGTH: 292
<212> TYPE: PRT
<213> ORGANISM: Oryctolagus cuniculus

<400> SEQUENCE: 46

Phe Arg Ser Gln Thr Arg Lys Leu Lys Thr Ser Glu Ala Arg Ala Met
1               5                   10                  15

Asp Asp Gln Arg Asp Leu Ile Ser Asn His Glu Gln Met Pro Met Leu
            20                  25                  30

Gly Gln Arg Pro Gly Ala Gln Glu Arg Lys Cys Ser Arg Gly Ala Leu
        35                  40                  45

Tyr Thr Gly Phe Ser Val Leu Val Ala Leu Leu Leu Ala Gly Gln Ala
    50                  55                  60

Thr Thr Ala Tyr Phe Leu Tyr Gln Gln Gln Asp Arg Leu Asp Lys Leu
65                  70                  75                  80

Thr Val Thr Ser Gln Asn Leu Gln Leu Glu Ser Leu Arg Met Lys Leu
                85                  90                  95

Pro Lys Ser Ala Lys Pro Met Ser Gln Met Arg Met Ala Ala Pro Met
            100                 105                 110

Met Met Gln Ala Leu Pro Met Glu Asn Leu Ser Gln Gly Pro Val Gln
        115                 120                 125

Asn Val Thr Lys Tyr Gly Asn Thr Thr Gln Asp Tyr Val Met His Leu
    130                 135                 140

Leu Leu Arg Ser Asp Pro Leu Lys Val Tyr Pro Gln Leu Lys Gly Ser

```
            145                 150                 155                 160
        Phe Pro Glu Asn Leu Lys Gln Leu Lys Gly Thr Met Asp Gly Leu Asn
                        165                 170                 175
        Trp Lys Val Phe Glu Ser Trp Leu His Gln Trp Leu Leu Phe Glu Met
                        180                 185                 190
        Ser Lys Asn Ser Leu Glu Glu Lys Pro Thr Glu Ala Pro Thr Lys Val
                        195                 200                 205
        Leu Ser Lys Cys Leu Glu Glu Ala Ser His Val Pro Asp Val His Pro
                        210                 215                 220
        Gly Arg Phe Lys Pro Gln Cys Asp Glu Asn Gly Asn Tyr Met Pro Leu
        225                 230                 235                 240
        Gln Cys His Gly Ser Ile Gly Tyr Cys Trp Cys Val Phe Pro Asn Gly
                        245                 250                 255
        Thr Glu Val Pro His Thr Arg Ser Arg Gly His His Asn Cys Ser Glu
                        260                 265                 270
        Pro Met Glu Phe Glu Tyr Pro Ser Ser Gly Leu Asp Met Ala Arg Pro
                        275                 280                 285
        Glu Met Gly Lys
                        290

<210> SEQ ID NO 47
<211> LENGTH: 282
<212> TYPE: PRT
<213> ORGANISM: Otolemur garnettii

<400> SEQUENCE: 47

Met Glu Asp Gln Arg Asp Leu Ile Ser Asn His Glu Gln Thr Pro Ile
1               5                   10                  15
Leu Ser Gln Arg Ala Gly Ala Pro Glu Arg Gln Cys Ser Arg Gly Ala
                20                  25                  30
Leu Tyr Thr Gly Phe Ser Val Leu Val Ala Leu Leu Leu Ala Gly Gln
                35                  40                  45
Ala Thr Thr Ala Tyr Phe Leu Tyr Gln Gln Gln Gly Arg Leu Asp Lys
        50                  55                  60
Leu Thr Val Thr Ser Gln Asn Leu Gln Leu Glu Asn Leu Arg Met Lys
65                  70                  75                  80
Leu Pro Lys Pro Pro Lys Pro Met Ser Lys Met Arg Met Ala Thr Pro
                85                  90                  95
Leu Met Met Gln Ala Leu Pro Met Glu Gly Leu Ala Gln Arg Pro Val
                100                 105                 110
Gln Asn Ala Thr Lys Tyr Gly Asn Met Thr Gln Asp His Val Met His
                115                 120                 125
Leu Leu Leu Lys Ala Asp Pro Leu Lys Val Tyr Pro Gln Met Lys Gly
        130                 135                 140
Asn Phe Pro Glu Asn Leu Lys His Leu Lys Ser Thr Met Glu Thr Leu
145                 150                 155                 160
Asp Trp Lys Val Phe Glu Ser Trp Met His Gln Trp Leu Leu Phe Glu
                165                 170                 175
Met Ser Lys Asn Ser Gly Glu Glu Lys Pro Thr Glu Ala Pro Pro Lys
                180                 185                 190
Val Leu Thr Lys Cys Gln Glu Glu Phe Ser Arg Val Pro Ala Ile His
                195                 200                 205
Pro Gly Thr Phe Arg Pro Lys Cys Asp Glu Asn Gly Asn Tyr Met Pro
        210                 215                 220
```

```
Leu Gln Cys His Gly Ser Ile Gly Tyr Cys Trp Cys Val Phe Pro Asn
225                 230                 235                 240

Gly Thr Glu Val Pro His Thr Arg Ser Arg Gly Gln His Asn Cys Ser
            245                 250                 255

Glu Pro Gln Asp Leu Glu Asp Pro Ser Ser Gly Leu Gly Phe Thr Lys
            260                 265                 270

Gln Glu Pro Gly Ile Gly Lys Gly Pro Val
            275                 280
```

<210> SEQ ID NO 48
<211> LENGTH: 375
<212> TYPE: PRT
<213> ORGANISM: Tupaia chinensis

<400> SEQUENCE: 48

```
Met Asp Asp Gln Arg Asp Leu Ile Ser Asn His Glu Gln Val Pro Ile
1               5                   10                  15

Leu Gly Gln Arg Pro Arg Glu Ala Glu Ser Lys Cys Gly Arg Gly Ala
            20                  25                  30

Leu Tyr Thr Gly Phe Ser Val Leu Val Ala Leu Leu Leu Ala Gly Gln
            35                  40                  45

Ala Thr Thr Ala Tyr Phe Leu Tyr Gln Gln Gln Gly Gln Leu His Lys
        50                  55                  60

Leu Thr Val Thr Ser Gln Asn Leu Gln Leu Glu Asn Leu Arg Met Lys
65                  70                  75                  80

Leu Pro Lys Pro Ala Lys Pro Leu Ser Lys Met Arg Met Ala Thr Pro
                85                  90                  95

Leu Leu Met Arg Ala Leu Pro Met Asp Gly Leu Pro Gln Gly Pro Val
            100                 105                 110

Gln Asn Ala Thr Lys Tyr Gly Asn Met Thr Gln Asp His Val Met His
        115                 120                 125

Leu Leu Leu Lys Ala Asp Pro Leu Lys Val Tyr Pro Gln Leu Lys Gly
    130                 135                 140

Ser Phe Pro Glu Asn Leu Lys His Leu Lys Ser Thr Met Glu Thr Met
145                 150                 155                 160

Asp Trp Lys Val Phe Glu Ser Trp Met His Gln Trp Leu Leu Phe Glu
                165                 170                 175

Met Ser Lys Asn Ser Met Glu Glu Lys Pro Thr Glu Pro Pro Thr Lys
            180                 185                 190

Ala Leu Thr Lys Cys Gln Glu Glu Val Ser Arg Ile Pro Ala Val His
        195                 200                 205

Pro Gly Thr Phe Arg Pro Lys Cys Asp Glu Asn Gly Asn Tyr Met Pro
    210                 215                 220

Leu Gln Cys His Gly Ser Ile Gly Tyr Cys Trp Cys Val Phe Pro Asn
225                 230                 235                 240

Gly Thr Glu Val Pro His Thr Arg Ser Arg Gly His His Asn Cys Ser
                245                 250                 255

Gly Pro Thr Cys Leu Ala Leu Trp Asp His Leu Asp Ala Arg Ala Ala
            260                 265                 270

Leu Leu Gln Glu Ala Tyr Leu Gly Leu Val Pro Val Ala Leu Arg Arg
        275                 280                 285

Ser Val Pro Leu Ser Ser Ser Val Gly Glu Lys Tyr Glu Arg Leu Leu
    290                 295                 300

Lys Leu Leu Trp Pro Pro Glu Gln Ile Leu Gly Leu Gln Gly Cys Leu
305                 310                 315                 320
```

```
Arg Ala Gly Gln Gly Ser Ala Ser Cys Thr Leu Gln Glu Gly Ala Arg
                325                 330                 335

Gly Ser Ala Leu Ile Thr Gln Gln Ala Leu Trp Ala Trp Val Glu Leu
            340                 345                 350

His Pro Cys Lys Val Trp Ala Val Gly His Glu His Ser Pro Cys Ser
        355                 360                 365

Gly Gly Ser Asp Thr Arg Lys
    370                 375

<210> SEQ ID NO 49
<211> LENGTH: 279
<212> TYPE: PRT
<213> ORGANISM: Ictidomys tridecemlineatus

<400> SEQUENCE: 49

Met Glu Asp Gln Arg Asp Leu Ile Ser Asn His Glu Gln Leu Pro Ile
1               5                   10                  15

Leu Gly Gln Arg Pro Arg Glu Gln Glu Arg Cys Ser Arg Gly Thr Leu
            20                  25                  30

Tyr Thr Gly Phe Ser Val Leu Val Ala Leu Leu Leu Ala Gly Gln Ala
        35                  40                  45

Thr Thr Ala Tyr Phe Leu Tyr Gln Gln Gln Gly Arg Leu Asp Lys Leu
    50                  55                  60

Thr Val Thr Ser Gln Asn Leu Gln Leu Glu Asn Leu Arg Met Lys Leu
65                  70                  75                  80

Pro Lys Pro Pro Lys Pro Val Ser Gln Leu Arg Met Ala Thr Pro Leu
                85                  90                  95

Leu Met Gln Ala Leu Pro Met Glu Gly Leu Arg Gln Gly Pro Lys Gln
            100                 105                 110

Asn Ala Thr Lys Tyr Gly Asn Met Thr Gln Asp His Val Met His Leu
        115                 120                 125

Leu Leu Lys Ser Asn Pro Leu Lys Val Tyr Pro Gln Leu Lys Gly Ser
    130                 135                 140

Phe Pro Glu Asn Leu Lys His Leu Lys Ser Thr Met Asp Asn Leu Asp
145                 150                 155                 160

Trp Lys Ile Phe Glu Asn Trp Leu His Gln Trp Leu Leu Phe Glu Met
                165                 170                 175

Ser Lys Asn Ser Leu Glu Glu Lys Pro Thr Glu Ala Pro Thr Arg Val
            180                 185                 190

Leu Thr Lys Cys Gln Glu Glu Val Ser His Ile Pro Ala Val His Pro
        195                 200                 205

Gly Ala Phe Arg Pro Lys Cys Asp Glu Asn Gly Asn Tyr Met Pro Leu
    210                 215                 220

Gln Cys His Gly Ser Ile Gly Tyr Cys Trp Cys Val Phe Pro Asn Gly
225                 230                 235                 240

Thr Glu Val Pro His Thr Arg Ser Arg Gly Arg His Asp Cys Ser Glu
                245                 250                 255

Pro Leu Glu Leu Glu Asp Val Ser Ser Gly Leu Gly Val Thr Lys Gln
            260                 265                 270

Asp Leu Gly Gln Val Ile Met
        275

<210> SEQ ID NO 50
<211> LENGTH: 209
<212> TYPE: PRT
```

<213> ORGANISM: Sarcophilus harrisii

<400> SEQUENCE: 50

Met Glu Asp Gln Arg Asp Leu Ile Ser Asn His Glu Gln Gln Pro Met
1               5                   10                  15

Leu Gly Gly Ser Ala Gly Gly Gln His Arg Ser Cys Asn Gln Gly Ala
            20                  25                  30

Phe Tyr Thr Gly Phe Ser Val Leu Val Ala Leu Leu Ile Ala Gly Gln
        35                  40                  45

Ala Ala Thr Val Tyr Phe Val Tyr Gln Gln Gln Gly Arg Leu Asp Lys
    50                  55                  60

Leu Thr Val Thr Ser Gln Asn Leu Gln Leu Glu Ser Leu Lys Met Lys
65                  70                  75                  80

Leu Pro Lys Ala Ser Ile Pro Met Asn Lys Leu Arg Leu Ala Thr Pro
                85                  90                  95

Met Leu Met Arg Glu Leu Glu Pro Glu Thr Leu Pro Ser Met Asp Leu
            100                 105                 110

Thr Lys Ile Gly Asn Asn Thr Lys Asp Gln Val Lys Tyr Leu Leu Leu
        115                 120                 125

Gln Ser Asp Pro Arg Arg Ser Phe Pro Glu Leu Thr Lys Ser Phe Gln
    130                 135                 140

Glu Asn Met Lys Lys Leu Lys Asn Asn Met Glu Thr Lys Asn Trp Lys
145                 150                 155                 160

Asn Phe Glu Asn Trp Met His Gln Trp Leu Leu Phe Glu Met Ser Lys
                165                 170                 175

Lys Pro Asn Glu Glu Asn Val Glu Lys Lys Thr Glu Pro Leu Gln Lys
            180                 185                 190

Gly Leu Leu Asp Glu Glu Met Phe Ser Ser Gly Leu Gly Phe Pro Lys
        195                 200                 205

Gln

<210> SEQ ID NO 51
<211> LENGTH: 9
<212> TYPE: PRT
<213> ORGANISM: Artificial Sequence
<220> FEATURE:
<223> OTHER INFORMATION: Amino acid sequence of the res linker

<400> SEQUENCE: 51

Ser Asp Arg Tyr Leu Asn Arg Arg Ala
1               5

<210> SEQ ID NO 52
<211> LENGTH: 27
<212> TYPE: DNA
<213> ORGANISM: Artificial sequence
<220> FEATURE:
<223> OTHER INFORMATION: Nucleotide sequence encoding the res linker

<400> SEQUENCE: 52
agcgatcgct atttaaatag gcgcgcc                                    27

<210> SEQ ID NO 53
<211> LENGTH: 9
<212> TYPE: PRT
<213> ORGANISM: Artificial Sequence
<220> FEATURE:
<223> OTHER INFORMATION: Amino acid sequence of the HA tag

<400> SEQUENCE: 53

Tyr Pro Tyr Asp Val Pro Asp Tyr Ala
1               5

<210> SEQ ID NO 54
<211> LENGTH: 27
<212> TYPE: DNA
<213> ORGANISM: Artificial Sequence
<220> FEATURE:
<223> OTHER INFORMATION: Nucleotide sequence encoding the HA tag

<400> SEQUENCE: 54
tacccatacg atgttccaga ttacgct                                         27

<210> SEQ ID NO 55
<211> LENGTH: 687
<212> TYPE: DNA
<213> ORGANISM: Murine

<400> SEQUENCE: 55
atggatgacc aacgcgacct catctctaac catgaacagt tgcccatact gggcaaccgc      60
cctagagagc cagaaaggtg cagccgtgga gctctgtaca ccggtgtctc tgtcctggtg     120
gctctgctct tggctgggca ggccaccact gcttacttcc tgtaccagca acagggccgc     180
ctagacaagc tgaccatcac ctcccagaac ctgcaactgg agagccttcg catgaagctt     240
ccgaaatctg ccaaacctgt gagccagatg cggatggcta ctcccttgct gatgcgtcca     300
atgtccatgg ataacatgct ccttgggcct gtgaagaacg ttacctccgg cggagagca      360 aggcgccgag cacggagatc tggacgaaag tacggcaaca tgacccagga ccatgtgatg     420
catctgctca cgaggtctgg acccctggag tacccgcagc tgaaggggac cttcccagag     480
aatctgaagc atcttaagaa ctccatggat ggcgtgaact ggaagatctt cgagagctgg     540
atgaagcagt ggctcttgtt tgagatgagc aagaactccc tggaggagaa aagcccacc      600 gaggctccac ctaaagagcc actggacatg gaagacctat cttctggcct gggagtgacc     660
aggcaggaac tgggtcaagt caccctg                                        687

<210> SEQ ID NO 56
<211> LENGTH: 229
<212> TYPE: PRT
<213> ORGANISM: Murine

<400> SEQUENCE: 56

Met Asp Asp Gln Arg Asp Leu Ile Ser Asn His Glu Gln Leu Pro Ile
1               5                   10                  15

Leu Gly Asn Arg Pro Arg Glu Pro Glu Arg Cys Ser Arg Gly Ala Leu
            20                  25                  30

Tyr Thr Gly Val Ser Val Leu Val Ala Leu Leu Leu Ala Gly Gln Ala
        35                  40                  45

Thr Thr Ala Tyr Phe Leu Tyr Gln Gln Gln Gly Arg Leu Asp Lys Leu
    50                  55                  60

Thr Ile Thr Ser Gln Asn Leu Gln Leu Glu Ser Leu Arg Met Lys Leu
65                  70                  75                  80

Pro Lys Ser Ala Lys Pro Val Ser Gln Met Arg Met Ala Thr Pro Leu
                85                  90                  95

Leu Met Arg Pro Met Ser Met Asp Asn Met Leu Leu Gly Pro Val Lys
            100                 105                 110

Asn Val Thr Ser Gly Arg Arg Ala Arg Arg Ala Arg Arg Ser Gly
        115                 120                 125

-continued

```
Arg Lys Tyr Gly Asn Met Thr Gln Asp His Val Met His Leu Leu Thr
    130                 135                 140

Arg Ser Gly Pro Leu Glu Tyr Pro Gln Leu Lys Gly Thr Phe Pro Glu
145                 150                 155                 160
Asn Leu Lys His Leu Lys Asn Ser Met Asp Gly Val Asn Trp Lys Ile
                165                 170                 175
Phe Glu Ser Trp Met Lys Gln Trp Leu Leu Phe Glu Met Ser Lys Asn
            180                 185                 190
Ser Leu Glu Glu Lys Lys Pro Thr Glu Ala Pro Pro Lys Glu Pro Leu
        195                 200                 205
Asp Met Glu Asp Leu Ser Ser Gly Leu Gly Val Thr Arg Gln Glu Leu
    210                 215                 220

Gly Gln Val Thr Leu
225

<210> SEQ ID NO 57
<211> LENGTH: 14
<212> TYPE: PRT
<213> ORGANISM: Artificial sequence
<220> FEATURE:
<223> OTHER INFORMATION: Exemplary furin cleavage site

<400> SEQUENCE: 57

Ser Gly Arg Arg Ala Arg Arg Arg Ala Arg Arg Ser Gly Arg
1               5                   10

<210> SEQ ID NO 58
<211> LENGTH: 55
<212> TYPE: DNA
<213> ORGANISM: Artificial sequence
<220> FEATURE:
<223> OTHER INFORMATION: Nucleotide sequence encoding SP-albumin

<400> SEQUENCE: 58
atgaagtggg tgaccttcat ctctctgctg ttcctgttta gctccgccta cagct          55

<210> SEQ ID NO 59
<211> LENGTH: 18
<212> TYPE: PRT
<213> ORGANISM: Artificial sequence
<220> FEATURE:
<223> OTHER INFORMATION: Amino acid sequence of SP-albumin

<400> SEQUENCE: 59

Met Lys Trp Val Thr Phe Ile Ser Leu Leu Phe Leu Phe Ser Ser Ala
1               5                   10                  15
Tyr Ser

<210> SEQ ID NO 60
<211> LENGTH: 1689
<212> TYPE: DNA
<213> ORGANISM: Artificial sequence
<220> FEATURE:
<223> OTHER INFORMATION: Nucleotide sequence encoding SP-ALB-CIDR 19-30

<400> SEQUENCE: 60
atgaagtggg tgaccttcat ctctctgctg ttcctgttta gctccgccta cagctattta      60
aataggcgcg ccccggactg tgtggttgtt tgtgaaggag gaaattgcaa agagaaaact     120
gaggacgata attgtaggtc tgaaatcatc aagaagatcc tgaagtacga gactcctact     180
ccgattgacg tgctgtacag cggtaaaggc cagggactta tcacgaaaaa gctggaggat     240
```

```
ttctgcagct cgaccaccaa ctacgaagga acgaacgtgc agaagtggaa atgctacaat    300
aagaacaagg actacaataa ctgcgagatg aacatttcca gctacaaaga tgcaactgat    360
cccaacgtga tgctttcggt cgagtgcttt cactcctggg ccaagaatct cctgatcgac    420
accatacggt gggaacacca gctgaagaat tgtatcaaca atactaatgt gactgattgt    480
acctcaaagt gcatcaaaaa ctgcgaatgc tacgaaaagt ggattaagga aaggagaag    540 gaatggccac aagtcaaagg cgtgctcaag aagaaagacg agacttcaca aactactat    600 gacaagctga aggatgtgtt cgatcgcttc ctgttcgagg tcaaggggc tctggaccag    660 gacgagaagg gaaagtggga ccaattcacc aaagatctcg aaaagaagtt tgggccttcc    720
gtggaatccg ccggcaccgc aaactcgcaa gatgcgatcg agctgctcct ggaccatctg    780
aacgacaacg cgactacctg taaggataac aacagcctgg ccgtggaaaa ctgcggcagc    840
ccggactgcg tggtgaagtg tgacggtaaa acgtgcgaac agaagaagga cgatgaaaac    900
tgcagatcga agatcatcca gaagatcctc caaggagaag aaccaaccgt gatcgacgtg    960
ttgtactcgg gaaagggaca aggtctgatc actaagaagc tgcatgactt ctgctccagc   1020
accaacaaag aggatgataa gtattacaaa aagtggaagt gctacaacaa aaactccgac   1080
tacaacaatt gtgagctcat ttcctcgctc tcaactgatc caaccgaccc gaaagtcatg   1140
ctctcgatta agtgcttcga ctcatgggcc cgcaatctgt tggtcgatgc cttgaagtgg   1200
gaacatcagc tcaagaattg catcaataac accaacgtca ccgactgcaa atcgaactgc   1260
aataacaact gcaagtgcta cgaagagtgg atcaagcaga aggaaaaaga atggcagaag   1320 gtgaagggg tgttgaagaa gaaggataag aattcagaca actactacaa gaatgtcaaa   1380
aatctgttct actcatttct cttccaagtg atctacgagc ttgagaagga agaaaagaac   1440
ggaaaatggg accagtttat ggaggacctg aaaagaaaa tcgaggcgag ccagaaaaac   1500
aaaggcaccg agaactccca agacgctatc gaactcctgc tggatcacct taaggataat   1560
gcaaccatct gcaaggacaa taacactaac gaagccggcc ggcctaaggt acccggggat   1620
cctctagagt cgacctgcag gcatgcaagc ttgggatctt tgtgaaggaa ccttacttct   1680
gtggtgtga                                                            1689
```

<210> SEQ ID NO 61
<211> LENGTH: 554
<212> TYPE: PRT
<213> ORGANISM: Artificial sequence
<220> FEATURE:
<223> OTHER INFORMATION: Amino acid sequence of SP-Alb-CIDR 19-30

<400> SEQUENCE: 61

```
Met Lys Trp Val Thr Phe Ile Ser Leu Leu Phe Leu Phe Ser Ser Ala
1               5                   10                  15

Tyr Ser Tyr Leu Asn Arg Arg Ala Pro Asp Cys Val Val Cys Glu
            20                  25                  30

Gly Gly Asn Cys Lys Glu Lys Thr Glu Asp Asp Asn Cys Arg Ser Glu
        35                  40                  45

Ile Ile Lys Lys Ile Leu Lys Tyr Glu Thr Pro Thr Pro Ile Asp Val
    50                  55                  60

Leu Tyr Ser Gly Lys Gly Gln Gly Leu Ile Thr Lys Lys Leu Glu Asp
65                  70                  75                  80

Phe Cys Ser Ser Thr Thr Asn Tyr Glu Gly Thr Asn Val Gln Lys Trp
                85                  90                  95
```

-continued

```
Lys Cys Tyr Asn Lys Asn Lys Asp Tyr Asn Asn Cys Glu Met Asn Ile
            100                 105                 110

Ser Ser Tyr Lys Asp Ala Thr Asp Pro Asn Val Met Leu Ser Val Glu
        115                 120                 125

Cys Phe His Ser Trp Ala Lys Asn Leu Leu Ile Asp Thr Ile Arg Trp
    130                 135                 140

Glu His Gln Leu Lys Asn Cys Ile Asn Asn Thr Asn Val Thr Asp Cys
145                 150                 155                 160

Thr Ser Lys Cys Ile Lys Asn Cys Glu Cys Tyr Glu Lys Trp Ile Lys
                165                 170                 175

Glu Lys Glu Lys Glu Trp Pro Gln Val Lys Gly Val Leu Lys Lys Lys
            180                 185                 190

Asp Glu Thr Ser His Asn Tyr Tyr Asp Lys Leu Lys Asp Val Phe Asp
        195                 200                 205

Arg Phe Leu Phe Glu Val Lys Gly Ala Leu Asp Gln Asp Glu Lys Gly
    210                 215                 220

Lys Trp Asp Gln Phe Thr Lys Asp Leu Glu Lys Lys Phe Gly Pro Ser
225                 230                 235                 240

Val Glu Ser Ala Gly Thr Ala Asn Ser Gln Asp Ala Ile Glu Leu Leu
                245                 250                 255

Leu Asp His Leu Asn Asp Asn Ala Thr Thr Cys Lys Asp Asn Asn Ser
            260                 265                 270

Leu Ala Val Glu Asn Cys Gly Ser Pro Asp Cys Val Val Lys Cys Asp
        275                 280                 285

Gly Lys Thr Cys Glu Gln Lys Lys Asp Asp Glu Asn Cys Arg Ser Lys
    290                 295                 300

Ile Ile Gln Lys Ile Leu Gln Gly Glu Glu Pro Thr Val Ile Asp Val
305                 310                 315                 320

Leu Tyr Ser Gly Lys Gly Gln Gly Leu Ile Thr Lys Lys Leu His Asp
                325                 330                 335

Phe Cys Ser Ser Thr Asn Lys Glu Asp Asp Lys Tyr Tyr Lys Lys Trp
            340                 345                 350

Lys Cys Tyr Asn Lys Asn Ser Asp Tyr Asn Asn Cys Glu Leu Ile Ser
        355                 360                 365

Ser Leu Ser Thr Asp Pro Thr Asp Pro Lys Val Met Leu Ser Ile Lys
    370                 375                 380

Cys Phe Asp Ser Trp Ala Arg Asn Leu Leu Val Asp Ala Leu Lys Trp
385                 390                 395                 400

Glu His Gln Leu Lys Asn Cys Ile Asn Asn Thr Asn Val Thr Asp Cys
                405                 410                 415

Lys Ser Asn Cys Asn Asn Asn Cys Lys Cys Tyr Glu Glu Trp Ile Lys
            420                 425                 430

Gln Lys Glu Lys Glu Trp Gln Lys Val Lys Gly Val Leu Lys Lys Lys
        435                 440                 445

Asp Lys Asn Ser Asp Asn Tyr Tyr Lys Asn Val Lys Asn Leu Phe Tyr
    450                 455                 460

Ser Phe Leu Phe Gln Val Ile Tyr Glu Leu Glu Lys Glu Lys Asn
465                 470                 475                 480

Gly Lys Trp Asp Gln Phe Met Glu Asp Leu Lys Lys Ile Glu Ala
                485                 490                 495

Ser Gln Lys Asn Lys Gly Thr Glu Asn Ser Gln Asp Ala Ile Glu Leu
            500                 505                 510

Leu Leu Asp His Leu Lys Asp Asn Ala Thr Ile Cys Lys Asp Asn Asn
```

515                 520                 525
Thr Asn Glu Ala Gly Arg Pro Lys Val Pro Gly Asp Pro Leu Glu Ser
    530                 535                 540

Thr Cys Arg His Ala Ser Leu Gly Ser Leu
545                 550

<210> SEQ ID NO 62
<211> LENGTH: 2310
<212> TYPE: DNA
<213> ORGANISM: Artificial sequence
<220> FEATURE:
<223> OTHER INFORMATION: Nucleotide sequence encoding Ii-CIDR 19-30

<400> SEQUENCE: 62

| | | | | | |
|---|---|---|---|---|---|
| atggatgacc | aacgcgacct | catctctaac | catgaacagt | tgcccatact | gggcaaccgc | 60 |
| cctagagagc | cagaaaggtg | cagccgtgga | gctctgtaca | ccggtgtctc | tgtcctggtg | 120 |
| gctctgctct | tggctgggca | ggccaccact | gcttacttcc | tgtaccagca | acagggccgc | 180 |
| ctagacaagc | tgaccatcac | ctcccagaac | ctgcaactgg | agagccttcg | catgaagctt | 240 |
| ccgaaatctg | ccaaacctgt | gagccagatg | cggatggcta | ctcccttgct | gatgcgtcca | 300 |
| atgtccatgg | ataacatgct | ccttgggcct | gtgaagaacg | ttaccaagta | cggcaacatg | 360 |
| acccaggacc | atgtgatgca | tctgctcacg | aggtctggac | ccctggagta | cccgcagctg | 420 |
| aagggggacct | tcccagagaa | tctgaagcat | cttaagaact | ccatggatgg | cgtgaactgg | 480 |
| aagatcttcg | agagctggat | gaagcagtgg | ctcttgtttg | agatgagcaa | gaactccctg | 540 |
| gaggagaaga | agcccaccga | ggctccacct | aaagagccac | tggacatgga | agacctatct | 600 |
| tctggcctgg | gagtgaccag | gcaggaactg | ggtcaagtca | ccctgagcga | tcgctattta | 660 |
| aataggcgcg | ccccggactg | tgtggttgtt | tgtgaaggag | gaaattgcaa | agagaaaact | 720 |
| gaggacgata | attgtaggtc | tgaaatcatc | aagaagatcc | tgaagtacga | gactcctact | 780 |
| ccgattgacg | tgctgtacag | cggtaaaggc | cagggactta | tcacgaaaaa | gctggaggat | 840 |
| ttctgcagct | cgaccaccaa | ctacgaagga | acgaacgtgc | agaagtggaa | atgctacaat | 900 |
| aagaacaagg | actacaataa | ctgcgagatg | aacatttcca | gctacaaaga | tgcaactgat | 960 |
| cccaacgtga | tgcttcggt | cgagtgcttt | cactcctggg | ccaagaatct | cctgatcgac | 1020 |
| accatacggt | gggaacacca | gctgaagaat | tgtatcaaca | atactaatgt | gactgattgt | 1080 |
| acctcaaagt | gcatcaaaaa | ctgcgaatgc | tacgaaaagt | ggattaagga | aaaggagaag | 1140 |
| gaatggccac | aagtcaaagg | cgtgctcaag | aagaaagacg | agacttcaca | caactactat | 1200 |
| gacaagctga | aggatgtgtt | cgatcgcttc | ctgttcgagg | tcaaggggc | tctggaccag | 1260 |
| gacgagaagg | gaaagtggga | ccaattcacc | aaagatctcg | aaaagaagtt | tgggccttcc | 1320 |
| gtggaatccg | ccggcaccgc | aaactcgcaa | gatgcgatcg | agctgctcct | ggaccatctg | 1380 |
| aacgacaacg | cgactacctg | taaggataac | aacagcctgg | ccgtggaaaa | ctgcggcagc | 1440 |
| ccggactgcg | tggtgaagtg | tgacggtaaa | acgtgcgaac | agaagaagga | cgatgaaaac | 1500 |
| tgcagatcga | agatcatcca | gaagatcctc | aaggagaag | aaccaaccgt | gatcgacgtg | 1560 |
| ttgtactcgg | aaagggaca | aggtctgatc | actaagaagc | tgcatgactt | ctgctccagc | 1620 |
| accaacaaag | aggatgataa | gtattacaaa | aagtggaagt | gctacaacaa | aaactccgac | 1680 |
| tacaacaatt | gtgagctcat | ttcctcgctc | tcaactgatc | caaccgaccc | gaaagtcatg | 1740 |
| ctctcgatta | agtgcttcga | ctcatgggcc | cgcaatctgt | tggtcgatgc | cttgaagtgg | 1800 |
| gaacatcagc | tcaagaattg | catcaataac | accaacgtca | ccgactgcaa | atcgaactgc | 1860 |

-continued

```
aataacaact gcaagtgcta cgaagagtgg atcaagcaga aggaaaaaga atggcagaag    1920
gtgaaagggg tgttgaagaa gaaggataag aattcagaca actactacaa gaatgtcaaa    1980
aatctgttct actcatttct cttccaagtg atctacgagc ttgagaagga agaaaagaac    2040
ggaaaatggg accagtttat ggaggacctg aaaaagaaaa tcgaggcgag ccagaaaaac    2100
aaaggcaccg agaactccca agacgctatc gaactcctgc tggatcacct taaggataat    2160
gcaaccatct gcaaggacaa taacactaac gaagccggcc ggcctaactc gagacctgca    2220
ggcatgcaag cttgggatct ttgtgaagga accttacttc tgtggtgtga cataattgga    2280
caaactacct acagagattt aaagctctaa                                    2310
```

<210> SEQ ID NO 63
<211> LENGTH: 769
<212> TYPE: PRT
<213> ORGANISM: Artificial sequence
<220> FEATURE:
<223> OTHER INFORMATION: Amino acid sequence of Ii-CIDR 19-30

<400> SEQUENCE: 63

```
Met Asp Asp Gln Arg Asp Leu Ile Ser Asn His Glu Gln Leu Pro Ile
1               5                   10                  15

Leu Gly Asn Arg Pro Arg Glu Pro Glu Arg Cys Ser Arg Gly Ala Leu
            20                  25                  30

Tyr Thr Gly Val Ser Val Leu Val Ala Leu Leu Leu Ala Gly Gln Ala
        35                  40                  45

Thr Thr Ala Tyr Phe Leu Tyr Gln Gln Gln Gly Arg Leu Asp Lys Leu
    50                  55                  60

Thr Ile Thr Ser Gln Asn Leu Gln Leu Glu Ser Leu Arg Met Lys Leu
65                  70                  75                  80

Pro Lys Ser Ala Lys Pro Val Ser Gln Met Arg Met Ala Thr Pro Leu
                85                  90                  95

Leu Met Arg Pro Met Ser Met Asp Asn Met Leu Leu Gly Pro Val Lys
            100                 105                 110

Asn Val Thr Lys Tyr Gly Asn Met Thr Gln Asp His Val Met His Leu
        115                 120                 125

Leu Thr Arg Ser Gly Pro Leu Glu Tyr Pro Gln Leu Lys Gly Thr Phe
    130                 135                 140

Pro Glu Asn Leu Lys His Leu Lys Asn Ser Met Asp Gly Val Asn Trp
145                 150                 155                 160

Lys Ile Phe Glu Ser Trp Met Lys Gln Trp Leu Leu Phe Glu Met Ser
                165                 170                 175

Lys Asn Ser Leu Glu Glu Lys Lys Pro Thr Glu Ala Pro Pro Lys Glu
            180                 185                 190

Pro Leu Asp Met Glu Asp Leu Ser Ser Gly Leu Gly Val Thr Arg Gln
        195                 200                 205

Glu Leu Gly Gln Val Thr Leu Ser Asp Arg Tyr Leu Asn Arg Arg Ala
    210                 215                 220

Pro Asp Cys Val Val Val Cys Glu Gly Gly Asn Cys Lys Glu Lys Thr
225                 230                 235                 240

Glu Asp Asp Asn Cys Arg Ser Glu Ile Ile Lys Ile Leu Lys Tyr
                245                 250                 255

Glu Thr Pro Thr Pro Ile Asp Val Leu Tyr Ser Gly Lys Gly Gln Gly
            260                 265                 270

Leu Ile Thr Lys Lys Leu Glu Asp Phe Cys Ser Ser Thr Thr Asn Tyr
```

```
                275                 280                 285
Glu Gly Thr Asn Val Gln Lys Trp Lys Cys Tyr Asn Lys Asn Lys Asp
            290                 295                 300
Tyr Asn Asn Cys Glu Met Asn Ile Ser Ser Tyr Lys Asp Ala Thr Asp
305                 310                 315                 320
Pro Asn Val Met Leu Ser Val Glu Cys Phe His Ser Trp Ala Lys Asn
                325                 330                 335
Leu Leu Ile Asp Thr Ile Arg Trp Glu His Gln Leu Lys Asn Cys Ile
                340                 345                 350
Asn Asn Thr Asn Val Thr Asp Cys Thr Ser Lys Cys Ile Lys Asn Cys
                355                 360                 365
Glu Cys Tyr Glu Lys Trp Ile Lys Glu Lys Glu Lys Glu Trp Pro Gln
            370                 375                 380
Val Lys Gly Val Leu Lys Lys Lys Asp Glu Thr Ser His Asn Tyr Tyr
385                 390                 395                 400
Asp Lys Leu Lys Asp Val Phe Asp Arg Phe Leu Phe Glu Val Lys Gly
                405                 410                 415
Ala Leu Asp Gln Asp Glu Lys Gly Lys Trp Asp Gln Phe Thr Lys Asp
            420                 425                 430
Leu Glu Lys Lys Phe Gly Pro Ser Val Glu Ser Ala Gly Thr Ala Asn
            435                 440                 445
Ser Gln Asp Ala Ile Glu Leu Leu Leu Asp His Leu Asn Asp Asn Ala
            450                 455                 460
Thr Thr Cys Lys Asp Asn Asn Ser Leu Ala Val Glu Asn Cys Gly Ser
465                 470                 475                 480
Pro Asp Cys Val Val Lys Cys Asp Gly Lys Thr Cys Glu Gln Lys Lys
                485                 490                 495
Asp Asp Glu Asn Cys Arg Ser Lys Ile Ile Gln Lys Ile Leu Gln Gly
            500                 505                 510
Glu Glu Pro Thr Val Ile Asp Val Leu Tyr Ser Gly Lys Gly Gln Gly
            515                 520                 525
Leu Ile Thr Lys Lys Leu His Asp Phe Cys Ser Ser Thr Asn Lys Glu
            530                 535                 540
Asp Asp Lys Tyr Tyr Lys Lys Trp Lys Cys Tyr Asn Lys Asn Ser Asp
545                 550                 555                 560
Tyr Asn Asn Cys Glu Leu Ile Ser Ser Leu Ser Thr Asp Pro Thr Asp
                565                 570                 575
Pro Lys Val Met Leu Ser Ile Lys Cys Phe Asp Ser Trp Ala Arg Asn
                580                 585                 590
Leu Leu Val Asp Ala Leu Lys Trp Glu His Gln Leu Lys Asn Cys Ile
            595                 600                 605
Asn Asn Thr Asn Val Thr Asp Cys Lys Ser Asn Cys Asn Asn Asn Cys
            610                 615                 620
Lys Cys Tyr Glu Glu Trp Ile Lys Gln Lys Glu Lys Glu Trp Gln Lys
625                 630                 635                 640
Val Lys Gly Val Leu Lys Lys Asp Lys Asn Ser Asp Asn Tyr Tyr
                645                 650                 655
Lys Asn Val Lys Asn Leu Phe Tyr Ser Phe Leu Phe Gln Val Ile Tyr
                660                 665                 670
Glu Leu Glu Lys Glu Glu Lys Asn Gly Lys Trp Asp Gln Phe Met Glu
            675                 680                 685
Asp Leu Lys Lys Lys Ile Glu Ala Ser Gln Lys Asn Lys Gly Thr Glu
            690                 695                 700
```

Asn Ser Gln Asp Ala Ile Glu Leu Leu Leu Asp His Leu Lys Asp Asn
705                 710                 715                 720

Ala Thr Ile Cys Lys Asp Asn Asn Thr Asn Glu Ala Gly Arg Pro Asn
            725                 730                 735

Ser Arg Pro Ala Gly Met Gln Ala Trp Asp Leu Cys Glu Gly Thr Leu
        740                 745                 750

Leu Leu Trp Cys Asp Ile Ile Gly Gln Thr Thr Tyr Arg Asp Leu Lys
        755                 760                 765

Leu

<210> SEQ ID NO 64
<211> LENGTH: 2352
<212> TYPE: DNA
<213> ORGANISM: Artificial sequence
<220> FEATURE:
<223> OTHER INFORMATION: Nucleotide sequence encoding Ii/fur/int-CIDR 19-30

<400> SEQUENCE: 64

| | |
|---|---|
| atggatgacc aacgcgacct catctctaac catgaacagt tgcccatact gggcaaccgc | 60 |
| cctagagagc cagaaaggtg cagccgtgga gctctgtaca ccggtgtctc tgtcctggtg | 120 |
| gctctgctct tggctgggca ggccaccact gcttacttcc tgtaccagca cagggccgc | 180 |
| ctagacaagc tgaccatcac ctcccagaac ctgcaactgg agagccttcg catgaagctt | 240 |
| ccgaaatctg ccaaacctgt gagccagatg cggatggcta ctcccttgct gatgcgtcca | 300 |
| atgtccatgg ataacatgct ccttgggcct gtgaagaacg ttacctccgg gcggagagca | 360 |
| aggcgccgag cacggagatc tggacgaaag tacggcaaca tgacccagga ccatgtgatg | 420 |
| catctgctca cgaggtctgg acccctggag tacccgcagc tgaagggac cttcccagag | 480 |
| aatctgaagc atcttaagaa ctccatggat ggcgtgaact ggaagatctt cgagagctgg | 540 |
| atgaagcagt ggctcttgtt tgagatgagc aagaactccc tggaggagaa gaagcccaca | 600 |
| gaggctccac ctaaagagcc actggacatg gaagacctat cttctggcct gggagtgacc | 660 |
| aggcaggaac tgggtcaagt caccctgagc gatcgctatt taaataggcg cgccccggac | 720 |
| tgtgtggttg tttgtgaagg aggaaattgc aaagagaaaa ctgaggacga taattgtagg | 780 |
| tctgaaatca tcaagaagat cctgaagtac gagactccta ctccgattga cgtgctgtac | 840 |
| agcggtaaag gccagggact tatcacgaaa aagctggagg atttctgcag ctcgaccacc | 900 |
| aactacgaag gaacgaacgt gcagaagtgg aaatgctaca ataagaacaa ggactacaat | 960 |
| aactgcgaga tgaacatttc cagctacaaa gatgcaactg atcccaacgt gatgctttcg | 1020 |
| gtcgagtgct tcactcctg ggccaagaat ctcctgatcg acaccatacg gtgggaacac | 1080 |
| cagctgaaga attgtatcaa caatactaat gtgactgatt gtacctcaaa gtgcatcaaa | 1140 |
| aactgcgaat gctacgaaaa gtggattaag gaaaaggaga aggaatggcc acaagtcaaa | 1200 |
| ggcgtgctca agaagaaaga cgagacttca cacaactact atgacaagct gaaggatgtg | 1260 |
| ttcgatcgct tcctgttcga ggtcaagggg gctctggacc aggacgagaa gggaaagtgg | 1320 |
| gaccaattca ccaaagatct cgaaaagaag tttgggcctt ccgtggaatc cgccggcacc | 1380 |
| gcaaactcgc aagatgcgat cgagctgctc ctggaccatc tgaacgacaa cgcgactacc | 1440 |
| tgtaaggata caacagcct ggccgtggaa aactgcggca gcccggactg cgtggtgaag | 1500 |
| tgtgacggta aaacgtgcga acagaagaag gacgatgaaa actgcagatc gaagatcatc | 1560 |
| cagaagatcc tccaaggaga agaaccaacc gtgatcgacg tgttgtactc gggaaaggga | 1620 |

-continued

```
caaggtctga tcactaagaa gctgcatgac ttctgctcca gcaccaacaa agaggatgat   1680
aagtattaca aaaagtggaa gtgctacaac aaaaactccg actacaacaa ttgtgagctc   1740
atttcctcgc tctcaactga tccaaccgac ccgaaagtca tgctctcgat taagtgcttc   1800
gactcatggg cccgcaatct gttggtcgat gccttgaagt gggaacatca gctcaagaat   1860
tgcatcaata acaccaacgt caccgactgc aaatcgaact gcaataacaa ctgcaagtgc   1920
tacgaagagt ggatcaagca gaaggaaaaa gaatggcaga aggtgaaagg ggtgttgaag   1980
aagaaggata agaattcaga caactactac aagaatgtca aaaatctgtt ctactcattt   2040
ctcttccaag tgatctacga gcttgagaag gaagaaaaga acggaaaatg ggaccagttt   2100
atggaggacc tgaaaaagaa aatcgaggcg agccagaaaa acaaaggcac cgagaactcc   2160
caagacgcta tcgaactcct gctggatcac cttaaggata atgcaaccat ctgcaaggac   2220
aataacacta acgaagccgg ccggcctaac tcgagacctg caggcatgca agcttgggat   2280
ctttgtgaag gaaccttact tctgtggtgt gacataattg gacaaactac ctacagagat   2340
ttaaagctct aa                                                        2352
```

<210> SEQ ID NO 65
<211> LENGTH: 783
<212> TYPE: PRT
<213> ORGANISM: Artificial sequence
<220> FEATURE:
<223> OTHER INFORMATION: Amino acid sequence of Ii/fur/int-CIDR 19-30

<400> SEQUENCE: 65

```
Met Asp Asp Gln Arg Asp Leu Ile Ser Asn His Glu Gln Leu Pro Ile
1               5                   10                  15

Leu Gly Asn Arg Pro Arg Glu Pro Glu Arg Cys Ser Arg Gly Ala Leu
            20                  25                  30

Tyr Thr Gly Val Ser Val Leu Val Ala Leu Leu Leu Ala Gly Gln Ala
        35                  40                  45

Thr Thr Ala Tyr Phe Leu Tyr Gln Gln Gln Gly Arg Leu Asp Lys Leu
    50                  55                  60

Thr Ile Thr Ser Gln Asn Leu Gln Leu Glu Ser Leu Arg Met Lys Leu
65                  70                  75                  80

Pro Lys Ser Ala Lys Pro Val Ser Gln Met Arg Met Ala Thr Pro Leu
                85                  90                  95

Leu Met Arg Pro Met Ser Met Asp Asn Met Leu Leu Gly Pro Val Lys
            100                 105                 110

Asn Val Thr Ser Gly Arg Arg Ala Arg Arg Ala Arg Ser Gly
        115                 120                 125

Arg Lys Tyr Gly Asn Met Thr Gln Asp His Val Met His Leu Leu Thr
    130                 135                 140

Arg Ser Gly Pro Leu Glu Tyr Pro Gln Leu Lys Gly Thr Phe Pro Glu
145                 150                 155                 160

Asn Leu Lys His Leu Lys Asn Ser Met Asp Gly Val Asn Trp Lys Ile
                165                 170                 175

Phe Glu Ser Trp Met Lys Gln Trp Leu Leu Phe Glu Met Ser Lys Asn
            180                 185                 190

Ser Leu Glu Glu Lys Lys Pro Thr Glu Ala Pro Pro Lys Glu Pro Leu
        195                 200                 205

Asp Met Glu Asp Leu Ser Ser Gly Leu Gly Val Thr Arg Gln Glu Leu
    210                 215                 220
```

```
Gly Gln Val Thr Leu Ser Asp Arg Tyr Leu Asn Arg Arg Ala Pro Asp
225                 230                 235                 240

Cys Val Val Cys Glu Gly Asn Cys Lys Glu Lys Thr Glu Asp
        245                 250                 255

Asp Asn Cys Arg Ser Glu Ile Ile Lys Lys Ile Leu Lys Tyr Glu Thr
            260                 265                 270

Pro Thr Pro Ile Asp Val Leu Tyr Ser Gly Lys Gly Gln Gly Leu Ile
        275                 280                 285

Thr Lys Lys Leu Glu Asp Phe Cys Ser Ser Thr Asn Tyr Glu Gly
        290                 295                 300

Thr Asn Val Gln Lys Trp Lys Cys Tyr Asn Lys Asn Lys Asp Tyr Asn
305                 310                 315                 320

Asn Cys Glu Met Asn Ile Ser Ser Tyr Lys Asp Ala Thr Asp Pro Asn
            325                 330                 335

Val Met Leu Ser Val Glu Cys Phe His Ser Trp Ala Lys Asn Leu Leu
            340                 345                 350

Ile Asp Thr Ile Arg Trp Glu His Gln Leu Lys Asn Cys Ile Asn Asn
            355                 360                 365

Thr Asn Val Thr Asp Cys Thr Ser Lys Cys Ile Lys Asn Cys Glu Cys
370                 375                 380

Tyr Glu Lys Trp Ile Lys Glu Lys Glu Lys Glu Trp Pro Gln Val Lys
385                 390                 395                 400

Gly Val Leu Lys Lys Asp Glu Thr Ser His Asn Tyr Tyr Asp Lys
                405                 410                 415

Leu Lys Asp Val Phe Asp Arg Phe Leu Phe Glu Val Lys Gly Ala Leu
            420                 425                 430

Asp Gln Asp Glu Lys Gly Lys Trp Asp Gln Phe Thr Lys Asp Leu Glu
        435                 440                 445

Lys Lys Phe Gly Pro Ser Val Glu Ser Ala Gly Thr Ala Asn Ser Gln
        450                 455                 460

Asp Ala Ile Glu Leu Leu Leu Asp His Leu Asn Asp Asn Ala Thr Thr
465                 470                 475                 480

Cys Lys Asp Asn Asn Ser Leu Ala Val Glu Asn Cys Gly Ser Pro Asp
            485                 490                 495

Cys Val Val Lys Cys Asp Gly Lys Thr Cys Glu Gln Lys Lys Asp Asp
            500                 505                 510

Glu Asn Cys Arg Ser Lys Ile Ile Gln Lys Ile Leu Gln Gly Glu Glu
        515                 520                 525

Pro Thr Val Ile Asp Val Leu Tyr Ser Gly Lys Gly Gln Gly Leu Ile
        530                 535                 540

Thr Lys Lys Leu His Asp Phe Cys Ser Ser Thr Asn Lys Glu Asp Asp
545                 550                 555                 560

Lys Tyr Tyr Lys Lys Trp Lys Cys Tyr Asn Lys Asn Ser Asp Tyr Asn
                565                 570                 575

Asn Cys Glu Leu Ile Ser Ser Leu Ser Thr Asp Pro Thr Asp Pro Lys
            580                 585                 590

Val Met Leu Ser Ile Lys Cys Phe Asp Ser Trp Ala Arg Asn Leu Leu
            595                 600                 605

Val Asp Ala Leu Lys Trp Glu His Gln Leu Lys Asn Cys Ile Asn Asn
            610                 615                 620

Thr Asn Val Thr Asp Cys Lys Ser Asn Cys Asn Asn Cys Lys Cys
625                 630                 635                 640

Tyr Glu Glu Trp Ile Lys Gln Lys Glu Lys Glu Trp Gln Lys Val Lys
```

```
              645                 650                 655
Gly Val Leu Lys Lys Asp Lys Asn Ser Asp Asn Tyr Tyr Lys Asn
        660                 665                 670

Val Lys Asn Leu Phe Tyr Ser Phe Leu Phe Gln Val Ile Tyr Glu Leu
        675                 680                 685

Glu Lys Glu Glu Lys Asn Gly Lys Trp Asp Gln Phe Met Glu Asp Leu
        690                 695                 700

Lys Lys Lys Ile Glu Ala Ser Gln Lys Asn Lys Gly Thr Glu Asn Ser
705                 710                 715                 720

Gln Asp Ala Ile Glu Leu Leu Leu Asp His Leu Lys Asp Asn Ala Thr
                725                 730                 735

Ile Cys Lys Asp Asn Asn Thr Asn Glu Ala Gly Arg Pro Asn Ser Arg
            740                 745                 750

Pro Ala Gly Met Gln Ala Trp Asp Leu Cys Glu Gly Thr Leu Leu Leu
                755                 760                 765

Trp Cys Asp Ile Ile Gly Gln Thr Thr Tyr Arg Asp Leu Lys Leu
        770                 775                 780

<210> SEQ ID NO 66
<211> LENGTH: 8
<212> TYPE: PRT
<213> ORGANISM: Gallus gallus

<400> SEQUENCE: 66

Ser Ile Ile Asn Phe Glu Lys Leu
1               5

<210> SEQ ID NO 67
<211> LENGTH: 43
<212> TYPE: PRT
<213> ORGANISM: Artificial sequence
<220> FEATURE:
<223> OTHER INFORMATION: Peptide of the Melanoma associated retrovirus
      p15E protein

<400> SEQUENCE: 67

Cys Phe Tyr Ala Asp His Thr Gly Leu Val Arg Asp Ser Met Ala Lys
1               5                   10                  15

Leu Arg Glu Arg Leu Ser Gln Arg Gln Lys Leu Phe Glu Ser Gln Gln
            20                  25                  30

Gly Trp Phe Glu Gly Leu Phe Asn Lys Ser Pro
        35                  40

<210> SEQ ID NO 68
<211> LENGTH: 762
<212> TYPE: DNA
<213> ORGANISM: Artificial sequence
<220> FEATURE:
<223> OTHER INFORMATION: IT4var19 antigen encoding polynucleotide
      sequence

<400> SEQUENCE: 68
ccggactgtg tggttgtttg tgaaggagga aattgcaaag agaaaactga ggacgataat     60
tgtaggtctg aaatcatcaa gaagatcctg aagtacgaga ctcctactcc gattgacgtg    120
ctgtacagcg gtaaaggcca gggacttatc acgaaaaagc tggaggattt ctgcagctcg    180
accaccaact acgaaggaac gaacgtgcag aagtggaaat gctacaataa gaacaaggac    240
tacaataact gcgagatgaa catttccagc tacaaagatg caactgatcc caacgtgatg    300
ctttcggtcg agtgctttca ctcctgggcc aagaatctcc tgatcgacac catacggtgg    360
```

```
gaacaccagc tgaagaattg tatcaacaat actaatgtga ctgattgtac ctcaaagtgc      420
atcaaaaact gcgaatgcta cgaaaagtgg attaaggaaa aggagaagga atggccacaa      480
gtcaaaggcg tgctcaagaa gaaagacgag acttcacaca actactatga caagctgaag      540
gatgtgttcg atcgcttcct gttcgaggtc aaggggctc tggaccagga cgagaaggga      600
aagtgggacc aattcaccaa agatctcgaa aagaagtttg gccttccgt ggaatccgcc      660 ggcaccgcaa actcgcaaga tgcgatcgag ctgctcctgg accatctgaa cgacaacgcg      720
actacctgta aggataacaa cagcctggcc gtggaaaact gc                        762
```

<210> SEQ ID NO 69
<211> LENGTH: 756
<212> TYPE: DNA
<213> ORGANISM: Artificial sequence
<220> FEATURE:
<223> OTHER INFORMATION: PFLCINvar30 antigen encoding polynucleotide sequence

<400> SEQUENCE: 69
ccggactgcg tggtgaagtg tgacggtaaa acgtgcgaac agaagaagga cgatgaaaac 60
tgcagatcga agatcatcca gaagatcctc caaggagaag aaccaaccgt gatcgacgtg 120
ttgtactcgg gaaagggaca aggtctgatc actaagaagc tgcatgactt ctgctccagc 180
accaacaaag aggatgataa gtattacaaa aagtggaagt gctacaacaa aaactccgac 240
tacaacaatt gtgagctcat ttcctcgctc tcaactgatc caaccgaccc gaaagtcatg 300
ctctcgatta agtgcttcga ctcatgggcc cgcaatctgt tggtcgatgc cttgaagtgg 360
gaacatcagc tcaagaattg catcaataac accaacgtca ccgactgcaa atcgaactgc 420
aataacaact gcaagtgcta cgaagagtgg atcaagcaga aggaaaaaga atggcagaag 480
gtgaaagggg tgttgaagaa gaaggataag aattcagaca actactacaa gaatgtcaaa 540
aatctgttct actcatttct cttccaagtg atctacgagc ttgagaagga agaaaagaac 600
ggaaaatggg accagtttat ggaggacctg aaaaagaaaa tcgaggcgag ccagaaaaac 660
aaaggcaccg agaactccca agacgctatc gaactcctgc tggatcacct taaggataat 720
gcaaccatct gcaaggacaa taacactaac gaagcc 756

<210> SEQ ID NO 70
<211> LENGTH: 4
<212> TYPE: PRT
<213> ORGANISM: Artificial Sequence
<220> FEATURE:
<223> OTHER INFORMATION: Synthetic: cleavage site
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa is Arg or Lys

<400> SEQUENCE: 70

Arg Xaa Xaa Arg
1